United States Patent
Selvey et al.

(10) Patent No.: US 9,801,856 B2
(45) Date of Patent: Oct. 31, 2017

(54) COMPOSITION OF A 5-HT$_{2A}$ SEROTONIN RECEPTOR MODULATOR USEFUL FOR THE TREATMENT OF DISORDERS RELATED THERETO

(71) Applicant: Arena Pharmaceuticals, Inc., San Diego, CA (US)

(72) Inventors: Lee Alani Selvey, Poway, CA (US); Marlon Carlos, Chula Vista, CA (US); Paul Maffuid, Carlsbad, CA (US); Yun Shan, San Diego, CA (US); William L. Betts, III, San Diego, CA (US); Deam Windate Given, III, San Diego, CA (US); Ryan M. Hart, San Francisco, CA (US); Zezhi Jesse Shao, San Diego, CA (US)

(73) Assignee: Arena Pharmaceuticals, Inc., San Diego, CA (US)

(*) Notice: Subject to any disclaimer, the term of this patent is extended or adjusted under 35 U.S.C. 154(b) by 0 days.

(21) Appl. No.: 14/679,487

(22) Filed: Apr. 6, 2015

(65) Prior Publication Data
US 2016/0067216 A1    Mar. 10, 2016

Related U.S. Application Data

(63) Continuation of application No. 13/126,564, filed as application No. PCT/US2009/005811 on Oct. 27, 2009, now Pat. No. 9,034,911.
(Continued)

(51) Int. Cl.
*A61K 31/415* (2006.01)
*C07D 231/16* (2006.01)
(Continued)

(52) U.S. Cl.
CPC .......... *A61K 31/415* (2013.01); *A61K 9/2027* (2013.01); *A61K 9/2054* (2013.01); *A61K 9/1635* (2013.01); *C07D 231/16* (2013.01)

(58) Field of Classification Search
CPC ........................... A61K 31/415; C07D 231/16
(Continued)

(56) References Cited

U.S. PATENT DOCUMENTS 4,099,012 A    7/1978    Gschwend
4,405,644 A    9/1983    Kabbe et al.
(Continued)

FOREIGN PATENT DOCUMENTS

CA    2135253        5/1996
CN    101272771 A    9/2008
(Continued)

OTHER PUBLICATIONS

Brittain, Polymorphism in Pharmaceutical Solids, Second Edition, Chapter 9 (2009), pp. 333-335.*
(Continued)

*Primary Examiner* — Kathrien Cruz
*Assistant Examiner* — Janet L Coppins
(74) *Attorney, Agent, or Firm* — Pepper Hamilton LLP

(57) ABSTRACT

The present invention relates to certain compositions of a 5-HT$_{2A}$ serotonin receptor modulator and methods for their preparation. The compositions disclosed herein are useful for increasing slow wave sleep, improvise sleep consolidation, improving sleep maintenance and improving sleep quality, and for treating insomnia and related sleep disorders, dyssomnias, parasomnias and nonrestorative sleep and the like. The compositions disclosed herein are further useful for treating platelet aggregation, coronary artery disease, myocardial infarction, transient ischemic attack, angina, stroke, atrial fibrillation, thrombosis, asthma or
(Continued)

symptoms thereof, agitation or symptoms thereof, behavioral disorders, drug induced psychosis, excitative psychosis, Gilles de la Tourette's syndrome, manic disorder, organic or NOS psychosis, psychotic disorders, psychosis, acute schizophrenia, chronic schizophrenia, NOS schizophrenia and related disorders, diabetic-related disorders and progressive multifocal leukoencephalopathy and the like.

28 Claims, 31 Drawing Sheets

Related U.S. Application Data

(60) Provisional application No. 61/197,542, filed on Oct. 28, 2008.

(51) Int. Cl.
*A61K 9/20* (2006.01)
*A61K 9/16* (2006.01)

(58) Field of Classification Search
USPC .......................................... 548/356; 514/406
See application file for complete search history.

(56) References Cited

U.S. PATENT DOCUMENTS

| | | | |
|---|---|---|---|
| 4,409,231 A | 10/1983 | Stenzel et al. |
| 4,482,534 A | 11/1984 | Blank |
| 4,555,399 A | 11/1985 | Hsiao |
| 4,985,352 A | 1/1991 | Julius et al. |
| 5,077,409 A | 12/1991 | Wissner |
| 5,128,351 A | 7/1992 | Wissner |
| 5,346,906 A | 9/1994 | Baker et al. |
| 5,523,280 A | 6/1996 | Chene et al. |
| 5,661,024 A | 8/1997 | Kao et al. |
| 5,856,326 A | 1/1999 | Anthony et al. |
| 5,861,431 A | 1/1999 | Hildebrand et al. |
| 5,885,785 A | 3/1999 | Kao et al. |
| 5,886,044 A | 3/1999 | Widdowson et al. |
| 5,905,080 A | 5/1999 | Duckworth et al. |
| 5,945,382 A | 8/1999 | Cantegril et al. |
| 5,990,133 A | 11/1999 | Gaster et al. |
| 6,005,008 A | 12/1999 | Widdowson et al. |
| 6,028,083 A | 2/2000 | Carr et al. |
| 6,028,085 A | 2/2000 | Bromidge |
| 6,054,472 A | 4/2000 | Armistead et al. |
| 6,063,808 A | 5/2000 | Fabiano et al. |
| 6,107,324 A | 8/2000 | Behan et al. |
| 6,110,498 A | 8/2000 | Rudnic et al. |
| 6,140,509 A | 10/2000 | Behan et al. |
| 6,150,393 A | 11/2000 | Behan et al. |
| 6,180,138 B1 | 1/2001 | Engh et al. |
| 6,204,285 B1 | 3/2001 | Fabiano et al. |
| 6,271,261 B1 | 8/2001 | Widdowson |
| 6,284,269 B1 | 9/2001 | Struengmann et al. |
| 6,297,261 B1 | 10/2001 | Christophersen et al. |
| 6,358,698 B1 | 3/2002 | Weiner et al. |
| 6,383,762 B1 | 5/2002 | Kao et al. |
| 6,417,393 B1 | 7/2002 | Christophersen et al. |
| 6,420,541 B1 | 7/2002 | Behan et al. |
| 6,469,006 B1 | 10/2002 | Blair et al. |
| 6,479,480 B1 | 11/2002 | Moyes et al. |
| 6,479,519 B1 | 11/2002 | Astles et al. |
| 6,531,291 B1 | 3/2003 | Kabbash et al. |
| 6,541,209 B1 | 4/2003 | Behan et al. |
| 6,541,477 B2 | 4/2003 | Goehring et al. |
| 6,696,475 B2 | 2/2004 | Dahl et al. |
| 6,706,749 B2 | 3/2004 | Dahl et al. |
| 6,753,442 B1 | 6/2004 | Benedini et al. |
| 6,784,183 B2 | 8/2004 | Lavielle et al. |
| 6,846,919 B2 | 1/2005 | Behan et al. |
| 7,091,236 B1 | 8/2006 | Roberts et al. |
| 7,368,539 B2 | 5/2008 | Behan et al. |
| 7,754,724 B2 | 7/2010 | Lorsbach et al. |
| 8,481,535 B2 | 7/2013 | Charbaoui et al. |
| 9,034,911 B2 * | 5/2015 | Selvey ................. A61K 31/415 514/406 |
| 2001/0022963 A1 | 9/2001 | Klaveness et al. |
| 2002/0025965 A1 | 2/2002 | Lavielle et al. |
| 2002/0025967 A1 | 2/2002 | Smith |
| 2002/0098548 A1 | 7/2002 | Kao et al. |
| 2003/0037274 A1 | 2/2003 | Shikata et al. |
| 2004/0077654 A1 | 4/2004 | Bouillot et al. |
| 2004/0082644 A1 | 4/2004 | Korsten |
| 2004/0092528 A1 | 5/2004 | Kelly et al. |
| 2004/0102636 A1 | 5/2004 | Miller et al. |
| 2005/0054691 A1 | 3/2005 | Potter et al. |
| 2005/0080124 A1 | 4/2005 | Teegarden et al. |
| 2005/0215526 A1 | 9/2005 | Hulme et al. |
| 2005/0267097 A1 | 12/2005 | Pinto et al. |
| 2006/0014705 A1 | 1/2006 | Howitz et al. |
| 2006/0018839 A1 | 1/2006 | Ieni et al. |
| 2006/0063754 A1 | 3/2006 | Edgar et al. |
| 2006/0142241 A1 | 6/2006 | Yoo |
| 2006/0172992 A1 | 8/2006 | Yokoyama et al. |
| 2006/0205792 A1 | 9/2006 | Wong et al. |
| 2006/0229335 A1 | 10/2006 | Teegarden et al. |
| 2007/0004750 A1 | 1/2007 | Lorsbach et al. |
| 2007/0037827 A1 | 2/2007 | Nunes et al. |
| 2007/0043058 A1 | 2/2007 | Bang-Anderson et al. |
| 2007/0072857 A1 | 3/2007 | Teegarden et al. |
| 2007/0078134 A1 | 4/2007 | Teegarden et al. |
| 2007/0207994 A1 | 9/2007 | Teegarden et al. |
| 2007/0244086 A1 | 10/2007 | Teegarden et al. |
| 2007/0293539 A1 | 12/2007 | Lansbury et al. |
| 2007/0293685 A1 | 12/2007 | Fritch et al. |
| 2008/0015223 A1 | 1/2008 | Strah-Pleynet et al. |
| 2008/0114014 A1 | 5/2008 | Rich |
| 2008/0194836 A1 | 8/2008 | Gharbaoui et al. |
| 2008/0200530 A1 | 8/2008 | Unett et al. |
| 2009/0053306 A1 | 2/2009 | Agarwal et al. |
| 2009/0076254 A1 | 3/2009 | Behan et al. |
| 2009/0186895 A1 | 7/2009 | Teegarden et al. |
| 2009/0197935 A1 | 8/2009 | Teegarden et al. |
| 2010/0004264 A1 | 1/2010 | Xiong et al. |
| 2010/0069367 A1 | 3/2010 | Boren et al. |
| 2010/0240653 A1 | 9/2010 | Santora et al. |
| 2011/0021538 A1 | 1/2011 | Krishnan et al. |
| 2011/0207790 A1 | 8/2011 | Carlos et al. |
| 2011/0207791 A1 | 8/2011 | Selvey et al. |
| 2011/0263592 A1 | 10/2011 | Xiong et al. |
| 2012/0088785 A1 | 4/2012 | Rich |
| 2013/0172379 A1 | 7/2013 | Rich |
| 2013/0172398 A1 | 7/2013 | Rich |
| 2013/0217700 A1 | 8/2013 | Xiong et al. |
| 2013/0237541 A1 | 9/2013 | Teegarden et al. |
| 2013/0331399 A1 | 12/2013 | Leahy et al. |
| 2014/0142140 A1 | 5/2014 | Bird |
| 2014/0349976 A1 | 11/2014 | Hacksell et al. |
| 2015/0031897 A1 | 1/2015 | Rich |
| 2015/0045372 A1 | 2/2015 | Krishnan |
| 2015/0073141 A1 | 3/2015 | Teegarden et al. |
| 2015/0210648 A1 | 7/2015 | Carlos et al. |
| 2016/0075660 A1 | 3/2016 | Xiong et al. |
| 2016/0361296 A1 | 12/2016 | Friedhoff et al. |
| 2016/0374990 A1 | 12/2016 | Teegarden et al. |
| 2017/0057924 A1 | 3/2017 | Carlos et al. |

FOREIGN PATENT DOCUMENTS

| | | |
|---|---|---|
| DE | 102004061593 | 6/2006 |
| EP | 0 371 431 | 6/1990 |
| EP | 1 108 720 | 6/2001 |
| EP | 1 558 582 | 12/2005 |
| EP | 1 683 516 | 7/2006 |
| EP | 1695966 A1 | 8/2006 |
| EP | 1 734 039 | 12/2006 |
| EP | 1727803 B1 | 3/2012 |
| EP | 2190844 B1 | 4/2013 |
| EP | 2066641 B1 | 6/2014 |
| FR | 2 722 369 | 1/1996 |
| GB | 1147379 | 12/1967 |

(56) References Cited

FOREIGN PATENT DOCUMENTS

| | | |
|---|---|---|
| JP | 04334357 B2 | 3/2010 |
| WO | WO96/02138 | 2/1996 |
| WO | WO96/10559 | 4/1996 |
| WO | WO96/23783 | 8/1996 |
| WO | WO96/32931 | 10/1996 |
| WO | WO97/03967 | 2/1997 |
| WO | WO97/45111 | 12/1997 |
| WO | WO98/24785 | 6/1998 |
| WO | WO99/06354 | 2/1999 |
| WO | WO99/32436 | 7/1999 |
| WO | WO99/32463 | 7/1999 |
| WO | WO99/32927 | 7/1999 |
| WO | WO99/52927 | 10/1999 |
| WO | WO00/57877 | 10/2000 |
| WO | WO 00/57877 | 10/2000 |
| WO | WO00/64866 | 11/2000 |
| WO | WO 01/07436 | 2/2001 |
| WO | WO01/21160 | 3/2001 |
| WO | WO01/29008 | 4/2001 |
| WO | WO 01/29008 A | 4/2001 |
| WO | WO 01/46166 | 6/2001 |
| WO | WO 01/64676 | 9/2001 |
| WO | WO02/39987 | 5/2002 |
| WO | WO02/051833 | 7/2002 |
| WO | WO02/076464 | 10/2002 |
| WO | WO03/002097 | 1/2003 |
| WO | WO03/062206 | 7/2003 |
| WO | WO2004/028450 | 4/2004 |
| WO | WO2004/045118 | 5/2004 |
| WO | WO 2004/046110 | 6/2004 |
| WO | WO2004/058722 | 7/2004 |
| WO | WO2004/071426 | 8/2004 |
| WO | WO2004/085433 | 10/2004 |
| WO | WO2004/096771 | 11/2004 |
| WO | WO2005/012254 | 2/2005 |
| WO | WO 2005/012254 A1 * | 2/2005 | ........... C07D 231/12 |
| WO | WO2005/021545 A | 3/2005 |
| WO | WO2005/077345 | 8/2005 |
| WO | WO 2015/012554 | 10/2005 |
| WO | WO2005/103011 | 11/2005 |
| WO | WO2006/018662 | 2/2006 |
| WO | WO2006/049734 | 5/2006 |
| WO | WO2006/049941 | 5/2006 |
| WO | WO2006/055734 | 5/2006 |
| WO | WO2006/059149 | 6/2006 |
| WO | WO2006/060654 | 6/2006 |
| WO | WO2006/070394 | 7/2006 |
| WO | WO2006/076592 | 7/2006 |
| WO | WO2006/078610 | 7/2006 |
| WO | WO2006/079637 | 8/2006 |
| WO | WO2006/081335 | 8/2006 |
| WO | WO2006/086705 | 8/2006 |
| WO | WO2006/089871 | 8/2006 |
| WO | WO2006/095205 | 9/2006 |
| WO | WO2006/097766 | 9/2006 |
| WO | WO2006/100519 | 9/2006 |
| WO | WO2006/112464 | 10/2006 |
| WO | WO2006/116614 | 11/2006 |
| WO | WO2007/002559 | 1/2007 |
| WO | WO2007/026959 | 3/2007 |
| WO | WO2007/041409 | 4/2007 |
| WO | WO2007/120600 | 10/2007 |
| WO | WO2007/129111 | 11/2007 |
| WO | WO2007/136680 | 11/2007 |
| WO | WO2007/136689 | 11/2007 |
| WO | WO2007/136703 | 11/2007 |
| WO | WO2007/136875 | 11/2007 |
| WO | WO2008/027483 | 3/2008 |
| WO | WO2008/042388 | 4/2008 |
| WO | WO2008/054748 | 5/2008 |
| WO | WO2009/023253 | 2/2009 |
| WO | WO2009/123714 | 10/2009 |
| WO | WO2010/062321 | 6/2010 |
| WO | WO 2010/062323 | 6/2010 |
| WO | 2014065437 A1 | 5/2014 |
| WO | 2014085362 A1 | 6/2014 |
| WO | 2015012554 A1 | 1/2015 |

OTHER PUBLICATIONS

Casey et al., "Constitutively active mutant 5HT 2A serotonin receptors: inverse agonist activity of classical 5HT 2A antagonists", Society for Neuroscience Abstracts, Nov. 16-21, 1996, vol. 22, p. 699.10.

Herrick-Davis et al., "Constitutively active 5HT2C serotonin receptor created by site-directed mutagenesis". Society of Neuroscience Abstracts. Nov. 16-21, 1996, vol. 22, p. 699.18.

Tang, et al. Bioorg. Med. Chem. Lett., Sep. 15, 2003, 203(13): 2985-88. See Table 1 and p. 2987.

Zhu et al., "Synthesis and mode of action of [125]- and 3H-labeled Thieno -2,3-c]pyridine antagonists of cell adhesion molecule expression", J. Org. Chem., Feb. 2002, 67:943-8.

Ancelin, et al. "Non-degenerative mild cognitive impairment in elderly people and use of anticholinergic drugs: longitudinal cohort study" (Feb. 1, 2006) *BMJ*, doi : 10.1136/bmj.38740.439664.DE.

Anonymous "Prevention of Atherosclerotic Complications: Controlled Trial of Ketanserin" (1989) *Br. Med. J.* 298:424-430.

Aschenbrenner et al., Drug Therapy in Nursing, 2009, TOC.

Campbell et al. "Use of anticholinergics and the risk of cognitive impairment in an African American population" (2010) *Neurology* 75:152-159.

Carnahan et al. "The Concurrent Use of Anticholinergics and Cholinesterase Inhibitors: Rare Event or Common Practice?" (2004) JAGS 52(12):2082-2087 (abstract).

Chew et al. "Serum Anticholinergic Activity and Cognition in Patients with Moderate-to-Severe Dementia" (Jun. 2005) *Am J Geriatr Psychiatry* 13:6 (abstract).

Cooke "Glycopyrrolate in Bladder Dysfunction", Jan. 1, 1983 *South African Medical Journal* 63(1):3 (abstract).

Cuvposa glycopyrrolate oral solution Product Information Sheet, Rev. Jul. 2010.

Database Beilstein [Online] Beilstein Institute for Organic Chem., Frankfurt-Main, DE; XP002535545 Database Accession No. 5926580 (BRN), the whole document.

Defilippi et al. "Drug Interactions with Cholinesterase Inhibitors" (2003) *Drugs Aging* 20(6):437-444 (abstract).

Dosa et al. "Synthesis and SAR of solubilized pyrazole derivatives as 5-HT2A inverse-agonists for platelet aggregation" 232nd ACS National Meeting, Sep. 2006, Medi 431, 1 page (abstract).

Douaud et al. "Preventing Alzheimer's disease-related gray matter atrophy by B-vitamin treatment" (2013) *PNAS* 110:9523-9528.

Drinka "Antimuscarinic Drugs for Overactive Bladder and Their Potential Effects on Cognitive Function in Older Patients" 2006 *JAGS* 54(6):1004-1005 (abstract).

Edwards et al. "Risk of delirium with concomitant use of tolterodine and and acetycholinesterase inhibitors". 2002 *J Amer Geriatric Society* 50(6):1165-1166 (abstract).

European Search Report for EP05025004.2 dated Jun. 30, 2006.

Ferguson "Modulation of lymphatic smooth muscle contraction responses by the endothelium" (1992) *Journal of Surgical Research* 52:359-363 (abstract).

Gish et al. "Memorandum: Age-dependent manifestations of central anticholinergic effects" Department of Health and Human Services Public Health Service Food and Drug Administration Center for Drug Evaluation and Research, Mar. 5, 2007.

Gottlieb et al. "NMR Chemical Shifts of Common Laboratory Solvents as Trace Impurities" (1997) *J Org. Chem.* 62:7512-7515.

Hashimoto et al. "Urinary Incontinence: an Unrecognised Adverse Effect with Donepezil" (Aug. 12, 2000) *The Lancet* 356:568 (abstract).

Iliff et al. "A Paravascular Pathway Facilitates CSF Flow Through the Brain Parenchyma and the Clearance of Interstitial Solutes, Including Amyloid β." (2012) *Sci. Transl. Med.* 4(147):147ra111.

International Preliminary Report on Patentability for International Application No. PCT/US2005/041726 dated Sep. 21, 2006 by Authorized Officer Stefan Hartinger.

(56) References Cited

OTHER PUBLICATIONS

International Preliminary Report on Patentability for International Application No. PCT/US2007/011810 dated Jul. 16, 2008 by Authorized Officer Bart De Jong.
International Preliminary Report on Patentability; PCT/US2007/021182 dated Nov. 4, 2008 by Authorized Officer P. Lauro.
International Search Report and Written Opinion for PCT/US2004/023488 dated Oct. 12, 2004.
International Search Report and Written Opinion for PCT/US2004/023880 dated Nov. 15, 2004.
International Search Report and Written Opinion for PCT/US2007/021182 dated Mar. 14, 2005.
International Search Report and Written Opinion for PCT/US2008/009740 dated Feb. 18, 2009.
International Search Report and Written Opinion for PCT/US2009/005811 dated Jul. 8, 2010.
International Search Report and Written Opinion for PCT/US2009/005809 dated Apr. 28, 2010.
International Search Report and Written Opinion for PCT/US2009/002019 dated Dec. 14, 2009.
International Search Report and Written Opinion for PCT/US2016/037090 dated Sep. 9, 2016.
International Search Report for International Application No. PCT/US2006/002721 dated Feb. 20, 2007.
International Search Report for International Application No. PCT/US2005/041726 dated May 18, 2006 by Authorized Officer Stefan Hartinger.
International Search Report for International Application No. PCT/US2006/001516 dated Jun. 7, 2006.
International Search Report for International Application No. PCT/US2007/011810 dated Oct. 30, 2007 by Authorized Officer Bart De Jong.
Janos et al. "Overactive bladder medicines and cognitive testing" (Nov. 2008) *Int J Clin Pract* 62(11):1637-1642 (abstract).
Jayakumar et al. "Synthesis and SAR of Alkoxyphenyl Pyrazole as 5-HT2A Inverse Agonists" (2006) ACS, 232nd ACS National Meeting, Medi 430, poster.
Jayakumar et al; "Synthesis and SAR of Substituted Diphenylamines as 5HT2A Inverse-Agonists" (2004) ACS, meeting abstract.
Jeon et al. "The synthesis of a new pyrazolylimidazolinone via 1,3-dipolar cycloaddition reaction of N-methyl sydnone with methyl propiolate" (1998) *Bull. Korean Chem. Soc.* 19(7):725-726.
Jewart et al. "Cognitive, Behavioral and Physiological Changes in Alzheimer Disease Patients as a Function of Incontinence Medications" (Apr. 2005) Am J Geriatr Psychiatry 13(4):324-328 (abstract).
Jhee et al. "Centrally Acting Antiemetics Mitigate Nausea and Vomiting in Patients with Alzheimer's Disease Who Receive Rivastigmine" (Mar./Apr. 2002) *Clinical Neuropharmacology* 25(2):122-123 (abstract).
Johnell et al. "Concurrent Use of Anticholinergic Drugs and Cholinesterase Inhibitors" (2008) *Drugs Aging* 25(10):871-877 (abstract).
Kay et al. "Antimuscarinic Drugs for Overactive Bladder and Their Potential Effects on Cognitive Function in Older Patients" (2005) *JAGS* 53:2195-2201 (abstract).
Kay et al. "Preserving cognitive function for patients with overactive bladder: evidence for a differential effect with darifenacin" (Nov. 2008) *Int J Clin Pract.* 62(11):1792-1800.
Khullar et al. "Prevalence of Faecal Incontinence Among Women with Urinary Incontinence" (1998) *Br. J. Obstet. Gynaecol.* 105:1211-1213.
Kubinyi "3D QSAR in Drug Design: Ligand-Protein Interactions and Molecular Similarity" (1998) *Springer*, 800 pages. p. 2-3:243 (abstract).
Levin et al. "Direct measurement of the anticholinergic activity of a series of pharmacological compounds on the canine and rabbit urinary bladder" (1982) *J. Urology* 128(2):396-398 (abstract).
Lewy Body Dementia Association, Inc., treatment options page, http://www.lbda.org/content/treatment-options, at least as early as Apr. 10, 2015.
Lopez et al. "Predictors of progression in patients with AD and Lewy bodies" (2000) *Neurology* 54:1774-1779 (abstract).
Lu et al. "Chronic Exposure to Anticholinergic Medications Adversely Affects the Course of Alzheimer Disease" (Jul.-Aug. 2003) *Am J Geriatr Psychiatry* 11(4):458-461 (abstract).
Major et al. "Establishment of a Line of Human Fetal Glial Cells That Supports JC Virus Multiplication" (1985) PNAS USA 82:1257-1261.
McKeith et al. "Efficacy of rivastigmine in dementia with Lewy bodies: a randomised, double-blind, placebo-controlled international study" (2000) *The Lancet* 356:2031-2036 (abstract).
MedlinePlus, MedlinePlus Medical Encyclopedia, 2009, pp. 1-5 (abstract).
Mestre et al. "5-Hydroxytryptamine 2A receptor antagonists as potential treatment for psychiatric disorders" (2013) *Expert Opin. Investig Drugs* 22(4):411-421.
Office Action for U.S. Appl. No. 11/883,043, mailed on Sep. 8, 2009.
Oken "Antihistamines, a Possible Risk Factor for Alzheimer's Disease" (1995)*Medical Hypotheses* 44:47-48 (abstract).
Olichney et al. "Cognitive Decline is Faster in Lewy Body Variant than in Alzheimer's Disease" (1998) *Neurology* 51:351-357 (abstract).
Ono Pharmaceutical Co., Ltd. "Launch of Rivistach.RTM. Patch, for the Treatment of Dementia of Alzheimer's Type" (2011) 2 pages.
Product Information Sheet, Detrol.RTM. LA (tolterodine tartrate) capsules, Rev. Mar. 2008.
Product Information Sheet, Enablex.RTM. (darifenacin) tablets, T2010-XX.
Product Information Sheet, Exelon.RTM. Patch (rivastigmine transdermal system), LTS Lohmann Therapie Systems AG, 2000.
Product Information Sheet, Robinul RTM. glycopyrrolate tablets, Rev. Apr. 2010.
Product Information Sheet, Sanctura.RTM. (trospium chloride), Rev. Jan. 2011.
Product Information Sheet, VESIcare.RTM. (solifenacin succinate) tablets, Rev. Apr. 2010.
Przyklenk et al. "Targeted inhibition of the serotonin 5HT2A receptor improves coronary patency in an in vivo model of recurrent thrombosis" (2010)*J. Thromb Haemost.* 8(2):331-340.
Ray et al. "Central Anticholinergic Hypersensitivity in Aging" (Apr.-Jun. 1992) *Journal of Geriatric Psychiatry and Neurology* 5:72-77 (abstract).
Roche Bioreversible Carriers in Drug Design ed (1987) (TOC only).
Roe et al. "Use of Anticholinergic Medications by Older Adults with Dementia" (2002) *JAGS* 50:836-842 (abstract).
Rudolph et al. "The Anticholinergic Risk Scale and Anticholinergic Adverse Effects in Older Persons" (Mar. 10, 2008)*Arch Intern Med* 168(5):508-513.
Sink et al. "Dual Use of Bladder Anticholinergics and Cholinesterase Inhibitors: Long-Term Functional and Cognitive Outcomes" (2008) *JAGS* 56:847-853.
Speer et al "Influence of Digestive Enzymes Combined with Sodium Lauryl Sulfate on Dissolution of Cross-linked Gelatin Capsules" 2005 *AAPS*, poster.
Strah-Pleynet et al. "5HT2A Receptor Inverse Agonists: Design and SAR of Novel Pyrazole Derivatives" (2006) meeting abstract.
Strah-Pleynet et al. "Bioisosteric Modifications of Urea Derivatives as 5HT2A Inverse-Agonists" 2004 ACS, meeting abstract.
Strah-Pleynet et al. "Discovery and SAR of novel 5-HT.sub.2A, inverse-agonists" 227th ACS National Meeting, MED1 270, Arena Pharmaceutical Inc. (Mar. 2004), 1 page, poster.
Strah-Pleynet et al. "Discovery and SAR of Novel 5-HT2A Inverse-Agonists" 2004 ACS, 227th ACS National Meeting, Medi 270, abstract.
Teegarden et al. "Discovery of 1-[3-(4-Bromo-2-methyl-2H-pyrazol-3-yl)-4-methoxy-phenyl]-3-(2,4-difluoro-  -phenyl)-urea (APD125) and Related 5-HT.sub.2A Inverse Agonists for the Treatment of Insomnia" (2009) *JMC* pp. 1-50.

(56) References Cited

OTHER PUBLICATIONS

Teramura-Gronblad et al. "Use of Anticholinergic Drugs and Cholinesterase Inhibitors and Their Association with Psychological Well-Being Among Frail Older Adults in Residential Care Facilities" (2011) Ann Pharmacotherapy 45:596-602 (abstract).
Terry et al. "The Cholinergic Hypothesis of Age and Alzheimer's Disease-Related Cognitive Deficits: Recent Challenges and Their Implications for Novel Drug Development" (2003) JPET 306(3):821-827.
Tsao et al. "Transient Memory Impairment and Hallucinations Associated with Tolterodine Use" (Dec. 4, 2003) New England Journal of Medicine 349(23):2274-2275 (abstract).
Vacante et al. "Extension of JC Virus Host Range to Monkey Cells by Insertion of a Simian Virus 40 Enhancer into the JC Virus Regulatory Region" Virology 170:353-361.
Van Eijk et al. "Effect of rivastigmine as an adjunct to usual care with haloperidol on duration of delirium and mortality in critically ill patients: a multicentre, double-blind, placebo-controlled randomised trial" (2010) The Lancet 376:1829-1837 (abstract).
Vanover et al. "Role of 5-HT2A receptor antagonists in the treatment of insomnia" (2010) Nature and Science of Sleep 2:139-150.
Vasilevskii "Oxidative Iodination of Substituted N-Methylpyrazoles," (1980) Bull. Acad. Sci. USSR 29(5):778-784.
Vasilevsky et al. "Study of the Heterocyclization of vic-Substituted Hydrazides of Actylenylpyrazolecarboxylic Acids into N-Amino Pyrazolpyridinones" (2002)J. Hetercycl. Chem. 39:1229-1233.
Verdejo et al. "Tratamiento con propantelina de la incontinencia urinaria por inestabilidad vesical en pacientes ancianos" (1992) Anales de Medicina 9(3):1160120.
Williams et al. "Survival and mortality differences between dementia with Lewy bodies vs Alzheimer disease" (1935) Neurology 67:1935-1941 (abstract).
"Arena Pharmaceuticals Announces Preliminary Results of Phase 2b Clinical Trial of APD125 for the Treatment of Insomnia" PRNewswire-FirstCall via COMTEX News Network, Press Release dated Dec. 9, 2008.
"QuaSAR" Research Monograph 22, 1978, NIDA, Barnett and Willette (eds.) See pp. 16-25 pp. 159-179, Tables 1-8.
Adams et al; "Antithrombotic and Vascular effects of AR246686, a novel 5-HT2A receptor antagonist" 2007 EJM, nn. 1-22.
Affolter, H., "CA2+ as Messenger of 5HT2-Receptor Stimulation in Human Blood Platelets," Naunyn Schmiedebergs Arch. Pharmacol., 1984, vol. 325(4), 337-42.
Al-Shamma et al., "Nelotanserin, a Novel Selective Human 5-Hydroxytryptamine $_{2A}$ Inverse Agonist for the Treatment ofInsomnia," J Pharmacol. Exp. Ther., 2009, 332:281-290.
Al-Shamma et al; "The Selective Serotonin 5HT2A Inverse Agonist APD125 Promotes Sleep Onset and Consolidation in Male Wistar Rats During the Normal Active Phase" 2004 APSS.
Al-Shamma; "APD125: A 5-HT2A Inverse Agonist for the Treatment of Sleep Maintenance Insomnia" 2008 DDST; DD. 1-7.
Al-Shamma; "The Selective Serotonin 5HT2A Inverse Agonist APD125 Promotes Sleep Onset and Consolidation" Jun. 22, 2005 APSS, DD. 1-5.
Andrzejewska-Buczko Jr. et al., Klin. Oczna, 98(2), 101-4, 1996.
Antinori et al., Neurology, 48:687-694, 1997.
Barluenga, Jr. et al., "A New and Specific Method for the Monomethylation of Primary Amines," J Chem. Soc. Chem. Commun., 1984, 20, 1334-1335.
Batey, R.A. et al., "An Efficient New Protocol for the Formation of Unsymmetrical Tri- and Tretrasubstituted Ureas," Tetra. Lett., 1998, 39, 6267-6270.
Berge et al., "Pharmaceutical salts", J. of Pharmaceutical Sciences (1977) 66(1):1-19.
Berger and Major, Seminars and Neurology, 19:193-200, 1999.
Bernatowicz, M. et al., "A Comparison of Acid Labile Linkage Agents for the Synthesis of Peptide C-Terminal Amides," Tetra. Lett., 1989, 30(35), 4645-4648.

Blier, P. et al., "Putative mechanisms of action of antidepressant drugs in affective and anxiety disorders and pain," Journal of Psychiatry and Neuroscience, 2000, vol. 26(1), 37-43.
Anonymous, Br. Med. J , 298: 424-430, 1989.
Burger, A., "Isosterism and Bioisosterism in Drug Design", Prag. Drug Res., 37 (1991), pp. 287-371.
Burla et al.,J Appl. Cryst., 38, 381, 2005.
Buysse et al.,Psychiatry Research, 28(2), 193-213, 1989.
Cameron and Cotter, Naunyn Schmiedebergs Arch. Pharmacol., 367(6): 607-14, Jun. 2003.
Carter, H.E. et al., "Carbobenzoxy Chloride and Derivatives," Org. Syn. Coll., 1955, vol. 3, 167-169.
Catalan, J. et al., "New Ultraviolet Stabilizers: 3- and 5-(2'-Hydroxyphenyl)pyrazoles," J Am. Chem. Soc., 114, 5039-5048 (1992).
Cazzola et al., "5-HT modifiers as a potential treatment of asthma", TIPS, 2000, vol. 21, p. 13.
Cazzola, M. and Matera, M.G., Trends Pharmacol. Sci. 21:201-202, 2000.
Chambers, et al. Bioorg., Med. Chem. Lett. 2002, 12 1997-99. See p. 1997-98.
Chang et al.,J Ocul. Pharmacol., 1:137-147, 1985.
Chang et al.,Shock, 24(4): 336-340, 2005.
Cohen-Mansfield J. and Billig, N., Agitated Behaviors in the Elderly. I.A. Conceptual Review,J Am. Geriatr. Soc. 34(10): 711-721, 1986.
Collier et al., "Radiosynthesis and in-vivo evaluation of the pseudopeptide 8-opioid antagonist [125]-ITIPP(\II)", J. Labeled Compd. Radiopharm., 1999, vol. 42, pp. S264-S266.
Collins et al., "N-Phenylamidines as Selective Inhibitors of Human Neuronal Nitric Oxide Synthase: Structure-Activity Studies and Demonstration of in Vivi Activity".Journal of Medicinal Chemistry, American Chemical Society, 41,No. 15,pp. 2858-2871, 1998:XP0022144154.
DeBie, J.J. et al.,British J Pharm., 124:857-864, 1998.
Deuchar, G. et al.,Pulm. Pharmacol. Ther., 18(1):23-31, 2005.
Dosa et al; "Solubilized phenyl-pyrazole ureas as potent, selective 5-HT2A inverse-agonists and their aDDlication as antiplatelet agents" 2010 BMCL; DD. 1-15.
Dosa et al; "Synthesis and SAR of Pyridinyl-Pyrazole Derivatives as Selective 5HT2A Inverse-Agonists for Platelet Aggregation" 2008 ACS, 235th ACS National Meeting, MEDI 44.
Dosa, P.I. et al., "Synthesis and SAR of Solubilized Pyrazole Derivatives as 5-HT2a Inverse-Agonists for Platelet Aggregration," 232th ACS National Meeting, Sep. 2006, MEDI-431, 1 page.
Elliott, J. M. et al., "4-0xospiro[benzopyran-2,4'-piperidines] as Class III Antiarrhythmic Agents. Pharmacological Studies on 3,4-Dihydro-1'-[2-(benzofurazan-5-yl)-ethyl]-
6methanesulfonamidospiro[(2H)-l-benzopyran-2,4'-piperidin]-4-one (L-691,121)", J Med. Chem., 35:3973-3976 (1992).
Elphick et al.,Science , 306:1380-1383, 2004.
Fujita, M. et al.,Am. Heart J 145:e16,2003.
Fujiwara, T., and Chiba, S.Journal of Cardiovascular Pharmacology 26: 503-510, 1995.
Glennon, et al., J. Med. Chem., 1982, 25(10), 1163-68. See p. 1166-67 and Table IL.
Greene et al., Protecting Groups in Organic Synthesis, 3rd Edition, 1999 (Wiley).
Grotewiel et al., "Receptors Exhibit Constitutive Activity that is Blocked by Inverse Agonists," Faseb J., Abstract 353, 8(7), May 21-25, 1994 (1 page).
Grunder et al., Time course of 5-HT2A receptor occupancy in the human brain after a single oral dose of the putative antipsychotic drug MDL 100,907 measured by positron emission tomography, Neuropsychopharmacology, Sep. 1997; 17(3):175-85.
Gutsche, C.D. et al., "2-Phenylcycloheptanone," Org. Syn. Coll., 1963, vol. 4, 780-783.
Hayashi, T. et al., Atherosclerosis 168: 23-31, 2003.
Herrick-Davis et al., "Activating mutations of the serotonin 5-HT2C receptor", J. Neurochem., Sep. 1997; 69(3):1138-44.

(56) References Cited

OTHER PUBLICATIONS

Higuchi et al., "Pro-drugs and Novel Delivery Systems", vol. 14 of the ACS Symposium Series; and in Bioreversible Carriers in Drug Design, ed. Edward B. Roche, American Pharmaceutical Association and Pergamon Press, 1987.
Hittner et al; "A Selective 5-HT2A Receptor Inverse Agonist with Preclinical Antipsychotic Profile in Rats" 2000 NEURO.
Holtje, the Practice of medicinal Chemistry, 2nd ed., 2003, Wermuth (editor), Academic Press, pp. 387-403. See p. 394.
Horibe, E., Circulation Research 68: 68-72, 2004.
ICSD-International Classification of Sleep Disorders: Diagnostic and Coding Manual: Diagnostic Classification SteerinR Committee, American Sleep Disorders Association, 1990.
Ieni, J. and Meyerson, L., "The 5-HT1A Receptor Probe[3H]8-0H-DPAT labels . . . ," Life Sciences, 1988, vol. 42, 311-320.
Ikeguchi, K. and Kuroda, A., "Mianserin Treatment of Patients with Pyschosis Induced by Antiparkinsonian Drugs," Eur. Arch. Psych. Clin. Neurosci., 1995, 244, 320-324.
Jayakumar et al; "Synthesis and SAR of Alkoxyphenyl Pyrazole as 5-HT2A Inverse Agonists" 2006, ACS, 232nd ACS National Meeting, MEDI 430.
Jayakumar et al; "Synthesis and SAR of Substituted Diphenylamines as 5HT2A Inverse-Agonists" 2005 ACS, 229th ACS National Meeting, MEDI 049.
John Mandel, "Statistical Analysis of Experimental Data", Chapter 3, pp. 28-57, Toronto, Ontario, (1964).
John Mandel, "Statistical Analysis of Experimental Data", Chapter 9, pp. 204-207, Toronto, Ontario, (1964).
Julius, D. et al., "The 5HT2 Receptor Defines a Family of Structurally Distinct but Functionally Conserved Serotonin Receptors," Proc. Natl. Acad. Sci. USA, 1990, vol. 87, 928-932.
Kanayama, M. et al., J Neurosurg. Spine, 2:441-446, 2005.
Kaneniwa, et al., Solubilization of Water-Insoluble Organic Powders by Ball-Milling in the Presence of Polyvinylpyrrolidone; Chem. Pharm. Bull; 23(11) 2973-2986; 1975.
Katz, LR. et al.,J Clin. Psychiatry, 60(2):107-115, 1999.
Kitagawa, 0. et al., "Beckmann Rearrangement of0-4 Pentenyl Oxime through N-Bromosuccinimide-Mediated Activating Process", Chem. Pharm. Bull., 45(1) 32-35 (1997).
Konig, W. et al., "A New Method for Synthesis of Peptides: Activation of the Carboxyl Group with Dicyclohexylcarbodiimide using 1-Hydroxybenzotriazoles as Additives," Chem. Ber., 1970, 103, 788-798 (English abstract included).
Koss E. et al., "Assessing patterns of agitation in Alzheimer's disease patients with the Cohen-Mansfield Agitation Inventory. The Alzheimer's Disease Cooperative Study",Alzheimer Dis. Assoc. Disord. ll(suDDL 2):S45-S50, 1997.
Krieger and Emre, Pediatr. Transplantation, 8:594-599, 2004.
Krystal et al; "The effects of APD125, a selective serotonin 5-HT2A, on sleep quality and sleep maintenance in a subiective study in patients with primary insomnia" 2009 SLEEP; DD. 1-23.
Landolt H.P. et al., Serotonin-2 Receptors and Human Sleep: Effect of Selective Antagonist on EEG Power Spectra, Neuropsvcho pharmacolo f!V, vol. 21(3):455-66, 1999.
Le Bas et al., "Radioiodinated analogs of EP 00652218 for the exploration of the tachykinin NKI receptor by spect", J. Labeled Compd. Radiopharm., 2001, vol. 44:S280-S282.
Luthringer et al; "Pharmacokinetic and Pharmacodynamic Effects of the Selective 5HT2A Inverse Agonist APD125 in Healthy Adults" 2005 APSS.
Marchini, P. et al., "Sodium Borohydride-Carboxylic Acid Systems. Useful Reagents for the Alkylation of Amines," J Orf;;. Chem., 1975, 40(23), 3453-3456.
Marcos, E. et al., Circ. Res., 94(9): 1263-70, 2004.
Mastropasqua et al.,Acta. Ophthalmol. Scand. Suppl., 224:24-25, 1997.
Menzaghi et al; "AR1 16081, A Novel Selective 5-HT2A Inverse Agonist as a Putative Atypical Antipsychotic: Comparative Studies with Clozapine and Haloperidol" 2000 CINP.
Menzaghi et al; "AR1 16081, A Novel High Affinity 5-HT2A Receptor Inverse Agonist With In Vivo Efficacy" Nov. 1999 NEURO.
Menzaghi et al; "Identification ofNovel Selective 5-HT2A Inverse Agonists as Putative Atypical Antipychotics Using Constitutively Activated Human 5-HT Receptors" Jun. 2000 ASPET.
Menzaghi et al; "Therapeutic Potential of Selective Serotonin 5HT2A Receptor Inverse Agonists: Pre-Clinical Evaluation of AR1 16081 as Antipsychotics in Rodents" 2002 FESN.
Miai, C., Clin. Exp. Pharmacol. Physiol., 30(3): 189-193, 2003.
Mizuki, Y. et al., "Effects of Mianserin on Negative Symptoms in Schizophrenia," Int. Clinical Psychopharmacolo5'Y, 1990,5:83-95.
Morairty, et al.; Selective $5HT_{2A}$ and $5HT_6$ Receptor Antagonists Promote Sleep in Rats;Sleep; vol. 31, No. 1, 2008.
Mueller, Ann. Thorac. Surg., 77:354-362, 2004.
Muto, T. et al.,Mal. Cell. Biochem. 272: 119-132, 2005.
National Institute of Health, National Heart, Lung and Blood Institute,Insomnia Facts Sheet, Oct. 1995.
Newton, R.A. and Elliot, J.M., "Mianserin-Induced Down-Regulation of Human 5-Hydrpxytryptamine2A and 5-Hydro . . . ," Journal of Neurochemistry, 1997, 69: 1031-1038.
Nichols, et al. J. Med Chem, 1991, 34, 276-81. See p. 279.
Nishiyama, T., Eur. J Pharmacol., 516:18-22, 2005.
Nomura et al., Blood Coagulation and Fibrinolysis 16: 423-428, 2005.
Otwinowski et al.,Methods Enzymology, 1997, 276, 307.
Pawlak, D. et al., Thrombosis Research 90: 259-270, 1998.
Pietraszek, M.H. et al., Thrombosis Res. 66(6): 765-74, 1992.
Portegies et al.,Eur. J Neural., 11:297-304, 2004.
Prosser et al., "Selective serotonin 5-HT2A inverse agonists promote sleep consolidation in male Wistar rats during the normal inactive phase", #29, Arena Pharmaceuticals, Inc., APSS Meeting (Jun. 2004) 1 page.
Querbes et al.,J Virology, 78:250-256, 2004.
Storey,R.,etal. "Automation ofSolid Form Screening Procedures in the Pharmaceutical Industry—How toAvoid the Bottlenecks", Crystallography Reviews,2004,vol. 10,No. 1,DD 45-46.

Remington, The Science and Practice of Pharmacy, $20_n$ Ed., 2000, Lippincott Williams & Wilkins, Editors: Gennaro, A.R. et al., 2000.
Rosenberg et al; "APD125, a selective serotonin 5-HT2A receptor inverse agonist, significantly improves the key parameters of sleep maintenance in patients with primary insomnia" 2007 AASM.
Rosenberg et al; "APD125, a selective serotonin 5-HT2A receptor inverse agonist, significantly improves the key PSG parameters of sleep maintenance in patients with primary insomnia" 2008 APA; pp. 1-37.
Rosenberg et al.; "APD125, a selective serotonin 5-HT(2A) receptor inverse agonist, significantly improves sleep maintenance in primary insomnia." Sleep (2008), 31(12), 1663-71.
Roth et al; "APD125, a selective serotonin 5-HT2A receptor inverse agonist, significantly improves the key parameters of sleep maintenance in patients with primary insomnia" 2008 APSS DD. 1-19.
Sahgal, A. (ed.), "Practical behavioural neuroscience: problems, pitfalls and suggestions," in Behavioral Neuroscience: A Practical Approach, IRL Press, New York, 1993, vol. 1, 1-8.
Satomura et al., "Sarpogrelate, a specific 5HT2-receptor antagonist, improves the coronary microcirculation in coronary artery disease", Clin. Cardiol. Jan. 2002; 25(1):28-32.
Sawnyok, J. et al., "Antidepressants as analgesics: an overview of central and peripheral mechanisms of action," Journal of Psychiatry and Neurosciences, 2001, vol. 26(1), 21-9.
Schmidt, C., "The Role of 5-HT2A Receptors in Antipsychotic Activity," Life Sciences, 1995, 56(25), 2209-2222.
Shan et al.; "Investigation of non-aqueous vehicles for a poorly soluble compound intended for softgel dosage form development". Abstract AAPS2005-000990, AAPS Journal, (2005).
Shan et al.; "Physicochemical characterization during salt selection process". Abstract AAPS2006-001961, AAPS Journal, (2006).
Shan et al.; "Physicochemical characterization during salt selection process". Abstract AAPS2005-000997, AAPS Journal, (2005).

(56) References Cited

OTHER PUBLICATIONS

Sharpley A.L., et al., "Slow Wave Sleep in Humans: Role of 5-HT$_{2A}$ and 5HT$_2$c Receptors", Neuropharmacolo fzy, vol. 33(3/4):467-71, 1994.

Sheehan, J.C. et al., "l-Ethyl-3-(3-Dimethylamiono)Proplycarbodiimide Hydrochloride and Methiodide," Or£. Svn. Coll., 1973, vol. 5, 555-558.

Shibata, R. et al., "Adiponectin protects against myocardial ischemiareperfusion injury through AMPK- and COX-2 dependent mechanisms," Nature Medicine, advanced online Publications: pp. 1-8, Published Online Sep. 11, 2005.

Silva, A., J Pharmacol., 518(2-3): 152-7,2005.

Singh et al., Transplantation, 69:467-472, 2000.

Smith et al., Test-retest variability of serotonin 5-HT2A receptor binding measured with positron emission tomography and [18F] altanserin in the human brain, Synapse, Dec. 1998; 30(4):380-92.

Sorenson et al., "Characterization of the 5-HT2 Receptor Antagonist MDL 100907 as Putative Atypical Antipshychotic: Behavioral, Electrophysiological and Neurchemical Studies," J Pharacol. Exp. Ther., 1993 266(2), 684-691.

Speer, et al.; "Influence of digestive enzymes on dissolution of a poorly water soluble compound from cross-linked gelatin capsules in sodium lauryl sulfate medium". Abstract AAPS2005-000998, AAPS Journal, (2005).

Speer, et al.; "Intrinsic dissolution characterization of different morphic forms of a poorly water soluble compound". Abstract AAPS2006-002324, AAPS Journal, (2006).

Staley et al., Comparison of [(18)F] altanerin and [(18)F]durteroaltanserin for PET imaging or serotonin (2A) receptors in baboon brain: pharmacological studies, Nucl Med Biol, Apr. 2001;28(3):271-9.

Strah-Pleynet, et al.; "Discovery and SAR of novel 5HT2A receptor inverse-agonists". Abstracts of Papers, 227th ACS National Meeting, Anaheim, CA, United States, Mar. 28-Apr. 1, 2004 (2004), MEDI-270.

Strah-Pleynet, et al.; "5-HT2A Receptor inverse-agonists: Design and structure-activity relationship of novel pyrazole derivatives". Abstracts of Papers, 231st ACS National Meeting, Atlanta, GA, United States, Mar. 26-30, 2006 (2006), MEDI-145.

Strah-Pleynet, et al.; "Bioisosteric modifications of urea derivatives as 5-HT2A inverse-agonists" Abstracts of Papers, 229th ACS National Meeting, San Diego, CA, United States, Mar. 13-17, 2005 (2005), MEDI-042.

Street et al., "Olanzapine treatment of psychotic and behavioral symptoms in patients with Alzheimer disease in nursing care facilities: a double-blind, randomized, placebo-controlled trial. The HGEU Study Group", Arch Gen Psychiatry, Oct. 2000; 57(10):968-76.

Takahashi, T. et al.,Diabetes. Res. Clin. Pract., 58(2): 123-9, Nov. 2002.

Takenaka et al., "The effect of anplag (sarpogrelate HCI), novel selective 5-HT$_2$ antagonist on intraocular pressure in glaucoma patients", Investig Ophthalmol Vis Sci, 36(4):5724 (3390-377) 1995.

Talvik-Lotfi et al., "High 5HT2A receptor occupancy in M100907-treated schizophrenic patients", Phychopharmacology (2000) 148:400-403.

Teegarden et al., "Discovery of1-[3-(4-Bromo-2-methyl-2H-pyrazol-3-yl)-4-methoxyphenyl]-3-(2,4-difluorophenyl(urea(Nelotanserin) and Related 5-Hydroxytryptamine $_{2A}$Inverse Agonists for the Treatment oflnsomnia", J Med. Chem. 2003, vol. 53, pp. 1923-1936.

Teegarden etal.; "5-HT2A inverse-agonists for the treatment of insomnia". Current Topics in Medicinal Chemistry, (2008), 8(11), 969-976.

The International Classification of Sleep Disorders, Revised Diagnostic and Coding Manual, American Academy of Sleep Medicine (2001) pp. 1-336 (also includes table of contents and glossary).

Topliss, John G. "A Manual Method for Applying the Hansch Approach to Drug Design", Journal of Medicinial Chemistry, vol. 20, No. 4, pp. 463-469, 1997.

Van Zwieten, PA, "Receptors Involved in the Regulation of Vascular Tone," Arzneimittelforschung. 1985, vol. 35(12A): 1904-9.

Verstraete, M., "Prevention of atherosclerotic complications: controlled trial of ketanserin," British Medical Journal, 1989, vol. 298, 424-30.

Vikenes, K. et al., "Serotonin is associated with coronary artery disease and cardiac events," Circulation, 1999, vol. 100,483-9.

Vippagunta, S. et al., "Crystalline solids," Advanced Drug Delivery Reviews, 48:3-26 (2001).

Westkaemper et al., Curr. Topics Med. Chem. 2002, 2, 575-598.

White, E., "Deamination of Amines. 2-Phenylethyl Benzoate Via the Nitrosoamide Decomposition," Org. Syn. Coll., 1973, vol. 5, 336-339.

Wikstrom, H. et al., "Synthesis and Pharmacological Testing of 1, 2, 3, 4, 10, 14b-Hexahydro-6-methoxy . . . ," J Med. Chem., 2002, vol. 45, 3280-3285.

Wilson, H.C. et al., Thromb. Haemost., 2:66(3):355-60, Sep. 2, 1991.

Winokur A. et al., Acute Effects of Mirtazapine on Sleep Continuity and Sleep Architecture in Depressed Patients: A Pilot Study,Soc. OfBiol. Psych., vol. 48:75-78, 2000.

Xiong et al; "Discovery and SAR of Highly Selective 5-HT2A Receptor Subtype Inverse-Agonists for Inhibition of Platelet Aggregation" 2008 ACS, 235[1] National Meeting, MEDI 45.

Xiong et al; "Synthesis and in Vivo Evaluation of Phenethylpiperazine Amides: Selective 5-Hydroxytryptamine2A Receptor Antagonists for the Treatment oflnsomnia", Journal of Medical Chemistry, 2010, vol. 53, 5696-5706 JMC.

Yamada et al., Clin. Diagn. Viral., 1:245-256, 1993.

Yamashita, T. et al.,Haemostatis 30:321-332, 2000.

Yevich et al. Curr. Med. Chem., 1997, 45(5), 295-312. See p. 302.

Guillory, "Generation of Polymorphs, Hydrates, Solvates, and Amorphous Solids, in Polymorphism in the Pharmaceutical Industry", 183-226, 202-209; Harry G. Britain, ed., 1999.

Griesser, The Importance of Solvates, in Polymorphism in the Pharmaceutical Industry; 211-23 3; Rolf Hilfzker, ed., 2006.

Morissette, et al., High-throughput Crystallization: Polymorphs, Salts, Co-crystals and Solvates of Pharmaceutical Solids,Advanced Dru£ Delivery Reviews, 56 (2004) 275-300.

Halberstadt et al., Neuropsychopharmacology (2009) 34, 1958-1967.

Bryn et al., Pharm. Res. V. 12 (1995), N. 7, p. 945-54.

Bryn, Solid-State Chemistry of Drugs, 2nd ed. (1999), Chapter 11—Hydrates and Solvates, 233-247.

Diagnostic and Statistical Manual of Mental Disorders, Fourth Edition, Text Revision: DSM-IV-TR, Washington, DC, American Psychiatric Association, 2000.

International Search Report and Written Opinion for PCT/US16/42556 dated Dec. 23, 2016.

Gill et al. "A Prescribing Cascade Involving Cholinesterase Inhibitors and Anticholinergic Drugs" (2005) Arch Intern Med 165:808-813.

Kaluef et al. "Hypolocomotion, anxiety and serotonin syndrome-like behavior contribute to the complex phenotype of serotonin transporter knockout mice" (2007) Genes, Brain and Behavior 6:389-400.

Monti "Serotonin 5-HT2A Receptor Antagonists in the Treatment of Insomnia: Present Status and Future Prospects" (2010) Drugs of Today 46(3):183-193.

Shapiro et al. "Differential Modes of Agonist Biinding to 5-Hydroxytryptamine2A Serotonin Receptors Revealed by Mutation and Molecular Modeling of Conserved Residues in Transmembrane Region 5" (2000) Molecular Pharmacol. 58(5):877-886.

* cited by examiner

A Pictorial Representation of the Hemi-acetonitrile Solvate of 1-[3-(4-Bromo-2-methyl-2H-pyrazol-3-yl)-4-methoxy-phenyl]-3-(2,4-difluoro-phenyl)-urea as Generated by Mercury v. 1.4.2 (Build 2) Based on Single-crystal X-ray Diffraction Analysis

COMPOSITION OF A 5-HT$_{2A}$ SEROTONIN RECEPTOR MODULATOR USEFUL FOR THE TREATMENT OF DISORDERS RELATED THERETO

CROSS REFERENCE TO RELATED APPLICATIONS

This application is a continuation of U.S. National Phase application Ser. No. 13/126,564, filed Apr. 28, 2011, which is a §371 National Stage Application of International Application PCT/US09/05811, filed Oct. 27, 2009, which claims the benefit of priority of U.S. Provisional Appl. No. 61/197,542, filed Oct. 28, 2008, each of which is incorporated herein by reference in its entirety.

FIELD OF THE INVENTION

The present invention relates to certain compositions of a 5-HT$_{2A}$ serotonin receptor modulator and methods for their preparation. The compositions disclosed herein are useful for increasing slow wave sleep, improving sleep consolidation, improving sleep maintenance and improving sleep quality, and for treating insomnia and related sleep disorders, dyssomnias, parasomnias and nonrestorative sleep and the like. The compositions disclosed herein are further useful for treating platelet aggregation, coronary artery disease, myocardial infarction, transient ischemic attack, angina, stroke, atrial fibrillation, thrombosis, asthma or symptoms thereof, agitation or symptoms thereof, behavioral disorders, drug induced psychosis, excitative psychosis, Gilles de la Tourette's syndrome, manic disorder, organic or NOS psychosis, psychotic disorders, psychosis, acute schizophrenia, chronic schizophrenia, NOS schizophrenia and related disorders, diabetic-related disorders and progressive multifocal leukoencephalopathy and the like.

BACKGROUND OF THE INVENTION

It has recently been discovered that certain 1,3-disubstituted urea compounds are modulators of the 5-HT$_{2A}$ serotonin-receptor and thus are useful for treating patients with disorders related thereto. Disorders related to the 5-HT$_{2A}$ serotonin receptor include, for example, insomnia and related sleep disorders, dyssomnias, parasomnias, nonrestorative sleep, platelet aggregation, coronary artery disease, myocardial infarction, transient ischemic attack, angina, stroke, atrial fibrillation, thrombosis, asthma or symptoms thereof, agitation or symptoms thereof, behavioral disorders, drug induced psychosis, excitative psychosis, Gilles de la Tourette's syndrome, manic disorder, organic or NOS psychosis, psychotic disorders, psychosis, acute schizophrenia, chronic schizophrenia, NOS schizophrenia and related disorders, diabetic-related disorders and progressive multifocal leukoencephalopathy and the like.

The 1,3-disubstituted urea compounds are disclosed and claimed in International Application No. PCT/US2004/023488 (published as International Publication No. WO 2005/012254), incorporated herein by reference in its entirety, and can be prepared according to the procedures described therein.

In particular, the Compound of Formula I, referred herein as 1-[3-(4-bromo-2-methyl-2H-pyrazol-3-yl)-4-methoxy-phenyl]-3-(2,4-difluoro-phenyl)-urea (APD125), has been found to be especially effective as a modulator of the 5-HT$_{2A}$ serotonin receptor.

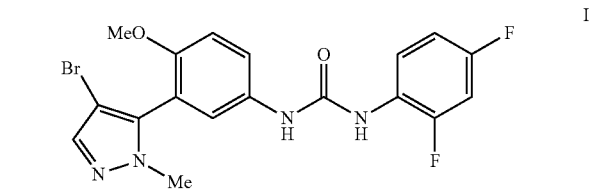 [SMILES: COc1ccc(NC(=O)Nc2ccc(F)cc2F)cc1-c1c(Br)cnn1C]

However, APD125 was observed to have aqueous solubility of about 10 μg/mL or less in each of the following aqueous systems: (a) deionized water, (b) 0.01 N HCl (about pH 2), (c) phosphate buffer (about pH 7) and (d) saline (about 0.9% NaCl solution). Accordingly, 1-[3-(4-bromo-2-2H-pyrazol-3-yl)-4-methoxy-phenyl]-3-(2,4-difluoro-phenyl)-urea is considered to possess extremely poor aqueous solubility and would be expected to provide very low oral bioavailability. It is well known that an active drug substance administered by any route must possess some aqueous solubility for systemic absorption and therapeutic response. Compounds that have poor solubility often exhibit either incomplete or erratic absorption and thus produce a minimal response at a desired dosage.

Recognizing the problems, it was discovered that pharmaceutical compositions for APD125, which were disclosed and claimed in International Application No. PCT/US2006/038267 (published as International Publication No. WO 2007/041409), incorporated herein by reference in its entirety, provide (a) substantial solubility, (b) pharmaceutical acceptability, (c) ease of processability during product manufacture, and (d) high oral bioavailability. In particular, it was observed that certain compositions allow for the preparation of pharmaceutical compositions containing APD125 in exceedingly high concentrations, such as concentrations up to about 350 mg/mL, thus allowing for convenient oral administration while at the same time achieving improved pharmacokinetic parameters, such as at least two fold higher bioavailability, compared to the aqueous suspension.

However, APD125 was found to be somewhat labile in solution at 25° C. forming a number of degradants, the most abundant of which are 2,4-difluoroaniline (DFA) and 3-(2'-methoxy-5-aminophenyl)-4-bromo-2-methyl-2H-pyrazole, compound II shown below.

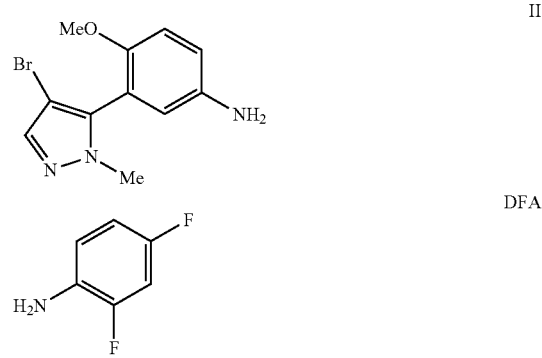

One aspect of the present invention relates to novel, solid-dosage formulations of APD125 which provide one or more of the following: (a) high oral-bioavailability, comparable to that of liquid formulations; (b) physical stability with respect to crystalline form; and (c) chemical stability better than that of liquid formulations. Consequently, the solid-dosage formulations disclosed herein are useful for treating certain 5-HT$_{2A}$ serotonin receptor-related disorders, such as insomnia and related sleep disorders.

Certain synthetic processes for preparing 1-[3-(4-bromo-2-methyl-2H-pyrazol-3-yl)-4-methoxy-phenyl]-3-(2,4-difluoro-phenyl)-urea have been described is PCT Applications PCT/US2004/023880 and PCT/US2006/002721, both of which are incorporated herein by reference in their entirety.

PCT Application PCT/US20004/023880 discloses processes that prepare 1-[3-(4-bromo-2-methyl-2H-pyrazol-3-yl)-4-methoxy-phenyl]-3-(2,4-difluoro-phenyl)-urea from 3-(4-bromo-2-methyl-2H-methyl-3-yl)-4-methoxy-phenylamine and 2,4-difluorophenyl-isocyanate in the presence of toluene (Example 5, PCT Application PCT/US2004/023880) with an impurity of 0.9 mole % identified as the desbromo of 1-[3-(4-bromo-2-methyl-2H-pyrazol-3-yl)-4-methoxy-phenyl]-3-(2,4-difluoro-phenyl)-urea and an overall purity of 98.2% purity by HPLC. While the solid state properties for 1-[3-(4-bromo-2-methyl-2H-pyrazol-3-yl)-4-methoxy-phenyl]-3-(2,4-difluoro-phenyl)-urea were not characterized, it was found in a subsequent experiment that the toluene process as described in Example 5 (PCT Application PCT/US2004/023880) was observed to be a mixture of at least Form I and Form II.

PCT Application PCT/US2006/002721 discloses processes that prepare 1-[3-(4-bromo-2-methyl-2H-pyrazol-3-yl)-4-methoxy-phenyl]-3-(2,4-difluoro-phenyl)-urea from 3-(4-bromo-2-methyl-2H-methyl-3-yl)-4-methoxy-phenylamine and 2,4-difluorophenyl-isocyanate in the presence of an alcoholic solvent, such as methanol and n-propanol (Examples 1-5, PCT Application PCT/US2006/002721) to give substantially Form II.

Although Form II is considered the more thermodynamically stable polymorph, Form I was identified as the desirable crystalline form based on, inter alia, improved pharmacokinetic characteristics.

SUMMARY OF THE INVENTION

One aspect of the present invention pertains to pharmaceutical compositions comprising:
 a. 1-[3-(4-bromo-2-methyl-2H-pyrazol-3-yl)-4-methoxy-phenyl]-3-(2,4-difluoro-phenyl)-urea; and
 b. an excipient selected from: PVP and coPVP.

One aspect of the present invention pertains to kits for treating a 5-HT$_{2A}$ serotonin receptor-related disorder in an individual comprising a container and a pharmaceutical composition of the present invention.

One aspect of the present invention pertains to methods for treating a 5-HT$_{2A}$ serotonin receptor-related disorder in an individual comprising administering to the individual in need thereof a therapeutically effective amount of a pharmaceutical composition of the present invention.

In some embodiments, the individual is a mammal.

In some embodiments, the mammal is a human.

In some embodiments, the pharmaceutical composition is administered orally, nasally sublingually, bucally, transdermally, vaginally or rectally.

In some embodiments, the pharmaceutical composition is administered orally.

One aspect of the present invention pertains to the use of a pharmaceutical composition of the present invention in the manufacture of a medicament for the treatment of a 5-HT$_{2A}$ serotonin receptor-related disorder.

One aspect of the present invention pertains to the use of a pharmaceutical composition of the present invention in the manufacture of a medicament for the treatment of a sleep disorder.

One aspect of the present invention pertains to the use of a pharmaceutical composition of the present invention in the manufacture of a medicament for the treatment of a dyssomnia.

One aspect of the present invention pertains to the use of a pharmaceutical composition of the present invention in the manufacture of a medicament for the treatment of insomnia.

One aspect of the present invention pertains to the use of a pharmaceutical composition of the present invention in the manufacture of a medicament for the treatment of a parasomnia.

One aspect of the present invention pertains to the use of a pharmaceutical composition of the present invention in the manufacture of a medicament for increasing slow wave sleep.

One aspect of the present invention pertains to the use of a pharmaceutical composition of the present invention in the manufacture of a medicament for improving sleep consolidation.

One aspect of the present invention pertains to the use of a pharmaceutical composition of the present invention in the manufacture of a medicament for improving sleep maintenance.

One aspect of the present invention pertains to the use of a pharmaceutical composition of the present invention in the manufacture of a medicament for improving sleep quality.

One aspect of the present invention pertains to the use of a pharmaceutical composition of the present invention in the manufacture of a medicament for the treatment of nonrestorative sleep.

One aspect of the present invention pertains to the use of a pharmaceutical composition of the present invention in the manufacture of a medicament for the treatment of a 5-HT$_{2A}$ serotonin receptor-related disorder selected from the group consisting of coronary artery disease, myocardial infarction, transient ischemic attack, angina, stroke, and atrial fibrillation.

One aspect of the present invention pertains to the use of a pharmaceutical composition of the present invention in the manufacture of a medicament for the treatment of a condition associated with platelet aggregation.

One aspect of the present invention pertains to the use of a pharmaceutical composition of the present invention in the manufacture of a medicament for the reduction of the risk of blood clot formation in an individual.

One aspect of the present invention pertains to the use of a pharmaceutical composition of the present invention in the manufacture of a medicament for the reduction of the risk of blood clot formation in an angioplasty or coronary bypass surgery individual.

One aspect of the present invention pertains to the use of a pharmaceutical composition of the present invention in the manufacture of a medicament for the reduction of the risk of blood clot formation in an individual suffering from atrial fibrillation.

One aspect of the present invention pertains to the use of a pharmaceutical composition of the present invention in the manufacture of a medicament for the treatment of a diabetic-related disorder.

One aspect of the present invention pertains to the use of a pharmaceutical composition of the present invention in the manufacture of a medicament for the treatment of progressive multifocal leukoencephalopathy.

One aspect of the present invention pertains to the use of a pharmaceutical composition of the present invention in the manufacture of a medicament for the treatment of hypertension.

One aspect of the present invention pertains to the use of a pharmaceutical composition of the present invention in the manufacture of a medicament for the treatment of pain.

One aspect of the present invention pertains to the use of a pharmaceutical composition of the present invention in the manufacture of a medicament for the treatment of a sleep disorder selected from: a dyssomnia, insomnia, and a parasomnia.

One aspect of the present invention pertains to the use of a pharmaceutical composition of the present invention in the manufacture of a medicament for increasing slow wave sleep, improving sleep consolidation, improving sleep maintenance, improving sleep quality, or treating nonrestorative sleep.

One aspect of the present invention pertains to the use of a pharmaceutical composition of the present invention in the manufacture of a medicament for the treatment of a 5-HT$_{2A}$ serotonin receptor-related disorder selected from: coronary artery disease, myocardial infarction, transient ischemic attack, angina, stroke, atrial fibrillation, a condition associated with platelet aggregation, blood clot formation in an individual, a diabetic-related disorder, progressive multifocal leukoencephalopathy, hypertension, and pain.

One aspect of the present invention pertains to pharmaceutical compositions of the present invention for use in a method of treatment of the human or animal body by therapy.

One aspect of the present invention pertains to pharmaceutical compositions of the present invention for use in a method for the treatment of 5-HT$_{2A}$ serotonin receptor-related disorder.

One aspect of the present invention pertains to pharmaceutical compositions of the present invention for use in a method for the treatment of a sleep disorder.

One aspect of the present invention pertains to pharmaceutical compositions of the present invention for use in a method for the treatment of a dyssomnia.

One aspect of the present invention pertains to pharmaceutical compositions of the present invention for use in a method for the treatment of insomnia.

One aspect of the present invention pertains to pharmaceutical compositions of the present invention for use in a method for the treatment of a parasomnia.

One aspect of the present invention pertains to pharmaceutical compositions of the present invention for use in a method for increasing slow wave sleep.

One aspect of the present invention pertains to pharmaceutical compositions of the present invention for use in a method for improving sleep consolidation.

One aspect of the present invention pertains to pharmaceutical compositions of the present invention for use in a method for improving sleep maintenance.

One aspect of the present invention pertains to pharmaceutical compositions of the present invention for use in a method for improving sleep quality.

One aspect of the present invention pertains to pharmaceutical compositions of the present invention for use in a method for the treatment of nonrestorative sleep.

One aspect of the present invention pertains to pharmaceutical compositions of the present invention for use in a method for the treatment of a 5-HT$_{2A}$ mediated disorder selected from the group consisting of coronary artery disease, myocardial infarction, transient ischemic attack, angina, stroke, and atrial fibrillation.

One aspect of the present invention pertains to pharmaceutical compositions of the present invention for use in a method for the treatment of a condition associated with platelet aggregation.

One aspect of the present invention pertains to pharmaceutical compositions of the present invention for use in a method for reducing the risk of blood clot formation in an individual.

One aspect of the present invention pertains to pharmaceutical compositions of the present invention for use in a method for reducing the risk of blood clot formation in an angioplasty or coronary bypass surgery individual.

One aspect of the present invention pertains to pharmaceutical compositions of the present invention for use in a method for reducing the risk of blood clot formation in an individual suffering from atrial fibrillation.

One aspect of the present invention pertains to pharmaceutical compositions of the present invention for use in a method for the treatment of a diabetic-related disorder.

One aspect of the present invention pertains to pharmaceutical compositions of the present invention for use in a method for the treatment of progressive multifocal leukoencephalopathy.

One aspect of the present invention pertains to pharmaceutical compositions of the present invention for use in a method for the treatment of hypertension.

One aspect of the present invention pertains to pharmaceutical compositions of the present invention for use in a method for the treatment of pain.

One aspect of the present invention pertains to pharmaceutical compositions of the present invention for use in a method for the treatment of a sleep disorder selected from: a dyssomnia, insomnia and a parasomnia.

One aspect of the present invention pertains to pharmaceutical compositions of the present invention for use in a method for increasing slow wave sleep, improving sleep consolidation, improving sleep maintenance, improving sleep quality, or treating nonrestorative sleep.

One aspect of the present invention pertains to pharmaceutical compositions of the present invention for use in a method for the treatment of a 5-HT$_{2A}$ mediated disorder selected from: coronary artery disease, myocardial infarction, transient ischemic attack, angina, stroke, atrial fibrillation, a condition associated with platelet aggregation, blood clot formation in an individual, atrial fibrillation, diabetic-related disorder, progressive multifocal leukoencephalopathy, hypertension, and pain.

One aspect of the present invention pertains to methods for preparing a pharmaceutical composition of the present invention comprising:

a. 1-[3-(4-bromo-2-methyl-2H-pyrazol-3-yl)-4-methoxy-phenyl]-3-(2,4-difluoro-phenyl)-urea; and b. an excipient selected from: PVP and coPVP;

comprising blending the 1-[3-(4-bromo-2-methyl-2H-pyrazol-3-yl)-4-methoxy-phenyl]-3-(2,4-difluoro-phenyl)-urea and the excipient in a blender.

One aspect of the present invention pertains to dosage forms comprising a. about 0.1 mg to about 500 mg of 1-[3-(4-bromo-2-methyl-2H-pyrazol-3-yl)-4-methoxy-phenyl]-3-(2,4-difluoro-phenyl)-urea; and b. PVP, methyl cellulose, or a mixture thereof.

A further aspect of the present invention is directed to compositions comprising Form I of 1-[3-(4-bromo-2-methyl-2H-pyrazol-3-yl)-4-methoxy-phenyl]-3-(2,4-difluoro-phenyl)-urea and less than 0.9 mole % of 1-(2,4-difluorophenyl)-3-(4-methoxy-3-(1-methyl-1H-pyrazol-5-yl)phenyl)urea.

One aspect of the present invention is directed to methods for treating a 5-HT$_{2A}$ serotonin receptor-related disorder in an individual comprising administering to the individual in need thereof a therapeutically effective amount of a composition of the present invention.

One aspect of the present invention pertains to the use of a composition of the present invention in the manufacture of a medicament for the treatment of a 5-HT$_{2A}$ serotonin receptor-related disorder.

One aspect of the present invention pertains to the use of a composition of the present invention in the manufacture of a medicament for the treatment of a sleep disorder.

One aspect of the present invention pertains to the use of a composition of the present invention in the manufacture of a medicament for the treatment of a dyssomnia.

One aspect of the present invention pertains to the use of a composition of the present invention in the manufacture of a medicament for the treatment of insomnia.

One aspect of the present invention pertains to the use of a composition of the present invention in the manufacture of a medicament for the treatment of a parasomnia.

One aspect of the present invention pertains to the use of a composition of the present invention in the manufacture of a medicament for increasing slow wave sleep.

One aspect of the present invention pertains to the use of a composition of the present invention in the manufacture of a medicament for improving sleep consolidation.

One aspect of the present invention pertains to the use of a composition of the present invention in the manufacture of a medicament for improving sleep maintenance.

One aspect of the present invention pertains to the use of a composition of the present invention in the manufacture of a medicament for improving sleep quality.

One aspect of the present invention pertains to the use of a composition of the present invention in the manufacture of a medicament for the treatment of nonrestorative sleep.

One aspect of the present invention pertains to the use of a composition of the present invention in the manufacture of a medicament for the treatment of a 5-HT$_{2A}$ serotonin receptor-related disorder selected from the group consisting of coronary artery disease, myocardial infarction, transient ischemic attack, angina, stroke, and atrial fibrillation.

One aspect of the present invention pertains to the use of a composition of the present invention in the manufacture of a medicament for the treatment of a condition associated with platelet aggregation.

One aspect of the present invention pertains to the use of a composition of the present invention is the manufacture of a medicament for the reduction of the risk of blood clot formation in an individual.

One aspect of the present invention pertains to the use of a composition of the present invention in the manufacture of a medicament for the reduction of the risk of blood clot formation in an angioplasty or coronary bypass surgery individual.

One aspect of the present invention pertains to the use of a composition of the present invention in the manufacture of a medicament for the reduction of the risk of blood clot formation in an individual suffering from atrial fibrillation.

One aspect of the present invention pertains to the use of a composition of the present invention in the manufacture of a medicament for the treatment of a diabetic-related disorder.

One aspect of the present invention pertains to the use of a composition of the present invention in the manufacture of a medicament for the treatment of progressive multifocal leukoencephalopathy.

One aspect of the present invention pertains to the use of a composition of the present invention in the manufacture of a medicament for the treatment of hypertension.

One aspect of the present invention pertains to the use of a composition of the present invention in the manufacture of a medicament for the treatment of pain.

One aspect of the present invention pertains to the use of a composition of the present invention in the manufacture of a medicament for the treatment of a sleep disorder selected from: a dyssomnia, insomnia, and a parasomnia.

One aspect of the present invention pertains to the use of a composition of the present invention in the manufacture of a medicament for increasing slow wave sleep, improving sleep consolidation, improving sleep maintenance, improving sleep quality, or treating nonrestorative sleep.

One aspect of the present invention pertains to the use of a composition of the present invention in the manufacture of a medicament for the treatment of a 5-HT$_{2A}$ serotonin receptor-related disorder selected from: coronary artery disease, myocardial infarction, transient ischemic attack, angina, stroke, atrial fibrillation, a condition associated with platelet aggregation, blood clot, formation in an individual, a diabetic-related disorder, progressive multifocal leukoencephalopathy, hypertension, and pain.

One aspect of the present invention pertains to compositions of the present invention for use in a method of treatment of the human or animal body by therapy.

One aspect of the present invention pertains to compositions of the present invention for use in a method of treatment of a 5-HT$_{2A}$ serotonin receptor-related disorder.

One aspect of the present invention pertains to compositions of the present invention for use in a method of treatment of a sleep disorder.

One aspect of the present invention pertains to compositions of the present invention for use in a method of treatment of a dyssomnia.

One aspect of the present invention pertains to compositions of the present invention for use in a method of treatment of insomnia.

One aspect of the present invention pertains to compositions of the present invention for use in a method of treatment of a parasomnia.

One aspect of the present invention pertains to compositions of the present invention for use in a method for increasing slow wave sleep.

One aspect of the present invention pertains to compositions of the present invention for use in a method for improving sleep consolidation.

One aspect of the present invention pertains to compositions of the present invention for use in a method for improving sleep maintenance.

One aspect of the present invention pertains to compositions of the present invention for use in a method for improving sleep quality.

One aspect of the present invention pertains to compositions of the present invention for use in a method for the treatment of nonrestorative sleep.

One aspect of the present invention pertains to compositions of the present invention for use in a method for the treatment of a 5-HT$_{2A}$ mediated disorder selected from the group consisting of coronary artery disease, myocardial infarction, transient ischemic attack, angina, stroke, and atrial fibrillation.

One aspect of the present invention pertains to compositions of the present invention for use in a method for the treatment of a condition associated with platelet aggregation.

One aspect of the present invention pertains to compositions of the present invention for use in a method for reducing the risk of blood clot formation in an individual.

One aspect of the present invention pertains to compositions of the present invention for use in a method for reducing the risk of blood clot formation in an angioplasty or coronary bypass surgery individual.

One aspect of the present invention pertains to compositions of the present invention for use in a method for reducing the risk of blood clot formation in an individual suffering from atrial fibrillation.

One aspect of the present invention pertains to compositions of the present invention for use in a method for the treatment of a diabetic-related disorder.

One aspect of the present invention pertains to compositions of the present invention for use in a method for the treatment of progressive multifocal leukoencephalopathy.

One aspect of the present invention pertains to compositions of the present invention for use in a method for the treatment of hypertension.

One aspect of the present invention pertains to compositions of the present invention for use in a method for the treatment of pain.

One aspect of the present invention pertains to compositions of the present invention for use in a method for the treatment of a sleep disorder selected from: a dyssomnia, insomnia and a parasomnia.

One aspect of the present invention pertains to compositions of the present invention for use in a method for increasing slow wave sleep, improving sleep consolidation, improving sleep maintenance, improving sleep quality, or treating nonrestorative sleep.

One aspect of the present invention pertains to compositions of the present invention for use in a method for the treatment of a 5-HT$_{2A}$ mediated disorder selected from: coronary artery disease, myocardial infarction, transient ischemic attack, angina, stroke, atrial fibrillation, a condition associated with platelet aggregation, blood clot formation in an individual, atrial fibrillation, diabetic-related disorder, progressive multifocal leukoencephalopathy, hypertension, and pain.

These and other aspects of the invention disclosed herein will be set forth in greater detail as the patent disclosure proceeds.

Figure 16:
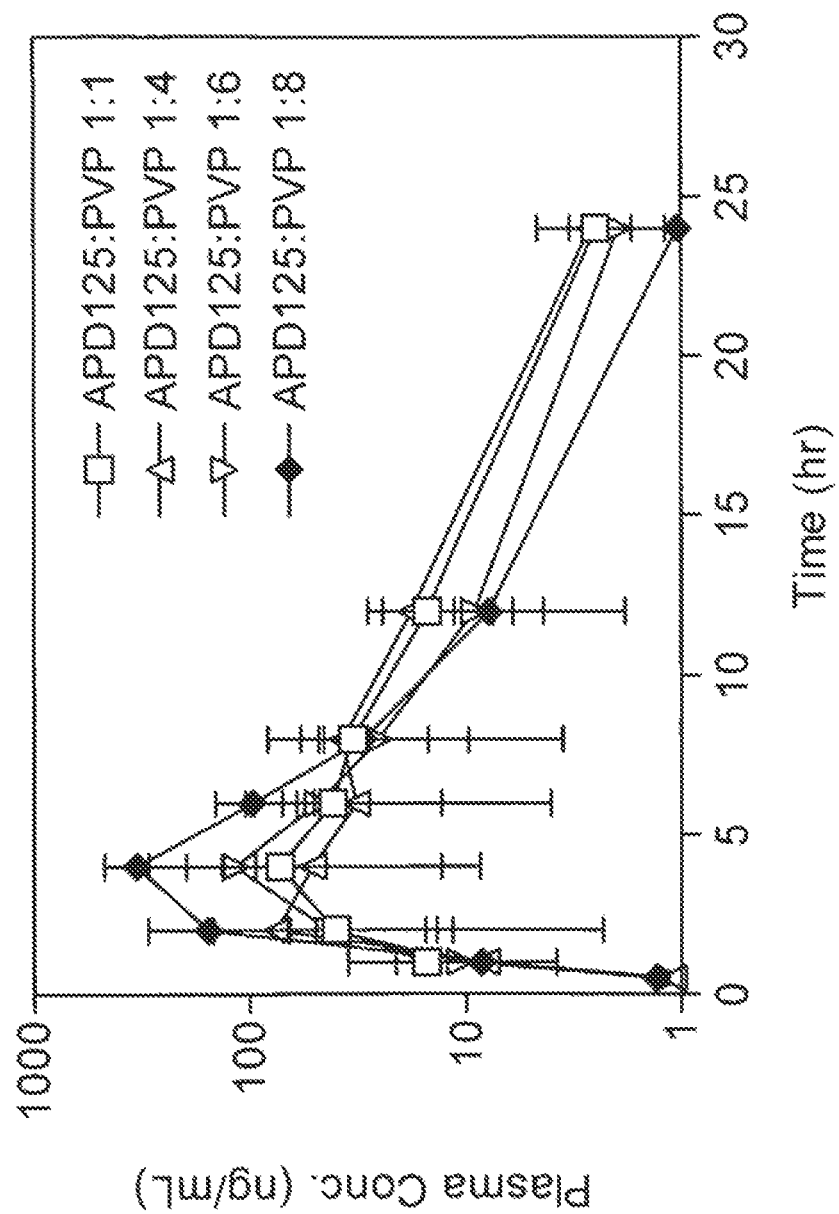

FIG. 16 depicts the effect of APD125/Pvp ratio on the APD125 plasma exposure in monkeys after oral administration of 10-mg direct-compression (dry) tablets.

Figure 17:
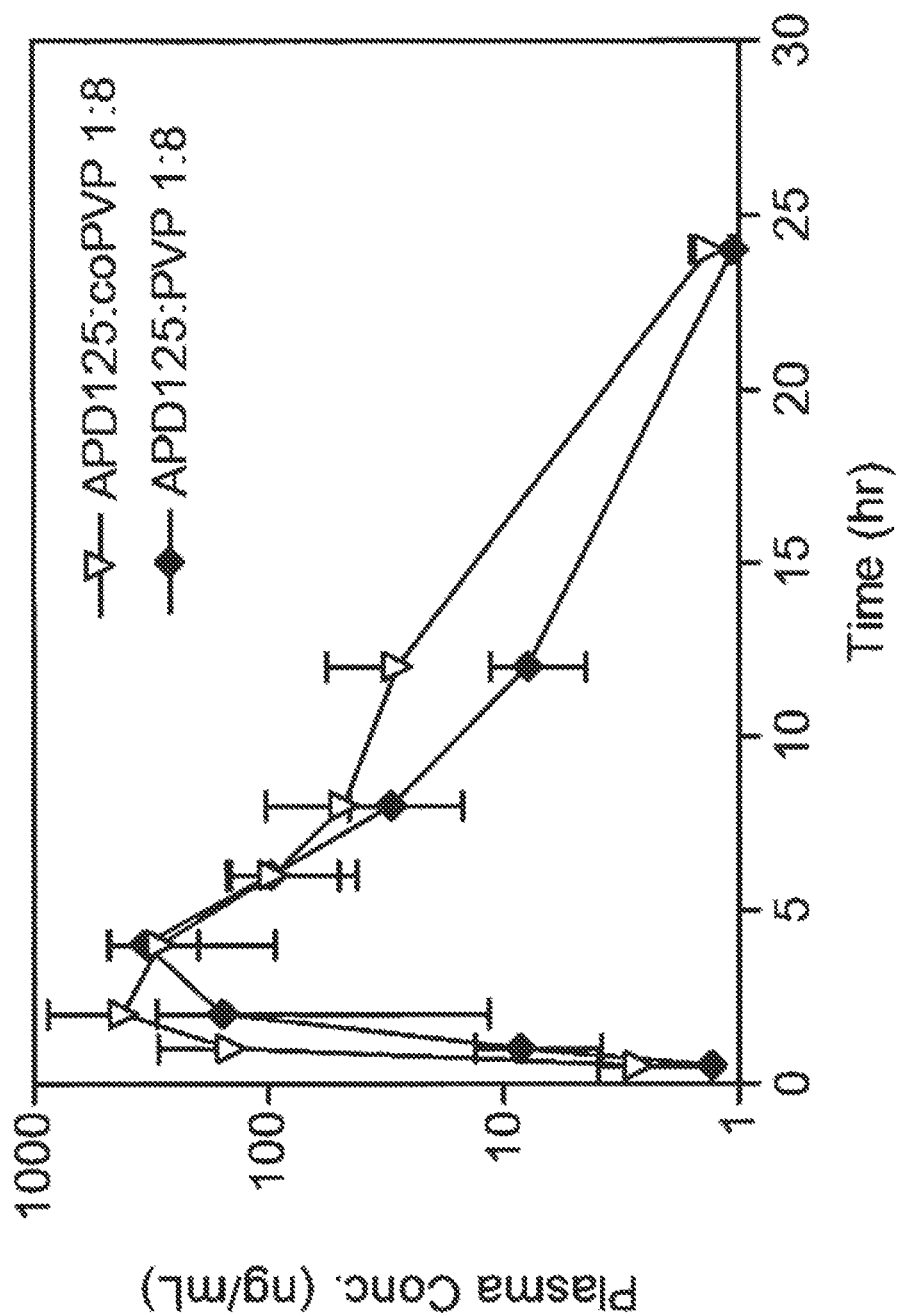

FIG. 17 depicts the effect of PVP and coPVP on the APD125 plasma exposure in monkeys after oral administration of 10-mg direct-compression (dry) tablets, containing either APD125:PVP (1:8) or APD125:coPVP (1:8).

Figure 18:
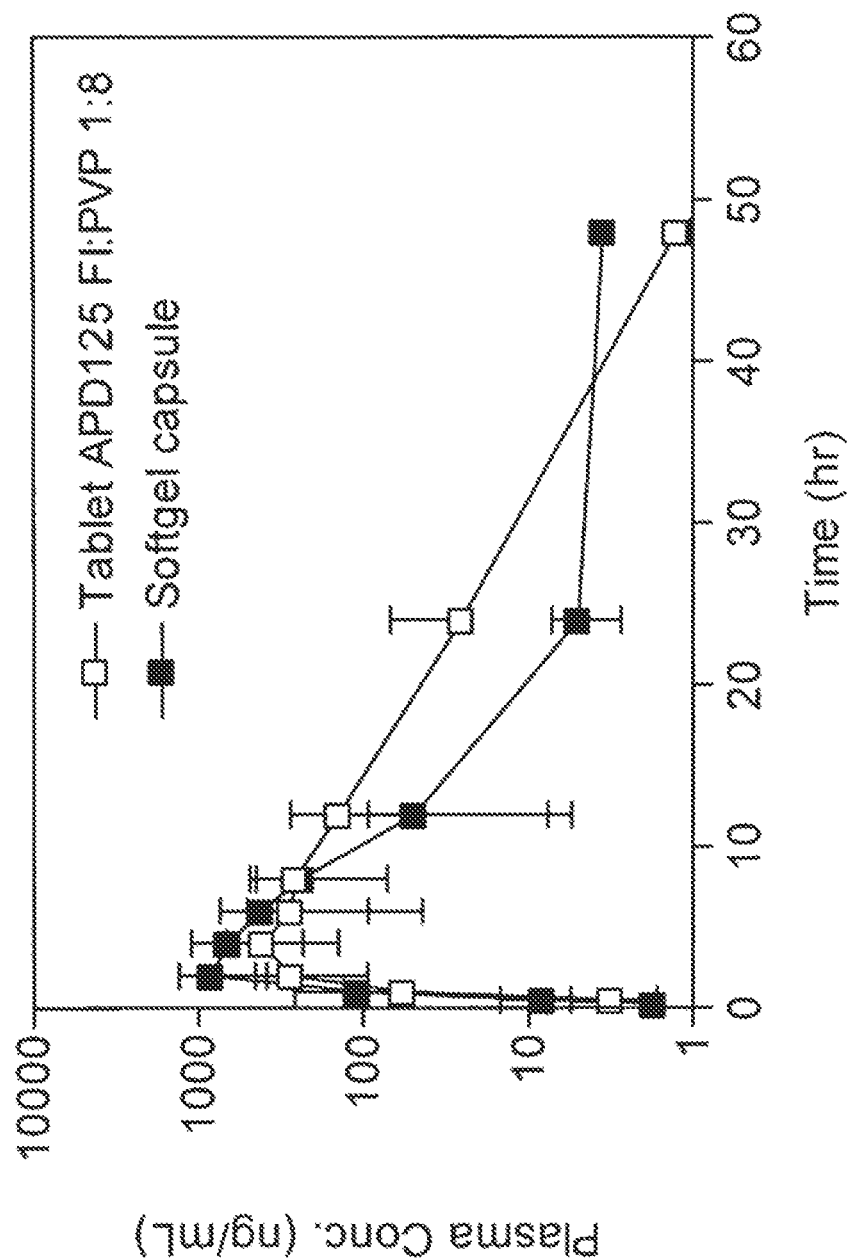

FIG. 18 depicts APD125 plasma exposure in monkeys after oral administration of direct-compression tablets (composition: 40 mg APD125 Form I:PVP [1:8], containing 2% w/w methyl cellulose) or SGCs (composition: 40 mg APD125 in Cremophor®:Labrasol® [1:1]).

Figure 19:
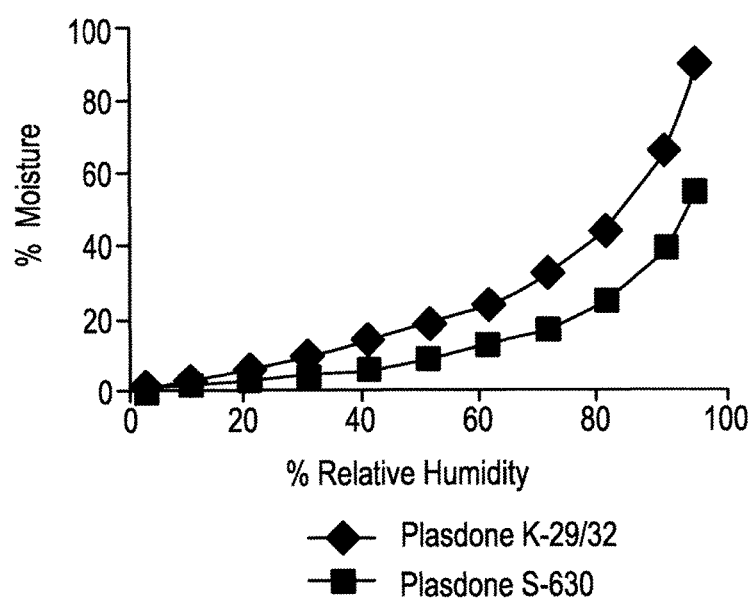

FIG. 19 depicts a hygroscopicity plot for Plasdone™ S-630 (coPVP) copolymer versus Plasdone™ K-29/32 (PVP) homopolymer.

Figure 20:
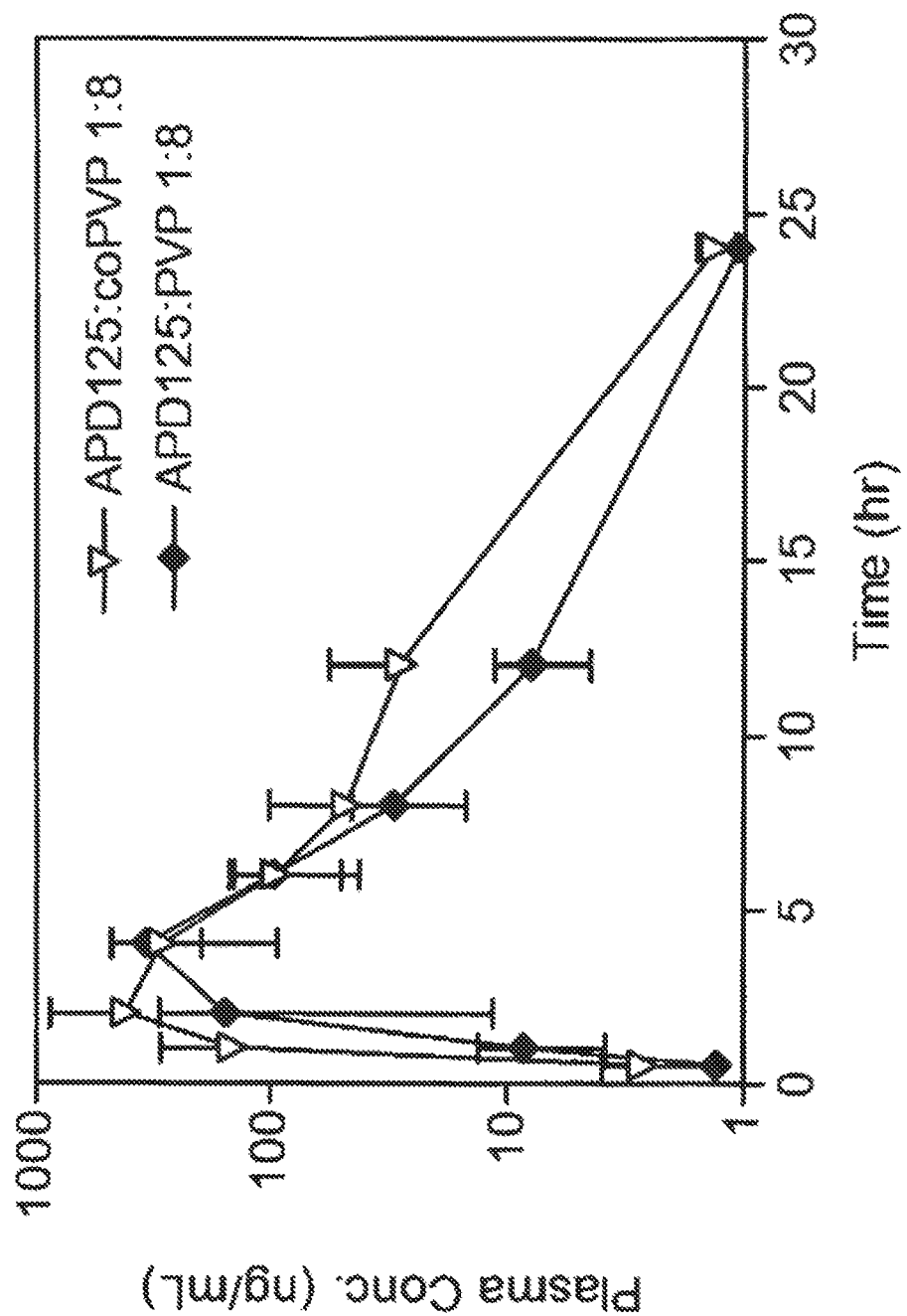

FIG. 20 depicts APD125 plasma exposure in monkeys after oral administration of direct-compression tablets (10 mg) containing either APD125:PVP (1:8) or APD125:coPVP (1:8).

Figure 21:
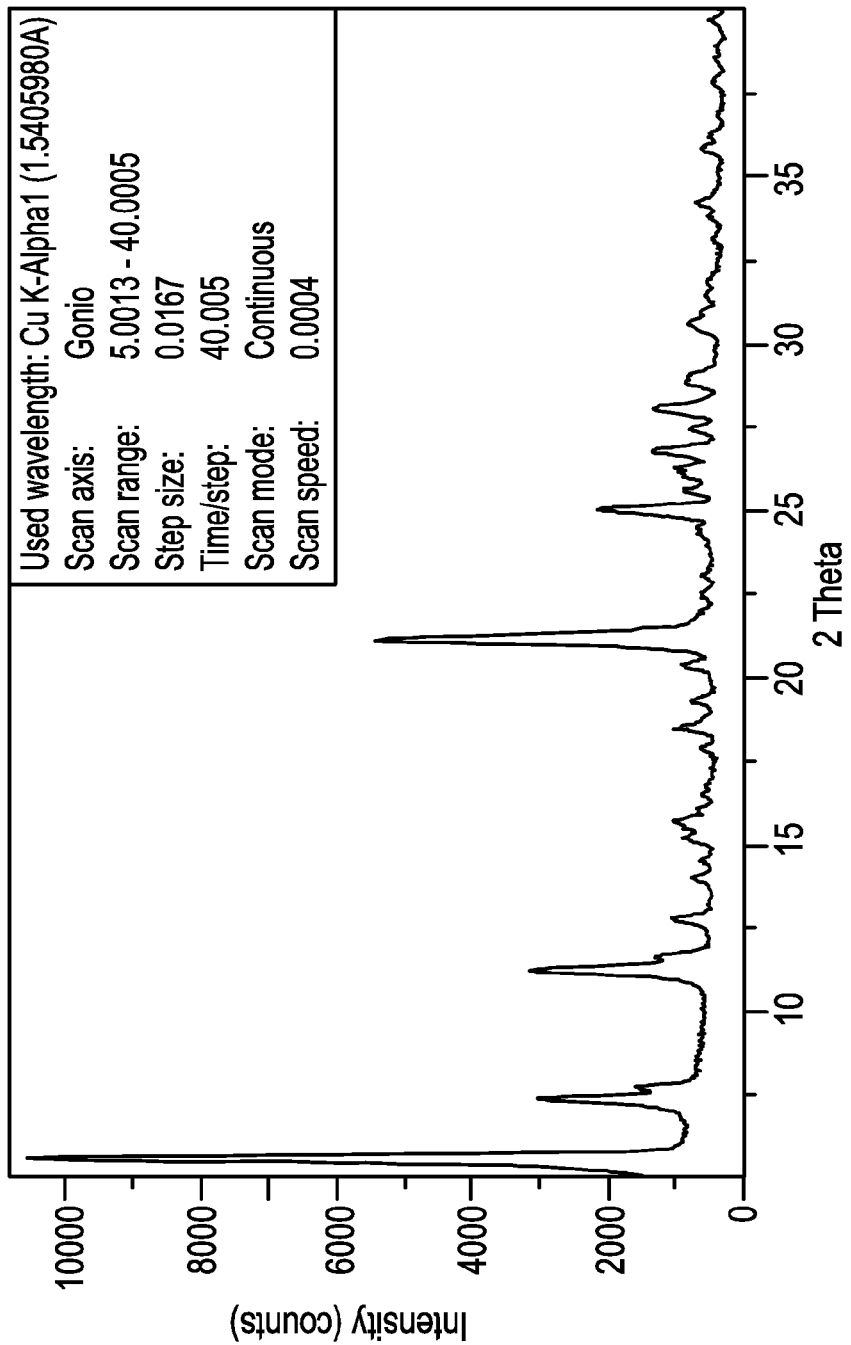

FIG. 21 depicts a powder X-ray diffraction (PXRD) pattern for Form I of 1-[3-(4-bromo-2-methyl-2H-pyrazol-3-yl)-4-methoxy-phenyl]-3-(2,4-difluoro-phenyl)-urea (Compound I), which was recorded using a PANalytical X'Pert Plus Powder X-Ray Diffractometer in the theta/theta geometry; scanning angles 5.0°-40.0° 2θ.

Figure 22:
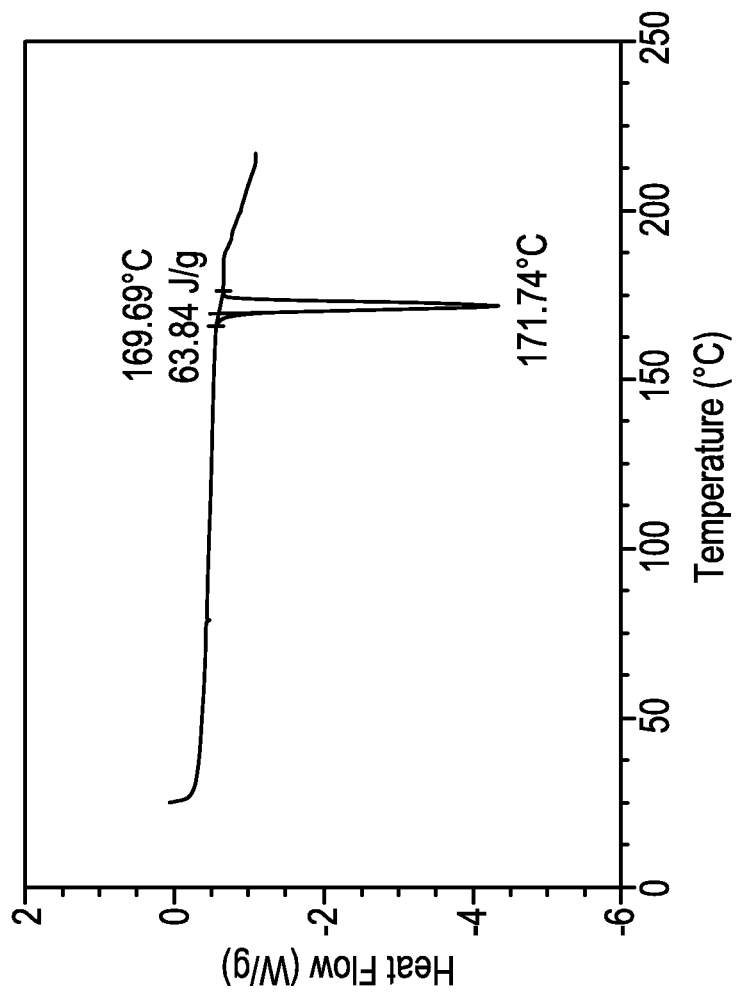

FIG. 22 depicts a differential scanning calorimetry (DSC) thermogram for Form I of 1-[3-(4-bromo-2-methyl-2H-pyrazol-3-yl)-4-methoxy-phenyl]-3-(2,4-difluoro-phenyl)-urea (Compound I), which was recorded using a TA Instruments DSC Q1000; at 10° C./min.

Figure 23:
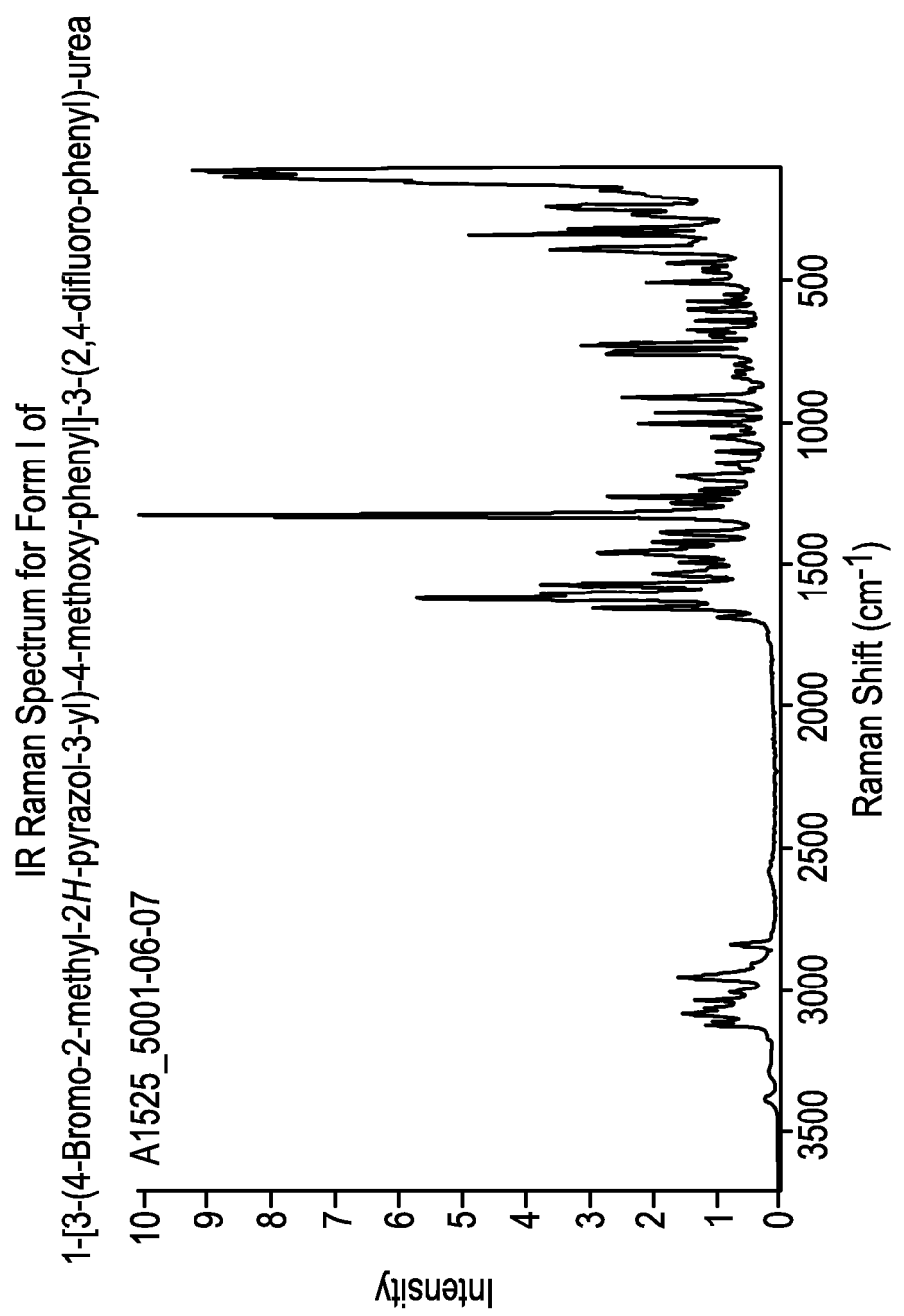

FIG. 23 deplete an FT Raman spectrum for Forms I 1-[3-(4-bromo-2-methyl-2H-pyrazol-3-yl)-4-methoxy-phenyl]-3-(2,4-difluoro-phenyl)-urea (Compound I), which was recorded using a ThermoFisher NXR6700 FT-Raman Spectrometer (EQ1874) using the FT-Raman Micro-Stage Accessory.

Figure 24:
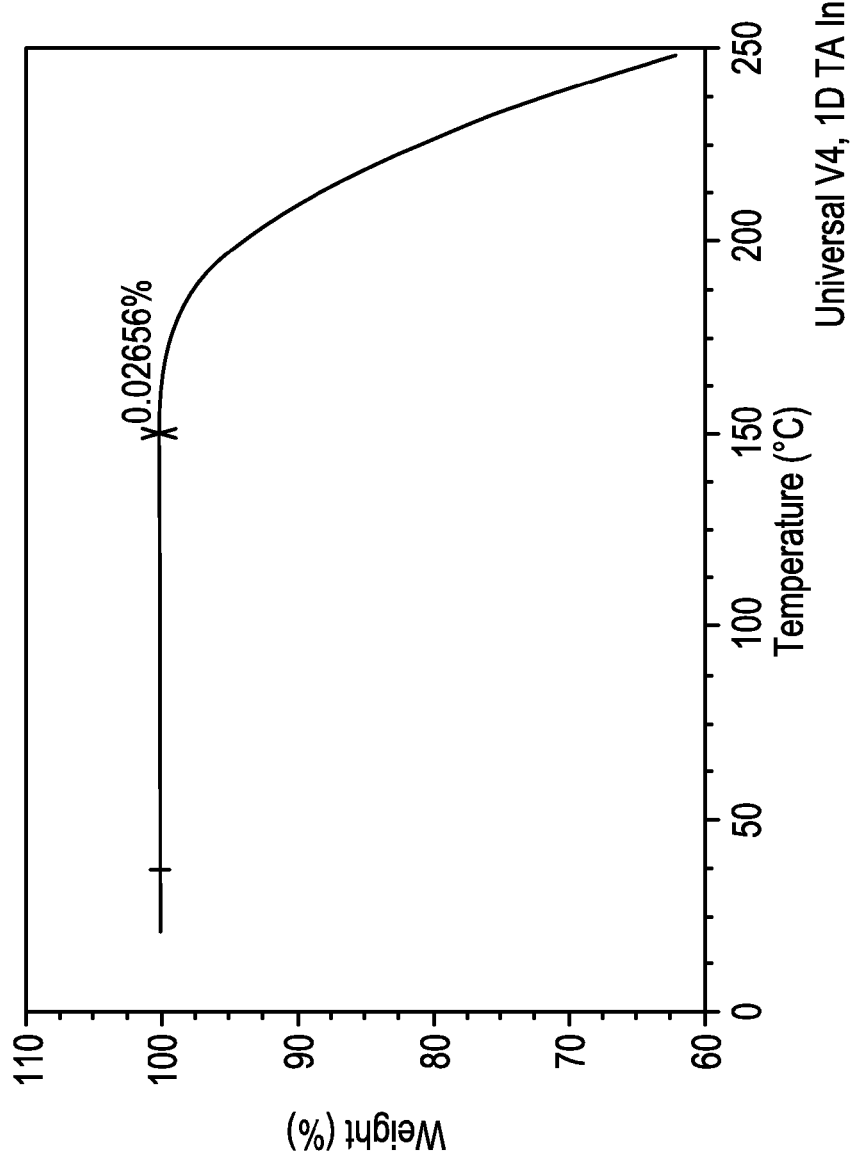

FIG. 24 depicts a thermogravimetric analysis (TGA) thermogram for Form I of 1-[3-(4-bromo-2-methyl-2H-pyrazol-3-yl)-4-methoxy-phenyl]-3-(2,4-difluoro-phenyl)-urea (Compound I), which was recorded using a TA Instruments TGA Q500 in a nitrogen atmosphere. The percent change in weight as a function of temperature was recorded.

Figure 25:
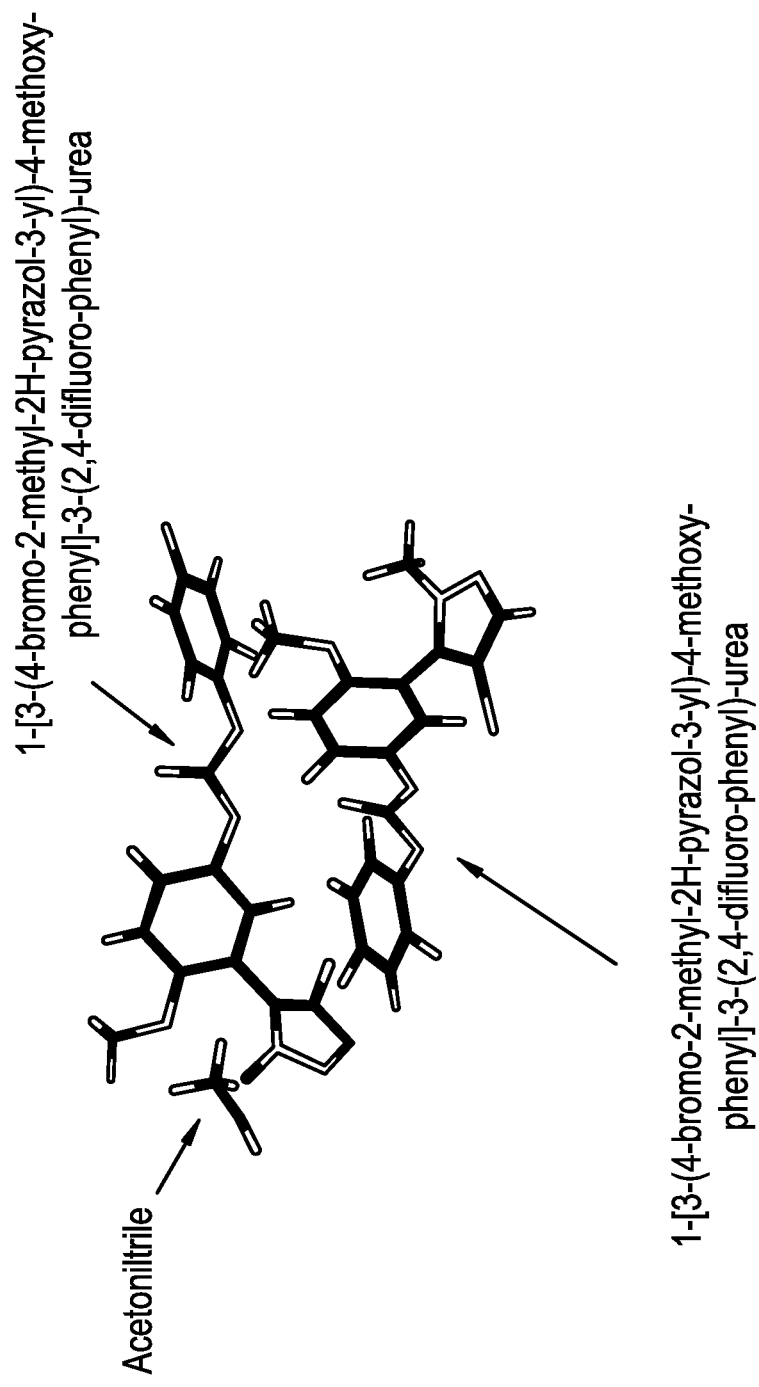

FIG. 25 depicts a pictorial representation of the hemi-acetonitrile solvate of 1-[3-(4-bromo-2-methyl-2H-pyrazol-3-yl)-4-methoxy-phenyl]-3-(2,4-difluoro-phenyl)-urea (Form IV) as generated by Mercury v. 1.4.2 (build 2) based on single-crystal X-ray diffraction analysis.

Figure 26:
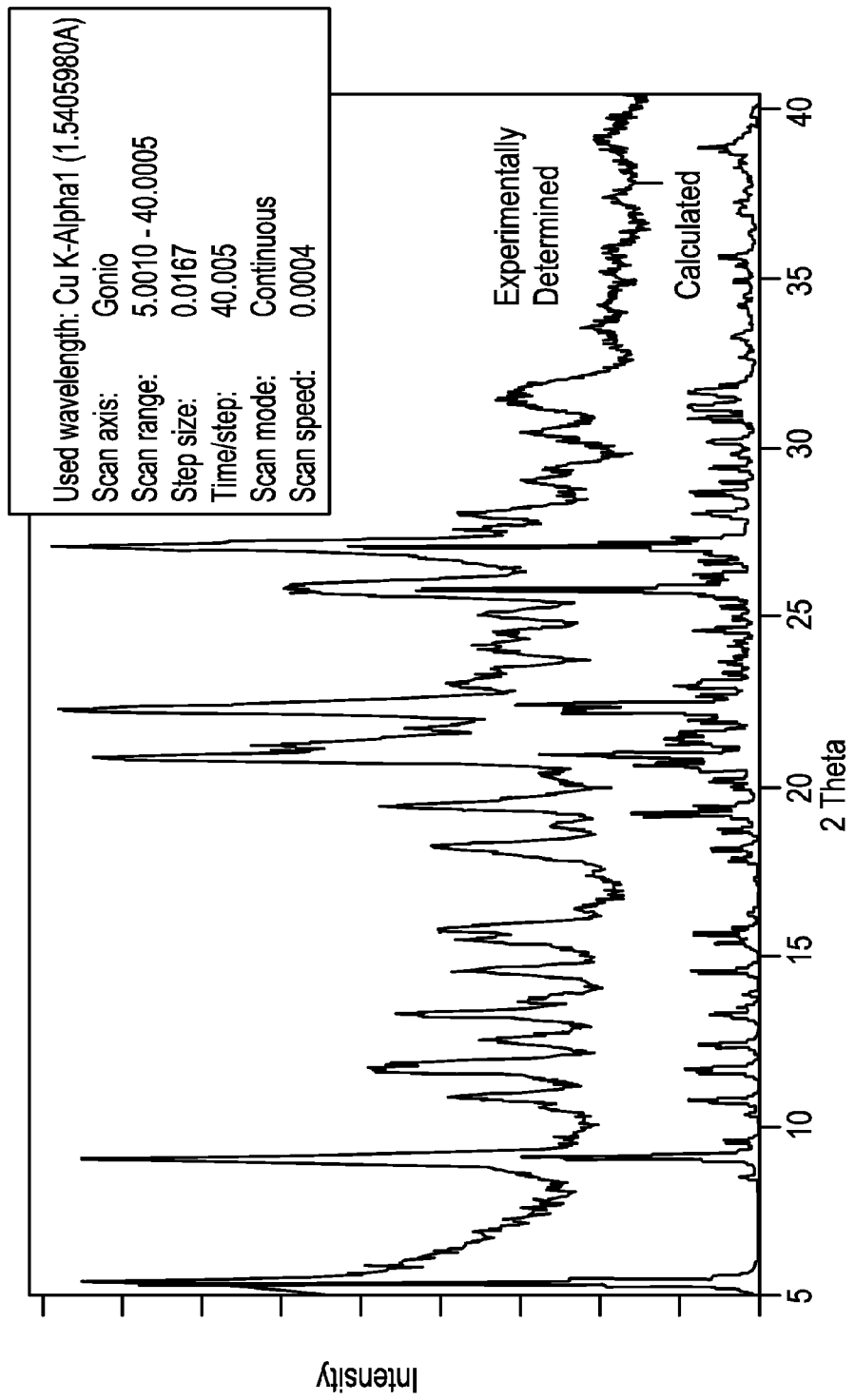

FIG. 26 depicts the comparison of calculated PXRD pattern of hemi-acetonitrile solvate of 1-[3-(4-bromo-2-methyl-2H-pyrazol-3-yl)-4-methoxy-phenyl]-3-(2,4-difluoro-phenyl)-urea (Form IV), based upon single-crystal X-diffraction results obtained at ca. 150° K. versus bulk Form IV isolated from acetonitrile and analyzed at ca. 298° K.

Figure 27:
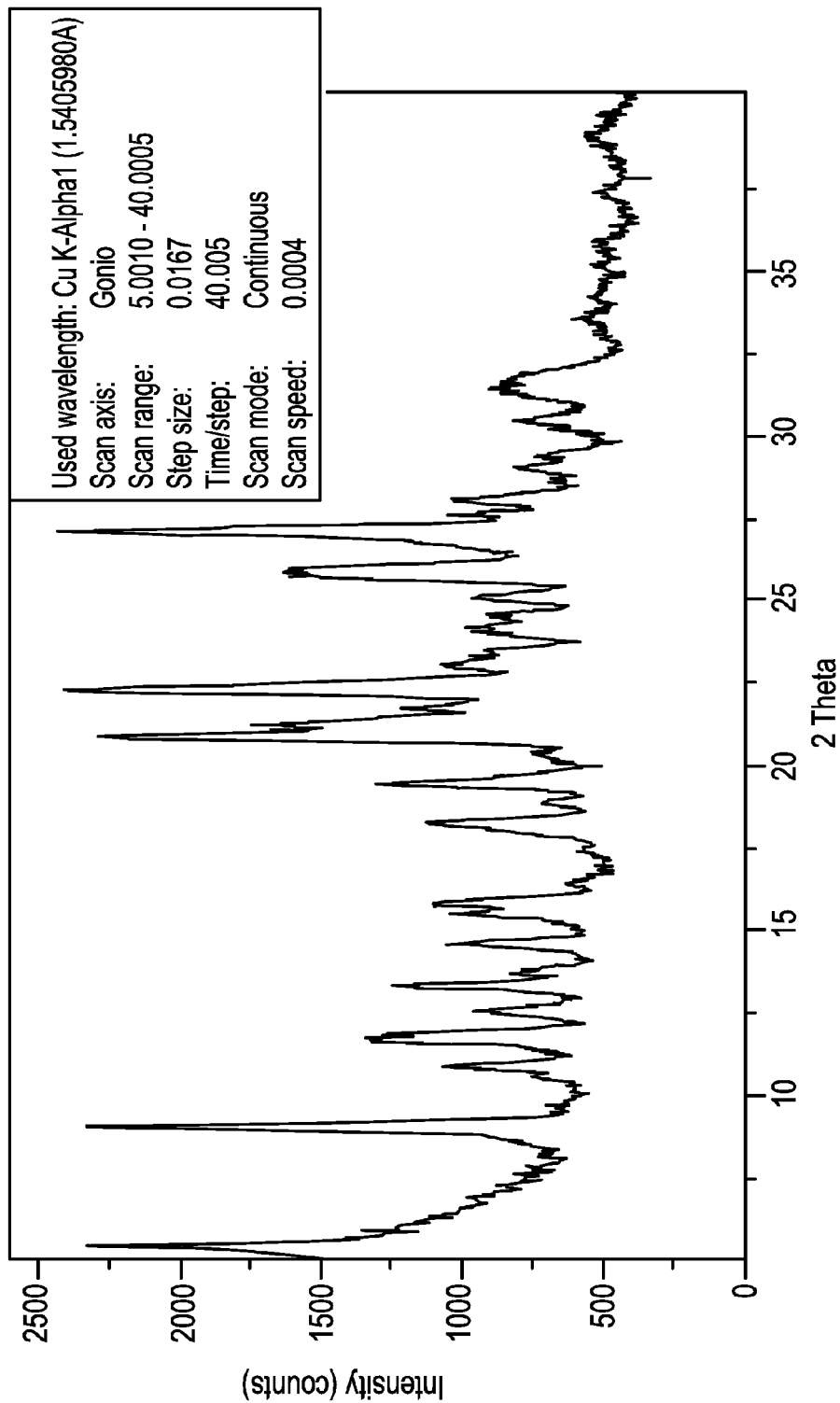

FIG. 27 depicts a powder X-ray diffraction (PXRD) pattern for a Acetonitrile Solvate of 1-[3-(4-bromo-2-methyl-2H-pyrazol-3-yl)-4-methoxy-phenyl]-3-(2,4-difluoro-phenyl)-urea, which was recorded using a PANalytical X'Pert Plus Powder X-Ray Diffractometer in the 2θ geometry; scanning angles 5.0°-40.0° 2θ.

Figure 28:
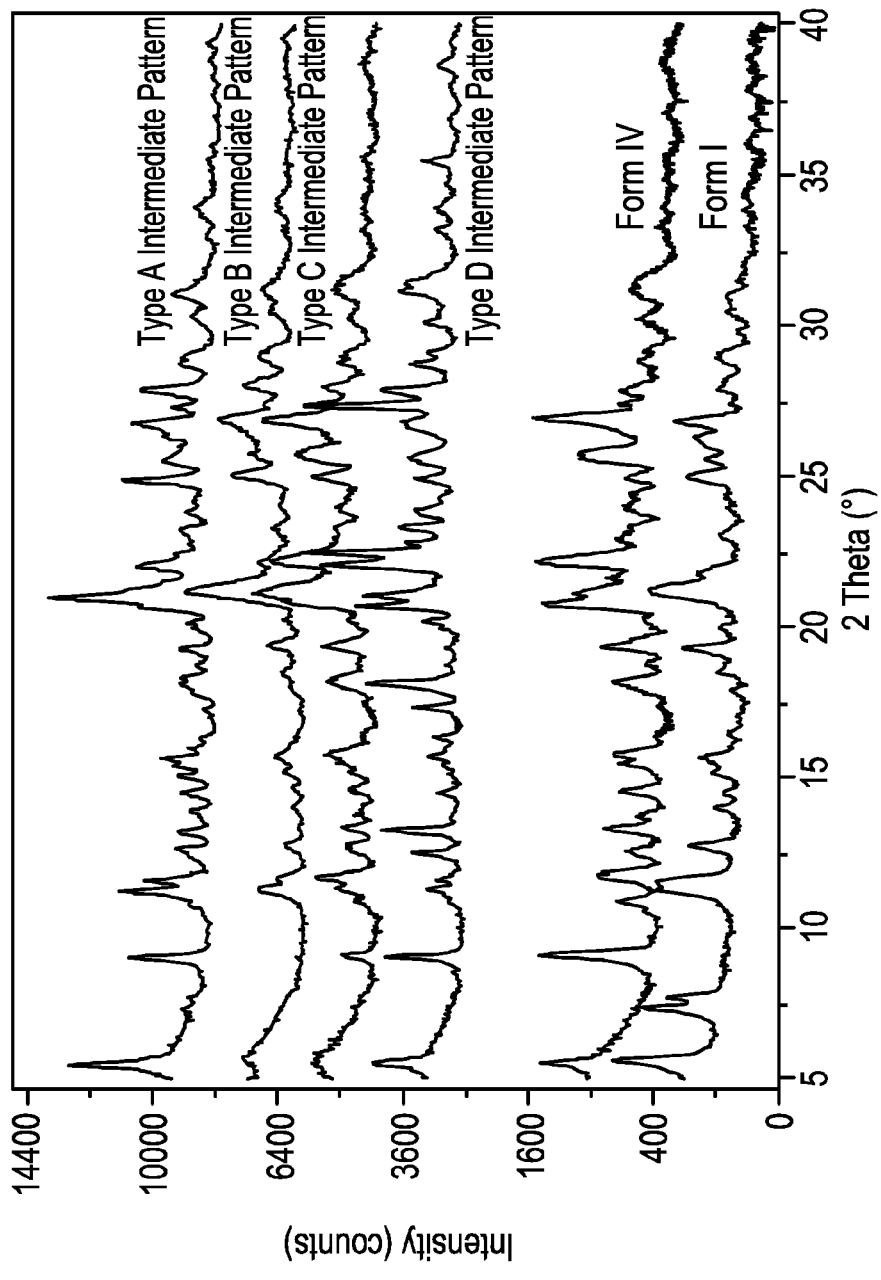

FIG. 28 depicts the transient X-ray powder diffraction patterns observed as Form IV of 1-[3-(4-bromo-2-methyl-2H-pyrazol-3-yl)-4-methoxy-phenyl]-3-(2,4-difluoro-phenyl)-urea converts in Form I, which was recorded using a PANalytical X'Pert Plus Powder X-Ray Diffractometer in the 2θ geometry; scanning angles 5.0°-40.0° 2θ.

Figure 29:
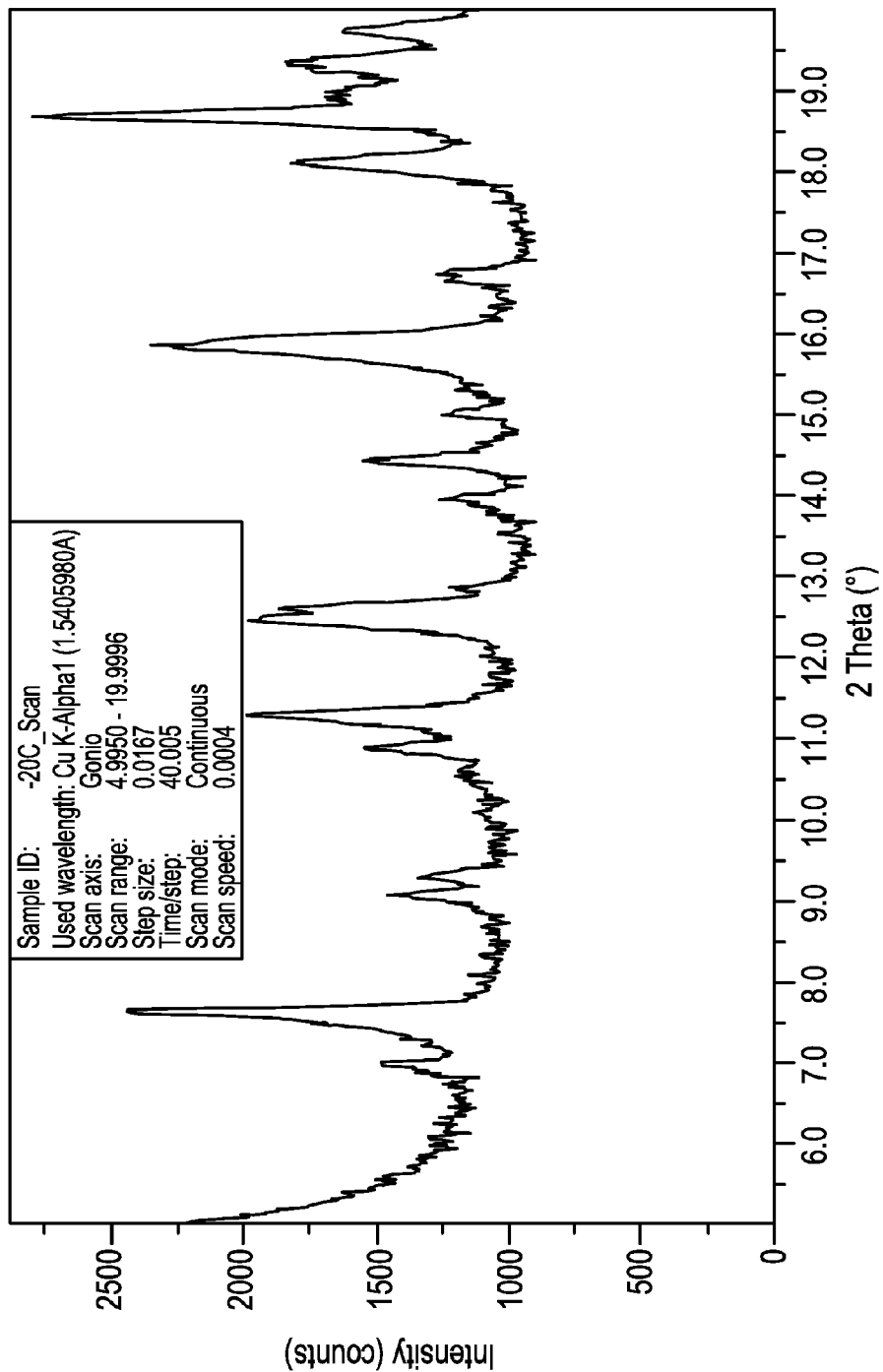

FIG. 29 depicts a powder X-ray diffraction (PXRD) pattern for a tetrahydrofuran solvate of 1-[3-(4-bromo-2-methyl-2H-pyrazol-3-yl)-4-methoxy-phenyl]-3-(2,4-difluoro-phenyl)-urea, which was recorded using a PANalytical X'Pert Plus Powder X-Ray Diffractometer in the 2θ geometry; scanning-angles 5.0°-40.0° 2θ.

Figure 30:
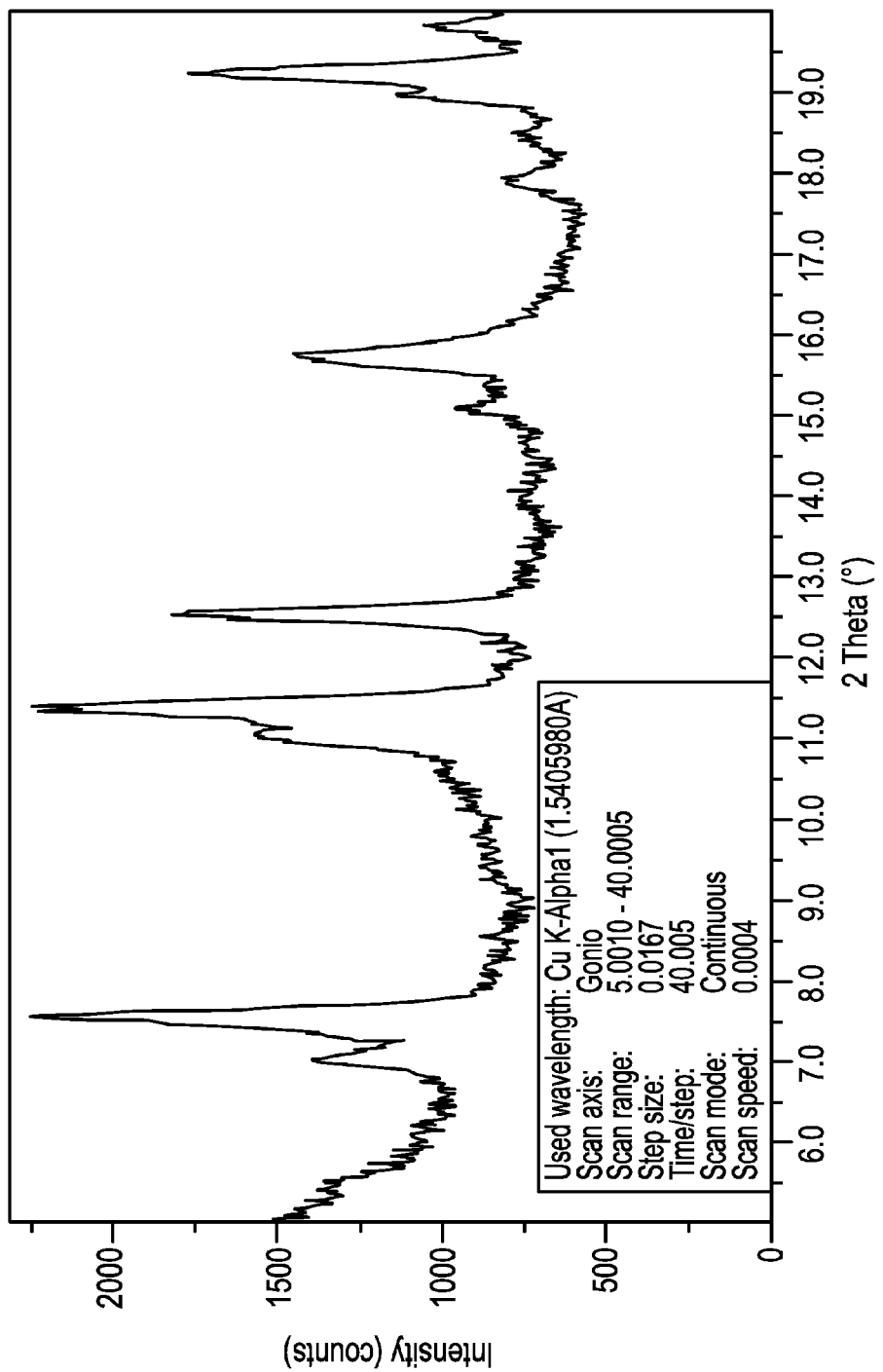

FIG. 30 depicts a powder X-ray diffraction (PXRD) pattern for a Heptane Solvate of 1-[3-(4-bromo-2-methyl-2H-pyrazol-3-yl)-4-methoxy-phenyl]-3-(2,4-difluoro-phenyl)-urea, which was recorded using a PANalytical X'Pert Plus Powder X-Ray Diffractometer in the theta/theta geometry; scanning angles 5.0°-40.0° 2θ.

Figure 31:
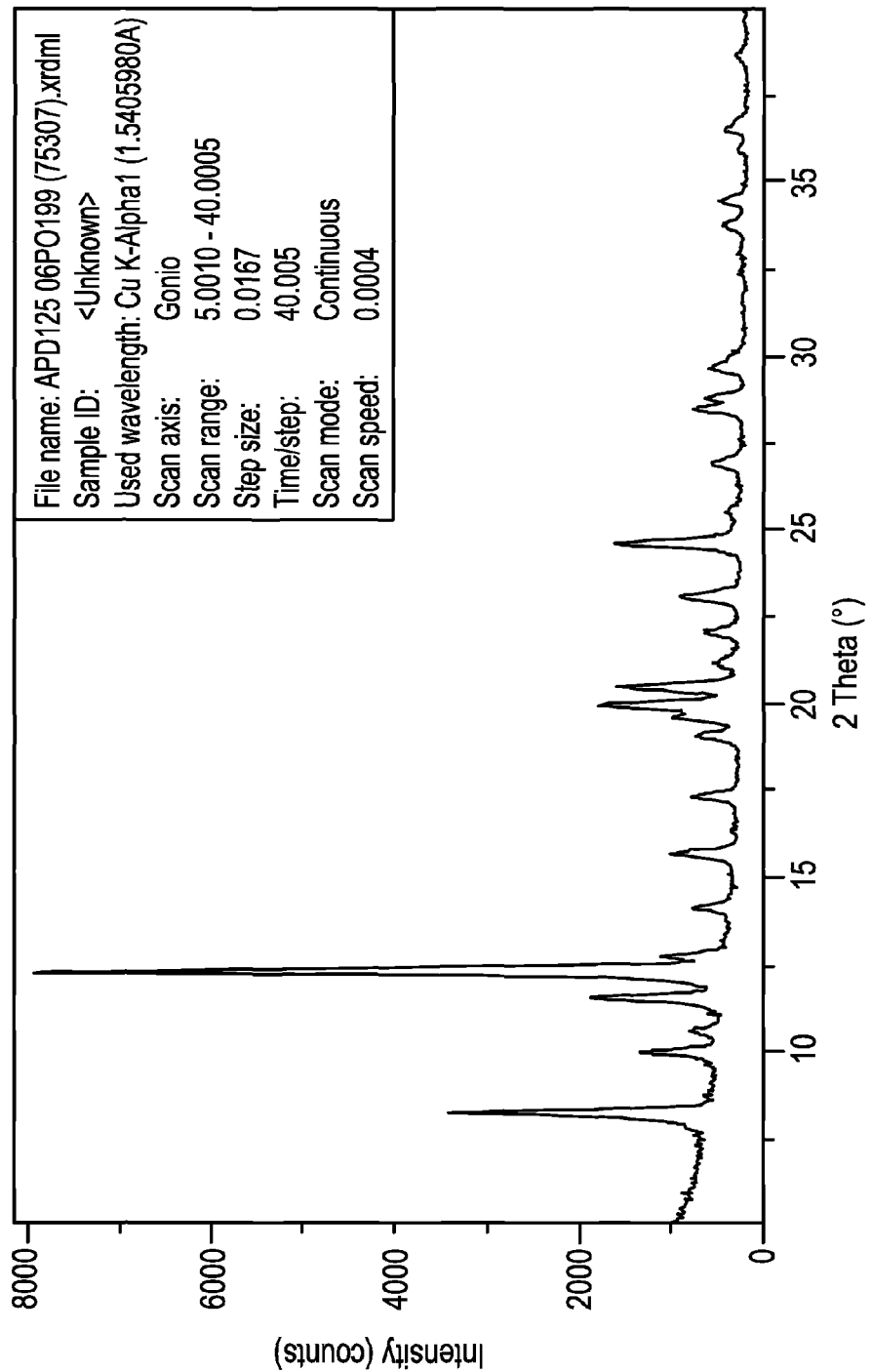

FIG. 31 depicts a powder X-ray diffraction (PXRD) pattern for Form II of 1-[3-(4-bromo-2-methyl-2H-pyrazol-3-yl)-4-methoxy-phenyl]-3-(2,4-difluoro-phenyl)-urea (Compound I), which was recorded using a PANalytical X'Pert Plus Powder X-Ray Diffractometer in the theta/theta geometry; scanning angles 5.0°-40.0° 2θ.

DETAILED DESCRIPTION OF THE INVENTION

Definitions

The terms "5-$HT_{2A}$ serotonin receptor-related disorder" and "5-$HT_{2A}$ serotonin receptor-related disease" as used herein respectively refer to a disorder or disease in an individual, which may be prevented, inhibited, ameliorated, treated or cured by modulation (e.g. agonism, antagonism or inverse agonism) of the 5-$HT_{2A}$ serotonin receptor, for example, by administering to the individual in need thereof a therapeutically effective amount of a pharmaceutical composition of the present invention comprising a 5-$HT_{2A}$ serotonin receptor modulator.

The term "in need of treatment" as used herein refers to a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

The term "individual" as used herein refers to any animal, including mammals, preferably mice, rats, other rodents, rabbits, dogs, cats, swine, cattle, sheep, horses, or primates, and most preferably humans.

The term "inverse agonists" as used herein refers to moieties that bind the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

The term "therapeutically effective amount" as used herein refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease;

(2) Inhibiting the disease; for example, inhibiting a disease, condition or disorder in an individual that is experiencing or displaying the pathology or symptomatology of the disease, condition or disorder (i.e., arresting further development of the pathology and/or symptomatology); and (3) Ameliorating the disease; for example, ameliorating a disease, condition, or disorder in an individual that is experiencing or displaying the pathology or symptomatology of the disease, condition or disorder (i.e., reversing the pathology and/or symptomatology).

The term "sleep maintenance" as used herein refers to the ability to sleep without persistent interruptions or extended periods of wakefulness. Sleep Maintenance Insomnia is a disturbance in maintaining sleep after sleep onset is achieved. It is characterized by persistently interrupted sleep without difficulty falling asleep, and sleep-continuity disturbance. Parameters used for measuring sleep maintenance include but are not limited to, wake time after sleep onset (WASO) and number of awakenings (NAW).

The term "sleep quality" as used herein refers to both the subjective assessment given by an individual of how restorative and undisturbed sleep has been (via a standardized questionnaire) and to a series of objective measures derived from polysomnography. Examples of standardized sleep questionnaires, include but are not limited to the Pittsburgh Sleep Quality Index (Buysse et al., *Psychiatry Research* (1989), 28(2), 193-213). Examples of objective measures of sleep quality include, but are not limited to, the amount and depth of nonREM sleep, the amount of REM sleep and the temporal organization of nonREM and REM stages. Subjective and objective measures of sleep quality are not necessarily concordant.

The term "nonrestorative sleep" as used herein refers to a disorder characterized by the subjective assessment given by an individual that sleep is restless, light, or of poor quality even though the duration may appear normal. NRS is associated with other symptoms including, but not limited to, excessive daytime sleepiness, mood swings and cognitive impairments.

The term "coPVP" as used herein refers to a vinylpyrrolidone-vinyl acetate copolymer, CAS registry number 25086-89-9. The term is used interchangeably with the terms copolyvidonum Plasdone™, copovidone and copolyvidone. coPVP has following structural formula:

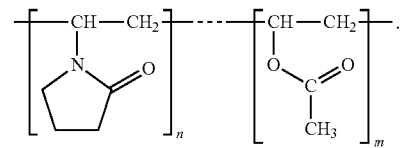

In some embodiments coPVP is a copolymer of 1-vinyl-2-pyrrolidone and vinyl acetate in a ratio of 6:4 by mass, wherein n≈1.2 m. Examples of coPVP include but are not limited to Kollidon™ VA 64, Plasdone™ S-630 and the like.

The term "cps" as used herein is intended to refer to the unit of dynamic viscosity known as the centipoise (cP). 1 cP=1 millipascal second.

The term "DFA" as used herein refers to 2,4-difluoroaniline, CAS registry number 367-25-9, which represented by the following formula:

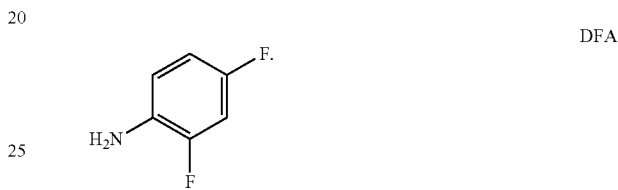

The term "HDPE" as used herein refers to high-density polyethylene.

The term "MCC" as used herein refers to microcrystalline cellulose, CAS registry number 9004-34-6. The term is used interchangeably with the terms cellulose gel, crystalline cellulose and E460. MCC has the following structural formula:

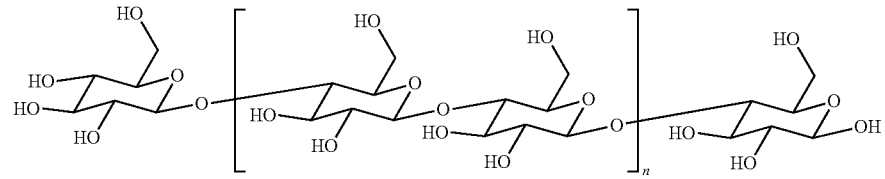

wherein n≈220.

Examples of MCC include, but are not limited to, Avicel™ PH, Avicel™ PH 102, Celex™, Celphere™, Ceolus™ KG, Emcocel™, Ethispheres™, Fibrocel™, Pharmacel™, Tabulose™ and Vivapur™.

The term "PIC" as used here in refers to powder in capsule.

The term "Poloxamer" as used herein refers to a class of pharmaceutical excipients comprising or consisting essentially of either a single compound or a mixture of compounds prepared from synthetic block copolymers of ethylene oxide and propylene oxide. In some embodiments, an excipient in this class comprises or consists essentially of a single compound or a mixture of compounds of the following formula:

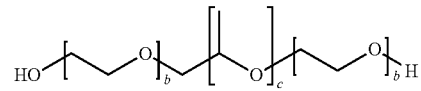

wherein "b" at each occurrence is independently an integer between 1 to 102; "c" is an integer between 1 and 57; b+c+b is 3 to 327, and the average molecule weight of the poloxamer is about 17500 or less. Poloxamers are known or can be prepared by methods in the art. A number of poloxamers are commercially available. Representative examples of a Poloxamer include, but are not limited to, Poloxamer 124 (Pluronic® L44NF), Poloxamer 188 (Pluronic® P68NF), Poloxamer 237 (Pluronic® F87NF), Poloxamer 338 (Pluronic® F108NF), Poloxamer 407 (Pluronic® F127NF) and the like.

The term "PVA" as used herein refers to polyvinyl alcohol, CAS registry number 9002-89-5. The term is used interchangeably with the term vinyl alcohol polymer. PVA has the following structural formula:

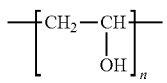

wherein n lies between 500 and 5000, equivalent to a molecular weight range of approximately 20,000 to 200,000. In some embodiments PVA is high viscosity with a molecular weight≈200,000. In some embodiments PVA is medium viscosity with a molecular weight≈130,000. In some embodiments PVA is medium viscosity with a molecular weight≈20,000. Examples of PVA include but are not limited to Airvol™, Elvanol™ and Gohsenol™.

The term "PVP" as used herein refers to polyvinylpyrrolidone. The term is used interchangeably with the terms, E1201, povidone, povidonum, poly[1-(2-oxo-1-pyrrolidinyl)ethylene, polyvidone and 1-vinyl-2-pyrrolidinone polymer. PVP has the following structural formula:

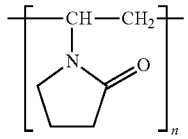

wherein the molecular weight is from about 2500 to about 3,000,000. Examples of PVP include, but are not limited to, Kollidon™, Kollidon™ VA 64, Plasdone™, Plasdone™ K-29/32 and Kollidon™ 30.

The term "% RSD" as used herein refers to the relative standard deviation, which is the absolute value of the coefficient of variation expressed as a percentage. The term is widely used in analytical chemistry to express the precision of an assay:

(standard deviation of array X)×100/(average of array X)=relative standard deviation.

The term "SGC" as used herein refers to a soft gelatin capsule.

The term "SLS" as used herein refers to sodium lauryl sulfate, which has the following structural formula:

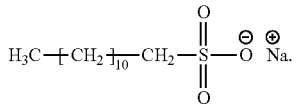

The term "xCMC" as used herein refers to crosscarmellose sodium, CAS Registry Number 74811-65-7. The term is used interchangeably with the terms carmellosum natricum conexum, crosslinked carboxymethyl cellulose sodium and modified cellulose gum. xCMC is a crosslinked polymer of carboxymethyl cellulose sodium. Carboxymethyl cellulose sodium has the following structural formula:

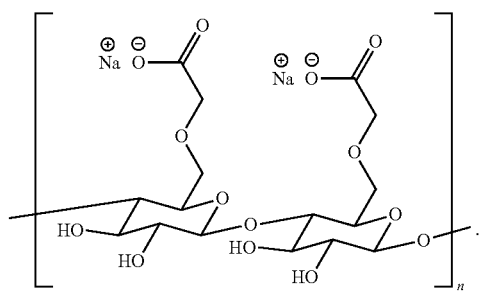

Examples of xCMC include, but are not limited to, Ac-Di-Sol™, Explocel™, Nymcel™ ZSX, Pharmacel™ XL, Primellose™, Solutab™ and Vivasol™.

The term "xPVP" as used herein refers to crosslinked povidone, CAS registry number 9003-39-8, wherein povidone has the same definition as described herein. The term is used interchangeably with the terms crospovidone, crospovidonum, E1202, polyvinylpolypyrrolidone, PVPP, 1-vinyl-2-pyrrolidinone and 1-ethenyl-2-pyrrolidinone homopolymer. Examples of xPVP include, bur are not limited to, PolyPlasdone™ XL, PolyPlasdone™ XL-10, Kollidon™ CL and Kollidon™ CL-M.

It is appreciated that certain features of the invention, which are, far clarity, described in the context of separate embodiments, may also be provided in combination in a single embodiment. Conversely, various features of the invention, which are, for brevity, described in the context of a single embodiment, may also be provided separately or in any suitable subcombination.

All combinations of the embodiments pertaining to the aspects described herein are specifically embraced by the present invention just as if each and every combination was individually explicitly recited, to the extent that such combinations embrace possible aspects. In addition, all subcombinations of the embodiments contained within the aspects described herein, as well as all subcombinations of the embodiments contained within all other aspects described herein, are also specifically embraced by the present invention just as if each and every subcombination of all embodiments are explicitly recited herein.

Pharmaceutical Compositions of the Present Invention

One aspect of the present invention pertains to pharmaceutical compositions comprising:

a. 1-[3-(4-bromo-2-methyl-2H-pyrazol-3-yl)-4-methoxy-phenyl]-3-(2,4-difluoro-phenyl)-urea; and b. an excipient selected from: PVP and coPVP.

In some embodiments, the 1-[3-(4-bromo-2-methyl-2H-pyrazol-3-yl)-4-methoxy-phenyl]-3-(2,4-difluoro-phenyl)-urea is Form I of 1-[3-(4-bromo-2-methyl-2H-pyrazol-3-yl)-4-methoxy-phenyl]-3-(2,4-difluoro-phenyl)-urea.

In some embodiments, the present invention pertains to pharmaceutical compositions comprising 1-[3-(4-bromo-2-methyl-2H-pyrazol-3-yl)-4-methoxy-phenyl]-3-(2,4-difluoro-phenyl)-urea and said excipient in a ratio from about 1:20 to about 1:1 by weight.

In some embodiments, the present invention pertains to pharmaceutical compositions comprising 1-[3-(4-bromo-2-methyl-2H-pyrazol-3-yl)-4-methoxy-phenyl]-3-(2,4-difluoro-phenyl)-urea and said excipient in a ratio from about 1:10 to about 1:5 by weight.

In some embodiments, the present invention pertains to pharmaceutical compositions comprising 1-[3-(4-bromo-2-methyl-2H-pyrazol-3-yl)-4-methoxy-phenyl]-3-(2,4-difluoro-phenyl)-urea and said excipient in a ratio of about 1:8 by weight.

In some embodiments, the pharmaceutical composition further comprises methyl cellulose.

In some embodiments, the methyl cellulose is 4000 cps methyl cellulose.

In some embodiments, the pharmaceutical composition comprises methyl cellulose in an amount between about 0.1% and about 10% by weight of the total composition.

In some embodiments, the pharmaceutical composition comprises methyl cellulose in an amount between about 0.5% and about 8% by weight of the total composition.

In some embodiments, the pharmaceutical composition comprises methyl cellulose in an amount between about 1% and about 5% by weight of the total composition.

In some embodiments, the pharmaceutical composition comprises methyl cellulose in an amount of about 2% by weight of the total composition.

In some embodiments, the excipient is PVP.

In some embodiments, the PVP is Plasdone™ K-29/32 PVP.

In some embodiments, the PVP is Kollidon™ 30 PVP.

In some embodiments, the excipient is coPVP.

In some embodiments, the coPVP is Kollidon™ VA 64 coPVP.

In some embodiments, the pharmaceutical composition further comprises at least one ingredient selected from: lactose monohydrate, microcrystalline cellulose, crospovidone, sodium lauryl sulfate, magnesium stearate and silicon dioxide.

In some embodiments, the lactose monohydrate is Fast-Flo™ 316 lactose monohydrate.

In some embodiments, the microcrystalline cellulose is Avicel™ PH102 microcrystalline cellulose.

In some embodiments, the crospovidone is selected from PolyPlasdone™ XL crospovidone and Kollidon™ CL crospovidone.

In some embodiments, the magnesium stearate is non-bovine HyQual™ 5712 magnesium stearate.

In some embodiments, the silicon dioxide is Cab-o-sil™ colloidal silicon dioxide.

In some embodiments, the 1-[3-(4-bromo-2-methyl-2H-pyrazol-3-yl)-4-methoxy-phenyl]-3-(2,4-difluoro-phenyl)-urea is in an amount of about 40% to about 0.001%, about 39% to about 0.001%, about 38% to about 0.001%, about 37% to about 0.001%, about 36% to about 0.001%, about 35% to about 0.001%, about 34% to about 0.001%, about 33% to about 0.001%, about 32% to about 0.001%, about 31% to about 0.001%, about 30% to about 0.001%, about 29% to about 0.001%, about 28% to about 0.001%, about 27% to about 0.001%, about 26% to about 0.001%, about 25% to about 0.001%, about 24% to about 0.001%, about 23% to about 0.001%, about 22% to about 0.001%, about 21% to about 0.001%, about 20% to about 0.001%, about 19% to about 0.001%, about 18% to about 0.001%, about 17% to about 0.001%, about 16% to about 0.001%, about 15% to about 0.001%, about 14% to about 0.001%, about 13% to about 0.001%, about 12% to about 0.001%, about 11% to about 0.001%, about 10% to about 0.001%, about 9% to about 0.001%, about 8% to about 0.001%, about 7% to about 0.001%, about 6% to about 0.001%, about 5% to about 0.001%, about 4% to about 0.001%, about 3% to about 0.001%, about 2% to about 0.001%, or about 1% to about 0.001%, each by weight of the total composition.

In some embodiments, the present invention pertains to pharmaceutical compositions comprising 1-[3-(4-bromo-2-methyl-2H-pyrazol-3-yl)-4-methoxy-phenyl]-3-(2,4-difluoro-phenyl)-urea in an amount between about 0.01% and about 30% by weight of the total composition.

In some embodiments, the present invention pertains to pharmaceutical compositions comprising 1-[3-(4-bromo-2-methyl-2H-pyrazol-3-yl)-4-methoxy-phenyl]-3-(2,4-difluoro-phenyl)-urea in an amount between about 1% and about 20% by weight of the total composition.

In some embodiments, the present invention pertains to pharmaceutical compositions comprising 1-[3-(4-bromo-2-methyl-2H-pyrazol-3-yl)-4-methoxy-phenyl]-3-(2,4-difluoro-phenyl)-urea in an amount between about 2% and about 10% by weight of the total composition.

In some embodiments, the present invention pertains to pharmaceutical compositions 1-[3-(4-bromo-2-methyl-2H-pyrazol-3-yl)-4-methoxy-phenyl]-3-(2,4-difluoro-phenyl)-urea in an amount between about 3% and about 7% by weight of the total composition.

In some embodiments, the present invention pertains to pharmaceutical compositions comprising 1-[3-(4-bromo-2-methyl-2H-pyrazol-3-yl)-4-methoxy-phenyl]-3-(2,4-difluoro-phenyl)-urea in an amount of about 5% by weight of the total composition.

In some embodiments, the present invention pertains to pharmaceutical compositions comprising the excipient in an amount between about 0.1% and about 90% by weight of the total composition.

In some embodiments, the present invention pertains to pharmaceutical compositions comprising the excipient in an amount between about 5% and about 80% by weight of the total composition.

In some embodiments, the present invention pertains to pharmaceutical compositions comprising the excipient in an amount between about 10% and about 70% by weight of the total composition.

In some embodiments, the present invention pertains to pharmaceutical compositions comprising the excipient in an amount between about 20% and about 50% by weight of the total composition.

In some embodiments, the present invention pertains to pharmaceutical compositions comprising the excipient in an amount of about 40% by weight of the total composition.

In some embodiments, the present invention pertains to pharmaceutical compositions comprising:

a. 1-[3-(4-bromo-2-methyl-2H-pyrazol-3-yl)-4-methoxy-phenyl]-3-(2,4-difluoro-phenyl)-urea in an amount from about 0.01% to about 30% by weight of the total composition;

b. said excipient in an amount from about 0.1% to about 90% by weight of the total composition; and c. methyl cellulose in an amount from about 0.1% to about 10% by weight of the total composition.

In some embodiments, the present invention pertains to pharmaceutical compositions comprising:

a. Form I of 1-[3-(4-bromo-2-methyl-2H-pyrazol-3-yl)-4-methoxy-phenyl]-3-(2,4-difluoro-phenyl)-urea in an amount from about 0.01% to about 30% by weight of the total composition;

b. said excipient in an amount from about 0.1% to about 90% by weight of the total composition; and c. methyl cellulose in an amount from about 0.1% to about 10% by weight of the total composition.

In some embodiments, the present invention pertains to pharmaceutical compositions comprising:
  a. 1-[3-(4-bromo-2-methyl-2H-pyrazol-3-yl)-4-methoxy-phenyl]-3-(2,4-difluoro-phenyl)-urea in an amount of about 5% by weight of the total composition;
  b. said excipient in an amount of about 40% by weight of the total composition; and
  c. methyl cellulose in an amount of about 2% by weight of the total composition.

In some embodiments, the present invention pertains to pharmaceutical compositions comprising:
  a. Form I of 1-[3-(4-bromo-2-methyl-2H-pyrazol-3-yl)-4-methoxy-phenyl]-3-(2,4-difluoro-phenyl)-urea in an amount of about 5% by weight of the total composition;
  b. said excipient in an amount of about 40% by weight of the total composition; and
  c. methyl cellulose in an amount of about 2% by weight of the total composition.

In some embodiments, the present invention pertains to pharmaceutical compositions comprising:
  a. 1-[3-(4-bromo-2-methyl-2H-pyrazol-3-yl)-4-methoxy-phenyl]-3-(2,4-difluoro-phenyl)-urea;
  b. PVP;
  c. methyl cellulose;
  d. lactose monohydrate;
  e. microcrystalline cellulose;
  f. crospovidone;
  g. sodium lauryl sulfate;
  h. magnesium stearate; and
  i. silicon dioxide.

In some embodiments, the present invention pertains to pharmaceutical compositions comprising:
  a. Form I of 1-[3-(4-bromo-2-methyl-2H-pyrazol-3-yl)-4-methoxy-phenyl]-3-(2,4-difluoro-phenyl)-urea;
  b. PVP;
  c. methyl cellulose;
  d. lactose monohydrate;
  e. microcrystalline cellulose;
  f. crospovidone;
  g. sodium lauryl sulfate;
  h. magnesium stearate; and
  i. silicon dioxide.

In some embodiments, the present invention pertains to pharmaceutical compositions comprising:
  a. 1-[3-(4-bromo-2-methyl-2H-pyrazol-3-yl)-4-methoxy-phenyl]-3-(2,4-difluoro-phenyl)-urea;
  b. coPVP;
  c. methyl cellulose;
  d. lactose monohydrate;
  e. microcrystalline cellulose;
  f. crospovidone;
  g. sodium lauryl sulfate;
  h. magnesium stearate; and
  i. silicon dioxide.

In some embodiments, the present invention pertains to pharmaceutical compositions comprising:
  a. Form I of 1-[3-(4-bromo-2-methyl-2H-pyrazol-3-yl)-4-methoxy-phenyl]-3-(2,4-difluoro-phenyl)-urea;
  b. coPVP;
  c. methyl cellulose;
  d. lactose monohydrate;
  e. microcrystalline cellulose;
  f. crospovidone;
  g. sodium lauryl sulfate;
  h. magnesium stearate; and
  i. silicon dioxide.

In some embodiments, the present invention pertains to pharmaceutical compositions comprising:
  a. 1-[3-(4-bromo-2-methyl-2H-pyrazol-3-yl)-4-methoxy-phenyl]-3-(2,4-difluoro-phenyl)-urea in an amount of about 5% by weight of the total composition;
  b. Plasdone™ K-29/32 PVP or Kollidon™ 30 PVP in an amount of about 40% by weight of the total composition;
  c. 4000 cps methyl cellulose in an amount of about 2% by weight of the total composition;
  d. Fast-Flo™ 316 lactose monohydrate in an amount of about 21.25% by weight of the total composition;
  e. Avicel™ PH102 microcrystalline cellulose in an amount of about 25% by weight of the total composition;
  f. Kollidon™ CL crospovidone in an amount of about 4% by weight of the total composition;
  g. sodium lauryl sulfate in an amount of about 2% by weight of the total composition;
  h. HyQual™ 5712 magnesium stearate in an amount of about 0.5% by weight of the total composition; and
  i. Cab-o-Sil™ colloidal silicon dioxide in an amount of about 0.25% by weight of the total composition.

In some embodiments, the present invention pertains to pharmaceutical compositions comprising:
  a. Form I of 1-[3-(4-bromo-2-methyl-2H-pyrazol-3-yl)-4-methoxy-phenyl]-3-(2,4-difluoro-phenyl)-urea in an amount of about 5% by weight of the total composition;
  b. Plasdone™ K-29/32 PVP or Kollidon™ 30 PVP in an amount of about 40% by weight of the total composition;
  c. 4000 cps methyl cellulose in an amount of about 2% by weight of the total composition;
  d. Fast-Flo™ 316 lactose monohydrate in an amount of about 21.25% by weight of the total composition;
  e. Avicel™ PH102 microcrystalline cellulose in an amount of about 25% by weight of the total composition;
  f. Kollidon™ CL crospovidone in an amount of about 4% by weight of the total composition;
  g. sodium lauryl sulfate in an amount of about 2% by weight of the total composition;
  h. HyQual™ 5712 magnesium stearate in an amount of about 0.5% by weight of the total composition; and
  i. Cab-o-sil™ colloidal silicon dioxide in an amount of about 0.25% by weight of the total composition.

In some embodiments, the present invention pertains to pharmaceutical compositions comprising:
  a. 1-[3-(4-bromo-2-methyl-2H-pyrazol-3-yl)-4-methoxy-phenyl]-3-(2,4-difluoro-phenyl)-urea in an amount of about 5% by weight of the total composition;
  b. Kollidon™ VA 64 coPVP in an amount of about 40% by weight of the total composition;
  c. 4000 cps methyl cellulose in an amount of about 2% by weight of the total composition;
  d. Fast-Flo™ 316 lactose monohydrate in an amount of about 21.25% by weight of the total composition;
  e. Avicel™ PH102 microcrystalline cellulose in an amount of about 25% by weight of the total composition;
  f. Kollidon™ CL crospovidone in an amount of about 4% by weight of the total composition;
  g. sodium lauryl sulfate in an amount of about 2% by weight of the total composition;
  h. HyQual™ 5712 magnesium stearate in an amount of about 0.5% by weight of the total composition; and
  i. Cab-o-sil™ colloidal silicon dioxide in an amount of about 0.25% by weight of the total composition.

In some embodiments, the present invention pertains to pharmaceutical compositions comprising:

a. Form I of 1-[3-(4-bromo-2-methyl-2H-pyrazol-3-yl)-4-methoxy-phenyl]-3-(2,4-difluoro-phenyl)-urea in an amount of about 5% by weight of the total composition;

b. Kollidon™ VA 64 coPVP in an amount of about 40% by weight of the total composition;

c. 4000 cps methyl cellulose in an amount of about 2% by weight of the total composition;

d. Fast-Flo™ 316 lactose monohydrate in an amount of about 21.25% by weight of the total composition;

e. Avicel™ PH102 microcrystalline cellulose in an amount of about 25% by weight of the total composition;

f. Kollidon™ CL crospovidone in an amount of about 4% by weight of the total composition;

g. sodium lauryl sulfate in an amount of about 2% by weight of the total composition;

h. HyQual™ 5712 magnesium stearate in an amount of about 0.5% by weight of the total composition; and i. Cab-o-sil™ colloidal silicon dioxide in an amount of about 0.25% by weight of the total composition.

In some embodiments, the present invention pertains to pharmaceutical compositions comprising 1-[3-(4-bromo-2-methyl-2H-pyrazol-3-yl)-4-methoxy-phenyl]-3-(2,4-difluoro-phenyl)-urea in an amount of about 0.1 mg to about 500 mg.

One aspect of the present invention pertains to pharmaceutical compositions of the present invention suitable for oral administration.

In some embodiments, the pharmaceutical composition is in the form of a tablet.

In some embodiments, the pharmaceutical composition is in the form of a wet granulation tablet.

In some embodiments, the pharmaceutical composition is in the form of a powder in capsule (PIC).

One aspect of the present invention pertains to pharmaceutical compositions of the present invention whereby oral administration to male cynomolgus monkeys of the pharmaceutical composition containing about 10 mg of the 1-[3-(4-bromo-2-methyl-2H-pyrazol-3-yl)-4-methoxy-phenyl]-3-(2,4-difluoro-phenyl)-urea provides an $AUC_{0-\infty}$ for the 1-[3-(4-bromo-2-methyl-2H-pyrazol-3-yl)-4-methoxy-phenyl]-3-(2,4-difluoro-phenyl)-urea of about 1.5 h·µg/mL.

One aspect of the present invention pertains to pharmaceutical compositions of the present invention whereby oral administration to male cynomolgus monkeys of the pharmaceutical composition containing about 10 mg of the 1-[3-(4-bromo-2-methyl-2H-pyrazol-3-yl)-4-methoxy-phenyl]-3-(2,4-difluoro-phenyl)-urea provides a $C_{max}$ for the 1-[3-(4-bromo-2-methyl-2H-pyrazol-3-yl)-4-methoxy-phenyl]-3-(2,4-difluoro-phenyl)-urea of about 0.23 µg/mL.

One aspect of the present invention pertains to pharmaceutical compositions of the present invention whereby oral administration to male cynomolgus monkeys of the pharmaceutical composition containing about 30 mg of the 1-[3-(4-bromo-2-methyl-2H-pyrazol-3-yl)-4-methoxy-phenyl]-3-(2,4-difluoro-phenyl)-urea provides an $AUC_{0-\infty}$ for the 1-[3-(4-bromo-2-methyl-2H-pyrazol-3-yl)-4-methoxy-phenyl]-3-(2,4-difluoro-phenyl)-urea of about 5.0 h·µg/mL.

One aspect of the present invention pertains to pharmaceutical compositions of the present invention whereby oral administration to male cynomolgus monkeys of the pharmaceutical composition containing about 30 mg of the 1-[3-(4-bromo-2-methyl-2H-pyrazol-3-yl)-4-methoxy-phenyl]-3-(2,4-difluoro-phenyl)-urea provides a $C_{max}$ for the 1-[3-(4-bromo-2-methyl-2H-pyrazol-3-yl)-4-methoxy-phenyl]-3-(2,4-difluoro-phenyl)-urea of about 0.50 µg/mL.

In some embodiments, the pharmaceutical composition is in the form of a direct compression tablet.

In some embodiments, the direct compression tablet is coated with a moisture barrier.

In some embodiments, the moisture barrier is Opadry® II Blue.

One aspect of the present invention pertains to pharmaceutical compositions of the present invention whereby oral administration to male cynomolgus monkeys of the pharmaceutical composition containing about 40 mg of the 1-[3-(4-bromo-2-methyl-2H-pyrazol-3-yl)-4-methoxy-phenyl]-3-(2,4-difluoro-phenyl)-urea provides an $AUC_{0-\infty}$ for the 1-[3-(4-bromo-2-methyl-2H-pyrazol-3-yl)-4-methoxy-phenyl]-3-(2,4-difluoro-phenyl)-urea of about 4.2 h·µg/mL.

One aspect of the present invention pertains to pharmaceutical compositions of the present invention whereby oral administration to male cynomolgus monkeys of the pharmaceutical composition containing about 40 mg of the 1-[3-(4-bromo-2-methyl-2H-pyrazol-3-yl)-4-methoxy-phenyl]-3-(2,4-difluoro-phenyl)-urea provides a $C_{max}$ for the 1-[3-(4-bromo-2-methyl-2H-pyrazol-3-yl)-4-methoxy-phenyl]-3-(2,4-difluoro-phenyl)-urea of about 0.46 µg/mL.

In some embodiments, the 1-[3-(4-bromo-2-methyl-2H-pyrazol-3-yl)-4-methoxy-phenyl]-3-(2,4-difluoro-phenyl)-urea is present in an amount of about 10 mg, about 20 mg, about 30 mg, about 40 mg or about 50 mg.

One aspect of the present invention pertains to pharmaceutical compositions of the present invention in tablet form for oral administration consisting essentially of:

a. 1-[3-(4-bromo-2-methyl-2H-pyrazol-3-yl)-4-methoxy-phenyl]-3-(2,4-difluoro-phenyl)-urea in an amount of about 0.01% to about 10% by weight of the total composition;

b. PVP in a ratio of about 8:1 by weight compared to the 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating;

whereby the composition in tablet form, after oral administration of a 40 mg dose of 1-[3-(4-bromo-2-methyl-2H-pyrazol-3-yl)-4-methoxy-phenyl]-3-(2,4-difluoro-phenyl)-urea to a male cynomolgus monkey provides an $AUC_{0-\infty}$ of about 4.2 µg/mL, or a $C_{max}$ of about 0.46 µg/mL.

One aspect of the present invention pertains to pharmaceutical compositions of the present invention in tablet form for oral administration consisting essentially of:

a. Form I of 1-[3-(4-bromo-2-methyl-2H-pyrazol-3-yl)-4-methoxy-phenyl]-3-(2,4-difluoro-phenyl)-urea in an amount of about 0.01% to about 10% by weight of the total composition;

b. PVP in a ratio of about 8:1 by weight compared to 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating;

whereby the composition in tablet form, after oral administration of a 40 mg dose of Form 1 of 1-[3-(4-bromo-2-methyl-2H-pyrazol-3-yl)-4-methoxy-phenyl]-3-(2,4-difluoro-phenyl)-urea to a male cynomolgus monkey provides an $AUC_{0-\infty}$ of about 4.2 h·µ/mL, or a $C_{max}$ of about 0.46 µg/mL.

One aspect of the present invention pertains to pharmaceutical compositions of the present invention in tablet form for oral administration consisting essentially of:

a. 1-[3-(4-bromo-2-methyl-2H-pyrazol-3-yl)-4-methoxy-phenyl]-3-(2,4-difluoro-phenyl)-urea in an amount of about 0.01% to about 10% by weight of the total composition;

b. coPVP in a ratio of about 8:1 by weight compared to the 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating;

whereby the composition in tablet form, after oral administration of a 40 mg dose of 1-[3-(4-bromo-2-methyl-2H-pyrazol-3-yl)-4-methoxy-phenyl]-3-(2,4-difluoro-phenyl)-urea to a male cynomolgus monkey provides an $AUC_{0-\infty}$ of about 4.2 h·μg/mL, or a $C_{max}$ of about 0.46 μg/mL.

One aspect of the present invention pertains to pharmaceutical compositions of the present invention in tablet form for oral administration consisting essentially of:

a. Form I of 1-[3-(4-bromo-2-methyl-2H-pyrazol-3-yl)-4-methoxy-phenyl]-3-(2,4-difluoro-phenyl)-urea in an amount of about 0.01% to about 10% by weight of the total composition;

b. coPVP in a ratio of about 8:1 by weight compared to the 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating;

whereby the composition in tablet form, after oral administration of a 40 mg dose of Form I of 1-[3-(4-bromo-2-methyl-2H-pyrazol-3-yl)-4-methoxy-phenyl]-3-(2,4-difluoro-phenyl)-urea to a male cynomolgus monkey provides an $AUC_{0-\infty}$ of about 4.2 h·μg/mL, or a $C_{max}$ of about 0.46 μg/mL.

One aspect of the present invention pertains to pharmaceutical compositions of the present invention in tablet form for oral administration consisting essentially of:

a. about 10 mg of 1-[3-(4-bromo-2-methyl-2H-pyrazol-3-yl)-4-methoxy-phenyl]-3-(2,4-difluoro-phenyl)-urea;

b. PVP in a ratio of about 8:1 by weight compared to the 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 10 mg of Form I of 1-[3-(4-bromo-2-methyl-2H-pyrazol-3-yl)-4-methoxy-phenyl]-3-(2,4-difluoro-phenyl)-urea;

b. PVP in a ratio of about 8:1 by weight compared to the Form I of 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 10 mg of 1-[3-(4-bromo-2-methyl-2H-pyrazol-3-yl)-4-methoxy-phenyl]-3-(2,4-difluoro-phenyl)-urea;

b. coPVP in a ratio of about 8:1 by weight compared to the 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 10 mg of Form I of 1-[3-(4-bromo-2-methyl-2H-pyrazol-3-yl)-4-methoxy-phenyl]-3-(2,4-difluoro-phenyl)-urea;

b. coPVP in a ratio of about 8:1 by weight compared to the Form I of 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 20 mg of 1-[3-(4-bromo-2-methyl-2H-pyrazol-3-yl)-4-methoxy-phenyl]-3-(2,4-difluoro-phenyl)-urea;

b. PVP in a ratio of about 8:1 by weight compared to the 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 20 mg of Form I of 1-[3-(4-bromo-2-methyl-2H-pyrazol-3-yl)-4-methoxy-phenyl]-3-(2,4-difluoro-phenyl)-urea;

b. PVP in a ratio of about 8:1 by weight compared to the Form I of 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 20 mg of 1-[3-(4-bromo-2-methyl-2H-pyrazol-3-yl)-4-methoxy-phenyl]-3-(2,4-difluoro-phenyl)-urea;

b. coPVP in a ratio of about 8:1 by weight compared to the 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 20 mg of Form I of 1-[3-(4-bromo-2-methyl-2H-pyrazol-3-yl)-4-methoxy-phenyl]-3-(2,4-difluoro-phenyl)-urea;

b. coPVP in a ratio of about 8:1 by weight compared to the Form I of 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 30 mg of 1-[3-(4-bromo-2-methyl-2H-pyrazol-3-yl)-4-methoxy-phenyl]-3-(2,4-difluoro-phenyl)-urea;

b. PVP in a ratio of about 8:1 by weight compared to the 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 30 mg of Form I of 1-[3-(4-bromo-2-methyl-2H-pyrazol-3-yl)-4-methoxy-phenyl]-3-(2,4-difluoro-phenyl)-urea;

b. PVP in a ratio of about 8:1 by weight compared to the Form I of 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 30 mg of 1-[3-(4-bromo-2-methyl-2H-pyrazol-3-yl)-4-methoxy-phenyl]-3-(2,4-difluoro-phenyl)-urea;

b. coPVP in a ratio of about 8:1 by weight compared to the 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 30 mg of Form I of 1-[3-(4-bromo-2-methyl-2H-pyrazol-3-yl)-4-methoxy-phenyl]-3-(2,4-difluoro-phenyl)-urea;

b. coPVP in a ratio of about 8:1 by weight compared to the Form I of 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 40 mg of 1-[3-(4-bromo-2-methyl-2H-pyrazol-3-yl)-4-methoxy-phenyl]-3-(2,4-difluoro-phenyl)-urea;

b. PVP in a ratio of about 8:1 by weight compared to the 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 40 mg of Form I of 1-[3-(4-bromo-2-methyl-2H-pyrazol-3-yl)-4-methoxy-phenyl]-3-(2,4-difluoro-phenyl)-urea;

b. PVP in a ratio of about 8:1 by weight compared to the 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 40 mg of 1-[3-(4-bromo-2-methyl-2H-pyrazol-3-yl)-4-methoxy-phenyl]-3-(2,4-difluoro-phenyl)-urea;

b. coPVP in a ratio of about 8:1 by weight compared to the 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 40 mg of Form I of 1-[3-(4-bromo-2-methyl-2H-pyrazol-3-yl)-4-methoxy-phenyl]-3-(2,4-difluoro-phenyl)-urea;

b. coPVP in a ratio of about 8:1 by weight compared to the Form I of 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 50 mg of 1-[3-(4-bromo-2-methyl-2H-pyrazol-3-yl)-4-methoxy-phenyl]-3-(2,4-difluoro-phenyl)-urea;

b. PVP in a ratio of about 8:1 by weight compared to the 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 50 mg of Form I of 1-[3-(4-bromo-2-methyl-2H-pyrazol-3-yl)-4-methoxy-phenyl]-3-(2,4-difluoro-phenyl)-urea;

b. PVP in a ratio of about 8:1 by weight compared to the Form I of 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 50 mg of 1-[3-(4-bromo-2-methyl-2H-pyrazol-3-yl)-4-methoxy-phenyl]-3-(2,4-difluoro-phenyl)-urea;

b. coPVP in a ratio of about 8:1 by weight compared to the 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

One aspect of the present invention pertains to pharmaceutical compositions of the present invention in tablet form for oral administration consisting essentially of:

a. about 50 mg of Form I of 1-[3-(4-bromo-2-methyl-2H-pyrazol-3-yl)-4-methoxy-phenyl]-3-(2,4-difluoro-phenyl)-urea;

b. coPVP in a ratio of about 8:1 by weight compared to the Form I of 1-[3-(4-bromo-2-methyl-2H-pyrazol-3-yl)-4-methoxy-phenyl]-3-(2,4-difluoro-phenyl)-urea;

c. methyl cellulose in an amount of about 2% by weight of the total composition;

d. at least one ingredient selected from: lactose monohydrate, microcrystalline cellulose, crospovidone, sodium lauryl sulfate, magnesium stearate and silicon dioxide; and e. a moisture barrier coating.

Kits of the Present Invention

One aspect of the present invention pertains to pharmaceutical compositions of the present invention in kit form that allow one of skill in the art to prepare a desired therapeutic regimen for treating a $5\text{-HT}_{2A}$ serotonin receptor-related disorder.

In some embodiments, the kits also comprise a container for the pharmaceutical compositions such as a bottle or a blister pack. Blister packs are well known in the packaging industry and are being widely used for the packaging of pharmaceutical unit dosage forms (tablets, capsules and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil that is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening. Additional examples of containers include, but are not limited to syringes, boxes, bags and the like. In some embodiments, the kits comprise directions for the administration of the pharmaceutical compositions.

One aspect of the present invention pertains to kits for treating a $5\text{-HT}_{2A}$ serotonin receptor-related disorder in an individual comprising a container and a pharmaceutical composition of the present invention.

In some embodiments the kit comprises single unit dosage forms of a pharmaceutical composition of the present invention.

In some embodiments the kit further comprises instructions for use of the pharmaceutical composition.

Methods of Preparing Pharmaceutical Compositions of the Present Invention

One aspect of the present invention pertains to methods for preparing a pharmaceutical composition of the present invention comprising:

a. 1-[3-(4-bromo-2-methyl-2H-pyrazol-3-yl)-4-methoxy-phenyl]-3-(2,4-difluoro-phenyl)-urea; and b. an excipient selected from: PVP and coPVP;

comprising blending said 1-[3-(4-bromo-2-methyl-2H-pyrazol-3-yl)-4-methoxy-phenyl]-3-(2,4-difluoro-phenyl)-urea and said excipient in a blender.

One aspect of the present invention pertains to methods for preparing a pharmaceutical composition of the present invention comprising:

a. 1-[3-(4-bromo-2-methyl-2H-pyrazol-3-yl)-4-methoxy-phenyl]-3-(2,4-difluoro-phenyl)-urea;

b. an excipient selected from: PVP and coPVP; and c. methyl cellulose comprising blending said 1-[3-(4-bromo-2-methyl-2H-pyrazol-3-yl)-4-methoxy-phenyl]-3-(2,4-difluoro-phenyl)-urea, said excipient and said methyl cellulose in a blender.

In some embodiments, the methyl cellulose is 4000 cps methyl cellulose.

In some embodiments, the 1-[3-(4-bromo-2-methyl-2H-pyrazol-3-yl)-4-methoxy-phenyl]-3-(2,4-difluoro-phenyl)-urea is Form I of 1-[3-(4-bromo-2-methyl-2H-pyrazol-3-yl)-4-methoxy-phenyl]-3-(2,4-difluoro-phenyl)-urea.

In some embodiments, the excipient is PVP.

In some embodiments, the PVP is Plasdone™ K-29/32 PVP or Kollidon™ 30 PVP.

In some embodiments, the excipient is coPVP.

In some embodiments, the coPVP is Kollidon™ VA 64 PVP.

In some embodiments, the pharmaceutical composition further comprises at least one ingredient selected from: lactose monohydrate, microcrystalline cellulose, crospovidone, sodium lauryl sulfate, magnesium stearate and silicon dioxide.

One aspect of the present invention pertains to methods for preparing a pharmaceutical composition of the present invention comprising:
  a. blending 1-[3-(4-bromo-2-methyl-2H-pyrazol-3-yl)-4-methoxy-phenyl]-3-(2,4-difluoro-phenyl)-urea, PVP, methyl cellulose, lactose monohydrate, microcrystalline cellulose, crospovidone, sodium lauryl sulfate and silicon-dioxide to produce a first blend;
  b. delumping said first blend in a conical mill; and
  c. blending said first blend with magnesium stearate.

One aspect of the present invention pertains to methods for preparing a pharmaceutical composition of the present invention comprising:
  a. 1-[3-(4-bromo-2-methyl-2H-pyrazol-3-yl)-4-methoxy-phenyl]-3-(2,4-difluoro-phenyl)-urea in an amount of about 0.01% to about 5% by weight of the total composition;
  b. Plasdone™ K-29/32 PVP or Kollidon™ 30 PVP in an amount of about 40% by weight of the total composition;
  c. methyl cellulose in an amount of about 2% fey weight of the total composition;
  d. lactose monohydrate, 316 in an amount of about 21.25% by weight of the total composition;
  e. microcrystalline cellulose, PH-102 in an amount of about 25% by weight of the total composition;
  f. Kollidon™ CL in an amount of about 4% by weight of the total composition;
  g. sodium lauryl sulfate in an amount of about 2% by weight of the total composition;
  h. magnesium stearate in an amount of about 0.5% by weight of the total composition; and
  i. silicon dioxide in an amount of about 0.25% by weight of the total composition.

One aspect of the present invention pertains to methods for preparing a pharmaceutical composition of the present invention comprising:
  a. blending Form I of 1-[3-(4-bromo-2-methyl-2H-pyrazol-3-yl)-4-methoxy-phenyl]-3-(2,4-difluoro-phenyl)-urea, PVP, methyl cellulose, lactose monohydrate, microcrystalline cellulose, crospovidone, sodium lauryl sulfate and silicon dioxide to produce a first blend;
  b. delumping said first blend in a conical mill; and
  c. blending said first blend with magnesium stearate.

One aspect of the present invention pertains to methods for preparing a pharmaceutical composition of the present invention comprising:
  a. Form I of 1-[3-(4-bromo-2-methyl-2H-pyrazol-3-yl)-4-methoxy-phenyl]-3-(2,4-difluoro-phenyl)-urea in an amount of about 0.01% to about 5% by weight of the total composition;
  b. Plasdone™ K-29/32 PVP or Kollidon™ 30 PVP in an amount of about 40% by weight of the total composition;
  c. methyl cellulose in an amount of about 2% by weight of the total composition;
  d. lactose monohydrate, 316 in an amount of about 21.25% by weight of the total composition;
  e. microcrystalline cellulose, PH-102 in an amount of about 25% by weight of the total composition;
  f. Kollidon™ CL in an amount of about 4% by weight of the total composition;
  g. sodium lauryl sulfate in as amount of about 2% by weight of the total composition;
  h. magnesium stearate in an amount of about 0.5% by weight of the total composition; and
  i. silicon dioxide in an amount of about 0.25% by weight of the total composition.

One aspect of the present invention pertains to methods for preparing a pharmaceutical composition of the present invention comprising:
  a. blending 1-[3-(4-bromo-2-methyl-2H-pyrazol-3-yl)-4-methoxy-phenyl]-3-(2,4-difluoro-phenyl)-urea, coPVP, methyl cellulose, lactose monohydrate, microcrystalline cellulose, crospovidone, sodium lauryl sulfate and silicon dioxide to produce a first blend;
  b. delumping said first blend in a conical mill; and
  c. blending said first blend with magnesium stearate.

One aspect of the present invention pertains to methods for preparing a pharmaceutical composition of the present invention comprising:
  a. 1-[3-(4-bromo-2-methyl-2H-pyrazol-3-yl)-4-methoxy-phenyl]-3-(2,4-difluoro-phenyl)-urea in an amount of about 0.01% to about 5% by weight of the total composition;
  b. Kollidon™ VA 64 coPVP in an amount of about 40% by weight of the total composition;
  c. methyl cellulose in an amount of about 2% by weight of the total composition;
  d. lactose monohydrate, 316 in an amount of about 21.25% by weight of the total composition;
  e. microcrystalline cellulose, PH-102 in an amount of about 25% by weight of the total composition;
  f. Kollidon™ CL in an amount of about 4% by weight of the total composition;
  g. sodium lauryl sulfate in an amount of about 2% by weight of the total composition;
  h. magnesium stearate in an amount of about 0.5% by weight of the total composition; and
  i. silicon dioxide in an amount of about 0.25% by weight of the total composition.

One aspect of the present invention pertains to methods for preparing a pharmaceutical composition of the present invention comprising:
  a. blending Form I of 1-[3-(4-bromo-2-methyl-2H-pyrazol-3-yl)-4-methoxy-phenyl]-3-(2,4-difluoro-phenyl)-urea, coPVP, methyl cellulose, lactose monohydrate, microcrystalline cellulose, crospovidone, sodium lauryl sulfate and silicon dioxide to produce a first blend;
  b. delumping said first blend in a conical mill; and
  c. blending said first blend with magnesium stearate.

One aspect of the present invention pertains to methods for preparing a pharmaceutical composition of the present invention comprising:
  a. Form I of 1-[3-(4-bromo-2-methyl-2H-pyrazol-3-yl)-4-methoxy-phenyl]-3-(2,4-difluoro-phenyl)-urea in an amount of about 0.01% to about 5% by weight of the total composition;
  b. Kollidon™ VA 64 co PVP in an amount of about 40% by weight of the total composition;
  c. methyl cellulose in an amount of about 2% by weight of the total composition;
  d. lactose monohydrate, 316 in an amount of about 21.25% by weight of the total composition;
  e. microcrystalline cellulose, PH-102 in an amount of about 25% by weight of the total composition;
  f. Kollidon™ CL in an amount of about 4% by weight of the total composition;
  g. sodium lauryl sulfate in an amount of about 2% by weight of the total composition;

h. magnesium stearate in an amount of about 0.5% by weight of the total composition; and i. silicon dioxide in an amount of about 0.25% by weight of the total composition.

In some embodiments the methods for preparing a pharmaceutical composition of the present invention further comprise the step of compressing said pharmaceutical composition into tablets.

In some embodiments the methods for preparing a pharmaceutical composition of the present invention further comprise the step of coating said tablets with a moisture barrier.

In some embodiments, the moisture barrier is Opadry® II Blue.

Dosage Forms of the Present Invention

One aspect of the present invention pertains to dosage forms comprising:
a. about 0.1 mg to about 500 mg of 1-[3-(4-bromo-2-methyl-2H-pyrazol-3-yl)-4-methoxy-phenyl]-3-(2,4-difluoro-phenyl)-urea; and
b. an excipient selected from PVP, or coPVP.

In some embodiments, the 1-[3-(4-bromo-2-methyl-2H-pyrazol-3-yl)-4-methoxy-phenyl]-3-(2,4-difluoro-phenyl)-urea is Form I of 1-[3-(4-bromo-2-methyl-2H-pyrazol-3-yl)-4-methoxy-phenyl]-3-(2,4-difluoro-phenyl)-urea.

In some embodiments, the dosage form further comprises methyl cellulose.

In some embodiments, the methyl cellulose is 4000 cps methyl cellulose.

In some embodiments, the excipient is Plasdone™ K-29/32 PVP or Kollidon™ 30 PVP.

In some embodiments, the excipient is Kollidon™ VA 64 coPVP.

One aspect of the present invention pertains to dosage forms comprising:
a. 1-[3-(4-bromo-2-methyl-2H-pyrazol-3-yl)-4-methoxy-phenyl]-3-(2,4-difluoro-phenyl)-urea and Plasdone™ K-29/32 PVP or Kollidon™ 30 PVP in a ratio of about 1:8; and
b. about 2% 4000 cps methyl cellulose.

One aspect of the present invention pertains to dosage forms comprising:
a. Form I of 1-[3-(4-bromo-2-methyl-2H-pyrazol-3-yl)-4-methoxy-phenyl]-3-(2,4-difluoro-phenyl)-urea and Plasdone™ K-29/32 PVP or Kollidon™ 30 PVP in a ratio of about 1:8; and
b. about 2% 4000 cps methyl cellulose.

One aspect of the present invention pertains to dosage forms comprising:
a. 1-[3-(4-bromo-2-methyl-2H-pyrazol-3-yl)-4-methoxy-phenyl]-3-(2,4-difluoro-phenyl)-urea and Kollidon™ VA 64 co PVP in a ratio of about 1:8; and
b. about 2% 4000 cps methyl cellulose.

One aspect of the present invention pertains to dosage forms comprising:
a. Form I of 1-[3-(4-bromo-2-methyl-2H-pyrazol-3-yl)-4-methoxy-phenyl]-3-(2,4-difluoro-phenyl)-urea and Kollidon™ VA 64 coPVP in a ratio of about 1:8; and
b. about 2% 4000 cps methyl cellulose.

In some embodiments, the dosage form is suitable for oral administration.

One aspect of the present invention pertains to dosage forms comprising: 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg of 1-[3-(4-bromo-2-methyl-2H-pyrazol-3-yl)-4-methoxy-phenyl]-3-(2,4-difluoro-phenyl)-urea.

One aspect of the present invention pertains to dosage forms comprising: 1 mg, 5 mg, 10 mg, 20 mg, 30 mg, 40 mg, 80 mg, or 100 mg of 1-[3-(4-bromo-2-methyl-2H-pyrazol-3-yl)-4-methoxy-phenyl]-3-(2,4-difluoro-phenyl)-urea.

Crystalline Forms of the Present Invention

One aspect of the present invention is directed to the preparation of Form I of 1-[3-(4-bromo-2-methyl-2H-pyrazol-3-yl)-4-methoxy-phenyl]-3-(2,4-difluoro-phenyl)-urea (Compound I) and compositions thereof. Form I can be identified by its unique solid state signature with respect to, for example, differential scanning calorimetry (DSC), powder X-ray diffraction (PXRD), IR. Raman spectroscopy and other solid state methods. Further characterization with respect to water or solvent content of the crystalline form can be gauged by any of the following methods for example, thermogravimetric analysis (TGA), DSC and the like. For DSC, it is known that the temperatures observed for thermal events will depend upon the rate of temperature change as well as sample preparation technique and the particular instrument employed. Thus, the values reported herein relating to DSC thermograms can vary by plus or minus about 4° C. The values reported herein relating to DSC thermograms can also vary by plus or minus about 20 Joules per gram. In samples contaminated with Form II of 1-[3-(4-bromo-2-methyl-2H-pyrazol-3-yl)-4-methoxy-phenyl]-3-(2,4-difluoro-phenyl)-urea the values reported herein relating to DSC thermograms can vary by plus or minus>20 joules per gram. For PXRD, the relative intensities of the peaks can vary, depending upon the sample preparation technique, the sample mounting procedure and the particular instrument employed. Moreover, instrument variation and other factors can often affect the 2θ values. Therefore, the peak assignments of diffraction patterns can vary by plus or minus about 0.2°2θ. For TGA, the features reported herein can vary by about ±5° C. The TGA features reported herein can also vary by about ±2% weight change due to, for example, sample variation. Further characterization with respect to hygroscopicity of the crystalline form can be gauged by, for example, dynamic vapor sorption (DVS). The DVS features reported herein can vary by about ±5% relative humidity. The DVS features reported herein can also vary and by about ±5% weight change.

The physical properties of crystalline Form I of 1-[3-(4-bromo-2-methyl-2H-pyrazol-3-yl)-4-methoxy-phenyl]-3-(2,4-difluoro-phenyl)-urea (Compound I) are summarized in Table A below.

TABLE A

Characterization of Form I of 1-[3-(4-bromo-2-methyl-2H-pyrazol-3-yl)-4-methoxy-phenyl]-3-(2,4-difluoro-phenyl)-urea (Compound I)

| | |
|---|---|
| PXRD | FIG. 21: Peaks of about 17% or greater relative intensity at 5.6°, 7.4°, 11.2°, 21.1° and 25.0° 2θ |
| DSC | FIG. 22: an endotherm with an extrapolated onset temperature of about 170° C., an associated heat flow of about 64 joules per gram and a peak temperature of about 172° C. |
| FT RAMAN | FIG. 23: Peaks at 3086, 2955, 2840, 1656, 1622, 1605, 1572, 1534, 1004, 1004, 964, 911, 759, 751, 732, 723, 673, 505, 390, 335 and 315 cm$^{-1}$ |
| TGA | FIG. 24: negligible weight loss below about 150° C. |

The negligible weight loss observed in the TGA data suggests that Form I of 1-[3-(4-bromo-2-methyl-2H-pyrazol-3-yl)-4-methoxy-phenyl]-3-(2,4-difluoro-phenyl)-urea (Compound I) is an anhydrous, non-solvated crystalline form. The DSC thermogram further reveals a melting endotherm with an onset at about 170° C.

One aspect of the present invention is directed to Form I of 1-[3-(4-bromo-2-methyl-2H-pyrazol-3-yl)-4-methoxyphenyl]-3-(2,4-difluoro-phenyl)-urea having a powder X-ray diffraction pattern comprising peaks expressed in terms of 2θ at about 5.6° C. and about 21.1°. In some embodiments, the crystalline form has an X-ray powder diffraction pattern comprising a peak, in terms of 2θ, at about 7.4° and about 11.2°. In some embodiments, the crystalline form has an X-ray powder diffraction pattern comprising a peak, in terms of 2θ, at about 5.6°, about 7.4°, about 11.2° and about 21.1°. In some embodiments, the crystalline form has an X-ray powder diffraction pattern comprising a peak, in terms of 2θ at about 5.6°, about 7.4°, about 11.2° about 21.1° and about 25.0°. In yet further embodiments, the crystalline form has an X-ray powder diffraction pattern substantially as shown in FIG. 21, wherein by "substantially" is meant that the reported peaks can vary by about ±0.2°2θ and also that the relative intensities of the reported peaks can vary.

In some embodiments, Form I of 1-[3-(4-bromo-2-methyl-2H-pyrazol-3-yl)-4-methoxy-phenyl]-3-(2,4-difluoro-phenyl)-urea has a differential scanning calorimetry thermogram comprising an endotherm with an extrapolated onset temperature of about 165° C. to about 175° C. In some embodiments, the crystalline form has a differential scanning calorimetry thermogram comprising an endotherm with an extrapolated onset temperature at about 170° C. In some embodiments, the crystalline form has a differential scanning calorimetry thermogram comprising an endotherm with a peak temperature between about 167° C. to about 177° C. In some embodiments, the crystalline form has a differential scanning calorimetry thermogram comprising an endotherm with a peak temperature at about 172° C. In some embodiments, the crystalline form has a differential scanning calorimetry thermogram comprising an endotherm with an associated heat flow of about 59 joules per gram to about 69 joules per gram. In some embodiments, the crystal line form has a differential scanning calorimetry thermogram comprising an endotherm with an associated heat flow of about 64 joules per gram. In further embodiments, the crystalline form has a differential scanning calorimetry thermogram substantially as shown in FIG. 22, wherein by "substantially" is meant that the reported DSC features can vary by about ±4° C. and also that the reported DSC features can vary by about ±20 joules per gram.

In some embodiments, Form I of 1-[3-(4-bromo-2-methyl-2H-pyrazol-3-yl)-4-methoxy-phenyl]-3-(2,4-difluoro-phenyl)-urea has a Raman spectrum comprising peaks at about 1327 cm$^{-1}$ and about 1657 cm$^{-1}$. In some embodiments, the crystalline form has a Raman spectrum comprising peaks at about 1327 cm$^{-1}$ about 1.622 cm$^{-1}$ and about 1657 cm$^{-1}$. In some embodiments, the crystalline form has a Raman spectrum comprising peaks at about 732 cm$^{-1}$, about 1327 cm$^{-1}$, about 1573 cm$^{-1}$, about 1622 cm$^{-1}$ about 1622 cm$^{-1}$ and about 1657 cm$^{-1}$. In some embodiments, the crystalline form has a Raman spectrum substantially as shown in FIG. 23.

In some embodiments, Form I of 1-[3-(4-bromo-2-methyl-2H-pyrazol-3-yl)-4-methoxy-phenyl]-3-(2,4-difluoro-phenyl)-urea has a weight loss of about 2% or less as determined by thermogravimetric analysis at a temperature up to about 150° C. In some embodiments, the crystalline form has a weight loss of about 0.5% or less as determined by thermogravimetric analysis at a temperature up to about 150° C. In some embodiments, the crystalline form has a weight loss of about 0.1% or less as determined by thermogravimetric analysis at a temperature up to about 150° C. In some embodiments, the crystalline form has a thermogravimetric analysis thermogram substantially as shown in FIG. 24, wherein by "substantially" is meant that the reported TGA features can vary by about ±5° C. and also that the reported TGA features can vary by about ±2% weight change In some embodiments, the crystalline form has a powder X-ray diffraction pattern comprising peaks expressed in terms of 2θ at about 5.6° and about 21.1°; a differential scanning calorimetry thermogram comprising an endotherm with an extrapolated onset temperature of about 165° C. to about 175° C.; and a Raman spectrum comprising peaks at about 1327 cm$^{-1}$ and about 1657 cm$^{-1}$.

In some embodiments, the crystalline form has a powder X-ray diffraction pattern comprising peaks expressed in terms of 2θ at about 7.4° and about 11.2°; a differential scanning calorimetry thermogram comprising an endotherm with an extrapolated onset temperature of about 170° C.; and; a Raman spectrum comprising peaks at about 1327 cm$^{-1}$, about 1622 cm$^{-1}$ and about 1657 cm$^{-1}$.

In some embodiments, the crystalline form has a powder X-ray diffraction pattern comprising peaks expressed in terms of 2θ at about 5.6°, about 7.4°, about 11.2° and about 21.1°; a differential spanning calorimetry thermogram comprising an endotherm with an extrapolated onset temperature of about 170° C., a peak temperature of about 172° C. and an associated heat flow of about 64 joules per gram; a Raman spectrum comprising peaks at about 732 cm$^{-1}$, about 1327 cm$^{-1}$, about 1573 cm$^{-1}$, about 1605 cm$^{-1}$, about 1622 cm$^{-1}$, and about 1657 cm$^{-1}$; and a weight loss of about 0.5% or less as determined by thermogravimetric analysis at a temperature up to about 150° C.

Compositions of the Present Invention

One aspect of the present invention is directed to compositions comprising Form I of 1-[3-(4-bromo-2-methyl-2H-pyrazol-3-yl)-4-methoxy-phenyl]-3-(2,4-difluoro-phenyl)-urea, wherein the compositions comprise less than 0.9 mole % of 1-(2,4-difluorophenyl)-3-(4-methoxy-3-(1-methyl-1H-pyrazol-5-yl)phenyl)urea. In some embodiments, Form I of 1-[3-(4-bromo-2-methyl-2H-pyrazol-3-yl)-4-methoxy-phenyl]-3-(2,4-difluoro-phenyl)-urea constitutes at least about 0.1% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 1% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 5% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 10% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 15% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 20% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 30% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 40% by weight of the composition. In some embodiments, Form 1-[3-(4-bromo- 2-methyl-2H-pyrazol-3-yl)-4-methoxy-phenyl]-3-(2,4-difluoro-phenyl)-urea constitutes at least about 50% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 60% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 70% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 80% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 90% by weight of the composition. In some embodiments, Form I of 1-[3-(4-bromo-2-methyl-2H-pyrazol-3-yl)-4-methoxy-phenyl]-3-(2,4-difluoro-phenyl)-urea constitutes at least about 95% by weight of the composition.

One aspect of the present invention is directed to compositions comprising Form I of 1-[3-(4-bromo-2-methyl-2H-pyrazol-3-yl)-4-methoxy-phenyl]-3-(2,4-difluoro-phenyl)-urea and less than 0.9 mole % of 1-(2,4-difluorophenyl)-3-(4-methoxy-3-(1-methyl-1H-pyrazol-5-yl)phenyl)urea and further comprising a pharmaceutically acceptable carrier. In some embodiments, the composition is formulated for oral administration. In some embodiments, the composition is in the form of a pill, capsule or tablet.

Indications and Methods of Treatment

In addition to the foregoing beneficial uses for the modulators of 5-HT$_{2A}$ serotonin receptor activity disclosed herein, the compounds disclosed herein are believed to be useful in the treatment of several additional diseases and disorders and in the amelioration of symptoms thereof. Without limitation, these include the following:

1. Sleep Disorders.

It is reported in the National Sleep Foundation's 2002 Sleep in America Poll, 58% of the adults surveyed report having experienced one or more symptoms of insomnia at least a few nights a week in the past year. Additionally, 35% of the adults surveyed say they have experienced insomnia-like symptoms every night or almost every night.

The normal sleep cycle and sleep architecture can be disrupted by a variety of organic causes as well as environmental influences. According to the International Classification of Sleep Disorders, there are over 80 recognized sleep disorders. Of these, compounds of the present invention are effective, for example, in any one or more of the following sleep disorders (ICSD—International Classification of Sleep Disorders: Diagnostic and Coding Manual. *Diagnostic Classification Steering Committee*, American Sleep Disorders Association, 1990):

A. Dyssomnias a. Intrinsic Sleep Disorders:

Psychophysiological insomnia, sleep state misperception, idiopathic insomnia, obstructive sleep apnea syndrome, central sleep apnea syndrome, central alveolar hypoventilation syndrome, periodic limb movement disorder, restless leg syndrome and intrinsic sleep disorder NOS (not otherwise specified).

b. Extrinsic Sleep Disorders:

Inadequate sleep hygiene, environmental sleep disorder, altitude insomnia, adjustment sleep disorder, insufficient sleep syndrome, limit-setting sleep disorder, sleep onset association disorder, nocturnal eating (drinking) syndrome, hypnotic-dependent sleep disorder, stimulant-dependent sleep disorder, alcohol-dependent sleep disorder, toxin-induced sleep disorder and extrinsic sleep disorder NOS.

c. Circadian Rhythm Sleep Disorders:

Time zone change (jet lag) syndrome, shift work sleep disorder, irregular sleep-wake pattern, delayed sleep phase syndrome, advanced sleep phase syndrome, non-24-hour sleep-wake disorder and circadian rhythm sleep disorder NOS.

B. Parasomnias a. Arousal Disorders:

Confusional arousals, sleepwalking and sleep terrors.

b. Sleep-Wake Transition Disorders:

Rhythmic movement disorder, sleep starts, sleep talking and nocturnal leg cramps.

C. Sleep Disorders Associated with Medical/Psychiatric Disorders a. Associated with Mental Disorders:

Psychoses, mood disorders, anxiety disorders, panic disorders and alcoholism.

b. Associated with Neurological Disorders:

Cerebral degenerative disorders, dementia, Parkinsonism, fatal familial insomnia, sleep-related epilepsy, electrical status epilepticus of sleep and sleep-related headaches.

c. Associated with Other Medical Disorders:

Sleeping sickness, nocturnal cardiac ischemia, chronic obstructive pulmonary disease, sleep-related asthma, sleep-related gastroesophageal reflux, peptic ulcer disease, fibrositis syndrome, osteoarthritis, rheumatoid arthritis, fibromyalgia and postsurgical.

The effects of sleep deprivation are more than excessive daytime sleepiness. Chronic insomniacs report elevated levels of stress, anxiety, depression and medical illnesses (National Institutes of Health, National Heart, lung and Blood Institute, *Insomnia Facts Sheet*, October 1995), Preliminary evidence suggests that having a sleep disorder that causes significant loss of sleep may contribute to increased susceptibility to infections due to immunosuppression, cardiovascular complications such as hypertension, cardiac arrhythmias, stroke and myocardial infarction, compromised glucose tolerance, increased obesity and metabolic syndrome. Compounds of the present invention are useful to prevent or alleviate these complications by improving sleep quality.

The most common class of medications for the majority of sleep disorders are the benzodiazepines, but the adverse effect profile of benzodiazepines includes daytime sedation, diminished motor coordination and cognitive impairments. Furthermore, at the National Institutes of Health Consensus Conference on Sleeping Pills and Insomnia in 1984 guidelines were developed discouraging the use of such sedative-hypnotics beyond 4-6 weeks because of concerns raised over drug misuse, dependency, withdrawal and rebound insomnia. Therefore, it is desirable to have a pharmacological agent for the treatment of insomnia, which is more effective and/or has fewer side effects than those currently used. In addition, benzodiazepines are used to induce sleep, but have little to no effect on the maintenance of sleep, sleep consolidation or slow wave sleep. Therefore, sleep maintenance disorders are not currently well treated.

Clinical studies with agents of a similar mechanism of action as compounds of the present invention have demonstrated significant improvements on objective and subjective sleep parameters in normal, healthy volunteers as well as patients with sleep disorders and mood disorders [Sharpley A. L., et al., Slow Wave Sleep in Humans: Role of 5-HT$_{2A}$ and 5-HT$_{2C}$ Receptors, *Neuropharmacology*, 1994, Vol. 33(3/4):467-71; Winokur A., et al., Acute Effects of Mirtazapine on Sleep Continuity and Sleep Architecture in Depressed Patients: A Pilot Study. *Soc. of Biol. Psych.,* 2000, Vol, 48:75-78; and Landolt H. P., et al., Serotonin-2 Receptors and Human Sleep: Effect of Selective Antagonist on EEG Power Spectra, *Neuropsychopharmacology,* 1999, Vol, 21(3): 455-66].

Some sleep disorders are sometimes found in conjunction with other conditions and accordingly those conditions are treatable by compositions of the present invention. For example, but not limited to, patients suffering from mood disorders typically suffer from a sleep disorder that can be treatable by compositions of the present invention. Having one pharmacological agent which treats two or more existing or potential conditions, as does the present invention, is more cost effective, leads to better compliance and has fewer side effects than taking two or more agents.

It is an object of the present invention to provide a therapeutic agent for the use in treating sleep disorders. It is another object of the present invention to provide one pharmaceutical agent, which may be useful in treating two or more conditions wherein one of the conditions is a sleep disorder. Compounds of the present invention described herein may be used alone or in combination with a mild sleep inducer (i.e. antihistamine).

Sleep Architecture:

Sleep comprises two physiological states: Non rapid eye movement (NREM) and rapid eye movement (REM) sleep. NREM sleep consists of four stages, each of which is characterized by progressively slower brain, wave patterns, with the slower patterns indicating deeper sleep. So called delta steep, stages 3 and 4 of NREM sleep, is the deepest and most refreshing type of sleep. Many patients with sleep disorders are unable to adequately achieve the restorative sleep of stages 3 and 4. In clinical terms, patients' sleep patterns are described as fragmented, meaning patients spend a lot of time alternating between stages 1 and 2 (semi-wakefulness) and being awake and very little time in deep sleep. As used herein, the term "fragmented sleep architecture" means an individual, such as a sleep disorder patient, spends the majority of their sleep time in NREM sleep stages 1 and 2, lighter periods of sleep from which the individual can be easily aroused to a waking state by limited external stimuli. As a result, the individual cycles through frequent bouts of light sleep interrupted by frequent awakenings throughout the sleep period. Many sleep disorders are characterized by fragmented sleep architecture. For example, many elderly patients with sleep complaints have difficulty achieving long bouts of deep, refreshing sleep (NREM stages 3 and 4) and instead spend the majority of their sleep time in NREM sleep stages 1 and 2.

In contrast to fragmented sleep architecture, as used herein the term "sleep consolidation" means a state in which the number of NREM sleep bouts, particularly stages 3 and 4 and the length of those sleep bouts are increased, while the number and length of waking bouts are decreased. In essence, the sleep architecture of the sleep disorder patient is consolidated to a sleeping state with increased periods of sleep and fewer awakenings during the night. More time is spent in slow wave sleep (stages 3 and 4) with fewer oscillations between stages 1 and 2. Compounds of the present invention can be effective in consolidating sleep patterns so that the patient with previously fragmented sleep can now achieve restorative, delta-wave sleep for longer, more consistent periods of time.

As sleep moves from stage 1 into later stages, heart rate and blood pressure drop, metabolic rate and glucose consumption fall and muscles relax. In normal sleep architecture, NREM sleep makes up about 75-80% of total sleep time; stage 1 accounting for 2-5% of total sleep time, stage 2 for about 45-50%, stage 3 approximately 3-8% and stage 4 approximately 10-15%. About 90 minutes after sleep onset, NREM sleep gives way to the first REM sleep episode of the night. REM makes up approximately 20-25% of total sleep time. In contrast to NREM sleep, REM sleep is characterized by high pulse, respiration and blood pressure, as well as other physiological patterns similar to those seen in the active waking stage. Hence, REM sleep is also known as "paradoxical sleep." Sleep onset occurs during NREM sleep and takes 10-20 minutes in healthy young adults. The four stages of NREM sleep together with a REM phase form one complete sleep cycle that is repeated throughout the duration of sleep, usually four or five times. The cyclical nature of sleep is regular and reliable: a REM period occurs about every 90 minutes during the night. However, the first REM period tends to be the shortest, often lasting less than 10 minutes, whereas the later REM periods may last up to 40 minutes. With aging, the time between retiring and sleep onset increases and the total amount of night-time sleep decreases because of changes in sleep architecture that impair sleep maintenance as well as sleep quality. Both NREM (particularly stages 3 and 4) and REM sleep are reduced. However, stage 1 NREM sleep, which is the lightest sleep, increases with age.

As used herein, the term "delta power" means a measure of the duration of EEG activity in the 0.5 to 3.5 Hz range during NREM sleep and is thought to be a measure of deeper, more refreshing sleep. Delta power is hypothesized to be a measure of a theoretical process called Process S and is thought to be inversely related to the amount of sleep an individual experiences during a given sleep period. Sleep is controlled by homeostatic mechanisms; therefore, the less one sleeps the greater the drive to sleep. It is believed that Process S builds throughout the wake period and is discharged most efficiently during delta power sleep. Delta power is a measure of the magnitude of Process S prior to the sleep period. The longer one stays awake, the greater Process S or drive to sleep and thus the greater the delta power during NREM sleep. However, individuals with sleep disorders have difficulty achieving and maintaining delta wave sleep and thus have a large build-up of Process S with limited ability to discharge this buildup during sleep. $5\text{-HT}_{2A}$ agonists tested preclinically and clinically mimic the effect of sleep deprivation on delta power, suggesting that subjects with sleep disorders treated with $5\text{-HT}_{2A}$ inverse agonist or antagonist will be able to achieve deeper sleep that is more refreshing. These same effects have not been observed with currently marketed pharmacotherapies. In addition, currently marketed pharmacotherapies for sleep have side effects such as hangover effects or addiction that are associated with the GABA receptor. $5\text{-HT}_{2A}$ inverse agonists do not target the GABA receptor and so these side effects are not a concern.

Subjective and Objective Determinations of Sleep Disorders:

There are a number of ways to determine whether the onset, duration or quality of sleep (e.g. non-restorative or restorative sleep) is impaired or improved. One method is a subjective determination of the patient, e.g., do they feel drowsy or rested upon waking. Other methods involve the observation of the patient by another during sleep, e.g., how long it takes the patient to fall asleep, how many times the patient wakes up during the night, how restless is the patient during sleep, etc. Another method is to measure the stages of sleep objectively using polysomnography.

Polysomnography is the monitoring of multiple electrophysiological parameters during sleep and generally includes measurement of EEG activity, electroculographic activity and electromyographic activity, as well as other measurements. These results, along with observations, can measure not only sleep latency (the amount of time required to fall asleep), but also sleep continuity (overall balance of sleep and wakefulness) and sleep consolidation (percent of sleeping time spent in delta-wave or restorative sleep) which may be an indication of the quality of sleep.

There are five distinct sleep stages, which can be measured by polysomnography: rapid eye movement (REM) sleep and four stages of non-rapid eye movement (NREM) sleep (stages 1, 2, 3 and 4). Stage 1 NREM sleep is a transition from wakefulness to sleep and occupies about 5% of time spent asleep in healthy adults. Stage 2 NREM sleep, which is characterized by specific EEG waveforms (sleep spindles and K complexes), occupies about 45-50% of time spent asleep. Stages 3 and 4 NREM sleep (also known collectively as slow-wave sleep and delta-wave sleep) are the deepest levels of sleep and occupy about 10-20% of sleep time. REM sleep, during which the majority of vivid dreams occur, occupies about 20-25% of total sleep.

These sleep stages have a characteristic temporal organization across the night. NREM stages 3 and 4 tend to occur in the first one-third to one-half of the night and increase in duration in response to sleep deprivation. REM sleep occurs cyclically through the night. Alternating with NREM sleep about every 80-100 minutes. REM sleep periods increase in duration toward the morning. Human sleep also varies characteristically across the life span. After relative stability with large amounts of slow-wave sleep in childhood and early adolescence, sleep continuity and depth deteriorate across the adult age range. This deterioration is reflected by increased wakefulness and stage 1 sleep and decreased stages 3 and 4 sleep.

In addition, the compounds of the invention can be useful for the treatment of the sleep disorders characterized by excessive daytime sleepiness such as narcolepsy. Inverse agonists at the serotonin 5-$HT_{2A}$ serotonin receptor improve the quality of sleep at nighttime which can decrease excessive daytime sleepiness.

Accordingly, another aspect of the present invention relates to the therapeutic use of compounds of the present invention for the treatment of sleep disorders. Compounds of the present invention are potent inverse agonists at the serotonin 5-$HT_{2A}$ serotonin receptor and can be effective in the treatment of sleep disorders by promoting one or more of the following: reducing the sleep onset latency period (measure of sleep induction), reducing the number of nighttime awakenings and prolonging the amount of time in delta-wave sleep (measure of sleep quality enhancement and sleep consolidation) without effecting REM sleep. In addition, compounds of the present invention can be effective either as a monotherapy or in combination with sleep inducing agents, for example but not limited to, antihistamines.

Pharmacodynamic Effects of the Selective 5-$HT_{2A}$ Inverse Agonist 1-[3-(4-Bromo-2-methyl-2H-pyrazol-3-yl)-4-methoxy-phenyl]-3-(2,4-difluoro-phenyl)-urea (APD125) in Healthy Adults APD125, a potent and selective 5-$HT_{2A}$ serotonin receptor inverse agonist is a member of the genus disclosed in the European Patent EP1558582. In Phase 1 trials, APD125 showed vigilance-lowering effects on waking EEG, with maximal effects at 40-80 mg; peak effects were observed at 2-4 h after dosing. In the afternoon nap model of insomnia in normal volunteers, APD125 increased slow wave sleep and associated parameters in a dose-dependent manner, primarily during the early part of sleep. These effects occurred at the expense of REM sleep. Sleep onset latency was not decreased by APD125. In the afternoon nap model, APD125 decreased microarousals, the number of sleep stage shifts and number of awakenings after sleep onset.

In a Phase 2 trial, when compared to placebo, patients treated with APD125 experienced statistically significant improvements in measurements of sleep maintenance, or the ability to maintain sleep during the night after falling asleep. The improvements in measurements of sleep maintenance were achieved without any limiting next day cognitive effects. The data from the APD125 Phase 2 study are consistent with Phase 1 data and support further development of APD125 for the treatment of insomnia patients who have difficulty maintaining sleep.

In conclusion, APD125, a 5-$HT_{2A}$ serotonin receptor inverse agonist, improved parameters of sleep consolidation and maintenance in humans.

2. Antiplatelet Therapies (Conditions Related to Platelet Aggregation).

Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction (heart attack), the heart muscle does not receive enough oxygen-rich blood because of a blockage in the coronary blood vessels. If taken while an attack is in progress or immediately afterward (preferably within 30 minutes), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs.

Angina is a temporary and often recurring chest pain, pressure or discomfort caused by inadequate oxygen-rich blood flow (ischemia) to some parts of the heart. In patients with angina, antiplatelet therapy can reduce the effects of angina and the risk of myocardial infarction.

Stroke is an event in which the brain does not receive enough oxygen-rich blood, usually due to blockage of a cerebral blood vessel by a blood clot. In high-risk patients, taking antiplatelets regularly has been found to prevent the formation of blood clots that cause first or second strokes.

Angioplasty is a catheter-based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrhythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism).

5-$HT_{2A}$ serotonin receptors are expressed on smooth muscle of blood vessels and 5-HT secreted by activated platelets causes vasoconstriction as well as activation of additional platelets during clotting. There is evidence that a 5-$HT_{2A}$ inverse agonist will inhibit platelet aggregation and thus be a potential treatment as an antiplatelet therapy (see Satimura, K., et al., *Clin. Cardiol.* 2002 Jan. 25 (1):28-32; and Wilson, H. C. et al., *Thromb Haemost.* 1991 Sep. 2; 66(3):355-60).

5-$HT_{2A}$ inverse agonists can be used to treat, for example, claudication or peripheral artery disease as well as cardiovascular complications (see *Br. Med. J.* 298: 424-430, 1989), arterial thrombosis (see, Pawlak, D. et al., *Thrombosis Research* 90:259-270, 1998), atherosclerosis (see, Hayashi, T. et al., Atherosclerosis 168:23-31, 2003), vasoconstriction caused by serotonin (see, Fujiwara, T. and Chiba, S. *Journal of Cardiovascular Pharmacology* 26: 503-510, 1995), restenosis of arteries following angioplasty or stent placement (see, Fujita, M. et al., *Am. Heart J.* 145: e16, 2003). It can also be used alone or in combination with thrombolytic therapy, for example, tissue plasminogen activator (tPA) (see, Yamashita, T. et al., *Haemostatis* 30:321-332, 2000), to provide cardioprotection following MI or postischemic myocardial dysfunction (see, Muto, T. et al., *Mol. Cell. Biochem.* 272: 119-132, 2005) or protection from ischemic injury during percutaneous coronary intervention (see, Horibe, E. *Circulation Research* 68: 68-72, 2004) and the like, including complications resulting therefrom.

5-$HT_{2A}$ inverse antagonists can increase circulating adiponectin in patients, suggesting that they would also be useful in protecting patients against indications that are linked to adiponectin, for example, myocardial ischemia reperfusion injury and atherosclerosis (see Nomura et al., *Blood Coagulation and Fibrinolysis* 2005, 16, 423-428).

The 5-$HT_{2A}$ inverse agonists disclosed herein provide beneficial improvement in microcirculation to patients in need of antiplatelet therapy by antagonizing the vasoconstrictive products of the aggregating platelets in, for example and not limited to the indications described above. Accordingly, in some embodiments, the present invention provides methods for reducing platelet aggregation in a patient in need thereof comprising administering to the patient a composition comprising a 5-$HT_{2A}$ inverse agonist disclosed herein. In further embodiments, the present invention provides methods for treating coronary artery disease, myocardial infarction, transient ischemic attack, angina, stroke, atrial fibrillation, or a symptom of any of the foregoing in a patient in need of the treatment, comprising administering to the patient a composition comprising a 5-$HT_{2A}$ inverse agonist disclosed herein.

In further embodiments, the present invention provides methods for reducing risk of blood clot formation is an angioplasty or coronary bypass surgery patient, or a patient suffering from atrial fibrillation, comprising administering to the patient a composition comprising a 5-$HT_{2A}$ inverse agonist disclosed herein at a time where such risk exists.

3. Asthma.

5-HT has been linked to the pathophysiology of acute asthma (see Cazzola, M. and Matera, M. G., *Trends Pharmacol. Sci.* 21: 201-202, 2000; and De Bie, J. J. et al., *British J. Pharm.*, 1998, 124, 857-864). The compounds of the present invention disclosed herein are useful in the treatment of asthma and the treatment of the symptoms thereof. Accordingly, in some embodiments, the present invention provides methods for treating asthma in a patient in need of the treatment, comprising administering to the patient a composition comprising a 5-$HT_{2A}$ inverse agonist disclosed herein. In further embodiments, methods are provided for treating a symptom of asthma in a patient in need of the treatment, comprising administering to the patient a composition comprising a 5-$HT_{2A}$ inverse agonist disclosed herein.

4. Agitation.

Agitation is a well-recognized behavioral syndrome with a range of symptoms, including hostility, extreme excitement, poor impulse control, tension and uncooperativeness (see Cohen-Mansfield J. and Billig, N., (1986), Agitated Behaviors in the Elderly, I. A. Conceptual Review, *J. Am. Geriatr. Soc.* 34(10): 711-721).

Agitation is a common occurrence in the elderly and is often associated with dementia such as those caused by Alzheimer's disease, Lewy Body, Parkinson's and Huntington's, which are degenerative diseases of the nervous system. Diseases that affect blood vessels, such as stroke, or multi-infarct dementia, which is caused by multiple strokes in the brain can also induce agitation. Alzheimer's disease accounts for approximately 50 to 70% of all dementias (see Koss E., et al., (1997), Assessing patterns of agitation in Alzheimer's disease patients with the Cohen-Mansfield Agitation Inventory. The Alzheimer's Disease Cooperative Study. *Alzheimer Dis. Assoc. Disord.* 11 (suppl 2):S45-S50).

An estimated 5% of people-aged 65 and older and up to 20% of those aged 80 and older are affected by dementia; of these sufferers, nearly half exhibit behavioral disturbances, such as agitation wandering and violent outbursts.

Agitated behaviors can also be manifested in cognitively intact elderly people and by those with psychiatric disorders other than dementia.

Agitation is often treated with antipsychotic medications such as haloperidol in nursing home and other assisted care settings. There is emerging evidence that agents acting at the 5-$HT_{2A}$ serotonin receptors in the brain have the effects of reducing agitation in patients, including Alzheimer's dementia (See Katz, I. R., et al., *J. Clin. Psychiatry* 1999 February, 60(2):107-115; and Street, J. S., et al., *Arch. Gen. Psychiatry* 2000 October, 57(10):968-976).

The compounds of the invention disclosed herein are useful for treating agitation and symptoms thereof. Thus, in some embodiments, the present invention provides methods for treating agitation in a patient in need of such treatment comprising administering to the patient a composition comprising a 5-$HT_{2A}$ inverse agonist disclosed herein. In some embodiments, the agitation is due to a psychiatric disorder other than dementia. In some embodiments, the present invention provides methods for treatment of agitation or a symptom thereof in a patient suffering from dementia comprising administering to the patient a composition comprising a 5-$HT_{2A}$ inverse agonist disclosed herein. In some embodiments of such methods, the dementia is due to a degenerative disease of the nervous system, for example and without limitation. Alzheimer's disease, Lewy Body, Parkinson's disease and Huntington's disease, or dementia due to diseases that affect blood vessels, including, without limitation, stroke and multi-infarct dementia. In some embodiments, methods are provided for treating agitation or a symptom thereof in a patient in need of such treatment, where the patient is a cognitively intact elderly patient, comprising administering to the patient a composition comprising a 5-$HT_{2A}$ inverse agonist disclosed herein.

5. Add-On Therapy to Haloperidol in the Treatment of Schizophrenia and Other Disorders.

Schizophrenia is a psychopathic disorder of unknown origin, which usually appears for the first time in early adulthood and is marked by a number of characteristics, psychotic symptoms, progression, phasic development and deterioration in social behavior and professional capability in the region below the highest level ever attained. Characteristic psychotic symptoms are disorders of thought content (multiple, fragmentary, incoherent, implausible or simply delusional contents of ideas of persecution) and of mentality (loss of association, flight of imagination, incoherence up to incomprehensibility), as well as disorders of perceptibility (hallucinations), of emotions (superficial or inadequate emotions), of self-perception, of intentions and impulses, of interhuman relationships and finally psychomotoric disorders (such as catatonia). Other symptoms are also associated with this disorder: see, *American Statistical and Diagnostic Handbook*.

Haloperidol (Haldol) is a potent dopamine $D_2$ receptor antagonist. It is widely prescribed for acute schizophrenic symptoms and is very effective for the positive symptoms of schizophrenia. However, Haldol is not effective for the negative symptoms of schizophrenia and may actually induce negative symptoms as well as cognitive dysfunction. In accordance with some methods of the invention, administering a 5-$HT_{2A}$ inverse agonist concomitantly with Haldol will provide benefits including the ability to use a lower dose of Haldol without losing its effects on positive symptoms, while reducing or eliminating its inductive effects on negative symptoms and prolonging relapse to the patient's next schizophrenic event.

Haloperidol is used for treatment of a variety of behavioral disorders, drug induced psychosis, excitative psychosis, Gilles de la Tourette's syndrome, manic disorders, psychosis (organic and NOS), psychotic disorder, psychosis, schizophrenia (acute, chronic and NOS). Further uses include in the treatment of infantile autism, Huntington's chorea and nausea and vomiting from chemotherapy and chemotherapeutic antibodies. Administration of 5-$HT_{2A}$ inverse agonists disclosed herein with haloperidol also will provide benefits in these indications.

In some embodiments, the present invention provides methods for treating a behavioral disorder, drug induced psychosis, excitative psychosis, Gilles de la Tourette's syndrome, manic disorders, psychosis (organic and NOS), psychotic disorder, psychosis, schizophrenia (acute, chronic and NOS) comprising administering to the patient a dopamine $D_2$ receptor antagonist and a 5-$HT_{2A}$ inverse agonist disclosed herein.

In some embodiments, the present invention provides methods for treating a behavioral disorder, drug induced psychosis, excitative psychosis, Gilles de la Tourette's syndrome, manic disorders, psychosis (organic and NOS), psychotic disorder, psychosis, schizophrenia (acute, chronic and NOS) comprising administering to the patient haloperidol and a 5-$HT_{2A}$ inverse agonist disclosed herein.

In some embodiments, the present invention provides methods for treating infantile autism, Huntington's chorea, or nausea and vomiting from chemotherapy or chemotherapeutic antibodies comprising administering to the patient a dopamine $D_2$ receptor antagonist and a 5-$HT_{2A}$ inverse agonist disclosed herein.

In some embodiments, the present invention provides methods for treating infantile autism, Huntington's chorea, or nausea and vomiting from chemotherapy or chemotherapeutic antibodies comprising administering to the patient haloperidol and a 5-$HT_{2A}$ inverse agonist disclosed herein.

In further embodiments, the present invention provides methods for treating schizophrenia in a patient in need of the treatment comprising administering to the patient a dopamine $D_2$ receptor antagonist and a 5-$HT_{2A}$ inverse agonist disclosed herein. Preferably, the dopamine $D_2$ receptor antagonist is haloperidol.

The administration of the dopamine $D_2$ receptor antagonist can be concomitant with administration of the 5-$HT_{2A}$ inverse agonist, or they can be administered at different times. Those of skill in the art will easily be able to determine appropriate dosing regimes for the most efficacious reduction, or elimination of deleterious haloperidol effects. In some embodiments, haloperidol and the 5-$HT_{2A}$ inverse agonist are administered in a single dosage form and in other embodiments, they are administered in separate dosage forms.

The present invention further provides methods of alleviating negative symptoms of schizophrenia induced by the administration of haloperidol to a patient suffering from schizophrenia, comprising administering to the patient a 5-$HT_{2A}$ inverse agonist as disclosed herein.

6. Diabetic-Related Pathologies.

Although hyperglycemia is the major cause for the pathogenesis of diabetic complications such as diabetic peripheral neuropathy (DPN), diabetic nephropathy (DN) and diabetic retinopathy (DR), some clinical work has implicated that increased plasma serotonin concentration is diabetic patients plays a role in disease progression (Pietraszek, M. H., et al., *Thrombosis Res.* 1992, 60(6), 765-74; and Andrzejewska-Buczko J., et al., *Klin. Oczna*. 1996; 98(2), 101-4). Serotonin is believed to play a role in vasospasm and increased platelet aggregability. Improving microvascular blood flow is beneficial to diabetic complications.

A recent study by Cameron and Cotter in *Naunyn Schmiedebergs Arch. Pharmacol.* 2005 June; 367(6):607-14, used a 5-$HT_{2A}$ antagonist experimental drug AT-1015 and other non-specific 5-$HT_{2A}$ antagonists including ritanserin and sarpogrelate. These studies found that all three drugs were able to produce a marked correction (82.6-99.7%) of a 19.8% sciatic motor conduction deficit in diabetic rats. Similarly, 44.7% and 14.9% reductions in sciatic endoneurial blood flow and saphenous sensory conduction velocity were completely reversed.

In a separate patient study, sarpogrelate was evaluated for the prevention of the development or progression of diabetic nephropathy (Takahashi, T., et al., *Diabetes. Res. Clin. Pract.* 2002 November; 58(2); 123-9). In the trial of 24 months of treatment, sarpogrelate significantly reduced urinary albumin excretion level.

7. Glaucoma.

Topical ocular administration of 5-$HT_2$ receptor antagonists result in a decrease in intra ocular pressure (IOP) in monkeys (Chang et al., *J. Ocul. Pharmacol.* 1:137-147 (1985)) and humans (Mastropasqua et al., *Acta. Ophthalmol. Scand. Suppl.* 224:24-25 (1997)) indicating utility for similar compounds such as 5-$HT_{2A}$ inverse agonists in the treatment of ocular hypertension associated with glaucoma. The 5-$HT_2$ receptor antagonist ketanserin (Mastropasqua supra) and sarpogrelate (Takenaka et al., *Investig. Ophthalmol. Vis. Sci.* 36:S734 (1995)) have been shown to significantly lower IOP in glaucoma patients.

8. Progressive Multifocal Leukoencephalopathy.

Progressive multifocal leukoencephalopathy (PML) is a lethal demyelinating disease caused by an opportunistic viral infection of oligodendrocytes in immunocompromised patients. The causative agent is JC virus, a ubiquitous papovavirus that infects the majority of the population before adulthood and establishes a latent infection in the kidney. In immunocompromised hosts, the virus can reactivate and productively infect oligodendrocytes. This previously rare condition, until 1984 repeated primarily in persons with underlying lymphoproliferative disorders, is now more common because it occurs in 4% of patients with AIDS. Patients usually present with relentlessly progressive focal neurologic detects, such as hemiparesis or visual field deficits, or with alterations in mental status. On brain MRI, one or more white matter lessons are present; they are hyperintense on T2-weighted images and hypointense on T1-weighted images. There is no mass effect and contrast enhancement is rare. Diagnosis can be confirmed by brain biopsy, with demonstration of virus by in situ hybridization or immunocytochemistry. Polymerase chain reaction amplification of JC virus sequences from the CSF can confirm diagnosis without the need for biopsy [Antinori et al., *Neurology* (1997) 48:687-694; Berger and Major, *Seminars in Neurology* (1999) 19:193-200; and Portegies, et al., *Eur. J. Neurol.* (2004) 11:297-304]. Currently, there is no effective therapy. Survival after diagnosis is about 3 to 5 months in AIDS patients.

JC virus enters cells by receptor-mediated clathrin-dependent endocytosis. Binding of JC virus to human glial cells (e.g., oligodendrocytes) induces an intracellular signal that is critical for entry and infection by a ligand-inducible clathrin-dependent mechanism [Querbes et al., *J. Virology* (2004) 78:250-256]. Recently, 5-HT$_{2A}$ was shown to be the receptor on human glial cells mediating infectious entry of JC virus by clathrin-dependent endocytosis [Elphick et al., *Science* (2004) 306:1380-1383]. 5-HT$_{2A}$ antagonists, including ketanserin and ritanserin, inhibited JC virus infection of human glial cells. Ketanserin and ritanserin have inverse agonist activity at 5-HT$_{2A}$.

5-HT$_{2A}$ antagonists including inverse agonists have been contemplated to be useful in the treatment of PML [Elphick et al., *Science* (2004) 306:1380-1383]. Prophylactic treatment of HIV-infected patients with 5-HT$_{2A}$ antagonists is envisioned to prevent the spread of JC virus to the central nervous system and the development of PML. Aggressive therapeutic treatment of patients with PML is envisioned to reduce viral spread within the central nervous system and prevent additional episodes of demyelination.

One aspect of the present invention encompasses methods for the treatment of progressive multifocal leukoencephalopathy in an individual comprising administering to the individual in need thereof a therapeutically effective amount of a compound according to any of the embodiments described herein or a pharmaceutical composition.

In some embodiments, the individual in need thereof has a lymphoproliferative disorder. In some embodiments, the lymphoproliferative disorder is leukemia or lymphoma. In some embodiments, the leukemia or lymphoma is chronic lymphocytic leukemia, Hodgkin's disease, or the like.

In some embodiments, the individual in need thereof has a myeloproliferative disorder.

In some embodiments, the individual in need thereof has carcinomatosis.

In some embodiments, the individual in need thereof has a granulomatous or inflammatory disease. In some embodiments, the granulomatous or inflammatory disease is tuberculosis or sarcoidosis.

In some embodiments, the individual in need thereof is immunocompromised. In some embodiments, the immunocompromised individual has impaired cellular immunity. In some embodiments, the impaired cellular immunity comprises impaired T-cell immunity.

In some embodiments, the individual in need thereof is infected with HIV. In some embodiments, the HIV-infected individual has a CD4+ cell count of ≤200/mm$^3$. In some embodiments, the HIV-infected individual has AIDS. In some embodiments, the HIV-infected individual has AIDS-related complex (ARC). In certain embodiments, ARC is defined as the presence of two successive CD4+ cell counts below 200/mm$^3$ and at least two of the following signs or symptoms: oral hairy leukoplakia, recurrent oral candidiasis, weight loss of at least 15 lb or 10% of body weight within last six months, multidermatomal herpes zoster, temperature above 38.5° C. for more than 14 consecutive days or more than 15 days in a 30-day period, or diarrhea with more than three liquid stools per day for at least 30 days [see, e.g., Yamada et al., *Clin. Diagn. Virol.* (1993) 1:245-256].

In some embodiments, the individual in need thereof is undergoing immunosuppressive therapy. In some embodiments, the immunosuppressive therapy comprises administering an immunosuppressive agent [see, e.g., Mueller, *Ann. Thorac. Surg.* (2004) 77:354-362; and Krieger and Emre, *Pediatr. Transplantation* (2004) 8:594-599]. In some embodiments, the immunosuppressive therapy comprises administering an immunosuppressive agent selected from the group consisting of: corticosteroids (for example, prednisone and the like), calcineurin inhibitors (for example, cyclosporine, tacrolimus and the like), antiproliferative agents (for example, azathioprine, mycophenolate mofetil, sirolimus, everolimus and the like), T-cell depleting agents (for example, OKT® 3 monoclonal antibody (mAb), anti-CD3 immunotoxin FN18-CRM9, Campath-1H (anti-CD52) mAb, anti-CD4 mAb, anti-T cell receptor mAb and the like), anti-IL-2 receptor (CD25) mAb (for example, basiliximab, daclizumab and the like), inhibitors of co-stimulation (for example, CTLA4-Ig, anti-CD154 (CD40 ligand) mAb and the like), deoxyspergualin and analogs thereof (for example, 15-DSG, LF-08-0299, LF14-0195 and the like), leflunomide and analogs thereof (for example, leflunomide, FK778, FK779 and the like), FTY720, anti-alpha-4-integrin monoclonal antibody and anti-CD45 RB monoclonal antibody. In some embodiments, the immunosuppressive agent and said compound or pharmaceutical composition are administered in separate dosage forms. In some embodiments, the immunosuppressive agent and said compound or pharmaceutical composition are administered in a single dosage form.

In some embodiments, the individual in need thereof is undergoing immunosuppressive therapy after organ transplantation. In some embodiments, the organ is liver, kidney, lung, heart, or the like [see, e.g., Singh et al., *Transplantation* (2000) 69:407-472].

In some embodiments, the individual in need thereof is undergoing treatment for a rheumatic disease. In some embodiments, the rheumatic disease is systemic lupus erythematosus or the like.

In some embodiments, the compound or the pharmaceutical composition inhibits JC virus injection of human glial cells 9. Hypertension.

Serotonin has been observed to play an important role in the regulation of vascular tone, vasoconstriction and pulmonary hypertension (Deuchar, G. et al., *Pulm. Pharmacol. Ther.* 18(1):23-31. 2005; and Marcos, E. et al., *Circ. Res.* 94(9): 1263-70 2004). Ketanserin, a 5-HT$_{2A}$ inverse agonist, have been demonstrated to protect against circulatory shocks, intracranial hypertension and cerebral ischemia during heatstroke (Chang, C. et al. *Shock* 24(4): 336-340 2005);

and to stabilize blood pressure in spontaneously hypertensive rats (Miao, C. *Clin. Exp. Pharmacol. Physiol.* 2003, 30(3): 189-193). Mainserin, a 5-HT$_{2A}$ inverse agonist, has been shown to prevent DOCA-salt induced hypertension in rats (Silva, A. *Eur. J. Pharmacol.* 518(2-3): 152-7 2005).

10. Pain.

5-HT$_{2A}$ inverse agonists are also effective for the treatment of pain. Sarpogrelate has been observed to provide a significant analgesic effect both on thermal induced pain in rats after intraperitoneal administration and on inflammatory pain in rats after either intrathecal or intraperitoneal administration (Nishiyama, T. *Eur. J. Pharmacol* 516:18-22, 2005). This same 5-HT$_{2A}$ inverse agonist in humans has been shown to be an effective treatment for lower back pain, leg pain and numbness associated with sciatica brought on by lumbar disc herniation (Kanayama, M. et al., *J. Neurosurg.: Spine* 2:441-446, 2005).

Representative Methods of the Invention

One aspect of the present invention pertains to methods for treating a 5-HT$_{2A}$ serotonin receptor-related disorder in an individual comprising administering to the individual in need thereof a therapeutically effective amount of a composition of the present invention.

One aspect of the present invention pertains to methods for treating a sleep disorder in an individual comprising administering to the individual in need thereof a therapeutically effective amount of a composition of the present invention.

One aspect of the present invention pertains to methods for treating a dyssomnia in an individual comprising administering to the individual in need thereof a therapeutically effective amount of a composition of the present invention.

One aspect of the present invention pertains to methods for treating insomnia in an individual comprising administering to the individual in need thereof a therapeutically effective amount of a composition of the present invention.

One aspect of the present invention pertains to methods for treating a parasomnia in an individual comprising administering to the individual in need thereof a therapeutically effective amount of a composition of the present invention.

One aspect of the present invention pertains to methods for treating a sleep disorder selected from: a dyssomnia, insomnia, and a parasomnia in an individual comprising administering to the individual in need thereof a therapeutically effective amount of a composition of the present invention.

One aspect of the present invention pertains to methods for increasing slow wave sleep in an individual comprising administering to the individual in need thereof a therapeutically effective amount of a composition of the present invention.

One aspect of the present invention pertains to methods for improving sleep consolidation in an individual comprising administering to the individual in need thereof a therapeutically effective amount of a composition of the present invention.

One aspect of the present invention pertains to methods for improving sleep maintenance in an individual comprising administering to the individual in need thereof a therapeutically effective amount of a composition of the present invention.

One aspect of the present invention pertains to methods for improving sleep quality in an individual comprising administering to the individual in need thereof a therapeutically effective amount of a composition of the present invention.

One aspect of the present invention pertains to methods for treating nonrestorative sleep in an individual comprising administering to the individual in need thereof a therapeutically effective amount of a composition of the present invention.

One aspect of the present invention pertains to methods for increasing slow wave sleep, improving sleep consolidation, improving sleep maintenance, improving sleep quality, or treating nonrestorative sleep in an individual comprising administering to the individual in need thereof a therapeutically effective amount of a composition of the present invention.

In some embodiments, the sleep disorder is a dyssomnia. In some embodiments, the dyssomnia is selected from psychophysiological insomnia, sleep state misperception, idiopathic insomnia, obstructive sleep apnea syndrome, central sleep apnea syndrome, central alveolar hypoventilation syndrome, periodic limb movement disorder, restless leg syndrome, inadequate sleep hygiene, environmental sleep disorder, altitude insomnia, adjustment sleep disorder, insufficient sleep syndrome, limit-setting sleep disorder, sleep-onset association disorder, nocturnal eating or drinking syndrome, hypnotic dependent sleep disorder, stimulant-dependent sleep disorder, alcohol-dependent sleep disorder, toxin-induced sleep disorder, time zone change, jet lag syndrome, shift work sleep disorder, irregular sleep-wake pattern, delayed sleep phase syndrome, advanced sleep phase syndrome and non-24-hour sleep-wake disorder.

In some embodiments, the sleep disorder is a parasomnia. In some embodiments, the parasomnia is selected from confusional arousals, sleepwalking and sleep terrors, rhythmic movement disorder, sleep starts, sleep talking and nocturnal leg cramps.

In some embodiments, the sleep disorder is associated with a medical or psychiatric disorder. In some embodiments, the medical or psychiatric disorder is selected from psychoses, mood disorders, anxiety disorders, panic disorders, alcoholism, cerebral degenerative disorders, dementia, parkinsonism, fatal familial insomnia, sleep-related epilepsy, electrical status epilepticus of sleep, sleep-related headaches, sleeping sickness, nocturnal cardiac ischemia, chronic obstructive pulmonary disease, sleep-related asthma, sleep-related gastroesophageal reflux, peptic ulcer disease, fibrositis syndrome, osteoarthritis, rheumatoid arthritis, fibromyalgia and post-surgical sleep disorder.

One aspect of the present invention pertains to methods of treating platelet aggregation in an individual comprising administering to the individual in need of such treatment a therapeutically effective amount of a composition of the present invention.

One aspect of the present invention pertains to methods of treating coronary artery disease, myocardial infarction, transient ischemic attack, angina, stroke and atrial fibrillation in an individual comprising administering to the individual in need of such treatment a therapeutically effective amount of a composition of the present invention.

One aspect of the present invention pertains to methods for reducing the risk of blood clot formation in an individual comprising administering to the individual in need thereof a therapeutically effective amount of a composition of the present invention.

One aspect of the present invention pertains to methods for reducing the risk of blood clot formation in an angioplasty or coronary bypass surgery individual comprising administering to the individual in need thereof a therapeutically effective amount of a composition of the present invention.

One aspect of the present invention pertains to methods for reducing the risk of blood clot formation in an individual suffering from atrial fibrillation, comprising administering to the individual in need thereof a therapeutically effective amount of a composition of the present invention.

One aspect of the present invention pertains to methods for treating asthma in an individual comprising administering to the individual in need thereof a therapeutically effective amount of a composition of the present invention.

One aspect of the present invention pertains to methods for treating a symptom of asthma in an individual comprising administering to the individual in need thereof a therapeutically effective amount of a composition of the present invention.

One aspect of the present invention pertains to methods for treating agitation or a symptom thereof in an individual comprising administering to the individual in need thereof a therapeutically effective amount of a composition of the present invention. In some embodiments, the individual is a cognitively intact elderly individual.

One aspect of the present invention pertains to methods for treating agitation or a symptom thereof in an individual suffering from dementia comprising administering to the individual in need thereof a therapeutically effective amount of a composition of the present invention. In some embodiments, the dementia is due to a degenerative disease of the nervous system. In some embodiments, the dementia is Alzheimer's disease, Lewy Body, Parkinson's disease or Huntington's disease. In some embodiments, the dementia is due to diseases that affect blood vessels. In some embodiments, the dementia is due to stroke or multi-infarct dementia.

One aspect of the present invention pertains to methods for treating an individual suffering from at least one of the indications selected from behavioral disorder, drug induced psychosis, excitative psychosis, Gilles de la Tourette's syndrome, manic disorder, organic or NOS psychosis, psychotic disorder, psychosis, acute schizophrenia, chronic schizophrenia and NOS schizophrenia comprising administering to the individual in need thereof a therapeutically effective amount of a composition of the present invention and a dopamine $D_2$ receptor antagonist. In some embodiments, the dopamine $D_2$ receptor antagonist is haloperidol.

One aspect of the present invention pertains to methods for treating an individual with infantile autism, Huntington's chorea or nausea and vomiting from chemotherapy or chemotherapeutic antibodies comprising administering to the individual in need thereof a therapeutically effective amount of a composition of the present invention and a dopamine $D_2$ receptor antagonist. In some embodiments, the dopamine $D_2$ receptor antagonist is haloperidol.

One aspect of the present invention pertains to methods for treating schizophrenia in an individual comprising administering to the individual in need thereof a therapeutically effective amount of a composition of the present invention and a dopamine $D_2$ receptor antagonist. In some embodiments, the dopamine $D_2$ receptor antagonist is haloperidol.

One aspect of the present invention pertains to methods for treating negative symptoms of schizophrenia induced by the administration of haloperidol to an individual suffering from the schizophrenia, comprising administering to the individual in need thereof a therapeutically effective amount of a composition of the present invention. In some embodiments, the dopamine $D_2$ receptor antagonist or haloperidol and the composition are administered in separate dosage forms.

One aspect of the present invention pertains to methods for treating a diabetic-related disorder in an individual comprising administering to the individual in need thereof a therapeutically effective amount of a composition of the present invention.

In some embodiments, the diabetic-related disorder is diabetic peripheral neuropathy. In some embodiments, the diabetic-related disorder is diabetic nephropathy. In some embodiments, the diabetic-related disorder is diabetic retinopathy.

One aspect of the present invention pertains to methods for the treatment of glaucoma or other diseases of the eye with abnormal intraocular pressure.

One aspect of the present invention pertains to methods for treating hypertension in an individual comprising administering to the individual in need thereof a therapeutically effective amount of a composition of the present invention.

One aspect of the present invention pertains to methods for treating pain in an individual comprising administering to the individual in need thereof a therapeutically effective amount of a composition of the present invention.

One aspect of the present invention pertains to methods for the treatment of progressive multifocal leukoencephalopathy in an individual comprising administering to the individual in need thereof a therapeutically effective amount of a composition of the present invention.

One aspect of the present invention pertains to methods for the treatment of progressive multifocal leukoencephalopathy in an individual comprising administering to the individual in need thereof a therapeutically effective amount of a composition of the present invention.

One aspect of the present invention pertains to methods for the treatment of a $5\text{-HT}_{2A}$ serotonin receptor-related disorder selected from: coronary artery disease, myocardial infarction, transient ischemic attack, angina, stroke, atrial fibrillation, a condition associated with platelet aggregation, blood clot formation, a diabetic-related disorder, progressive multifocal leukoencephalopathy, hypertension, and pain, in an individual comprising administering to the individual in need thereof a therapeutically effective amount of a composition of the present invention.

In some embodiments, the individual in need thereof has a lymphoproliferative disorder. In some embodiments, the lymphoproliferative disorder is leukemia or lymphoma. In some embodiments, the leukemia or lymphoma is chronic lymphocytic leukemia, Hodgkin's disease, or the like.

In some embodiments, the individual in need thereof has a myeloproliferative disorder.

In some embodiments, the individual in need thereof has carcinomatosis.

In some embodiments, the individual in need thereof has a granulomatous or inflammatory disease. In some embodiments, the granulomatous or inflammatory disease is tuberculosis or sarcoidosis.

In some embodiments, the individual in need thereof is immunocompromised. In some embodiments, the immunocompromised individual has impaired cellular immunity. In some embodiments, the impaired cellular immunity comprises impaired T-cell immunity.

In some embodiments, the individual in need thereof is infected with HIV. In some embodiments, the HIV-infected individual has a CD4+ cell count of $\leq 200/\text{mm}^3$. In some embodiments, the HIV-infected individual has AIDS. In some embodiments, the HIV-infected individual has AIDS-related complex (ARC). In certain embodiments, ARC is defined as the presence of two successive CD4+ cell counts below $200/\text{mm}^3$ and at least two of the following signs or symptoms: oral hairy leukoplakia, recurrent oral candidiasis, weight loss of at least 2.5 kg or 10% of body weight within last six months, multidermatomal herpes zoster, temperature above 38.5° C. for more than 14 consecutive days or more than 15 days in a 30-day period, or diarrhea with more than three liquid stools per day for at least 30 days [see, e.g., Yamada et al., *Clin. Diagn. Virol.* (1993) 1:245-256].

In some embodiments, the individual in need thereof is undergoing immunosuppressive therapy. In some embodiments, the immunosuppressive therapy comprises administering an immunosuppressive agent [see, e.g., Mueller, *Ann Thorac Surg* (2004) 77:354-362; and Krieger and Emre, *Pediatr Transplantation* (2004) 8:594-599]. In some embodiment, the immunosuppressive therapy comprises administering an immunosuppressive agent selected from the group consisting of: corticosteroids (for example, prednisone and the like), calcineurin inhibitors (for example, cyclosporine, tacrolimus and the like), antiproliferative agents (for example, azathioprine, mycophenolate mofetil, sirolimus, everolimus and the like), T-cell depleting agents (for example, OKT® 3 monoclonal antibody (mAb), anti-CD3 immunotoxin FN18-CRM9, Campath-1H (anti-CD52) mAb, anti-CD4 mAb, anti-T cell receptor mAb and the like), anti-IL-2 receptor (CD25) mAb (for example, basiliximab, daclizumab and the like), inhibitors of co-stimulation (for example, CTLA4-Ig, anti-CD154 (CD40 ligand) mAb and the like), deoxyspergualin and analogs thereof (for example, 15-DSG, LF-08-0299, LF14-0195 and the like), leflunomide and analogs thereof (for example, leflunomide, FK778, FK779 and the like), FTY720, anti-alpha-4-integrin monoclonal antibody and anti-CD45 RB monoclonal antibody. In some embodiments, the immunosuppressive agent and the compound or composition are administered in separate dosage forms. In some embodiments, the immunosuppressive agent and the compound or composition are administered in a single dosage form.

In some embodiments, the individual in need thereof is undergoing immunosuppressive therapy after organ transplantation. In some embodiments, the organ is liver, kidney, lung, heart, or the like [see, e.g., Singh et al., *Transplantation* (2000) 69:467-472].

In some embodiments, the individual in need thereof is undergoing treatment for a rheumatic disease. In some embodiments, the rheumatic disease is systemic lupus erythematosus or the like.

In some embodiments, the composition inhibits JC virus infection of human glial cells.

If desired, the compositions of the present invention may further comprise conventional pharmaceutical additives such as co-surfactants, coloring agents, flavoring agents, fragrances, preserving agents, stabilizers, antioxidant and/or thickening agents.

It is noted that when the compositions described herein are not only intended for use in humans but also in other non-human mammals as well. Indeed, recent advances in the area of animal health-care suggests that consideration be given for the use of active agents, such as 5-$HT_{2A}$ serotonin receptor modulators, for the treatment of a 5-$HT_{2A}$ serotonin receptor-related disease or disorder in companion animals (e.g., cats and dogs) and in livestock animals (e.g., cows, chickens, fish, etc.). Those of ordinary skill in the art are readily credited with understanding the utility of such compounds in such settings.

One aspect of the present invention pertains to methods for treating a 5-$HT_{2A}$ serotonin receptor-related disorder in an individual comprising administering to the individual in need thereof a therapeutically effective amount of a pharmaceutical composition of the present invention.

One aspect of the present invention pertains to methods for treating a sleep disorder in an individual comprising administering to the individual in need thereof a therapeutically effective amount of a pharmaceutical composition of the present invention.

One aspect of the present invention pertains to methods for treating a dyssomnia in an individual comprising administering to the individual in need thereof a therapeutically effective amount of a pharmaceutical composition of the present invention.

One aspect of the present invention pertains to methods for treating insomnia in an individual comprising administering to the individual in need thereof a therapeutically effective amount of a pharmaceutical composition of the present invention.

One aspect of the present invention pertains to methods for treating a parasomnia in an individual comprising administering to the individual in need thereof a therapeutically effective amount of a pharmaceutical composition of the present invention.

One aspect of the present invention pertains to methods for treating a sleep disorder selected from: a dyssomnia, insomnia, and a parasomnia in an individual comprising administering to the individual in need thereof a therapeutically effective amount of a pharmaceutical composition of the present invention.

One aspect of the present invention pertains to methods for increasing slow wave sleep in an individual comprising administering to the individual in need thereof a therapeutically effective amount of a pharmaceutical composition of the present invention.

One aspect of the present invention pertains to methods for improving sleep consolidation in an individual comprising administering to the individual in need thereof a therapeutically effective amount of a pharmaceutical composition of the present invention.

One aspect of the present invention pertains to methods for improving sleep maintenance in an individual comprising administering to the individual in need thereof a therapeutically effective amount of a pharmaceutical composition of the present invention.

One aspect of the present invention pertains to methods for improving sleep quality in an individual comprising administering to the individual in need thereof a therapeutically effective amount of a pharmaceutical composition of the present invention.

One aspect of the present invention pertains to methods for treating nonrestorative sleep in an individual comprising administering to the individual in need thereof a therapeutically effective amount of a pharmaceutical composition of the present invention.

One aspect of the present invention pertains to methods for increasing slow wave sleep, improving sleep consolidation, improving sleep maintenance, improving sleep quality, or treating nonrestorative sleep in an individual comprising administering to the individual in need thereof a therapeutically effective amount of a pharmaceutical composition of the present invention.

In some embodiments, the sleep disorder is a dyssomnia. In some embodiments, the dyssomnia is selected from psychophysiological insomnia, sleep state misperception, idiopathic insomnia, obstructive sleep apnea syndrome, central sleep apnea syndrome, central alveolar hypoventilation syndrome, periodic limb movement disorder, restless leg syndrome, inadequate sleep hygiene, environmental sleep disorder, altitude insomnia, adjustment sleep disorder, insufficient sleep syndrome, limit-setting sleep disorder, sleep-onset association disorder, nocturnal eating or drinking syndrome, hypnotic dependent sleep disorder, stimulant-dependent sleep disorder, alcohol-dependent sleep disorder, toxin-induced sleep disorder, time zone change, jet lag syndrome, shift work sleep disorder, irregular sleep-wake pattern, delayed sleep phase syndrome, advanced sleep phase syndrome and non-24-hour sleep-wake disorder.

In some embodiments, the sleep disorder is a parasomnia. In some embodiments, the parasomnia is selected from confusional arousals, sleepwalking and sleep terrors, rhythmic movement disorder, sleep starts, sleep talking and nocturnal leg cramps.

In some embodiments, the sleep disorder is associated with a medical or psychiatric disorder. In some embodiments, the medical or psychiatric disorder is selected from psychoses, mood disorders, anxiety disorders, panic disorders, alcoholism, cerebral degenerative disorders, dementia, parkinsonism, fatal familial insomnia, sleep-related epilepsy, electrical status epilepticus of sleep, sleep-related headaches, sleeping sickness, nocturnal cardiac ischemia, chronic obstructive pulmonary disease, sleep-related asthma, sleep-related gastroesophageal reflux, peptic ulcer disease, fibrositis syndrome, osteoarthritis, rheumatoid arthritis, fibromyalgia and post-surgical sleep disorder.

One aspect of the present invention pertains to methods of treating platelet aggregation in an individual comprising administering to the individual in need of such treatment a therapeutically effective amount of a pharmaceutical composition of the present invention.

One aspect of the present invention pertains to methods of treating coronary artery disease, myocardial infarction, transient ischemic attack, angina, stroke and atrial fibrillation in an individual comprising administering to the individual in need of such treatment a therapeutically effective amount of a pharmaceutical composition of the present invention.

One aspect of the present invention pertains to methods for reducing the risk of blood clot formation in an individual comprising administering to the individual in need thereof a therapeutically effective amount of a pharmaceutical composition of the present invention.

One aspect of the present invention pertains to methods for reducing the risk of blood clot formation in an angioplasty or coronary bypass surgery individual comprising administering to the individual in need thereof a therapeutically effective amount of a pharmaceutical composition of the present invention.

One aspect of the present invention pertains to methods for reducing the risk of blood clot formation in an individual suffering from atrial fibrillation, comprising administering to the individual in need thereof a therapeutically effective amount of a pharmaceutical composition of the present invention.

One aspect of the present invention pertains to methods for treating asthma in an individual comprising administering to the individual in need thereof a therapeutically effective amount of a pharmaceutical composition of the present invention.

One aspect of the present invention pertains to methods for treating a symptom of asthma in an individual comprising administering to the individual in need thereof a therapeutically effective amount of a pharmaceutical composition of the present invention.

One aspect of the present invention pertains to methods for treating agitation or a symptom thereof in an individual comprising administering to the individual in need thereof a therapeutically effective amount of a pharmaceutical composition of the present invention. In some embodiments, the individual is a cognitively intact elderly individual.

One aspect of the present invention pertains to methods for treating agitation or a symptom thereof in an individual suffering from dementia comprising administering to the individual in need thereof a therapeutically effective amount of a pharmaceutical composition of the present invention. In some embodiments, the dementia is due to a degenerative disease of the nervous system. In some embodiments, the dementia is Alzheimer's disease, Lewy Body, Parkinson's disease or Huntington's disease. In some embodiments, the dementia is due to diseases that affect blood vessels. In some embodiments, the dementia is due to stroke or multi-infarct dementia.

One aspect of the present invention pertains to methods for treating an individual suffering from at least one of the indications selected from behavioral disorder, drug induced psychosis, excitative psychosis, Gilles de la Tourette's syndrome, manic disorder, organic or NOS psychosis, psychotic disorder, psychosis, acute schizophrenia, chronic schizophrenia and NOS schizophrenia comprising administering to the individual in need thereof a therapeutically effective amount of a pharmaceutical composition of the present invention and a dopamine $D_2$ receptor antagonist. In some embodiments, the dopamine $D_2$ receptor antagonist is haloperidol.

One aspect of the present invention pertains to methods for treating an individual with infantile autism, Huntington's chorea or nausea and vomiting from chemotherapy or chemotherapeutic antibodies comprising administering to the individual in need thereof a therapeutically effective amount of a pharmaceutical composition of the present invention and a dopamine $D_2$ receptor antagonist. In some embodiments, the dopamine $D_2$ receptor antagonist is haloperidol.

One aspect of the present invention pertains to methods for treating schizophrenia in an individual comprising administering to the individual in need thereof a therapeutically effective amount of a pharmaceutical composition of the present invention and a dopamine $D_2$ receptor antagonist. In some embodiments, the dopamine $D_2$ receptor antagonist is haloperidol.

One aspect of the present invention pertains to methods for treating negative symptoms of schizophrenia induced by the administration of haloperidol to an individual suffering from the schizophrenia, comprising administering to the individual in need thereof a therapeutically effective amount of a pharmaceutical composition of the present invention. In some embodiments, the dopamine $D_2$ receptor antagonist or haloperidol and the pharmaceutical composition are administered in separate dosage forms.

One aspect of the present invention pertains to methods for treating a diabetic-related disorder in an individual comprising administering to the individual in need thereof a therapeutically effective amount of a pharmaceutical composition of the present invention.

In some embodiments, the diabetic-related disorder is diabetic peripheral neuropathy. In some embodiments, the diabetic-related disorder is diabetic nephropathy. In some embodiments, the diabetic-related disorder is diabetic retinopathy.

One aspect of the present invention pertains to methods for the treatment of glaucoma or other diseases of the eye with abnormal intraocular pressure.

One aspect of the present invention pertains to methods for treating hypertension in an individual comprising administering to the individual in need thereof a therapeutically effective amount of a pharmaceutical composition of the present invention.

One aspect of the present invention, pertains to methods for treating pain in an individual comprising administering to the individual in need thereof a therapeutically effective amount of a pharmaceutical composition of the present invention.

One aspect of the present invention pertains to methods for the treatment of progressive multifocal leukoencephalopathy in an individual comprising administering to the individual in need thereof a therapeutically effective amount of a pharmaceutical composition of the present invention.

One aspect of the present invention pertains to methods for the treatment of progressive multifocal leukoencephalopathy in an individual comprising administering to the individual in need thereof a therapeutically effective amount of a pharmaceutical composition of the present invention.

One aspect of the present invention pertains to methods for the treatment of a $5\text{-HT}_{2A}$ serotonin receptor-related disorder selected from: coronary artery disease, myocardial infarction, transient ischemic attack, angina, stroke, atrial fibrillation, a condition associated with platelet aggregation, blood clot formation, a diabetic-related disorder, progressive multifocal leukoencephalopathy, hypertension, and pain, in an individual comprising administering to the individual in need thereof a therapeutically effective amount of a pharmaceutical composition of the present invention.

In some embodiments, the individual in need thereof has a lymphoproliferative disorder. In some embodiments, the lymphoproliferative disorder is leukemia or lymphoma. In some embodiments, the leukemia or lymphoma is chronic lymphocytic leukemia, Hodgkin's disease, or the like.

In some embodiments, the individual in need thereof has a nonproliferative disorder.

In some embodiments, the individual in need thereof has carcinomatosis.

In some embodiments, the individual in need thereof has a granulomatous or inflammatory disease. In some embodiments, the granulomatous or inflammatory disease is tuberculosis or sarcoidosis.

In some embodiments, the individual in need thereof is immunocompromised. In some embodiments, the immunocompromised individual has impaired cellular immunity. In some embodiments, the impaired cellular immunity comprises impaired T-cell immunity.

In some embodiments, the individual in need thereof is infected with HIV. In some embodiments, the HIV-infected individual has a CD4+ cell count of ≤200/mm$^3$. In some embodiments, the HIV-infected individual has AIDS. In some embodiments, the HIV-infected individual has AIDS-related complex (ARC). In certain embodiments, ARC is defined as the presence of two successive CD4+ cell counts below 200/mm$^3$ and at least two of the following signs or symptoms: oral hairy leukoplakia, recurrent oral candidiasis, weight loss of at least 2.5 kg or 10% of body weight within last six months, multidermatomal herpes zoster, temperature above 38.5° C. for more than 14 consecutive days or more than 15 days in a 30-day period, or diarrhea with more than three liquid stools per day for at least 30 days [see, e.g., Yamada et al., *Clin. Diagn Virol.* (1993) 1:245-256].

In some embodiments, the individual in need thereof is undergoing immunosuppressive therapy. In some embodiments, the immunosuppressive therapy comprises administering an immunosuppressive agent [see, e.g., Mueller, *Ann Thorac Surg* (2004) 77:354-362; and Krieger and Emre, *Pediatr Transplantation* (2004) 8:594-599]. In some embodiments, the immunosuppressive therapy comprises administering an immunosuppressive agent selected from the group consisting of: corticosteroids (for example, prednisone and the like), calcineurin inhibitors (for example, cyclosporine, tacrolimus and the like), antiproliferative agents (for example, azathioprine, mycophenolate mofetil, sirolimus, everolimus and the like), T-cell depleting agents (for example, OKT® 3 monoclonal antibody (mAb), anti-CD3 immunotoxin FN18-CRM9, Campath-1H (anti-CD52) mAb, anti-CD4 mAb, anti-T cell receptor mAb and the like), anti-IL-2 receptor (CD25) mAb (for example, basiliximab, daclizumab and the like), inhibitors of co-stimulation (for example, CTLA4-Ig anti-CD154 (CD40 ligand) mAb and the like), deoxyspergualin and analogs thereof (for example, 15-DSG, LP-08-0299, LF14-0195 and the like), leflunomide and analogs thereof (for example, leflunomide, FK778, FK779 and the like), FTY720, anti-alpha-4-integrin monoclonal antibody and anti-CD45 RB monoclonal antibody. In some embodiments, the immunosuppressive agent and the compound or pharmaceutical composition are administered in separate dosage forms. In some embodiments, the immunosuppressive agent and the compound or pharmaceutical composition are administered in a single dosage form.

In some embodiments, the individual is need thereof is undergoing immunosuppressive therapy after organ transplantation. In some embodiments, the organ is liver, kidney, lung, heart, or the like [see, e.g., Singh et al., *Transplantation* (2000) 69:467-472].

In some embodiments, the individual in need thereof is undergoing treatment for a rheumatic disease. In some embodiments, the rheumatic disease is systemic lupus erythematosus or the like.

In some embodiments, the pharmaceutical composition inhibits JC virus infection of human glial cells.

If desired, the pharmaceutical compositions of the present invention may further comprise conventional pharmaceutical additives such as co-surfactants, coloring agents, flavoring agents, fragrances, preserving agents, stabilizers, antioxidant and/or thickening agents.

It is noted that when the pharmaceutical compositions described herein are not only intended for use in humans but also in other non-human mammals as well. Indeed, recent advances in the area of animal health-care suggests that consideration be given for the use of active agents, such as $5\text{-HT}_{2A}$ serotonin receptor modulators, for the treatment of a $5\text{-HT}_{2A}$ serotonin receptor-related disease or disorder in companion animals (e.g., cats and dogs) and in livestock animals (e.g., cows, chickens, fish, etc.). Those of ordinary skill in the art are readily credited with understanding the utility of such compounds in such settings.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Pharmacokinetic Experiments

General Experimental Descriptions:

Male cynomolgus monkeys were administered an oral dose of APD125 in combination with excipients delivered as either a liquid in SGC (composition: 10 mg APD125 in Cremophor®:Labrasol® [1:1]), wet-granulated tablets (see Example 2) or as dry-granulated tablets (see Example 7). APD125 dose levels were 10 mg, 30 mg, or 40 mg and the monkeys received approximately 10 mL of tap water after dose administration. Animals were fasted prior to dosing. Three to six monkeys were dosed per treatment group. In two cases, a 2×6 crossover study design was employed. Blood samples were collected via venous puncture at pre-dose (t=0) and 0.25 h, 0.5 h, 1 h, 2 h, 4 h, 6 h, 8 h, 12 h, 24 h and 48 h post-dose. Blood was treated with an anticoagulant and plasma was separated by centrifugation. Plasma samples were frozen and stored at or below −20° C. prior to analysis.

Pharmacokinetic Data Analysis:

Noncompartmental PK analysis was performed with a commercial software package (WinNonlin® Professional, version 5.2., Pharsight Mountain View, Calif.; Computer System Validation report CSV-004-SM-R1), with calculation of the following parameters:

| Parameter | Definition |
| --- | --- |
| $t_{max}$ | Time of maximum observed plasma concentration |
| $C_{max}$ | Plasma concentration corresponding to $t_{max}$ |
| $AUC_{0-\infty}$ | Area under the plasma concentration versus time curve from the time of dosing to extrapolated to infinity |

Bioanalytical Method:

Anticoagulated male cynomolgus monkey plasma samples were analyzed for APD125 and the internal standard using a selective liquid chromatography-tandem mass spectrometry (LC/MS/MS) method. Plasma proteins were removed with the addition of acetonitrile at two-fold the tissue volume, followed by centrifugation. The supernatant was injected onto an HPLC system equipped with a SCIEX API 3000 mass spectrometer. Peak areas were measured against the internal standard in the positive ion MRM mode. Quantitation was performed with regression analyses of the external calibration standards.

Example 1.1

Figure 1:
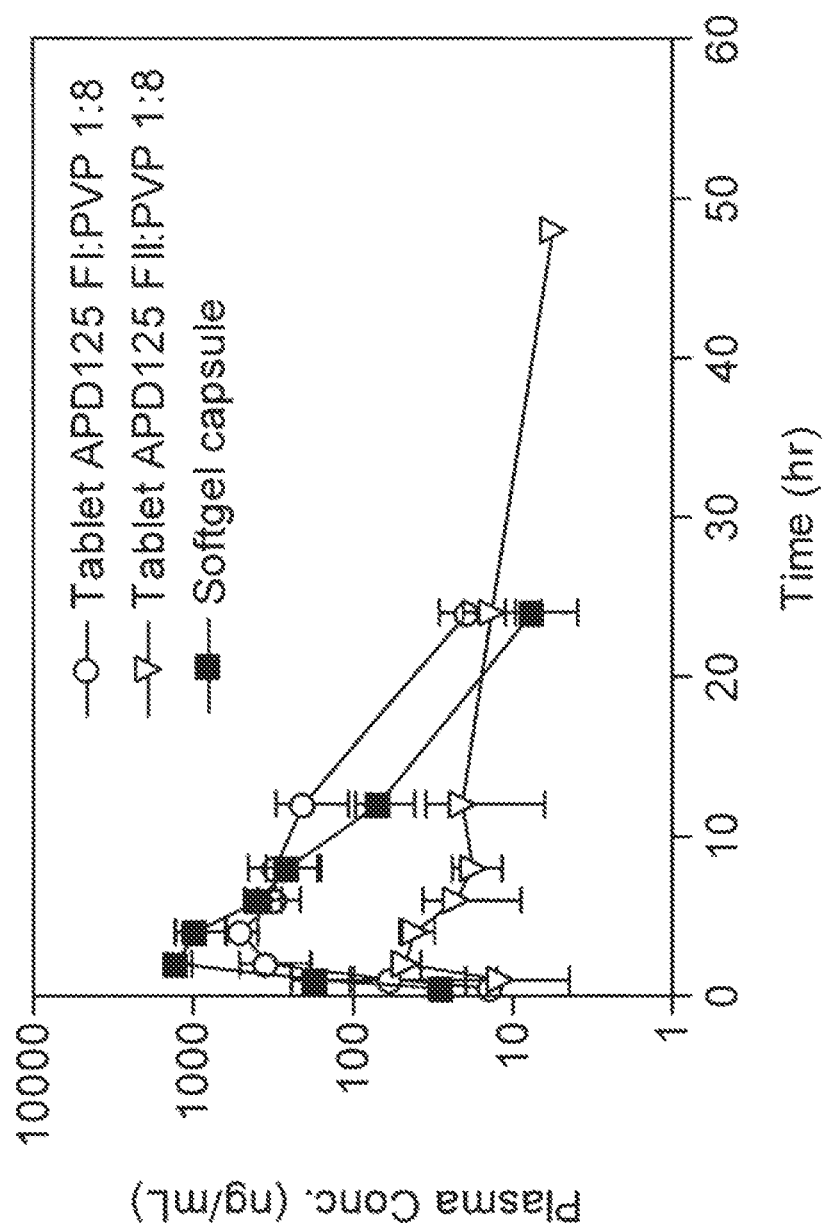
FIG. 1 depicts APD125 plasma exposure in monkeys after oral administration of wet-granulation tablets (composition: 30 mg APD125 Form I or Form II in a ratio of 1:8 to PVP) or SGCs (composition: 40 mg APD125 in Cremophor®: Labrasol® [1:1], Dose Adjusted to 30 mg).

Preliminary Wet Granulation-Based Tablet Formulation: Monkey APD125 Plasma Exposure Monkey APD125 plasma exposure after oral administration of SGCs or wet granulation tablets are shown in FIG. 1. PK parameters are presented in Table 1. APD125 absorption into the systemic circulation occurred over a 2-h to 4-h period followed by a mono-exponential terminal phase. The time to maximal plasma concentration ($t_{max}$) was most rapid for the liquid filled SGCs at 2 h. The $t_{max}$ increased with tablet administration to 2.7 h and 4 h, for APD125 Form II and APD125 Form I, respectively. The SGC $C_{max}$ (0.953 μg/mL±0.180 μg/mL; dose adjusted to 30 mg) was 19-fold and 2-fold greater than the $C_{max}$ for APD125 Form II (0.051 μg/mL±0.007 μg/mL) and APD125 Form 1 (0.504 μg/mL±0.109 μg/mL). The integrated plasma-exposures ($AUC_{0-\infty}$) were highest for SGC (4.540 h·μg/mL±1.394 h·μg/mL; dose adjusted to 30 mg) and APD125 Form I tablets (4.998 h·μg/mL±1.739 h·μg/mL), APD125 Form II tablet exposure (0.727 h·μg/mL±0.362 h·μg/mL) was at least 6-fold lower compared to SGC and APD125 Form I tablets.

TABLE 1

| Formulation | Dose (mg) | N | Cmax(μg/mL) Mean | Cmax(μg/mL) SD | $AUC_{0-\infty}$(h·μg/mL) Mean | $AUC_{0-\infty}$(h·μg/mL) SD |
| --- | --- | --- | --- | --- | --- | --- |
| APD125 Form I:PVP (1:8) | 10 | 6 | 0.227 | 0.153 | 1.507 | 1.218 |
| APD125 Form I:PVP (1:8) | 30 | 3 | 0.504 | 0.109 | 4.998 | 1.739 |
| APD125 Form II:PVP (1:8) | 30 | 3 | 0.051 | 0.007 | 0.727 | 0.362 |
| SGC: | 10 | 6 | 0.942 | 0.303 | 3.192 | 1.291 |
| APD125 in [1:1] Cremophor ®:Labrasol ® | 30[a] | 2 | 0.953 | 0.180 | 4.540 | 1.394 |
| | 40 | 2 | 1.270 | 0.240 | 6.054 | 1.859 |

[a]40-mg SGC dose adjusted to 30 mg for comparison purposes.

Figure 2:
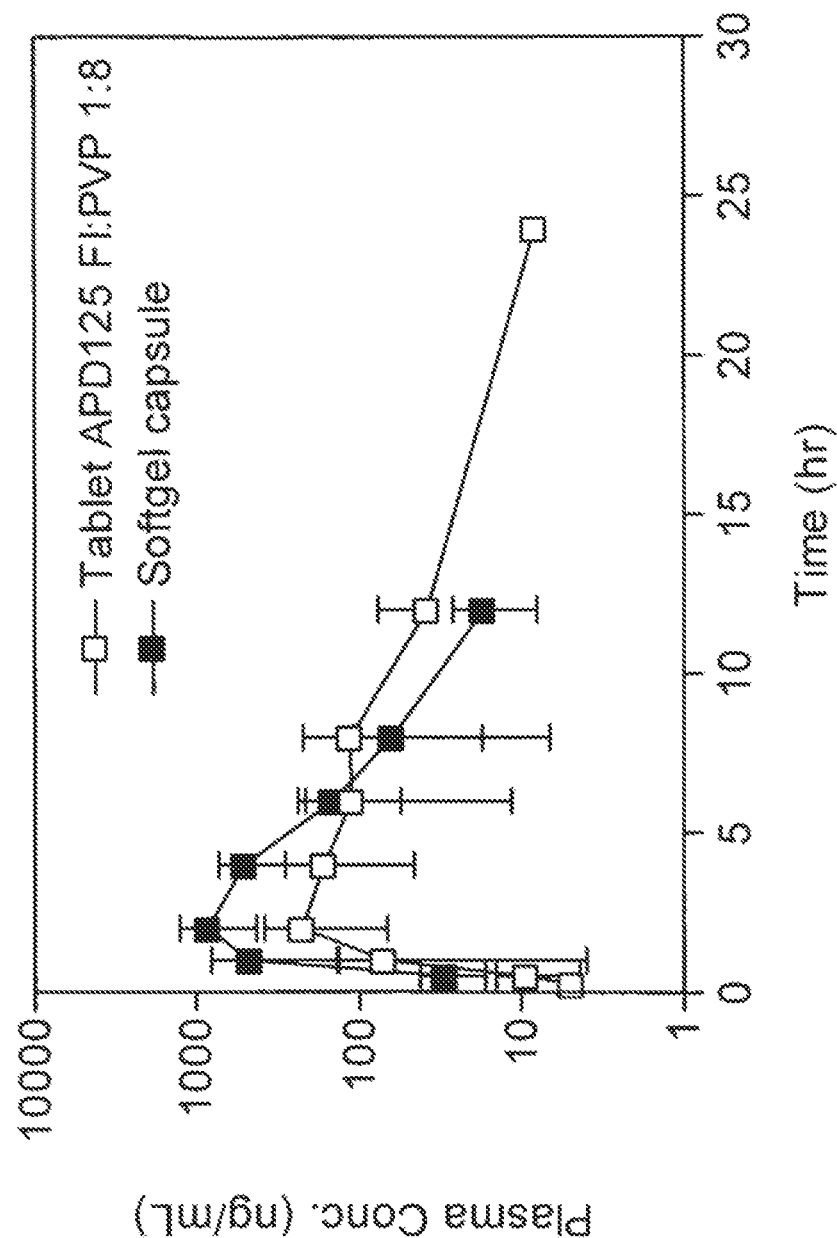
FIG. 2 depicts APD125 plasma exposure in monkeys after oral administration of wet-granulation tablets (composition: 10 mg APD125 Form I:PVP [1:8]) or SGC (composition: 10 mg APD125 in Cremophor®:Labrasol® [1:1]).
Figure 3:
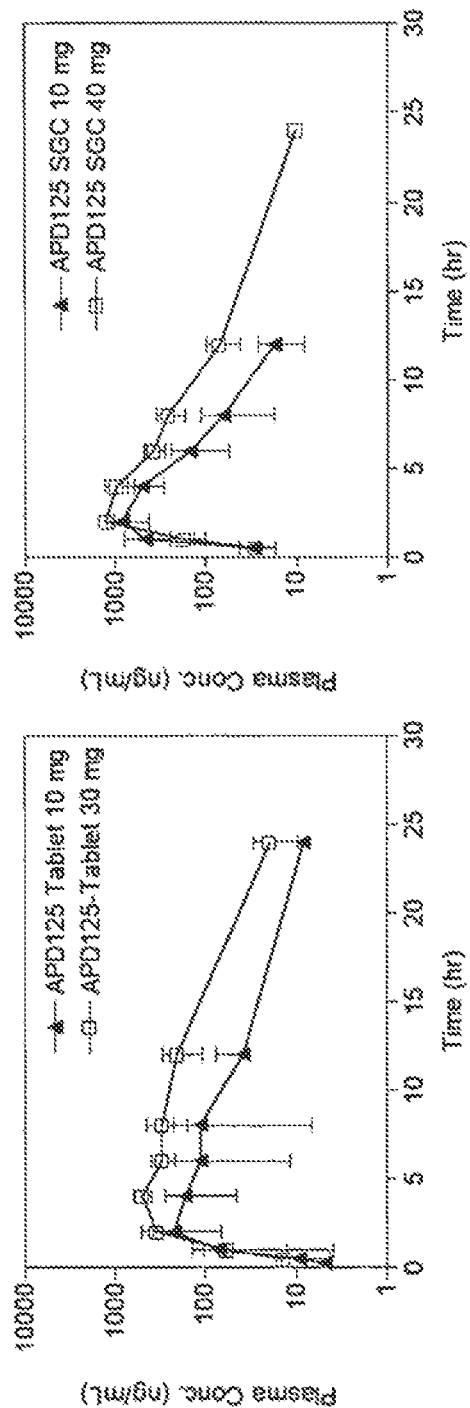
FIG. 3: depicts monkey PK exposure results for 10-mg and 30-mg APD125 Form I wet-granulation tablets versus 10-mg and 40-mg SGCs.

APD125 Form II-based tablets exhibited poor exposure ($C_{max}$ and $AUC_{0-\infty}$) relative to SGCs and therefore, were removed from further consideration. In contrast, APD125 Form I-based tablets exhibited similar integrated exposures ($AUC_{0-\infty}$) to SGCs, with approximately half the $C_{max}$ of the SGCs, a not uncommon finding when comparing liquid and solid-based formulations. It should be noted, however, that at a lower dose there was disparity between all exposure parameters. At a 10-mg dose, SGC $C_{max}$ and $AUC_{0-\infty}$ values were four-fold and two-fold higher, respectively, compared to the wet granulation tablet exposure parameters suggesting tablets and SGC become dissimilar with decreasing dose (FIG. 2, FIG. 3, Table 2).

TABLE 2

| Formulation | Dose (mg) | Cmax(μg/mL) Mean | Cmax(μg/mL) SD | $AUC_{0-\infty}$(h·μg/mL) Mean | $AUC_{0-\infty}$(h·μg/mL) SD |
| --- | --- | --- | --- | --- | --- |
| Form I tablet | 10 | 0.227 | 0.153 | 1.507 | 1.218 |
| | 30 | 0.504 | 0.109 | 4.998 | 1.739 |
| SGC | 10 | 0.942 | 0.303 | 3.192 | 1.291 |
| | 40 | 1.270 | 0.240 | 6.054 | 1.859 |

Example 2

Wet-Granulation Tablet

Example 2.1

Tablet Manufacturing

Using a 1-L bowl of high-shear granulator, PVP, APD125, mannitol, methyl cellulose, half of the xPVP, and half of the SLS were added to the key high shear granulator. The resulting mixture was dry-mixed for 5 minutes with impeller and chopper running. After which, water was added slowly using a transfer pipette through the addition port on the lid of the granulator bowl, while the impeller and chopper were still running. The process was stopped once power consumption started to rise quickly. The lid was then opened, and the granulation visually and texturally inspected to ensure proper moisture content had been achieved. The wet granulation was spread evenly over tray paper and dried in an oven at 55° C., until a loss on drying (LOD) of less than 5% w/w was achieved. Next, the dried granulation was passed through a mill with round-hole screen size of 0.063". A 1-qt. blender was charged with this screened material, and the other half of the SLS and xPVP was added, followed by blending for 5 minutes. Finally, magnesium stearate was added and the mixture was blended for 1 minute. Tableting was performed as follows: For each tablet (30 mg), 600 mg final blend was dispensed onto weigh paper and filled into dies (0.730"×0.365"). The granulation was then pressed into tablets using a carver press to achieve a hardness of about 11 kp. General tablet composition is provided in Table 3.

TABLE 3

| Ingredient | % (w/w) |
| --- | --- |
| APD125 Form I or Form II (micronized)[a] | 5.0 |
| PVP K-29/32 | 40.0 |
| Mannitol powdered | 22.0 |
| xPVP | 30.0 |
| Methyl cellulose | 0.5 |
| SLS | 2.0 |
| Magnesium stearate | 0.5 |
| Total | 100.0 |

[a]For placebo APD125 was replaced with mannitol

Example 2.2

Stability Testing

Figure 4:
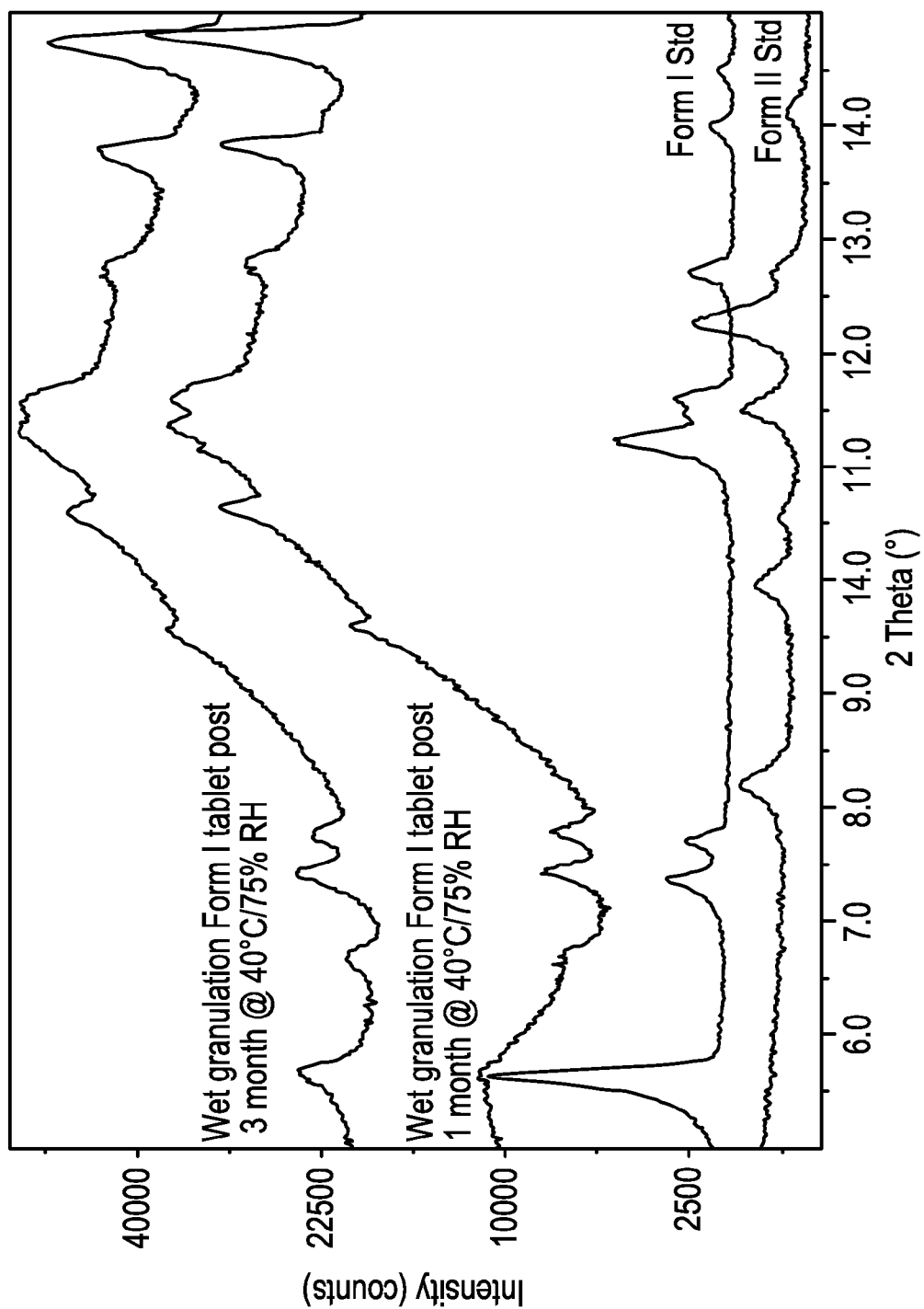
FIG. 4 depicts the 1-month and 3-month PXRD results for the wet-granulation Form I based tablet. The PXRD patterns show that the samples substantially comprise Form I at both time points.
Figure 5:
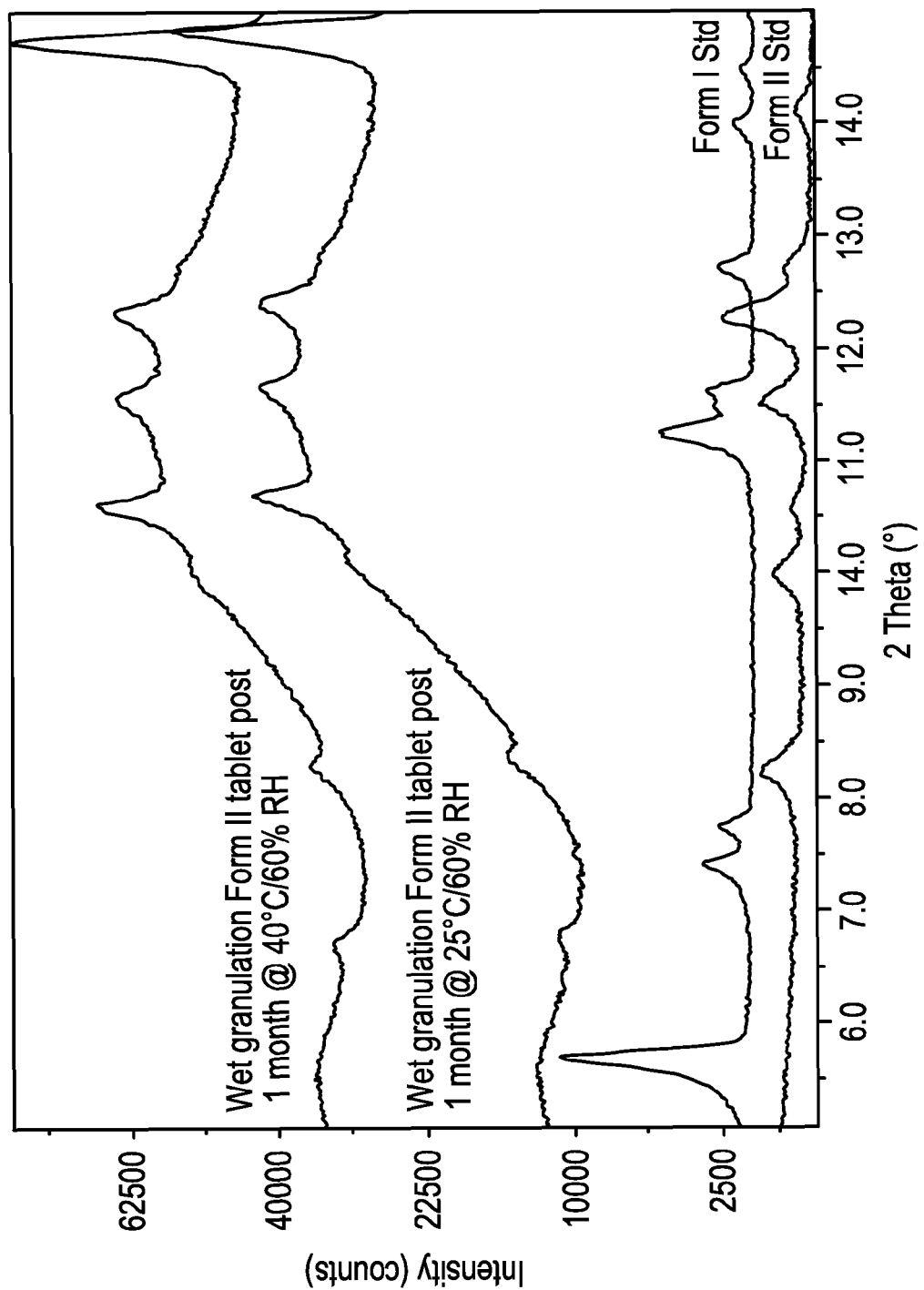
FIG. 5 depicts the 1-month and 3-month PXRD results for the wet-granulation Form II based tablet. The PXRD patterns show that the samples substantially comprise Form II at both time points.

Wet-granulation based placebo, 30-mg Form I, and 30-mg Form II tablets were placed on stability at 25° C./60% RH and 40° C./75% RH, using 60-mL HDPE bottles (non-induction sealed). Appearance, Assay, DFA, Dissolution, Water Content by Karl Fischer (except at Initial), Tablet Hardness, Related Substances, and Powder X-ray Diffraction (PXRD) testing were performed at initial (t=0), and at 1-month, 3-month and 6-month time points. Results for the wet-granulation Form I and Form II based tablets are provided in Table 4. Form I and Form II based tablet initial, 1-month, 3-month and 6-month dissolution results are provided in Table 5. Three-month and 6-month DFA results are provided in Table 6. Results of the water content determination by Karl Fischer at 1-month, 3-month and 6-month time points are provided in Table 7. Initial (t=0), 1-month, 3-month and 6-month tablet hardness results are provided in Table 8, while initial (t=0), 1-month, 3-month and 6-month PXRD results are provided in Table 9. PXRD results obtained at the 3-month time point are provided in FIG. 4 and FIG. 5.

TABLE 4

| | | % Assay (% RSD) n = 2 | | | |
| --- | --- | --- | --- | --- | --- |
| Formulation | Conditions | t = 0 | 1 month | 3 month | 6 month |
| Form I tablet | 25° C./ 60% RH | 100.3 (0.4) | 108.2 (2.4) | 101.8 (1.8) | 89.8 (0.2) |
| | 40° C./ 75% RH | | 106.9 (5.4) | 99.1 (0.5) | 84.3 (2.6) |

TABLE 4-continued

| | | % Assay (% RSD) n = 2 | | | |
| --- | --- | --- | --- | --- | --- |
| Formulation | Conditions | t = 0 | 1 month | 3 month | 6 month |
| Form II tablet | 25° C./ 60% RH | 97.7 (3.4) | 96.8 (0.1) | 101.3 (2.5) | 91.1 (2.3) |
| | 40° C./ 75% RH | | 96.9 (0.7) | 99.3 (1.2) | 84.3 (3.0) |

TABLE 5

| Formulation | Storage Conditions | Dissolution % Released (% RSD) | | | |
| --- | --- | --- | --- | --- | --- |
| | | 15 min | 30 min | 45 min | 60 min |
| Form I tablet | Initial | 68.3 (3.7) | 79.7 (0.8) | 81.6 (0.7) | 82.9 (0.4) |
| | 1 month at 25° C./ 60% RH | 73.9 (3.8) | 85.9 (0.2) | 88.4 (0.8) | 89.9 (0.6) |
| | 1 month at 40° C./ 75% RH | 70.3 (11.8) | 84.9 (3.1) | 88.1 (1.7) | 89.6 (1.8) |
| | 3 months at 25° C./ 60% RH | 76.8 (3.2) | 87.6 (1.1) | 90.2 (1.3) | 91.3 (1.3) |
| | 3 months at 40° C./ 75% RH | 71.1 (8.2) | 85.8 (0.8) | 89.1 (0.4) | 90.6 (0.7) |
| | 6 months at 25° C./ 60% RH | 77.0 (3.8) | 82.2 (0.7) | 86.1 (0.3) | 85.1 (1.5) |
| | 6 months at 40° C./ 75% RH | 65.7 (3.1) | 73.5 (1.2) | 74.4 (3.7) | 75.0 (2.7) |
| Form II tablet | Initial | 47.5 (4.9) | 55.9 (0.5) | 57.8 (0.7) | 58.4 (0.5) |
| | 1 month at 25° C./ 60% RH | 48.1 (12.5) | 58.3 (1.5) | 60.7 (1.3) | 61.8 (0.6) |
| | 1 month at 40° C./ 75% RH | 49.1 (5.9) | 57.5 (1.3) | 60.0 (1.0) | 61.0 (0.4) |
| | 3 months at 25° C./ 60% RH | 54.1 (4.5) | 60.4 (0.4) | 62.3 (0.3) | 63.4 (0.3) |
| | 3 months at 40° C./ 75% RH | 54.5 (2.9) | 59.8 (1.1) | 61.7 (0.7) | 63.8 (4.3) |
| | 6 months at 25° C./ 60% RH | 41.4 (3.3) | 48.1 (3.6) | 48.1 (1.1) | 48.0 (0.8) |
| | 6 months at 40° C./ 75% RH | 46.4 (0.0) | 48.7 (2.2) | 49.7 (0.8) | 50.9 (0.8) |

TABLE 6

| Formulation | DFA (ppm) post 3 months at 25°/ 60% RH n = 2 (rep1/rep2) | DFA (ppm) post 3 months at 40°/ 75% RH n = 2 (rep1/rep2) | DFA (ppm) 6 months at 25° C./ 60% RH n = 2 (rep1/rep2) | DFA (ppm) 6 months at 40° C./ 75% RH n = 2 (rep1/rep2) |
| --- | --- | --- | --- | --- |
| Form I tablet | ND | 165/166 | <35 | 833/834 |
| Form II tablet | ND | 253/245 | <35 | 1400/1414 |
| SGC | 542 (est.)[a] | 4387 (est.)[a] | ND | ND |

[a]The 3-month SGC results estimated using three times mean 28 day data (APD125 5-mg and 40-mgSGC capsule results 189.3 ppm and 172.3 ppm at 25° C./60% RH, respectively, and 1658.2 ppm and 1266.5 ppm at 40° C./75% RH, respectively).
ND = not determined

TABLE 7

| Formulation | Storage Conditions | 1 month n = 1 | 3 months n = 2 | 6 months n = 2 |
|---|---|---|---|---|
| | | % H$_2$O (rep1/rep2)[a] | | |
| Placebo | 25° C./60% RH | 7.59 | 9.55/9.43 | 9.36/9.18 |
| | 40° C./75% RH | 8.96 | 10.50/10.53 | 10.51/11.15 |
| Form I tablet | 25° C./60% RH | 8.68 | 8.32/8.55 | 8.92/9.24 |
| | 40° C./75% RH | 9.56 | 10.05/9.82 | 11.93/12.04 |
| Form II tablet | 25° C./60% RH | 8.75 | 8.67/8.77 | 9.40/9.22 |
| | 40° C./75% RH | 8.86 | 10.91/10.69 | 13.35/13.46 |

[a] Water Content by Karl Fischer was not performed at t = 0

TABLE 8

| Condition | Material | Target Hardness (kp) t = 0 | Average Hardness and Range (kp) n = 4 | | |
|---|---|---|---|---|---|
| | | | 1 month | 3 months | 6 months |
| 25° C. 60% RH | Form I/PVP (1:8) Wet granulation | 11.0 | 7.2 (4.6-10.1) | 7.8 (3.9-10.1) | 4.8 (3.8-7.0) |
| | Form II/PVP (1:8) Wet granulation | 11.0 | 6.4 (4.5-9.4) | 7.8 (5.6-12.4) | 9.4 (8.2-12.1) |
| | Placebo | 10.0 | 12.9 (9.0-21.2) | 11.0 (7.7-14.4) | 11.5 (7.6-16.2) |
| 40° C. 75% RH | Form I/PVP (1:8) Wet granulation | 11.0 | 5.5 (3.5-7.3) | 5.9 (3.9-9.9) | 9.3 (7.8-11.1) |
| | Form II/PVP (1:8) Wet granulation | 11.0 | 7.6 (6.0-10.0) | 6.8 (4.3-8.0) | 22.2 (23.1-23.6) |
| | Placebo | 10.0 | 8.7 (7.4-10.6) | 9.9 (6.5-14.8) | 14.9 (12.6-13.5) |

TABLE 9

| Condition | Material | t = 0 | APD125 Polymorphic Form(s) Detected | | |
|---|---|---|---|---|---|
| | | | 1 month | 3 months | 6 months |
| 25° C. 60% RH | Form I/PVP (1:8) Wet granulation | Form I | Form I | Form I | Form I |
| | Form II/PVP (1:8) Wet granulation | Form II | Form II | Form II | —[b] |
| | Placebo | NA | NA | NA | NA |
| 40° C. 75% RH | Form I/PVP (1:8) Wet granulation | Form I | Form I | Form I | Form I[a] |
| | Form II/PVP (1:8)Wet granulation | Form II | Form II | Form II | —[b] |
| | Placebo | NA | NA | NA | NA |

[a] Some reduction in Form I peak intensity was observed, but no Form II was detected.
[b] PXRD measurements were not collected for the Form II tablets at 6 months.
NA = not applicable The Form I and Form II based wet-granulation tablets exhibited similar chemical stability (Table 4), although it was not possible to accurately determine if a significant drop in assay was occurring for either tablet formulation, due, in part, to the significant assay variation observed. For example, both formulations showed near 100% assay at t=0, but the Form I tablets showed 106.9% assay and 108.2% assay at 1 month, at 40° C./75% RH and 25° C./60% RH, respectively. In addition, since water content determination was not added to the stability testing protocol until the 1-month time point, none of the assay results were corrected for water content. This is a significant point, since water contents increased from 9.56% w/w to 11.99% w/w at 40° C./75% RH for the Form I based tablets (Table 7). Therefore, assay results were only used to consider the relative stability of Form I and Form II based tablets. Chemical stability of the tablet, relative to SGCs, was evaluated on the basis of DFA formation rates. For both tablet formulations, low DFA formation rates (Table 6) were observed over the course of the R&D stability study, far superior to SGCs. Dissolution (Table 5) results showed no significant changes as a function of time, with Form II tablets exhibiting consistently slower dissolution relative to Form I tablets, in agreement with monkey plasma exposure results, supra. Tablet hardness measurements (Table 8), on the other hand, showed significant variability. However, since the tablets were hand pressed rather than pressed using automated equipment, the wet granulation based tablet R&D stability hardness results might not be indicative of long-term tablet hardness stability. Water content determination by Karl Fischer at 1-month and 3-months (Table 7) suggests a possible water uptake of about 3% w/w to about 5% w/w between 1 month and 6 months at 40° C./75% RH, suggesting some level of moisture control would be advisable for future tablet development. PXRD results (Table 9, FIG. 4 and FIG. 5) showed good solid-state form control, supporting the potential use of metastatic Form I for further tablet development. However, the Form I tablet 6-month PXRD results at 40° C./75% RH showed some loss in Form I peak intensity. The water content of the Form I tablets at 6 months and 40° C./75% RH was 11.99% w/w (Table 7), as compared to 9.94% w/w water at 3 months and 40° C./75% RH and 9.08% w/w water at 6 months and 25° C./60% RH, both of which did not show a loss in Form I content, suggesting water contents of 12% w/w or higher might result in Form I content reduction. Therefore, these results suggest future Form I tablet development should focus upon dry rather than wet-based formulations, and efforts to minimize water uptake, such as utilizing a water barrier tablet coating, should be considered. In addition, the 0.5% w/w methyl cellulose loading used in the wet-granulation tablets was based upon Form I API stabilization results (see Example 5).

Example 3

Thermal Activity Monitoring MicroWatt Excipient Compatibility Screening

Test Blend Preparation:

Materials for each of the nine formulations shown in Tables 10 through 18 were dispensed into separately labeled 60 mL glass jars and manually blended (tumbled) for about 5 min.

TABLE 10

| Blend 1: APD125/PVP (1:8) | | |
|---|---|---|
| Ingredient | % (w/w) | Amount (g) |
| APD125 | 5.0 | 0.50 |
| Mannitol (powdered) | 21.5 | 2.15 |
| PVP | 40.0 | 4.00 |
| xPVP | 30.0 | 3.00 |
| Methyl cellulose | 0.5 | 0.05 |

TABLE 10-continued

Blend 1: APD125/PVP (1:8)

| Ingredient | % (w/w) | Amount (g) |
|---|---|---|
| SLS | 2.0 | 0.20 |
| Magnesium stearate | 1.0 | 0.10 |
| Total | 100.0 | 10.00 |

TABLE 11

Blend 2: APD125/PVP (1:5)

| Ingredient | % (w/w) | Amount (g) |
|---|---|---|
| APD125 | 5.0 | 0.50 |
| Mannitol (powdered) | 55.0 | 5.50 |
| PVP | 25.0 | 2.50 |
| xPVP | 12.0 | 1.20 |
| SLS | 2.0 | 0.20 |
| Magnesium stearate | 1.0 | 0.10 |
| Total | 100.0 | 10.00 |

TABLE 12

Blend 3: APD125/PVP (1:8) Dical phosphate/MCC

| Ingredient | % (w/w) | Amount (g) |
|---|---|---|
| APD125 | 5.0 | 0.50 |
| Dical phosphate | 20.0 | 2.00 |
| MCC | 20.0 | 2.00 |
| PVP | 40.0 | 4.00 |
| xPVP | 11.5 | 1.15 |
| Methyl cellulose | 0.5 | 0.05 |
| SLS | 2.0 | 0.20 |
| Magnesium stearate | 1.0 | 0.10 |
| Total | 100.0 | 10.00 |

TABLE 13

Blend 4: APD125/PVP (1:8) Mannitol/MCC

| Ingredient | % (w/w) | Amount (g) |
|---|---|---|
| APD125 | 5.0 | 0.50 |
| Mannitol (powdered) | 20.0 | 2.00 |
| MCC | 20.0 | 2.00 |
| PVP | 40.0 | 4.00 |
| xPVP | 11.5 | 1.15 |
| Methyl cellulose | 0.5 | 0.05 |
| SLS | 2.0 | 0.20 |
| Magnesium stearate | 1.0 | 0.10 |
| Total | 100.0 | 10.00 |

TABLE 14

Blend 5: APD125/coPVP (1:8)

| Ingredient | % (w/w) | Amount (g) |
|---|---|---|
| APD125 | 5.0 | 0.50 |
| Mannitol (powdered) | 21.5 | 2.15 |
| coPVP | 40.0 | 4.00 |
| xPVP | 30.0 | 3.00 |
| Methyl cellulose | 0.5 | 0.05 |

TABLE 14-continued

Blend 5: APD125/coPVP (1:8)

| Ingredient | % (w/w) | Amount (g) |
|---|---|---|
| SLS | 2.0 | 0.20 |
| Magnesium stearate | 1.0 | 0.10 |
| Total | 100.0 | 10.00 |

TABLE 15

Blend 6: APD125/coPVP (1:8) xCMC

| Ingredient | % (w/w) | Amount (g) |
|---|---|---|
| APD125 | 5.0 | 0.50 |
| Mannitol (powdered) | 21.5 | 2.15 |
| coPVP | 40.0 | 4.00 |
| xCMC | 30.0 | 3.00 |
| Methyl cellulose | 0.5 | 0.05 |
| SLS | 2.0 | 0.20 |
| Magnesium stearate | 1.0 | 0.10 |
| Total | 100.0 | 10.00 |

TABLE 16

Blend 7: APD125/PVP (1:8) Dical phosphate/MCC, xCMC

| Ingredient | % (w/w) | Amount (g) |
|---|---|---|
| APD125 | 5.0 | 0.50 |
| Dical phosphate | 20.0 | 2.00 |
| MCC | 20.0 | 2.00 |
| PVP | 40.0 | 4.00 |
| xCMC | 11.5 | 1.15 |
| Methyl cellulose | 0.5 | 0.05 |
| SLS | 2.0 | 0.20 |
| Magnesium stearate | 1.0 | 0.10 |
| Total | 100.0 | 10.00 |

TABLE 17

Blend 8: APD125/PVP (1:5) Dical phosphate/MCC without methyl cellulose

| Ingredient | % (w/w) | Amount (g) |
|---|---|---|
| APD125 | 5.0 | 0.50 |
| Dical phosphate | 27.5 | 2.75 |
| MCC | 27.5 | 2.75 |
| PVP | 25.0 | 2.50 |
| xPVP | 12.0 | 1.20 |
| SLS | 2.0 | 0.20 |
| Magnesium stearate | 1.0 | 0.10 |
| Total | 100.0 | 10.00 |

TABLE 18

Blend 9: APD125/PVP (1:8) Poloxamer

| Ingredient | % (w/w) | Amount (g) |
|---|---|---|
| APD125 | 5.0 | 0.50 |
| Mannitol (powdered | 21.5 | 2.15 |
| PVP | 40.0 | 4.00 |
| xPVP | 30.0 | 3.00 |
| Methyl cellulose | 0.5 | 0.05 |

TABLE 18-continued

Blend 9: APD125/PVP (1:8) Poloxamer

| Ingredient | % (w/w) | Amount (g) |
|---|---|---|
| Poloxamer | 2.0 | 0.20 |
| Magnesium stearate | 1.0 | 0.10 |
| Total | 100.0 | 10.00 |

Experimental Method:

The formulation screening studies were performed at Aptuit Inc., Kansas City, Mo. 64137. Measurements were performed at 40° C. using a thermal activity monitoring (TAM) model 2277 consisting of four calorimetric units (2277-201) and standard amplifiers. All data were collected using Digitam® for Windows, version 4.1, software. Prior to initiating the series of experiments, each calorimeter unit was calibrated at 100 µW using a static electrical calibration procedure. Samples of APD125, APD125 formulation blend, or formulation blend placebo were weighed into separate 5-mL stainless steel ampoules. Approximately 100 mg of each material was used. The reference ampoules were loaded with approximately 150 mg of 4-mm borosilicate glass balls. Each ampoule was loaded onto an ampoule lifter and placed into the equilibrium position. After an initial pause, a baseline heat flow was recorded prior to lowering the samples into the measurement position. After sufficient data had been collected, the ampoules were returned to the equilibrium position and a final baseline heat flow was collected. The raw heat flow data were baseline corrected and exported for further data analysis.

Results:

The results for the nine APD125 formulation blends are provided in Table 19. The desired result is zero net heat flow, with results within about 2 µW/g of zero being indistinguishable from baseline noise. With these facts in mind, it can be seen that formulation blends 1, 4, 8 and 9 are the most compatible blends, while blend 7 is the least compatible.

TABLE 19

| Formulation Blend | Net Heat Flow Output (µW/g) |
|---|---|
| 1[a] | 0.87 |
| 2 | -13.63 |
| 3 | 8.88 |
| 4[a] | -0.23 |
| 5 | -13.10 |
| 6 | -8.92 |
| 7 | -62.36 |
| 8[a] | -0.78 |
| 9[a] | -1.19 |

[a]Most stable formulation blends

These results suggest that summit (diluent/filler), PVP (dispersing agent), xPVP (dispersing agent), methyl cellulose (APD125 Form I stabilizer), poloxamer (wetting agent), magnesium stearate (lubricant), dical phosphate (diluent/filler), MCC (diluent/filler) and SLS (wetting agent), the excipients used in one or more of the four most stable blends (i.e., blends 1, 4, 8 and 9), are suitable for further consideration as excipients. The remaining two excipients used in the study, xCMC and coPVP, were not in any of the most stable formulations, and therefore, should be considered to be potentially problematic.

Example 4

Effect of Milling and Compression Upon APD125 Form I

Sample Preparation:

Micronized APD125 Form I, was ground using a mortar and pestle, with samples withdrawn at 1-min, 5-min and 10-min time points for PXRD analyses to evaluate the impact of grinding upon the solid-state form of APD125 Form I. PXRD patterns were obtained pre- and post-milling. Additionally, micronized APD125 Form I, was compressed at 2 kp, 5 kp and 10 kp for 1 min per sample using a Carver press. The samples were then removed from the Carver press and lightly broken up using a mortar and pestle, prior to PXRD analysis to evaluate the impact of compression upon the solid-state form of APD125 Form I. PXRD patterns were obtained pre- and post-compression.

Powder X-Ray Diffraction:

PXRD measurements were obtained using a Philips (PANalytical) X'Pert PRO theta/theta diffractometer (EQ 0233) equipped with an X'Celerator RTMS detector and utilizing copper Kα radiation, operating at 45 kV and 40 mA. The instrument radius was 239.5 mm, the mask filter was 20 mm, the soller slit was 0.04 radians, and a nickel filter and sample spinning were used during data acquisition. The application and instrument control software used were X'Pert Data Collector®, version 2.0c and XPERT-PRO®, version 1.6, respectively. The samples were scanned from 5° to 40° 2θ in continuous mode, using a step size of 0.0167° 2θ.

Figure 6:
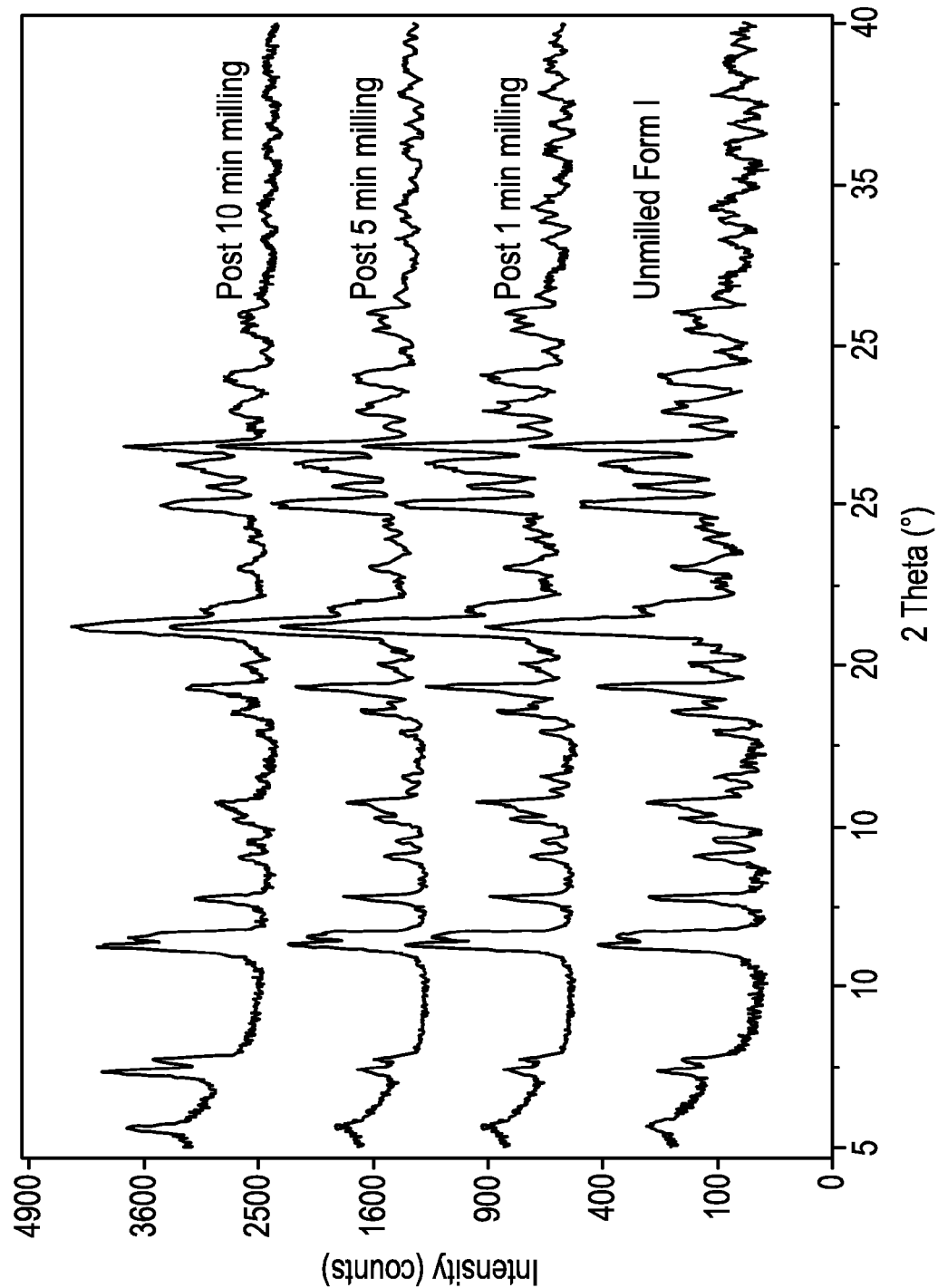
FIG. 6 depicts PXRD patterns for micronized APD125 Form I, before and after grinding with a mortar and pestle for 1 minute, 5 minutes and 10 minutes. The PXRD patterns show that the samples all substantially comprise Form I.
Figure 7:
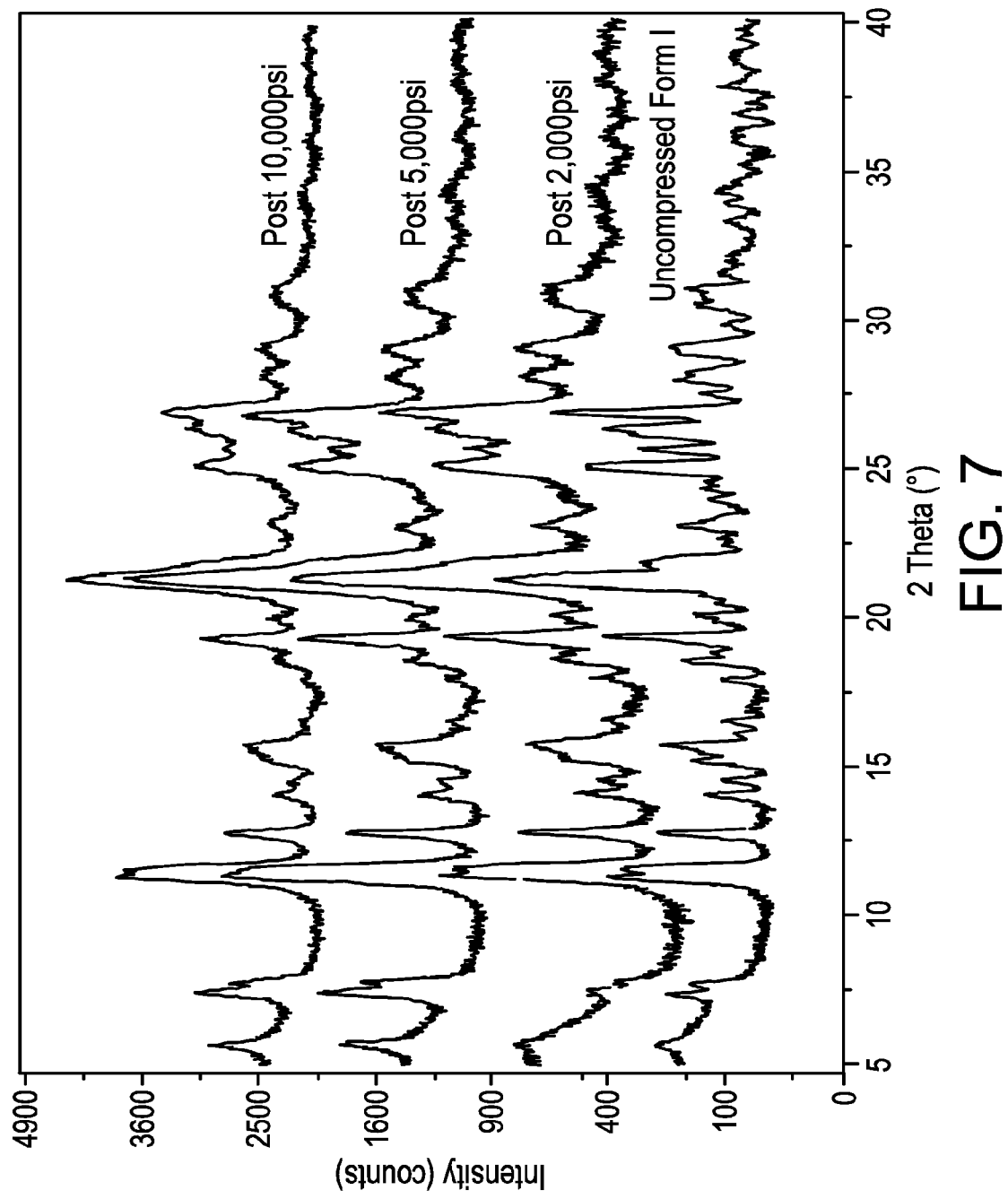
FIG. 7 depicts PXRD patterns of APD125 Form I compressed at 2 kp, 5 kp and 10 kp compared with uncompressed Form I. The PXRD patterns show that the samples all substantially comprise Form I.

Results:

In FIG. 6, an overlay of PXRD patterns for micronized APD125 Form I, before and after grinding with a mortar and pestle for 1 minute, 5 minutes and 10 minutes are compared. No significant changes in the PXRD patterns were observed, suggesting that Form I is stable to grinding/milling forces. In FIG. 7, PXRD patterns of APD125 Form I compressed at 2 kp, 5 kp and 10 kp are compared with uncompressed Form I. All of the PXRD patterns are consistent with APD125 Form I, although with the possibility of a slight reduction in crystallinity, as suggested by peak broadening and a loss of peak resolution/intensity for the compressed samples, relative to the uncompressed control sample.

Example 5

Methyl Cellulose Optimization

Example 5.1

Test Blend Preparation

Example 5.1.1

Form I API Slurries in Water

In a small scintillation vial, 152.13 mg of micronized APD125 Form I, was spiked with sufficient deionized water to make a paste; the weight of the water added, 844.60 mg was recorded, and the resulting mixture was stirred using a spatula to obtain a paste. The resulting sample, post-collection of an initial PXRD pattern, was capped, wrapped in tinfoil and stored at 40° C. until the next day, when a second PXRD pattern was obtained.

Using another small scintillation vial, 2.1183 g of micronized APD125 Form I, was mixed with 3.3619 g of a 0.5% w/v methyl cellulose to obtain a paste, which was immediately sampled for PXRD analysis to verify starting APD125 solid-state form, post-methyl cellulose addition. The remaining sample in the scintillation vial was split into two portions, placed in capped, parafilm-wrapped scintillation vials, which were then wrapped in tinfoil and stored at 40° C. and room temperature, respectively. PXRD patterns were collected at initial (t=0), 2-day and 16-day time points for each sample.

Example 5.1.2

Tablet Granulation Slurries in Water

APD125 micronized Form I/PVP (1:8) blend, weighing 3.0081 g and containing 0.5% w/w methyl cellulose, was mixed with 3.71277 g of water to form a paste. After sampling the paste for an initial PXRD pattern, the remaining paste was split into two portions, placed in capped, parafilm-wrapped scintillation vials, which were then wrapped in tinfoil and stored at 40° C. and room temperature, respectively. PXRD patterns were collected at initial (t=0), 1-day, 7-day and 21-day time points.

Example 5.1.3

Tablets (10 mg) Prepared Using 0% w/w, 2% w/w, 5% w/w and 8% w/w Methyl Cellulose For each blend, materials were dispensed (minus magnesium stearate) into a glass vial and blended for about 5 minutes. Magnesium stearate was added and the mixture was blended an additional 2 minutes. The final blend was compacted into standard round concave tablets (5/16" diameter) with a total tablet weight of 200 mg and hardness of 10 kp using a Carver press. For each batch of tablets, several were crushed using a mortar and pestle to obtain a fine powder, from which a small sample was taken for PXRD analysis to confirm the initial APD125 polymorphic form. The remaining powder was weighed into a Qorpak® bottle, and ca. 50% w/w deionized water was added. The resulting mixture was stirred using a micro-spatula to wet the powder and form a paste. A Teflon® lid was screwed on tightly, and the prepared samples were stored in a 40° C. oven. Ground tablet and water weights for each methyl cellulose loading are provided in Table 20. PXRD patterns were collected for the five tablet granulation/water blends, according to the schedule provided in Table 21.

TABLE 20

| Formulation Used | Weight of Powder (g) | Weight of Water (g) |
| --- | --- | --- |
| APD125:PVP (1:8) 2% methyl cellulose | 1.4767 | 1.4802 |
| APD125:PVP (1:8) 5% methyl cellulose | 1.3173 | 1.5822 |
| APD125:CoPVP (1:8) 5% methyl cellulose | 1.5436 | 1.5172 |
| APD125:PVP (1:8) 8% methyl cellulose | 1.5355 | 1.5049 |
| APD125:PVP (1:8) | 1.64810 | 1.63835 |

TABLE 21

| Formulation Used | Time Point | XRD Results Suggest Major Presence of: |
| --- | --- | --- |
| 2% methyl cellulose | Initial (no water) | Form I |
|  | 1 day | Form I |
|  | 1 week | Form II |
|  | 4 weeks | — |
| 5% methyl cellulose, PVP | Initial (no water) | Form I |
|  | 1 day | Form I |
|  | 1 week | Form I |
|  | 4 weeks | Form I |
| 5% methyl cellulose, coPVP | Initial (no water) | Form I |
|  | 1 day | Form I |
|  | 1 week | Form I |
|  | 4 weeks | Form II |
| 8% methyl cellulose | Initial (no water) | Form I |
|  | 1 day | Form I |
|  | 1 week | Form I |
|  | 4 weeks | Form I and Form II |
| 0% methyl cellulose | Initial (no water) | Form I |
|  | 1 day | Form II |
|  | 1 week | — |
|  | 4 weeks | — |

Example 5.2

Powder X-Ray Diffraction

PXRD measurements were obtained using a Philips (PANalytical) X'Pert PRO theta/theta diffractometer (EQ 0233) equipped with an X'Celerator RTMS detector and utilizing copper Kα radiation, operating at 45 kV and 40 mA. The instrument radius was 239.5 mm, the mask filter was 20 mm, the soller slit was 0.04 radians, and a nickel filter and sample spinning were used during data acquisition. The application and instrument control software used were X'Pert Data Collector®, version 2.0c and XPERT-PRO®, version 1.6, respectively. The API-based paste samples were scanned from 5° to 40° 2θ in continuous mode, using a step size of 0.0167° 2θ and a counting time of 40.005 seconds. The tablet granulation samples were scanned from 2° to 15° 2θ in continuous mode, using a step size of 0.0167° 2θ and a counting time of 1063.625 s.

Figure 8:
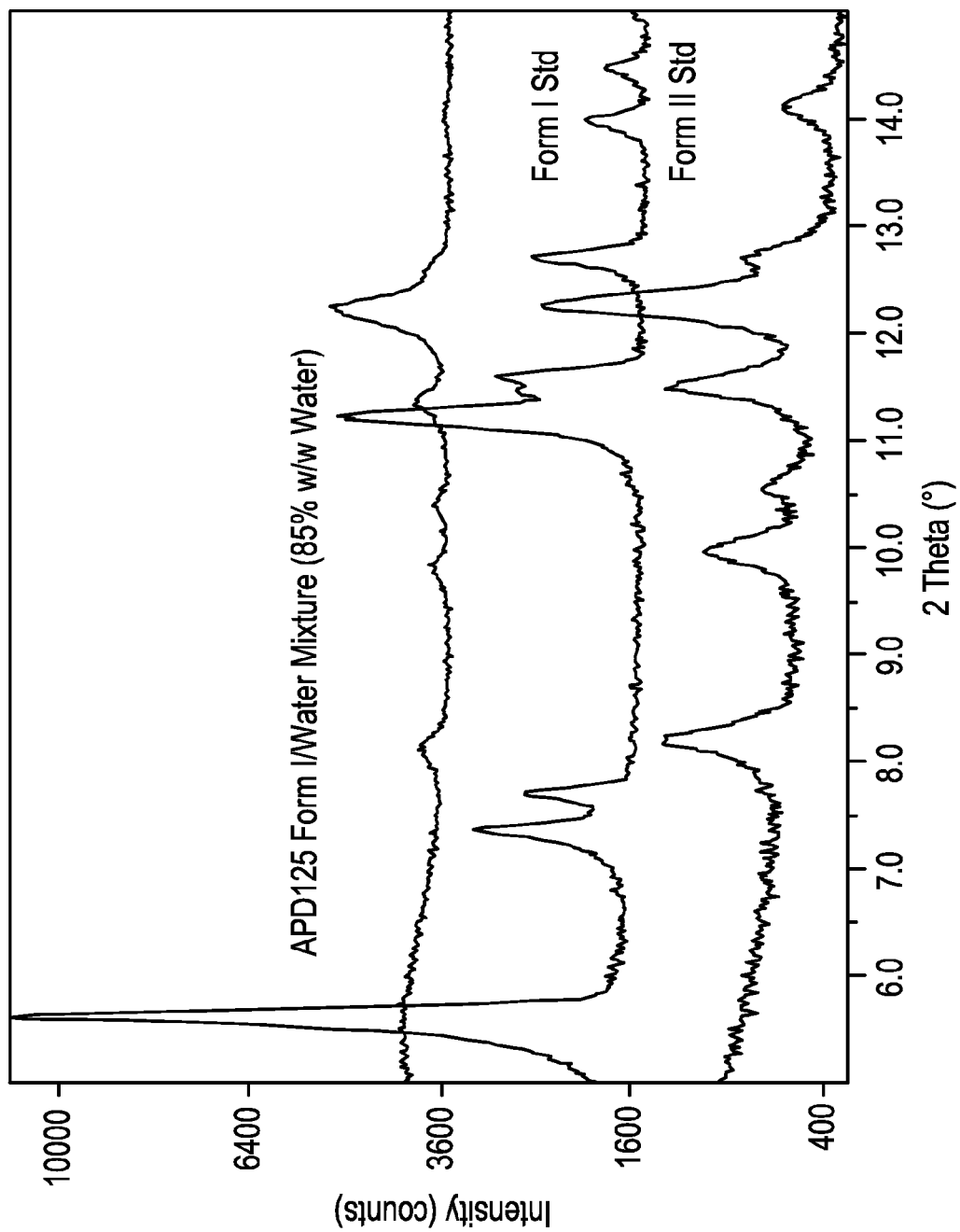
FIG. 8 depicts a PXRD pattern of an aqueous 0.5% w/w methyl cellulose solution of Form I at room temperature and 40° C. after 16 days. The PXRD pattern shows that the sample has substantially converted to Form II.
Figure 9:
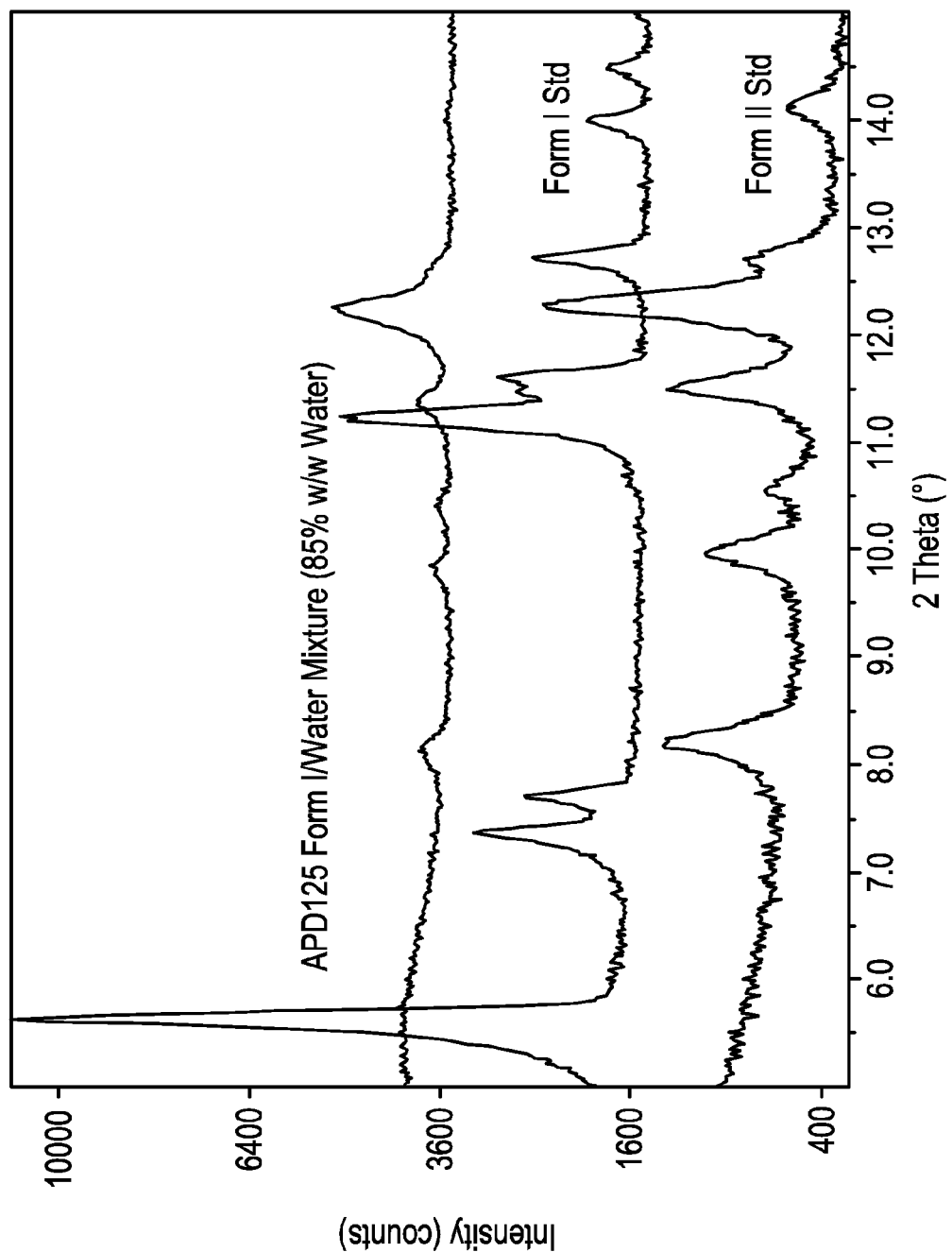
FIG. 9 depicts PXRD patterns of a Form I paste in water alone at room temperature and 40° C. after 24 h. The PXRD pattern shows that the sample has substantially converted to Form II.
Figure 10:
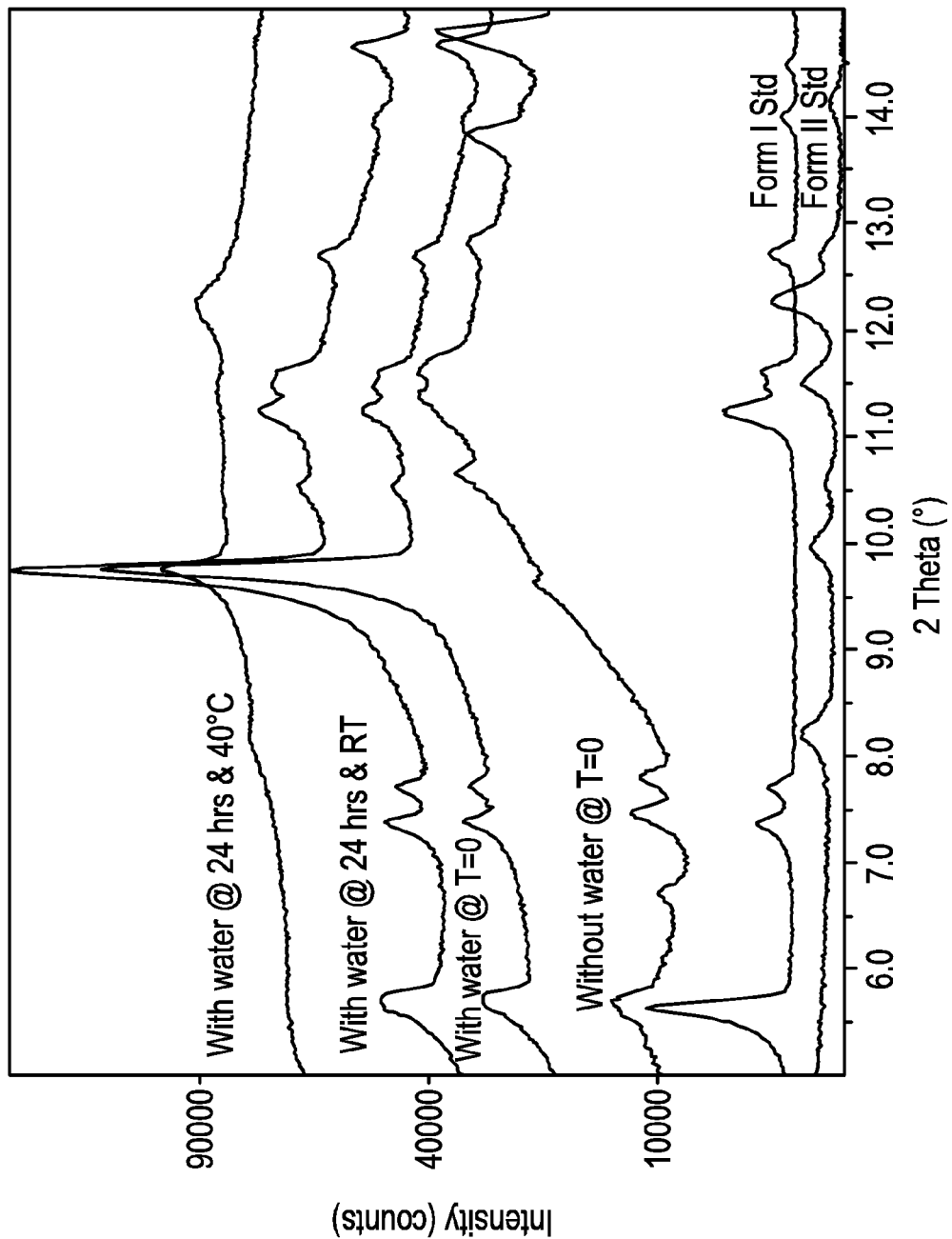
FIG. 10 depicts PXRD patterns for the wet-granulation Form I tablet blend post-mixing without water at t=0, and with 50% w/w water at t=0 and 24-h storage at room temperature and 40° C. The PXRD patterns show that each sample substantially comprises Form I.
Figure 11:
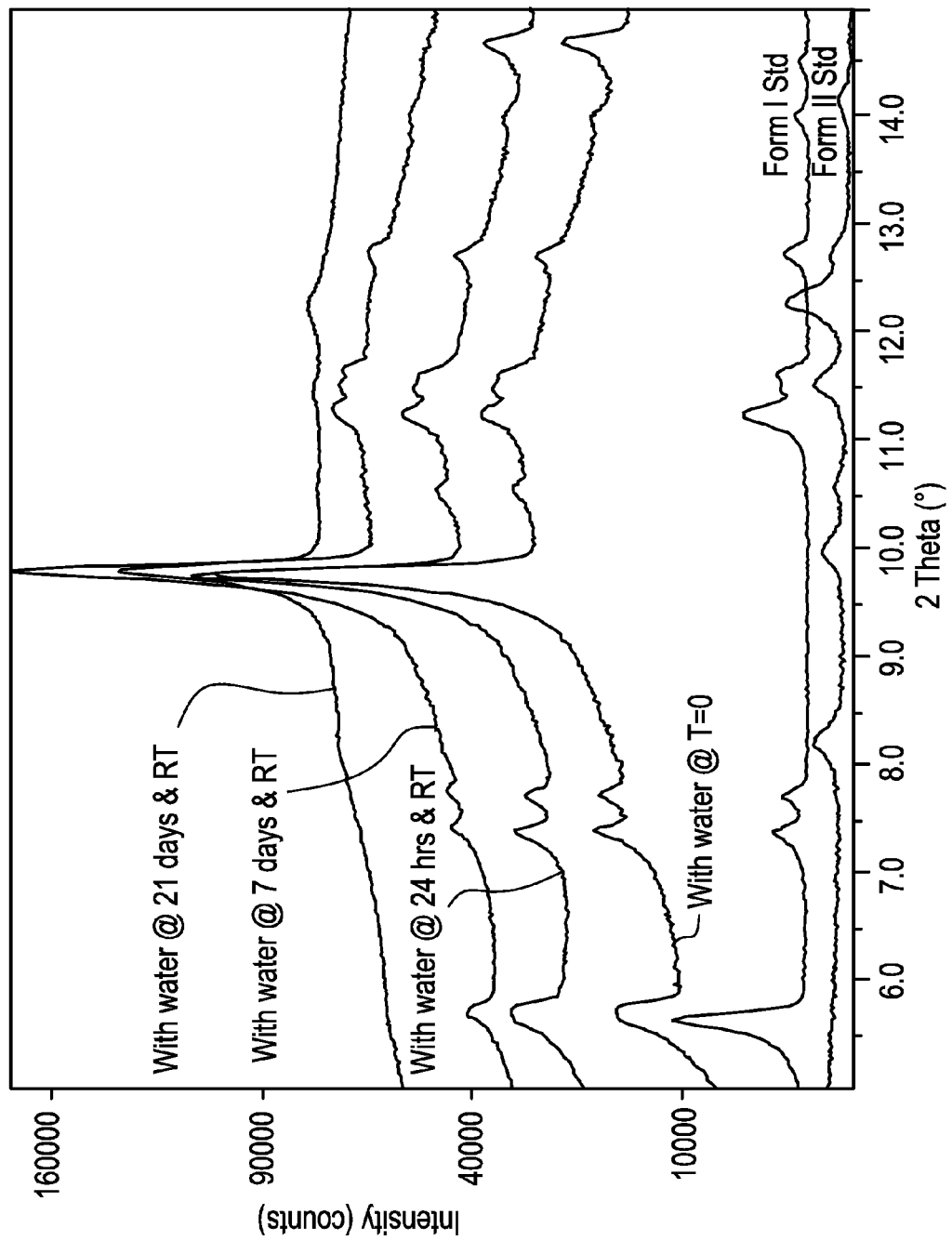
FIG. 11 depicts PXRD patterns for the Form I wet-granulation tablet blend post-mixing with 50% w/w water at t=0, 24-h, 7-days and 21-days storage at room temperature. The PXRD patterns show that at t=0, 24-h and 7-days the samples substantially comprise Form I, and at t=21 days the sample has substantially converted to Form II.

An aqueous 0.5% w/w methyl cellulose solution of Form I at 40° C. showed no evidence of conversion to Form II after 10 days (FIG. 8), in sharp contract to a Form I paste in water alone at 40° C., which converted to Form II within 24 hours (FIG. 9). As a result, 0.5% w/w methyl cellulose was added to the first APD125 wet-granulation tablet to hinder the conversion of Form I to Form II. However, the effectiveness of methyl cellulose in a tablet matrix has not been previously investigated. Therefore, as a first step, the wet-granulation tablet blend, containing 0.5% w/w methyl cellulose, was mixed with 50% w/w water to form a paste and stored at room temperature and 40° C. to determine if conversion to Form II was inhibited. Initial (t=0) and 24 hour PXRD patterns for the wet samples are shown in FIG. 10. After 24 hours, the sample stored at 40° C. showed conversion to Form II, while the room-temperature sample was still Form I. As shown in FIG. 11, the room-temperature sample remains Form I at 7 days, finally converting to Form II at 21 days.

Figure 12:
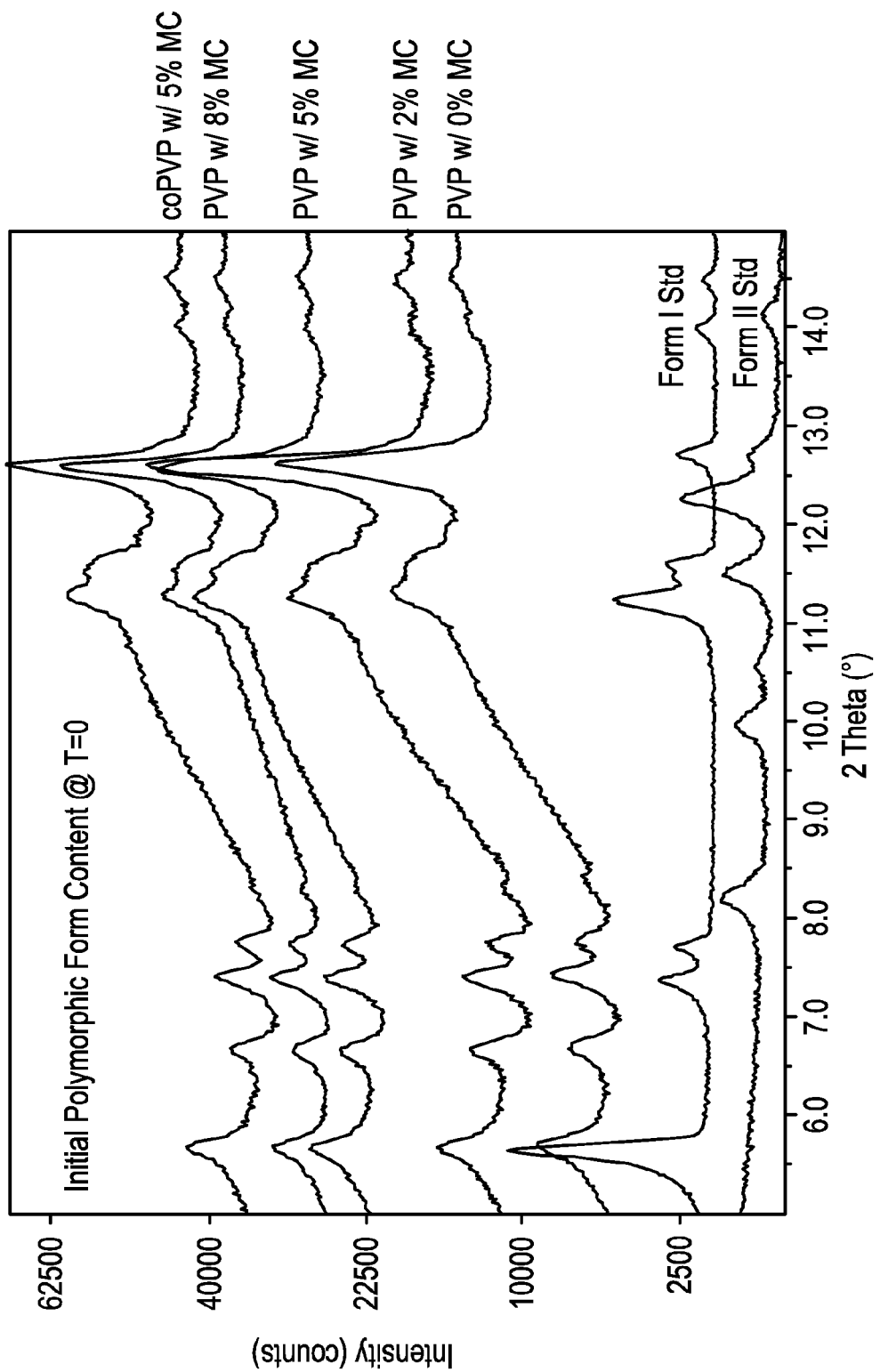
FIG. 12 depicts PXRD patterns for PVP-based direct-compression Form I tablets, containing 0% w/w, 2% w/w, 5% w/w and 8% w/w methyl cellulose and a coPVP-based direct-compression Form I tablet, containing 5% w/w methyl cellulose, post-mixing with 50% w/w water at t=0. The PXRD patterns show that each sample substantially comprises Form I.
Figure 13:
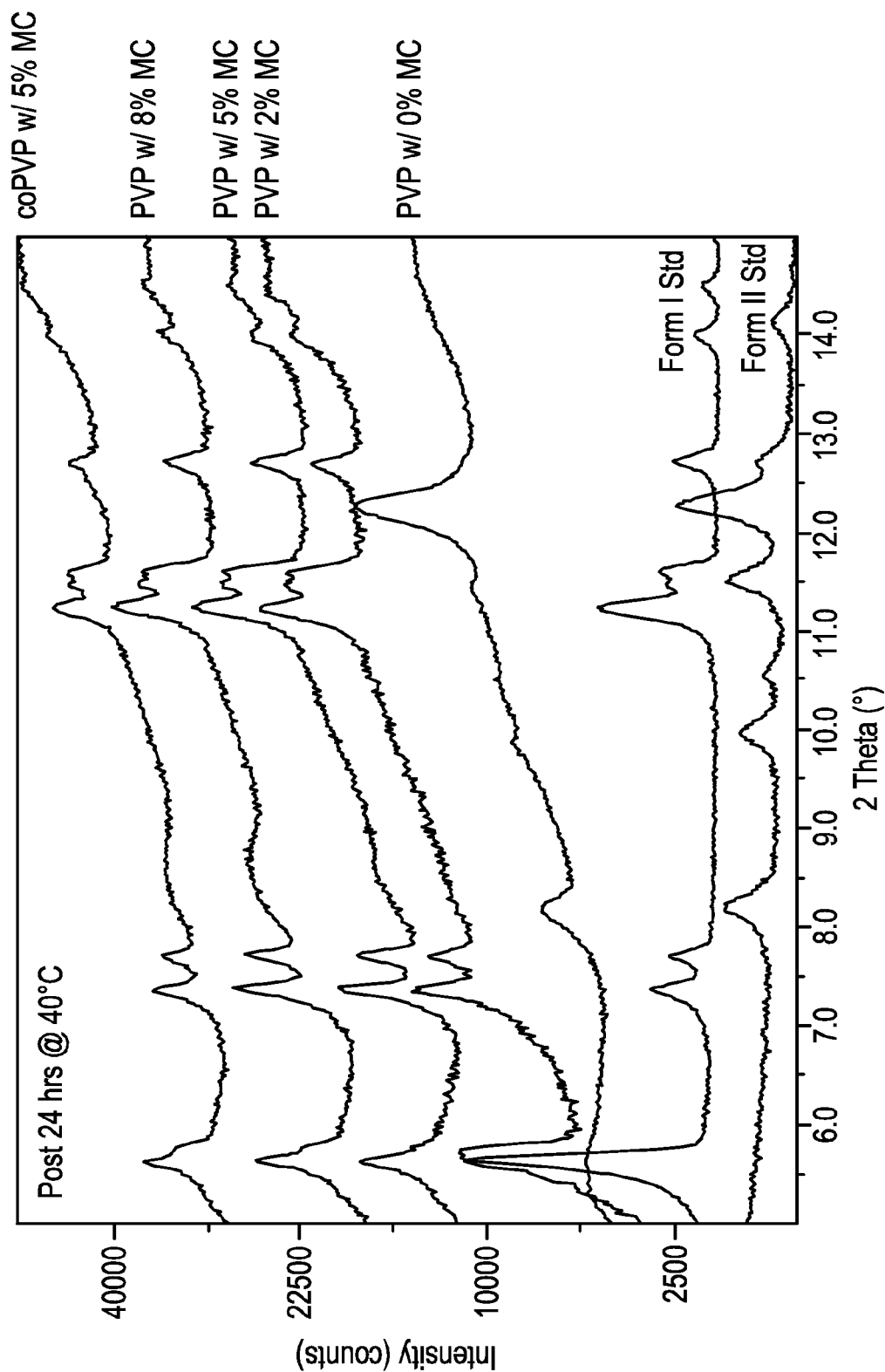
FIG. 13 depicts PXRD patterns for PVP-based direct-compression Form I tablets, containing 0% w/w, 2% w/w, 5% w/w and 8% w/w methyl cellulose, and a coPVP-based direct-compression tablet, containing 5% w/w methyl cellulose, post-mixing with 50% w/w water after 24 h at 40° C. The PXRD patterns show that the sample containing 0% methyl cellulose has substantially converted to Form II and all other samples substantially comprise Form I.

In contrast to pure APD125 Form I suspended in aqueous 0.5% w/w methyl cellulose, which did not convert to Form II in 21 days at room temperature, the tablet did show conversion to Form II. Therefore, it was decided to evaluate higher methyl cellulose concentrations to determine if conversion to Form II could be more effectively inhibited. PVP-based direct compression tablets were prepared containing 0% w/w, 2% w/w, 5% w/w and 8% w/w methyl cellulose. In addition, coPVP-based direct compression tablets were prepared containing 5% w/w methyl cellulose. In each case, the tablets were ground, mixed with 50% w/w water and stored at 40° C., with PXRD patterns collected at t=0, 24 h, 1 week and 4 weeks (1 month). As shown in FIG. 12, all samples contained Form I initially, but by 24 hours (FIG. 13), the sample without methyl cellulose showed conversion to Form II, as was previously observed for the 0.5% w/w methyl cellulose tablet blend.

Figure 14:
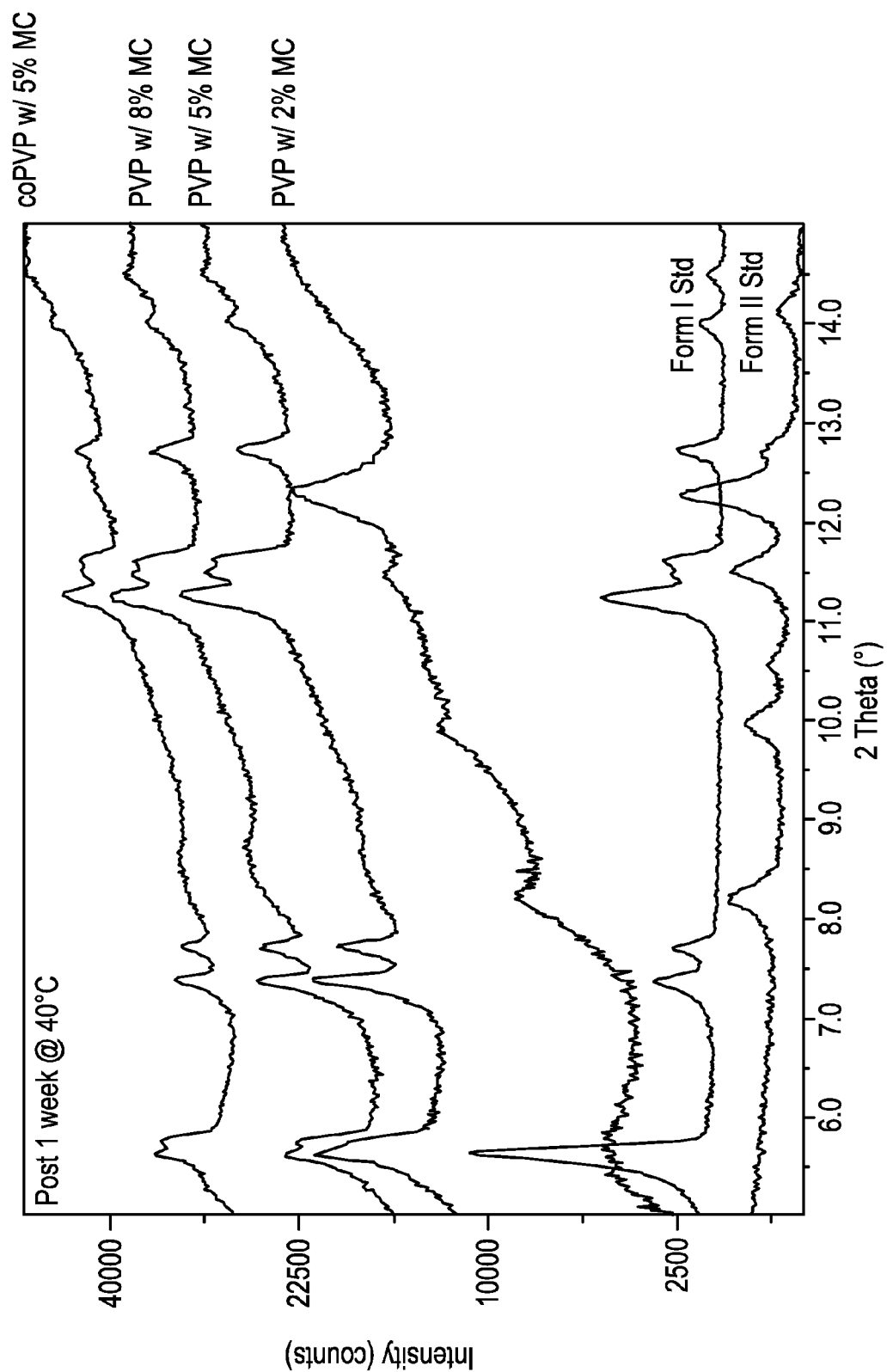
FIG. 14 depicts PXRD patterns for PVP-based direct-compression Form I tablets, containing 0% w/w, 2% w/w, 5% w/w and 8% w/w methyl cellulose, and a coPVP-based direct-compression Form I tablet, containing 5% w/w methyl cellulose, post-mixing with 50% w/w water after 1 week at 40° C. The PXRD patterns show that the sample containing 2% methyl cellulose has substantially converted to Form II and all other samples substantially comprise Form I.
Figure 15:
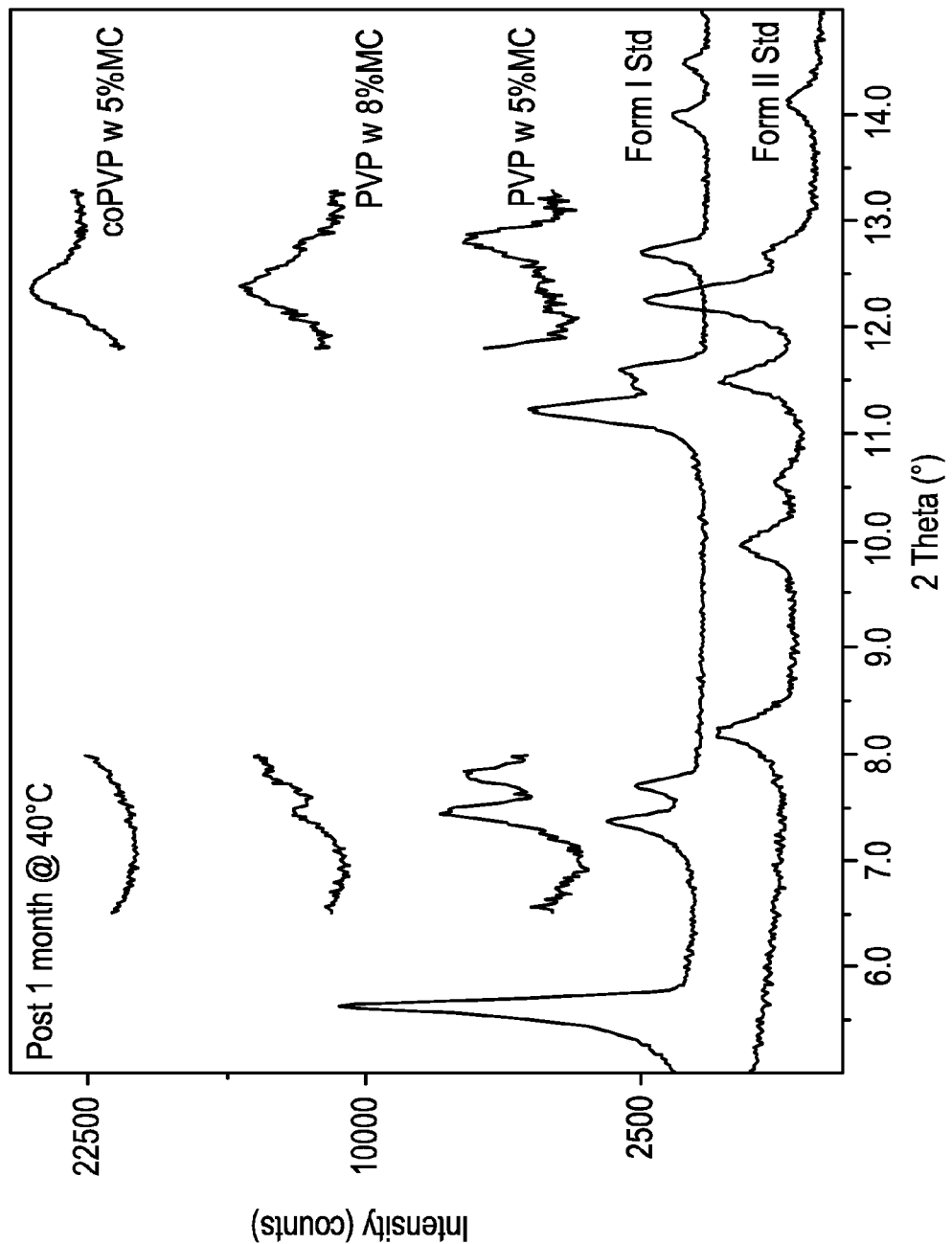
FIG. 15 depicts PXRD patterns for PVP-based direct-compression Form I tablets, containing 5% w/w and 8% w/w methyl cellulose, and a coPVP-based direct-compression From I tablet, containing 5% w/w methyl cellulose, post-mixing with 50% w/w water after 1 month at 40° C. The PXRD patterns show that the sample containing PVP and 5% methyl cellulose substantially comprises Form I, the sample containing PVP and 8% methyl cellulose has partially converted to Form II, and the sample containing coPVP has substantially converted to Form II. Note that the tablet PXRD data acquisition scan window was reduced to two smaller regions of 6.5° to 8° 2θ and 11.8° to 13.3° 2θ so reduce the overall sample analysis time, while maintaining the ability to discriminate Form I from Form II.

After 1 week at 40° C., the 2% w/w methyl cellulose sample showed conversion to Form II (FIG. 14), while the remaining samples, containing 5% w/w and 8% w/w methyl cellulose, started to show conversion to Form II at 1 month (FIG. 15). Thus, 2% w/w, 5% w/w and 8% w/w methyl cellulose containing tablets showed retarded conversion to Form II relative to the 0% w/w methyl cellulose control and the previously studied 0.5% w/w methyl cellulose containing tablet.

In addition to maintaining Form I, a primary goal of APD125 tablet formulation development is to minimize DFA formation. As can be seen in Table 25, although methyl cellulose loadings of 5% w/w and 8% w/w exhibited the best inhibition of Form II, they also resulted in increased DFA formation, relative to the 0% w/w methyl cellulose control. In addition, at the 5% w/w methyl cellulose loading, the coPVP-based tablets showed over three times the DFA formation of the PVP-based tablets, suggesting, as in the case of the TAM results, that coPVP might be less desirable as an excipient than PVP. The 2% w/w methyl cellulose loading provided the best overall balance of optimal chemical stability, while retaining a reasonable ability to inhibit the formation of Form II (FIG. 13, Table 25), and therefore, was used as the basis of further tablet development.

Example 5.3

DFA Assay

In addition to maintaining Form I, a primary goal of APD125 tablet formulation development was to minimize DFA formation. The 4-week 40° C./75% RH samples were pulled from their stability chambers and allowed to dry over the course of a couple of days under nitrogen. The material was then broken up using a micro-spatula until enough material was available for the DFA HPLC analysis. The samples were allowed to sit in solution for 4 hours before being filtered by centrifugation and transferred into an HPLC vial for analysis. Manual integration was used for all chromatograms.

As can be seen in Table 22, although methyl cellulose loadings of 5% w/w and 8% w/w exhibited the best inhibition of Form II, they also resulted in increased DFA formation, relative to the 0% w/w methyl cellulose control. In addition, at the 5% w/w methyl cellulose loading, the coPVP-based tablets showed over three times the DFA formation of the PVP-based tablets, suggesting, as in the case of the TAM results, that coPVP might be less desirable as an excipient than PVP. The 2% w/w methyl cellulose loading provided the best overall balance of optimal chemical stability, while retaining a reasonable ability to inhibit the formation of Form II (FIG. 13, Table 22), and therefore, was used as the basis of further tablet development.

TABLE 22

| Formulation | Form Detected | | | DFA (n = 1) |
| | (1 day) | (1 week) | (4 weeks) | (4 weeks) |
| --- | --- | --- | --- | --- |
| APD125 Form I/PVP (1:8) No methyl cellulose | Form II | Not applicable | Not applicable | 37 ppm |
| APD125 Form I/PVP (1:8) 2% w/w methyl cellulose | Form I | Form II | Not applicable | 34 ppm |
| APD125 Form I/PVP (1:8) 5% w/w methyl cellulose | Form I | Form I | Form I | 80 ppm |
| APD125 Form I/coPVP (1:8) 5% w/w methyl cellulose | Form I | Form I | Form II | 292 ppm |
| APD125 Form I/PVP (1:8) 8% w/w methyl cellulose | Form I | Form I | Form I/Form II mixture | 105 ppm |

Example 6

PVP/API and coPVP/API Ratio Optimization

Example 6.1

Sample Preparation

APD125 Form I and either PVP or coPVP were weighed out and mixed to obtain API/PVP or API/coPVP ratios of 1:1, 1:3, 1:5 and 1:8. The resulting mixtures were blended for ca. 5 min, screened through a #40 screen, and blended for an additional ca. 5 minutes.

Example 6.2

Scanning Electron Microscopy Analysis

Each sample was lightly stirred with a micro-spatula and a small portion of the material was tapped onto double-sided adhesive on a disposable scanning electron microscopy (SEM) stage at a height no greater than 0.5 cm. The SEM stage was lightly tapped to remove any loose material that did not adhere to the adhesive, and the prepared sample was placed in the SEM chamber. Images were collected using a FEI Quanta 200 (S/N D7554-R).

The 1:1 blend showed significant amounts of residual APD125 not coated onto the PVP particles, whereas the 1:3, 1:5 and 1:8 SEM images showed similar and significantly less residual APD125, not coated onto PVP, suggesting an API:PVP ratio of greater than 1:1, but no more than 1:3 is required to disperse most of the APD125 onto the PVP. APD125 does not uniformly coat the PVP particles, but tends to adhere more thickly to some areas than others, possibly due to variations in electrostatics.

Similar SEM results were obtained for API/coPVP blends. Once again, based upon the SEM images, it would appear that the least residual APD125 was observed at API:coPVP ratios of 1:3 or greater.

Example 6.3

Monkey APD125 Plasma Exposure—APD125 Form I:PVP and APD125 Form I:coPVP Tablet Formulations The effects of PVP and coPVP in various ratios with APD125 on APD125 plasma exposure in monkeys after oral administration of direct (dry) compression tablets containing 10 mg of APD125 were examined. APD125 plasma exposure ($AUC_{0-\infty}$) at APD125:PVP ratios of 1:1, 1:4 and 1:6 were similar at 0.548±0.321 h·µg/mL, 0.575±0.379 h·µg/mL and 0.572±0.556 h·µg/mL, respectively. At an APD125:PVP ratio of 1:8, however, plasma exposure (1.262±0.660 h·µg/mL) increased twofold compared to the 1:1, 1:4 and 1:6 ratios (FIG. 16, Table 23). The replacement of PVP with coPVP in the direct compression tablet at a ratio of 1:8 did not affect APD125 exposure: APD125:PVP, 1.262±0.660 h·µg/mL; APD125:coPVP, 1.889±1.162 h·µg/mL (FIG. 20, Table 23). Therefore, the final prototype tablets were 1:8 APD125:PVP or 1:8 APD125:coPVP ratio based formulations.

TABLE 23

| Formulation | Dose (mg) | N | $C_{max}$ (µg/mL) Mean | $C_{max}$ (µg/mL) SD | $AUC_{0-\infty}$ (h·µg/mL) Mean | $AUC_{0-\infty}$ (h·µg/mL) SD | $t_{max}$ (h) Mean | $t_{max}$ (h) SD |
|---|---|---|---|---|---|---|---|---|
| APD125 Form I:PVP (1:1) DC | 10 | 6 | 0.077 | 0.057 | 0.548 | 0.321 | 4.7 | 2.1 |
| APD125 Form I:PVP (1:4) DC | 10 | 6 | 0.085 | 0.071 | 0.575 | 0.379 | 4.7 | 4.3 |
| APD125 Form I:PVP (1:6) DC | 10 | 6 | 0.125 | 0.174 | 0.572 | 0.556 | 4.3 | 2.3 |
| APD125 Form I:PVP (1:8) DC | 10 | 3 | 0.335 | 0.138 | 1.262 | 0.660 | 2.7 | 0.8 |
| APD125 Form I:coPVP (1:8) DC | 10 | 5 | 0.471 | 0.413 | 1.889 | 1.162 | 2.4 | 0.9 |
| APD125 Form I:PVP (1:8) WET | 10 | 6 | 0.227 | 0.153 | 1.507 | 1.218 | 2.2 | 1.0 |
| Soft gelatin capsule | 10 | 6 | 0.942 | 0.303 | 3.192 | 1.291 | 2.2 | 1.0 |

Example 7

Direct Compression Tablet

Example 7.1

Micronization of APD125 Form I

APD125 Form I (12.5 kg, particle size $d_{10}$ of 1.75 µm, $d_{50}$ of 6.98 µm, $d_{90}$ of 38.45 µm) (Sympatec Helos wet dispersion laser-diffraction particle size analyzer) was micronized in a 300 mm spiral jet mill at a solid feed rate of 20.0 kg/h with a grinding pressure of 6.5±0.5 bar and a filtered nitrogen gas feed pressure of 10±0.5 bar to produce APD125 Form I (11.55 kg, 92.4% yield) of 99.93% purity by HPLC peak area. The micronized product was found to have a particle size $d_{90}$ of 6.16 µm with a Sympatec Helos wet dispersion laser diffraction particle size analyzer.

Example 7.2

Tablet Manufacturing for 5% w/w Methyl Cellulose-Loaded Tablets

Materials were dispensed according to the target tablet quantitative composition. Micronized APD125, PVP and methyl cellulose were preblended in a bag, and then hand-screened through a #40-mesh sieve. A 2-qt. blender was charged with the preblend, and all other remaining materials were added, minus the magnesium stearate, followed by blending for 300 rotations (12 min at 25 rpm). Finally, the magnesium stearate was added, and the resulting mixture was blended for an additional 100 rotations (4 minutes at 25 rpm). This material was compressed into 200-mg tablets using a Piccola PLC tablet press equipped with two stations of 5/16" standard round concave tooling to achieve a target 5-kp to 8-kp tablet hardness.

Example 7.3

Tablet Manufacturing for 2% w/w Methyl Cellulose-Loaded Tablets

Materials were dispensed according to the target tablet quantitative composition. A blender was charged with all of the tablet components, minus magnesium stearate, and blended for 300 rotations (12 min at 25 rpm). The resulting blend was delumped using a Comill (equipped with an R045 screen and round-arm impeller), transferred into a blender, and blended for 300 rotations (12 min at 25 rpm). The magnesium stearate was added, followed by blending for an additional 100 rotations (4 min at 25 rpm). The resulting final blend was compressed into 200-mg tablets (containing 10 mg of micronized APD125 Form I API) to a target hardness of 5 kp to 8 kp, using a Piccola PLC tablet press, equipped with 5/16" standard round concave tooling. For the 40-mg active tablets, the final blend was compressed into 800-mg tablets to a target hardness of 12 kp to 16 kp, using 0.730"×0.365" plain oval tooling. Finally, all tablet cores were film coated with Opadry® II Blue 85F90996 to a 5% weight gain, using a fully perforated 11.5" pan. Final tablet composition is provided in Table 24.

TABLE 24

| Ingredient | % (w/w) | Amount (g) |
|---|---|---|
| Core tablet | | |
| APD125 (Micronized) | 5.00 | 50.0 |
| PVP, Plasdone™ K-29/32 or coPVP, Kollidon™ VA 64 | 40.00 | 400.0 |
| Lactose monohydrate, 316 | 21.25 | 212.5 |
| Microcrystalline cellulose, PH102 | 25.00 | 250.0 |
| Crospovidone, Kollidon™ CL | 4.00 | 40.0 |
| Methyl cellulose | 2.00 | 20.0 |
| Sodium lauryl sulfate | 2.00 | 20.0 |
| Magnesium stearate | 0.50 | 5.0 |
| Silicon dioxide | 0.25 | 2.5 |
| Total | 100.00 | 1000.0 |
| Film coat | | |
| Opadry ® II Blue 85F90996 | 5 | NA |

NA = not applicable

Example 7.4

Monkey APD125 Plasma Exposure

Monkey APD125 exposure studies conducted with wet granulation based APD125 Form I 10-mg tablets, containing 0.5% w/w methyl cellulose, were shown to exhibit roughly one-half the $AUC_{0-\infty}$ and one-fourth the $C_{max}$ of SGCs (Example 1.1). Additionally, monkey studies using uncoated direct compression APD125 Form I 10-mg tablets, containing 5% w/w methyl cellulose found the direct compression tablets to exhibit essentially the same exposure as previously observed for the wet-granulation tablets (Example 6.3). Based on the PK data and the methyl cellulose formulation stability results (Table 22), a decision was made to prepare two final, separate R&D batches of coated direct-compression tablets with 40 mg APD125 Form I, containing methyl cellulose at 2% w/w, and either PVP or coPVP.

Six monkeys were dosed in a 2×6 crossover design. APD125 plasma exposure after oral administration of 40 mg APD125 in SGC or dry compression tablets are shown in FIG. 18. Pharmacokinetic parameters are presented in Table 25. APD125 absorption into the systemic circulation occurred over a 3-h period followed by a mono-exponential terminal phase. The time to maximal plasma concentration ($t_{max}$) was most rapid for the liquid filled SGC at 2.2 h. The $t_{max}$ increased with tablet administration to 3.3 h. The SGC $C_{max}$ (0.850±0.462 µg/mL) was approximately twofold greater than the $C_{max}$ for APD125 Form I tablet (0.464±0.236 µg/mL). The integrated plasma exposures ($AUC_{0-\infty}$) for SGC and APD125 Form I tablet were similar (4.395±3.122 h·µg/mL) and APD125 Form I (4.223±2.660 h·µg/mL). The extended $t_{max}$ reduced Cmax and similar overall exposures ($AUC_{0-\infty}$) of the tablet formulation compared to the SGC formulation corroborate the exploratory formulations discussed in Example 1.1 (Table 1).

TABLE 25

| Formulation | Dose (mg) | N | $C_{max}$ (µg/mL) Mean | SD | $AUC_{0-\infty}$ (h·µg/mL) Mean | SD | $t_{max}$ (h) Mean | SD |
|---|---|---|---|---|---|---|---|---|
| Tablet APD125 Form I:PVP (1:8) coated | 40 | 6 | 0.46 | 0.236 | 4.223 | 2.660 | 3.3 | 1.0 |

TABLE 25-continued

| Formulation | Dose (mg) | N | $C_{max}$ (µg/mL) Mean | SD | $AUC_{0-\infty}$ (h·µg/mL) Mean | SD | $t_{max}$ (h) Mean | SD |
|---|---|---|---|---|---|---|---|---|
| direct-compression, 2% w/w methyl cellulose Soft gelatin capsule | 40 | 6 | 0.850 | 0.462 | 4.395 | 3.122 | 2.2 | 1.0 |

As can be seen in Table 25, APD125 Form I:PVP (1:8) coated direct-compression tablets exhibit essentially identical $AUC_{0-\infty}$ results to the SGC at a 40-mg dose, as was expected on the basis of the previous wet-granulation tablet monkey PK results. Additionally, the 40-mg tablets exhibited roughly one-half the $C_{max}$ of the SGCs and a slightly longer $t_{max}$, which is also consistent with previous wet granulation tablet PK results.

Example 7.5

R&D Stability Testing 10-mg and 40-mg, PVP and coPVP-based prototype APD125 tablets were placed on stability at 25° C./60% RH and 40° C./75% RH, contained in HDPE bottles with induction seal and desiccant. Appearance, dissolution, water content by Karl Fischer, PXRD, related substances and tablet hardness tests were performed at initial and 8-week time points only. Compound II, DFA and related substances were assayed at initial, 2-week and 4-week time points. Additional tablets were also stored in open containers at 40° C./75% RH, pulled and analyzed at the 4-week time point for DFA and compound II.

PVP-based and coPVP-based tablet formulations showed comparable overall chemical stability during the 8-week study, with no significant loss in APD125 observed, as demonstrated by the assay results shown in Table 26. The DFA results for she final two R&D formulations are provided in Table 27.

TABLE 26

| | | | APD125 % Assay (% RSD) | | | |
|---|---|---|---|---|---|---|
| Formulation | Conditions | Dose (mg) | Initial n = 3 | 2 weeks n = 3 | 4 weeks n = 3 | 8 weeks n = 3 |
| APD125 Form I:PVP (1:8) 2% w/w methyl cellulose, direct-compression (coated) | 40° C. 75% RH | 10 | 90.5 (0.5) | 93.0 (0.6) | 102.3 (4.9) | 93.7 (2.4) |
| | | 40 | 93.1 (0.5) | 91.3 (0.7) | 102.3 (3.6) | 97.7 (2.1) |
| | 25° C. | 10 | 90.5 (0.5) | NT | NT | 95.4 (2.1) |
| | 60% RH | 40 | 93.1 (0.5) | NT | NT | 96.9 (2.0) |
| APD125 Form I:coPVP (1:8) 2% w/w methyl cellulose, direct-compression (coated) | 40° C. 75% RH | 10 | 90.4 (0.5) | 91.8 (1.8) | 92.6 (0.9) | 95.1 (1.5) |
| | | 40 | 92.5 (1.5) | 97.5 (5.9) | 93.1 (0.9) | 97.0 (0.9) |
| | 25° C. | 10 | 90.4 (0.5) | NT | NT | 93.3 (1.1) |
| | 60% RH | 40 | 92.5 (1.5) | NT | NT | 96.7 (2.7) |

NT = not tested

TABLE 27

| | | | DFA Concentration as ppm (% RSD) | | | |
|---|---|---|---|---|---|---|
| Formulation | Conditions | Dose (mg) | Initial n = 2 | 2 weeks n = 2 | 4 weeks n = 2 | 8 weeks n = 2 |
| APD125 Form I:PVP (1:8) 2% w/w methyl cellulose, | 40° C. 75% RH | 10 | ND[a] | <35 | <35 | <35 |
| | | 40 | ND[a] | <35 | <35 | <35 |

TABLE 27-continued

| Formulation | Conditions | Dose (mg) | Initial n = 2 | 2 weeks n = 2 | 4 weeks n = 2 | 8 weeks n = 2 |
|---|---|---|---|---|---|---|
| | | | DFA Concentration as ppm (% RSD) | | | |
| direct-compression (coated), HDPE bottle with desiccant | 25° C. 60% RH | 10 40 | ND[a] ND[a] | NA NA | NA NA | ND[a] ND[a] |
| APD125 Form I:coPVP (1:8) 2% w/w methyl cellulose, direct-compression (coated), HDPE bottle with desiccant | 40° C. 75% RH 25° C. 60% RH | 10 40 10 40 | ND[a] ND[a] ND[a] ND[a] | 69 (1.8) 67 (1.2) NA NA | 114 (1.7) 145 (0.6) NA NA | 142 (2.4) 161 (1.1) ND[a] ND[a] |
| APD125 Form I:PVP (1:8) 2% w/w methyl cellulose, direct-compression (coated), open container | 40° C. 75% RH | 10 40 | ND[a] ND[a] | NA NA | 645 (0.2) 918 (0.5 | NA NA |
| APD125 Form I:coPVP (1:8) 2% w/w methyl cellulose, direct-compression (coated), open container | 40° C. 75% RH | 10 40 | ND[a] ND[a] | NA NA | 648 (1.7) 788 (1.4) | NA NA |

[a]DFA limit of detection and limit of quantitation are 10 ppm and 35 ppm respectively
NA = not applicable
ND = Not detected As was previously observed during the methyl cellulose optimization studies (Table 22), the coPVP-based tablets were found to exhibit faster DFA formation rates than the corresponding PVP-based tablets, which is also consistent with TAM results (Example 3), suggesting potential compatibility issues with coPVP. Interestingly, the open-container results (Table 27) show similar DFA formation rates for both PVP-based and coPVP-based tablets, in contrast with HDPE bottle stability and methyl cellulose optimization results, which suggested tablets containing coPVP exhibit faster DFA formation than PVP-based tablets. This apparent discrepancy might be due to water content differences. In the cases of the HDPE bottle stability and methyl cellulose optimization studies, the amount of water present in the samples is very similar, which allows one to better assess the impact of changing from PVP to coPVP. However, in the case of the open-container stability study results, each sample would equilibrate to quite different water contents, as shown in FIG. 20. At a relative humidity of 75%, the PVP-based tablets could be expected to absorb significantly more water than the coPVP-based tablets, and since hydrolysis is a major pathway for DFA formation, it is not unreasonable that the open container PVP-based tablets would begin to show faster DFA formation, becoming nearly identical to the open container coPVP-based tablets. It is therefore possible that the observed increased DFA formation rate in the presence of coPVP, relative to PVP, is not the result of chemical incompatibility with coPVP. Instead, at a fixed water content in a closed system, the more hygroscopic PVP, relative to coPVP, might reduce the amount of free water available for hydrolysis of APD125.

As shown in Table 28 and Table 29, both PVP-based and coPVP-based tablets exhibited no evidence of significant Compound II assay and dissolution rate changes post-8 weeks at 40° C./75% RH, with the exception of the open container results, consistent with the DFA results, shown in Table 27. The PXRD results show that all samples tested contain Form I, indicating good solid-state form stability for both PVP-based and coPVP-based tablets (Table 30). The water content determination by Karl Fischer showed essentially no change in water content over the 8-week study (Table 31). There was, however, a slightly higher water content observed for the PVP-based tablets, relative to the coPVP-based tablets, which is consistent with the fact that PVP is somewhat more hygroscopic than coPVP (FIG. 19).

TABLE 28

| Formulation | Conditions | Dose (mg) | Initial n = 2 | 2 weeks n = 2 | 4 weeks n = 2 | 8 weeks n = 2 |
|---|---|---|---|---|---|---|
| | | | Compound II Concentration as % area (% RSD) | | | |
| APD125 Form I:PVP (1:8) 2% w/w methyl cellulose, direct-compression (coated), HDPE bottle with desiccant | 40° C. 75% RH 25° C. 60% RH | 10 40 10 40 | ND[a] ND[a] ND[a] ND[a] | ND[a] ND[a] NA NA | ND[a] ND[a] NA NA | <0.05 <0.05 <0.05 <0.05 |
| APD125 Form I:coPVP (1:8) 2% w/w methyl cellulose, direct-compression (coated), HDPE bottle with desiccant | 40° C. 75% RH 25° C. 60% RH | 10 40 10 40 | ND[a] ND[a] ND[a] ND[a] | ND[a] ND[a] NA NA | ND[a] ND[a] NA NA | <0.05 <0.05 <0.05 <0.05 |
| APD125 Form I:PVP (1:8) 2% w/w methyl cellulose, direct-compression (coated), open container | 40° C. 75% RH | 10 40 | ND[a] ND[a] | NA NA | 0.24 (5.89) 0.26 (2.77) | NA NA |
| APD125 Form I:coPVP (1:8) 2% w/w methyl cellulose, direct-compression (coated), open container | 40° C. 75% RH | 10 40 | ND[a] ND[a] | NA NA | 0.24 (5.89) 0.33 (15.23) | NA NA |

TABLE 29

| Formulation | Conditions | Dose (mg) | APD125 % Released at 60 min (% RSD) | |
|---|---|---|---|---|
| | | | Initial n = 4 | 8 weeks n = 4 |
| APD125 Form I:PVP (1:8) 2% w/w methyl cellulose, direct-compression (coated) | 40° C. 75% RH 25° C. 60% RH | 10 40 10 40 | 103.9 (3.4) 98.9 (2.5) 103.9 (3.4) 98.9 (2.5) | 97.0 (3.1) 95.9 (1.4) 101.0 (1.7) 100.4 (2.0) |
| APD125 Form I:coPVP (1:8) 2% w/w methyl cellulose, direct-compression (coated) | 40° C. 75% RH 25° C. 60% RH | 10 40 10 40 | 100.0 (0.7) 98.3 (1.3) 100.0 (0.7) 98.3 (1.3) | 95.6 (0.9) 94.5 (0.8) 99.0 (0.9) 98.9 (0.8) |

TABLE 30

| Formulation | Conditions | Dose (mg) | APD125 Polymorph(s) Detected | |
|---|---|---|---|---|
| | | | Initial | 8 weeks |
| APD125 Form I:PVP (1:8) 2% w/w methyl cellulose, direct-compression (coated) | 40° C. 75% RH 25° C. 60% RH | 10 40 10 40 | Form I Form I Form I Form I | Form I Form I Form I Form I |
| APD125 Form I:coPVP (1:8) 2% w/w methyl cellulose, direct-compression (coated) | 40° C. 75% RH 25° C. 60% RH | 10 40 10 40 | Form I Form I Form I Form I | Form I Form I Form I Form I |

TABLE 31

| Formulation | Conditions | Dose (mg) | % water Content (% RSD) | |
|---|---|---|---|---|
| | | | Initial n = 3 | 8 weeks n = 3 |
| APD125 Form I:PVP (1:8) 2% w/w methyl cellulose, direct-compression (coated) | 25° C. 60% RH 40° C. 75% RH | 10 40 10 40 | 6.7 (4.5) 5.7 (3.7) 6.7 (4.5) 5.7 (3.7) | 4.8 (0.9) 4.5 (1.1) 6.5 (0.0)[a] 5.7 (5.9)[a] |
| APD125 Form I:coPVP (1:8) 2% w/w methyl cellulose, direct-compression (coated) | 25° C. 60% RH 40° C. 75% RH | 10 40 10 40 | 4.7 (5.2) 4.3 (0.8) 4.7 (5.2) 4.3 (0.8) | 4.1 (19.2) 3.9 (0.7)[a] 4.9 (1.7)[a] 4.5 (0.8)[a] |

[a] n = 2

Example 7.6

Nine Months Stability Testing 10-mg and 40-mg, PVP and coPVP-based prototype APD125 tablets were placed on stability testing packaged in HDPE bottles 60 cc with and without desiccant. See Table 32.

TABLE 32

| Batch | Formulation | Strength | Packaging |
|---|---|---|---|
| 1 | APD125/PVP | 10 mg | HDPE bottles with desiccant |
| 2 | | 40 mg | |
| 3 | APD125/coPVP | 10 mg | |
| 4 | | 40 mg | |
| 5 | APD125/PVP | 10 mg | HDPE bottles |

TABLE 32-continued

| Batch | Formulation | Strength | Packaging |
|---|---|---|---|
| 6 | | 40 mg | without desiccant |
| 7 | APD125/coPVP | 10 mg | |
| 8 | | 40 mg | |
| 9 | Placebo/PVP | (10 mg) | HDPE bottles with desiccant |
| 10 | | (10 mg) | HDPE bottles without desiccant |
| 11 | | (40 mg) | HDPE bottles with desiccant |
| 12 | | (40 mg) | HDPE bottles without desiccant |

The stability samples were stored at 25° C./60% relative humidity, 30° C./65% relative humidity and 40° C./75% relative humidity to examine the effect of heat and humidity. The studies are conducted according to ICH Q1A(R) guidelines (stability testing of new drug substances and products).

After a storage duration of 6 months, the stability tests with tablets in bottles without desiccant were stopped and only the stability tests with tablets in bottles with desiccant were measured after a storage duration of 9 months.

After a storage duration of 9 months at 25° C./60% relative humidity in bottles with desiccant, the tablets show an increase of the water content compared with the initial values (PVP max.+2.4%, coPVP max.+4%, placebo tablets max.+1.6%). The tablets were tested again after 10.5 months and the water content was found to be lower than it had been at 9 months. The water content at 10.5 months compared with the initial values was: PVP max.+0.5%; coPVP max.+ 0.5%; placebo tablets max.+0.1%). The difference in water content at 9 months and 10.5 months is probably due to the testing protocols used. At 9 months the tablets were ground on one day but the water content was not measured until the following day. During this delay it is believed the ground tablets picked up moisture from the air. At 10.5 months however, the tablets were ground and tested for water content on the same day.

After a storage duration of 9 months at 25° C./60% relative humidity in bottles with desiccant, a decrease of the crushing strength of the tablets was observed compared with the initial values. The decrease of the 10 mg tablets was higher than the 40 mg tablets (10 mg max.=–24 N; 40 mg max.=–8 N). No significant differences were observed between the active and the placebo tablets and between the PVP and the coPVP formulation.

After a storage duration of 9 months at 25° C./60% relative humidity in bottles with desiccant, no significant decrease of the dissolution rate can be observed.

After a storage duration of 9 months at 25° C./60% relative humidity in bottles with desiccant, the assay results for APD125 were in the same range as the initial conditions. No significant trends of the assay results can be observed and all results are within the specification.

After a storage duration of 9 months at 25° C./60% relative humidity in bottles with desiccant, small amounts of DFA were detected but all results were below the quantitation limit of 75 ppm. For other impurities, no increase were observed and all results were ≤0.05%.

Example 8

Preparation of Intermediate N-[4-Methoxy-3-(2-methyl-2H-pyrazol-3-yl)phenyl]-acetamide

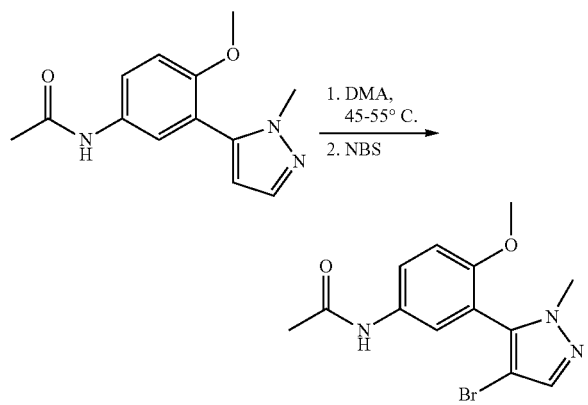

To a solution of N-[4-methoxy-3-(2-methyl-2H-pyrazol-3-yl)phenyl]-acetamide (25.0 kg) in N,N-dimethylacetamide (DMA, 140.5 kg) in a 400 L glass lined jacketed reactor with overhead stirring under nitrogen as 45 to 55° C. internal temperature N-bromosuccinimide (NBS, 19.0 kg) was charged in portions at such a rate as to maintain internal temperature to less than 55° C. The reaction mixture remained a solution at this dilution of DMA and internal temperature of 50.9° C. An "in process check" of the reaction mixture to determine reaction completion after at least 1 hr of stirring at 50° C. showed that the reaction mixture was substantially free of the starting material. Upon cooling of the reaction mixture to an internal temperature of 34° C. water (150 kg) was added in a controlled manner into the reactor to maintain an internal temperature between 40-55° C. A slight exotherm was observed during the reaction quench. The product slurry was then cooled to −5 to 5° C. and filtered through a corrosion resistant filter/dryer. The wetcake was re-slurried, washed with water (2×25 kg), and dried under full house vacuum (~30 in Hg) with a jacket temperature of 65° C. producing N-[3-(4 bromo-2-methyl-2H-pyrazol-3-yl)-4-methoxyphenyl]-acetamide (31.6 kg, 100% purity by HPLC, 90.1% yield).

Example 9

Preparation of Intermediate 3-(4-Bromo-2-methyl-2H-methyl-3-yl)-4-methoxy-phenylamine

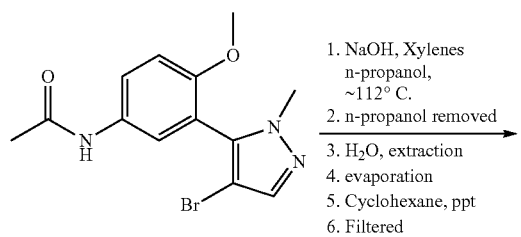

N-[3-(4-Bromo-2-methyl-2H-pyrazol-3-yl)-4-methoxy-phenyl]-acetamide (15.6 kg), xylenes (67.1 kg), n-propanol (12.5 kg), and sodium hydroxide pellets (4.1 kg) were charged into a 400 L Hastelloy jacketed reactor with overhead stirring and nitrogen blanket. The reaction mixture was heated and held at reflux for at least four hours with a peak internal temperature of 107° C. at which point the HPLC analysis of the reaction mixture indicated substantially complete deacetylation of the starting material to product. The reactor condenser was then switched from redox to distillation configuration to remove most of the n-propanol solvent. This was accomplished by monitoring the temperature profile of the reactor contents and monitoring when the temperature stabilized (126-127° C. $T_{internal}$ with up to 145° C. $T_{jacket}$) indicating near-complete removal of n-propanol. The product mixture was cooled to 80° C. and water (15.6 L) was added to extract the inorganic material from the product dissolved in xylenes. The aqueous extraction was repeated by adding water (11.7 kg) at 70-80° C. and performing a second extraction to remove residual inorganics from the product solution. Upon cooling to 65° C. vacuum was applied to effect distillation of approximately 40% of initial xylenes charge at which point precipitation was observed. The reaction slurry was further cooled to 40° C. Cyclohexane (10.5 L) was charged in portions to control precipitation at an internal temperature 36.6 to 41.1° C. Upon completion of the cyclohexane anti-solvent addition, the reaction mixture was cooled to −11.9° C. (maximize the yield). The solid product was filtered using a filter/dryer, washed with cyclohexane (2×12.2 kg), and dried under full house vacuum (~30 in Hg) and with increasing internal temperature up to 40° C. isolating 3-(4-bromo-2-methyl-2H-methyl-3-yl)-4-methoxy-phenylamine (12.29 kg, 100% purity by HPLC, and 92% yield).

Example 10

Preparation of Form I of 1-[3-(4-Bromo-2-methyl-2H-pyrazol-3-yl)-4-methoxy-phenyl]-3-(2,4-difluoro-phenyl)-urea, Direct Method, (Compound I)

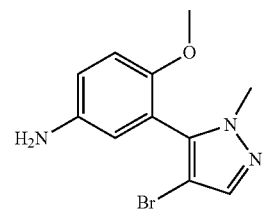

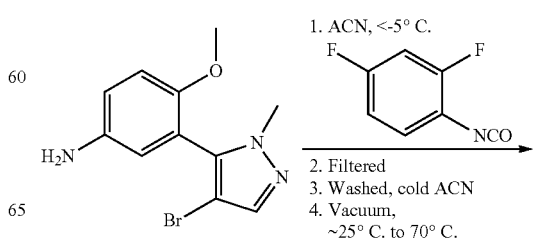

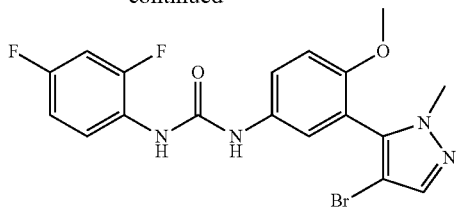

To a solution of 3-(4-bromo-2-methyl-2H-methyl-3-yl)-4-methoxy-phenylamine (16.7 kg) in acetonitrile (78.6 kg) in a 200 L-glass jacketed reactor with overhead stirring and nitrogen blanket at an internal temperature of <−10° C. 2,4-difluorophenyl-isocyanate (9.68 kg) was controlled charged through a 1 micron line filter at a rate substantially slow enough to prevent co-precipitation of the starting material in the product. After continued stirring at <−10° C. for approximately 1 hour post completion of the 2,4-difluorophenyl-isocyanate addition, the conversion of starting material to product was substantially complete. The product slurry was filtered and washed with cold acetonitrile (26.3 kg) at <−5° C. producing the acetonitrile solvate of the product. Full house vacuum (~30 in Hg) was applied to the bottom outlet filter/dryer while nitrogen flowed through from the top enhancing the removal of volatile solvents without application of heat. Samples were removed from the bulk material and LOD was determined using an IR-200 Moisture Analyzer Instrument (Denver Instrument Company). The time course is shown below:

| Sample No. | LOD % | Time (h) |
|---|---|---|
| 1 | 38.48 | 0 |
| 2 | 29.63 | 7 |
| 3 | 20.96 | 13.5 |
| 4 | 7.28 | 19.5 |

Drying of the "wetcake" was maintained at ambient temperature under full house vacuum (~30 in Hg) for about 19.5 h at which time the LOD was 7.28%. At this point, the temperature was raised to 70° C. under full house vacuum (~30 in Hg) for 11 hrs to afford 1-[3-(4-bromo-2-methyl-2H-pyrazol-3-yl)-4-methoxy-phenyl]-3-(2,4-difluoro-phenyl)-urea (24.2 kg, 99.94% HPLC purity, form I determined by PXRD, and 92.9% yield).

Example 11

Conversion of Form II of 1-[3-(4-Bromo-2-methyl-2H-pyrazol-3-yl)-4-methoxy-phenyl]-3-(2,4-difluoro-phenyl)-urea to Form I of 1-[3-(4-Bromo-2-methyl-2H-pyrazol-3-yl)-4-methoxy-phenyl]-3-(2,4-difluoro-phenyl)-urea

1. THF, heat
2. <−5° C.
3. Heptane
4. Filtered
5. ACN wash, ~0° C.
6. Vacuum, ~25° C. to 70° C.

Form II

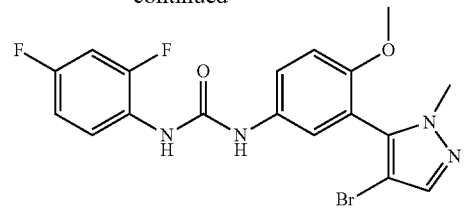

Form I

1-[3-(4-Bromo-2-methyl-2H-pyrazol-3-yl)-4-methoxy-phenyl]-3-(2,4-difluoro-phenyl)-urea (24.2 kg) was dissolved in tetrahydrofuran (85.6 kg) in a 200 L Hastelloy jacketed reactor with overhead stirring and nitrogen blanket at or near reflux (62.4° C.). Solids which had precipitated on the wall were washed down with THF (8.6 kg). The THF solution was transferred through a line filter into a 400 L glass lined reactor. At a reduced THF solution internal temperature of <−5° C. heptane (128.5 kg) was added into the reactor at a controlled rate such that internal temperature did not exceed −5° C. After having been stirred at <−5° C. for 17 min, the resulting slurry was filtered through a Hastelloy filter/dryer, and the solid product was washed with precooled acetonitrile (18.9 kg) at −11° C. (without the acetonitrile wash, the heptane level in the dried product would be about 10,000 ppm, which would exceed the ICH guideline of <5000 ppm). Full house vacuum (~30 in Hg) was applied to the bottom outlet filter/dryer while nitrogen flows through from the top enhancing the removal of volatile solvents without application of heat. The volatile solvent content of the wetcake was 4.85% prior to application of heat. Upon drying at 70° C. under full house vacuum (~30 in Hg), 1-[3-(4-bromo-2-methyl-2H-pyrazol-3-yl)-4-methoxy-phenyl]-3-(2,4-difluoro-phenyl)-urea (21.9 kg, Form I determined by PXRD, and 90.5% yield) was isolated.

Example 12

Powder X-Ray Diffraction of Form I of 1-[3-(4-Bromo-2-methyl-2H-pyrazol-3-yl)-4-methoxy-phenyl]-3-(2,4-difluoro-phenyl)-urea (Compound I)

Powder X-ray Diffraction (PXRD) data were collected on an X'Pert PRO MPD powder diffractometer (PANalytical, Inc.) with a Cu source set at 45 kV and 40 mA, a Ni-filter to remove Cu Kβ radiation, and an X'Celerator detector. The instrument was calibrated by the vendor using a silicon powder standard NIST #640c. The calibration was found to be correct when it was tested with NIST #675 low-angle diffraction standard. The sample was prepared for PXRD scanning by placing several milligrams of compound onto a sample holder and smoothing as flat as possible by pressing weigh paper down on the sample with a flat object. The sample was analyzed using a spinning-sample stage. Scans covered the range of 5 to 40° 2θ. A continuous scan mode was used with a step size of 0.0170° 2θ. Diffraction data were viewed and analyzed with the X'Pert Data Viewer Software, version 1.0a and X'Pert HighScore Software, version 1.0b.

The PXRD pattern for Form I of 1-[3-(4-bromo-2-methyl-2H-pyrazol-3-yl)-4-methoxy-phenyl]-3-(2,4-difluoro-phenyl)-urea (Compound I) is shown in FIG. 21.

TABLE 33

Observed Peaks for Form I of 1-[3-(4-Bromo-2-methyl-2H-pyrazol-3-yl)-4-methoxy-phenyl]-3-(2,4-difluoro-phenyl)-urea (Compound I) Ranging from 5 °2θ to 30 °2θ

| Pos. [°2θ] | Rel. Int. [%] |
|---|---|
| 5.6* | 100.0 |
| 7.4* | 23.4 |
| 7.7 | 9.5 |
| 9.2 | 0.1 |
| 9.7 | 0.3 |
| 11.2* | 25.7 |
| 11.6 | 7.6 |
| 12.8 | 4.9 |
| 12.8 | 4.9 |
| 14.0 | 2.8 |
| 14.5 | 1.4 |
| 15.2 | 4.3 |
| 15.5 | 3.5 |
| 15.7 | 5.5 |
| 16.1 | 2.2 |
| 16.5 | 1.5 |
| 17.9 | 1.9 |
| 18.5 | 5.1 |
| 19.3 | 3.2 |
| 20.3 | 3.5 |
| 20.4 | 4.4 |
| 21.1* | 49.3 |
| 22.0 | 2.0 |
| 22.5 | 1.9 |
| 23.1 | 1.7 |
| 23.9 | 1.3 |
| 24.3 | 2.3 |
| 24.5 | 2.9 |
| 25.0* | 17.4 |
| 25.6 | 4.2 |
| 26.0 | 4.8 |
| 26.3 | 5.8 |
| 26.8 | 9.5 |
| 26.9 | 8.3 |
| 27.4 | 4.0 |
| 28.0 | 8.1 |
| 28.1 | 7.9 |
| 28.8 | 4.8 |
| 29.1 | 3.9 |

*Peaks of about 17% or greater relative intensity.

The PXRD pattern for a tetrahydrofuran solvate of 1-[3-(4-bromo-2-methyl-2H-pyrazol-3-yl)-4-methoxy-phenyl]-3-(2,4-difluoro-phenyl)-urea (Compound I) is shown in FIG. 29.

The PXRD pattern for a heptane solvate of 1-[3-(4-Bromo-2-methyl-2H-pyrazol-3-yl)-4-methoxy-phenyl]-3-(2,4-difluoro-phenyl)-urea (Compound I) is shown in FIG. 30.

Example 13

Differential Scanning Calorimetry for Form I of 1-[3-(4-Bromo-2-methyl-2H-pyrazol-3-yl)-4-methoxy-phenyl]-3-(2,4-difluoro-phenyl)-urea (Compound I)

Differential Scanning Calorimetry (DSC) was performed on a TA Instruments, Inc. DSC Q2000 at 10° C./min. The instrument was calibrated at this scan rate by the vendor for temperature and energy using the melting point and enthalpy of fusion of an indium standard. Samples were prepared by taring a sample-pan lid along with a sample-pan bottom on a Mettler Toldeo MX5 balance. Sample was placed in the bottom of the tared sample pan. The sample-pan lid fitted snuggly in the sample-pan bottom. The sample and pan were reweighed to get the sample weight. Thermal events (for example, onset temperature, enthalpy of fusion) are calculated using the Universal Analysis 2000 software, version 4.1D, Build 4.1.0.16.

The DSC thermogram for Form I of 1-[3-(4-Bromo-2-methyl-2H-pyrazol-3-yl)-4-methoxy-phenyl]-3-(2,4-difluoro-phenyl)-urea (Compound I) is shown in FIG. 22.

Example 14

FT-Raman Spectroscopy for Form I of 1-[3-(4-Bromo-2-methyl-2H-pyrazol-3-yl)-4-methoxy-phenyl]-3-(2,4-difluoro-phenyl)-urea (Compound I)

The Raman spectrum for Form I of 1-[3-(4-bromo-2-methyl-2H-pyrazol-3-yl)-4-methoxy-phenyl]-3-(2,4-difluoro-phenyl)-urea (Compound I) was recorded using the ThermoFisher NXR6700 FT-Raman Spectrometer (EQ1874). NXR6700 FT-Raman Spectrometer (ThermoFisher Scientific, Serial #AHR0700837), NXR FT-Raman Module (ThermoFisher Scientific AEU0700442) and using the FT-Raman Micro-Stage Accessory (ThermoFisher Scientific AIS0800151). The instrument comprises a NdYAg laser operating at a wavelength of 1064 nm, an interferometer with a calcium fluoride beam-splitter, and an InGaAs detector. No background spectrum was required, and the Raman spectra were recorded by placing approximately 1 mg of each sample directly into the powder cup on the sample stage.

In order to collect the spectra, 1024 transients of an interferogram containing 8192 points were acquired with 4 $cm^{-1}$ resolution. The spectrum was recorded from 100 $cm^{-1}$ to 3700 $cm^{-1}$. The interferogram was apodized with a Happ-Genzel function and the data was zero-filled once prior to the application of a power spectrum for phase correction.

Collection and Processing Information

Number of sample scans: 2048; Collection length: 4240.4 sec; Resolution: 4.000; Levels of zero filling: 1; Number of scan points: 16672; Number of FFT points: 32768; Laser frequency: 15798.3 $cm^{-1}$; Interferogram peak position: 8192; Apodization: Happ-Genzel; Phase correction: Power spectrum; Number of background scans: 0; and Background gain: 0.0.

Data Description:

Number of points: 3737, X-axis: Raman shift (cm-1), Y-axis: Raman intensity, First X value: 99.2486, Last X value: 3701.6821, Raman laser frequency: 9393.6416, Data spacing: 0.064249.

Spectrometer Description:

Spectrometer: Nicolet 6700, Source: Off, Detector: InGaAs, Smart Accessory ID: Unknown, Beamsplitter: CaF2, Sample spacing: 1.0000, Digitizer bits: 24, Mirror velocity: 0.3165, Aperture: 59.00, Sample gain: 64.0, High pass filter: 200.0000, Low pass filter: 11000.0000.

Data Processing:

Final format: Shifted spectrum, Resolution: 4.000 from 99.2486 to 3701.6821, Laser power at sample: 0.699 W.

The FT-Raman Spectrum for Form I of 1-[3-(4-bromo-2-methyl-2H-pyrazol-3-yl)-4-methoxy-phenyl]-3-(2,4-difluoro-phenyl)-urea (Compound I) is shown in FIG. 23.

Example 15

Thermogravimetric Analysis (TGA) for Form I of 1-[3-(4-Bromo-2-methyl-2H-pyrazol-3-yl)-4-methoxy-phenyl]-3-(2,4-difluoro-phenyl)-urea (Compound I)

Thermal Gravimetric Analysis (TGA) was performed on the TA Instruments, Inc. TGA Q500. The instrument is calibrated by the vendor at 10° C./min. for temperature using the curie point of a ferromagnetic standard. The balance is calibrated with a standard weight. Sample scans are performed at 10° C./min. Sample was placed into an open sample part, previously tared on the TGA balance. Thermal events such as weight-loss are calculated using the Universal Analysis 2000 software, version 4.1D, Build 4.1.0.16.

The TGA thermogram for Form I of 1-[3-(4-bromo-2-methyl-2H-pyrazol-3-yl)-4-methoxy-phenyl]-3-(2,4-difluoro-phenyl)-urea (Compound I) is shown in FIG. 24.

Example 16

Single-Crystal X-Ray Structure of Hemi-Acetonitrile Solvate of 1-[3-(4-Bromo-2-methyl-2H-pyrazol-3-yl)-4-methoxy-phenyl]-3-(2,4-difluoro-phenyl)-urea Crystal structure determination was carried out under non-GMP conditions at Purdue Crystallography Laboratory, West Lafayette, Ind.

1. Data Collection

A colorless needle of $C_{18}H_{15}BrF_2N_4O_2$, 0.5 $(CH_3CN)$ having approximate dimensions of 0.47×0.13×0.11 mm was mounted on a glass fiber in a random orientation. Preliminary examination and data collection were performed Mo $K_\alpha$ radiation (λ=0.71073Å) on a Nonius KappaCCD equipped with a graphite crystal, incident beam monochromator.

Cell constants for data collection were obtained from least-squares refinement, using the setting angles of 17249 reflections in the range 3<θ<25°. The refined mosaicity from DENZO/SCALEPACK (Otwinowski et al., *Methods Enzymology* 1997, 276, 307) was 0.51° indicating moderate crystal quality. The space group was determined by the program XPREP (Broker, XPREP in SHELXTL version 6.12, Bruker AXS Inc., Madison, Wis., USA, (2002)). There were no systematic absences; the space group was determined to be P-1 (no 2).

The data were collected at a temperature of 150° K. Data were collected to a maximum 2θ of 51.2°.

2. Data Reduction

A total of 17249 reflections were collected, of which 6818 were unique. Frames were integrated with DENZO-SMN (Otwinowski et al., *Methods Enzymology* 1997, 276, 307).

Lorentz and polarization corrections were applied to the data. The linear absorption coefficient is 21.3/cm for Mo $K_\alpha$ radiation. An empirical absorption correction using SCALEPACK (Otwinowski et al., *Methods Enzymology* 1997, 276, 307) was applied.

Transmission coefficients ranged from 0.688 to 0.791. Intensities of equivalent reflections were averaged. The agreement factor for the averaging was 6.1% based on intensity.

3. Structure Solution and Refinement

The structure was solved by direct methods using SIR2004 (Burla et al., *J. Appl. Cryst.*, 2005, 38, 381). The remaining atoms were located in succeeding difference Fourier syntheses. Hydrogen atoms were included in the refinement but restrained to ride on the atom to which they are banded. The structure was refined in full-matrix least-squares by minimizing the function:

$$\Sigma w(|F_o|^2-|F_c|^2)^2$$

The weight w is defined as:

$$1/[\sigma^2(F_o^2)+(0.0600P)^2+7.0096P] \text{ where } P=(F_o^2+2F_c^2)/3$$

Scattering factors were taken from the "International Tables for Crystallography" (International Tables for Crystallography, Vol. C, Kluwer Academic Publishers, Utrecht, The Netherlands, (1992), Tables 4.2.6.8 and 6.1.1.4.). Of the 6818 reflections were used in the refinements, only 5185 reflections with $F_o^2>2\sigma$ $(F_o^2)$ were used in calculating R I. The final cycle of refinement included 575 variable parameters and converged (largest parameter shift was <0.01 times its estimated standard deviation) with unweighted and weighted agreement factors of:

$$R=\Sigma|F_o-F_c|/\Sigma F_o=0.079$$

$$R_w=\sqrt{(\Sigma w(F_o^2-F_c^2)^2/\Sigma w(F_o^2)^2)}=0.161$$

The standard deviation of an observation of unit weight was 1.11. The highest peak in the final difference Fourier had a height of 0.62 e/Å$^3$. The minimum negative peak had a height of −1.07 e/Å$^3$.

Refinement was performed on a LINUX PC using SHELX-97 (Sheldrick, SHELXL97, A Program for Crystal Structure Refinement, Univ. of Gottingen, Germany, (1997)).

The crystallographic drawing in FIG. 25 was done using Mercury v. 1.4.2 (build 2).

Example 17

Powder X-Ray Diffraction of Form II of 1-[3-(4-Bromo-2-methyl-2H-pyrazol-3-yl)-4-methoxy-phenyl]-3-(2,4-difluoro-phenyl)-urea (Compound I)

Powder X-ray Diffraction (PXRD) data were collected on an X'Pert PRO MPD powder diffractomer (PANalytical, Inc.) with a Cu source set at 45 kV and 40 mA, a Ni-filter to remove Cu Kβ radiation, and an X'Celerator detector. The instrument was calibrated by the vendor using a silicon powder standard NIST #640c. The calibration was found to be correct when it was tested with NIST #675 low-angle diffraction standard. The sample was prepared for PXRD scanning by placing several milligrams of compound onto a sample holder and smoothing as flat as possible by pressing weigh paper down on the sample with a flat object. The sample was analyzed using a spinning-sample stage. Scans covered the range of 5 to 40° 2θ. A continuous scan mode was used with a step size of 0.0170° 2θ. Diffraction data were viewed and analyzed with the X'Pert Data Viewer Software, version 1.0a and X'Pert HighScore Software, version 1.0b.

The PXRD pattern for Form II of 1-[3-(4-bromo-2-methyl-2H-pyrazol-3-yl)-4-methoxy-phenyl]-3-(2,4-difluoro-phenyl)-urea (Compound I) is shown in FIG. 31.

TABLE 34

Observed Peaks for Form II of 1-[3-(4-Bromo-2-methyl-2H-pyrazol-3-yl)-4-methoxy-phenyl]-3-(2,4-difluoro-phenyl)-urea (Compound I) Ranging from 5 °2θ to 30 °2θ

| Pos. [°2θ] | Rel. Int. [%] |
|---|---|
| 5.3 | 0.4 |
| 5.9 | 0.3 |
| 6.8 | 0.2 |
| 8.2* | 37.6 |
| 8.7 | 1.0 |
| 9.9 | 10.9 |
| 10.5 | 4.1 |
| 11.5* | 18.6 |
| 12.3* | 100.0 |

TABLE 34-continued

Observed Peaks for Form II of 1-[3-(4-Bromo-2-methyl-2H-pyrazol-3-yl)-4-methoxy-phenyl]-3-(2,4-difluoro-phenyl)-urea (Compound I) Ranging from 5 °2θ to 30 °2θ

| Pos. [°2θ] | Rel. Int. [%] |
|---|---|
| 12.7 | 8.9 |
| 14.1 | 5.5 |
| 15.6 | 8.8 |
| 16.5 | 0.2 |
| 17.3 | 6.5 |
| 19.0 | 6.2 |
| 19.1 | 5.5 |
| 19.6 | 9.7 |
| 19.9* | 20.0 |
| 20.4* | 16.2 |
| 21.1 | 3.3 |
| 22.0 | 4.7 |
| 22.1 | 5.0 |
| 23.0 | 8.9 |
| 24.6* | 18.4 |
| 24.7* | 14.5 |
| 25.5 | 2.0 |
| 26.9 | 4.4 |
| 27.6 | 0.5 |
| 28.4 | 5.2 |
| 28.5 | 7.3 |
| 28.8 | 5.6 |
| 29.6 | 4.8 |
| 30.0 | 2.1 |
| 31.6 | 0.4 |
| 32.4 | 0.5 |
| 33.0 | 0.8 |
| 33.8 | 3.1 |
| 34.5 | 3.8 |
| 35.0 | 0.4 |
| 36.0 | 1.2 |
| 36.5 | 2.9 |
| 37.3 | 0.3 |
| 38.7 | 1.7 |
| 39.7 | 0.4 |

*Peaks of about 14% or greater relative intensity.

Those skilled in the art will recognize that various modifications, additions, substitutions and variations to the illustrative examples set forth herein can be made without departing from the spirit of the invention and are, therefore, considered within the scope of the invention. All documents referenced above, including, but not limited to, printed publications and provisional and regular patent applications, are incorporated herein by reference in their entirety.

The invention claimed is:

1. A pharmaceutical composition comprising:
   a. 1-[3-(4-bromo-2-methyl-2H-pyrazol-3-yl)-4-methoxy-phenyl]-3-(2,4-difluoro-phenyl)-urea; and
   b. an excipient selected from: PVP and coPVP
   wherein 1-[3-(4-bromo-2-methyl-2H-pyrazol-3-yl)-4-methoxy-phenyl]-3-(2,4-difluoro-phenyl)-urea and said excipient are present in a ratio of between about 1:20 and about 1:1 by weight, and
   wherein the composition comprises less than 0.9 mole % of 1-(2,4-difluorophenyl)-3-(4-methoxy-3-(1-methyl-1H-pyrazol-5-yl)phenyl)urea.

2. The pharmaceutical composition according to claim 1, wherein said 1-[3-(4-bromo-2-methyl-2H-pyrazol-3-yl)-4-methoxy-phenyl]-3-(2,4-difluoro-phenyl)-urea is Form I of 1-[3-(4-bromo-2-methyl-2H-pyrazol-3-yl)-4-methoxy-phenyl]-3-(2,4-difluoro-phenyl)-urea which has an x-ray powder diffraction pattern comprising a peak expressed in terms of 2θ, at about 5.6°, about 7.4°, about 11.2°, about 21.1°, and about 25.0.

3. The pharmaceutical composition according to claim 1, comprising said 1-[3-(4-bromo-2-methyl-2H-pyrazol-3-yl)-4-methoxy-phenyl]-3-(2,4-difluoro-phenyl)-urea and said excipient in a ratio of about 1:8 by weight.

4. The pharmaceutical composition according to claim 1, further comprising methyl cellulose.

5. The pharmaceutical composition according to claim 1, wherein said excipient is PVP.

6. The pharmaceutical composition according to claim 1, wherein said excipient is coPVP.

7. The pharmaceutical composition according to claim 1, wherein said pharmaceutical composition further comprises at least one ingredient selected from: lactose monohydrate, microcrystalline cellulose, crospovidone, sodium lauryl sulfate, magnesium stearate and silicon dioxide.

8. The pharmaceutical composition according to claim 1, comprising said 1-[3-(4-bromo-2-methyl-2H-pyrazol-3-yl)-4-methoxy-phenyl]-3-(2,4-difluoro-phenyl)-urea in an amount of about 5% by weight of the total composition.

9. The pharmaceutical composition according to claim 1, comprising said excipient in an amount of about 40% by weight of the total composition.

10. The pharmaceutical composition according to claim 2, comprising:
    a. Form I of 1-[3-(4-bromo-2-methyl-2H-pyrazol-3-yl)-4-methoxy-phenyl]-3-(2,4-difluoro-phenyl)-urea in an amount of about 5% by weight of the total composition;
    b. said excipient in an amount of about 40% by weight of the total composition; and
    c. methyl cellulose in an amount of about 2% by weight of the total composition.

11. The pharmaceutical composition according to claim 2, comprising:
    a. Form I of 1-[3-(4-bromo-2-methyl-2H-pyrazol-3-yl)-4-methoxy-phenyl]-3-(2,4-difluoro-phenyl)-urea in an amount of about 5% by weight of the total composition;
    b. Plasdone™ K-29/32 PVP or Kollidon™ 30 PVP in an amount of about 40% by weight of the total composition;
    c. 4000 cps methyl cellulose in an amount of about 2% by weight of the total composition;
    d. Fast-Flo™ 316 lactose monohydrate in an amount of about 21.25% by weight of the total composition;
    e. Avicel™ PH102 microcrystalline cellulose in an amount of about 25% by weight of the total composition;
    f. Kollidon™ CL crospovidone in an amount of about 4% by weight of the total composition;
    g. sodium lauryl sulfate in an amount of about 2% by weight of the total composition;
    h. HyQual™ 5712 magnesium stearate in an amount of about 0.5% by weight of the total composition; and
    i. Cab-o-sil™ colloidal silicon dioxide in an amount of about 0.25% by weight of the total composition.

12. The pharmaceutical composition according to claim 2, comprising:
    a. Form I of 1-[3-(4-bromo-2-methyl-2H-pyrazol-3-yl)-4-methoxy-phenyl]-3-(2,4-difluoro-phenyl)-urea in an amount of about 5% by weight of the total composition;
    b. Kollidon™ VA 64 coPVP in an amount of about 40% by weight of the total composition;
    c. 4000 cps methyl cellulose in an amount of about 2% by weight of the total composition;
    d. Fast-Flo™ 316 lactose monohydrate in an amount of about 21.25% by weight of the total composition;
    e. Avicel™ PH102 microcrystalline cellulose in an amount of about 25% by weight of the total composition;

f. Kollidon™ CL crospovidone in an amount of about 4% by weight of the total composition;

g. sodium lauryl sulfate in an amount of about 2% by weight of the total composition;

h. HyQual™ 5712 magnesium stearate in an amount of about 0.5% by weight of the total composition; and i. Cab-o-sil™ colloidal silicon dioxide in an amount of about 0.25% by weight of the total composition.

13. The pharmaceutical composition according to claim 1, wherein said pharmaceutical composition is in the form of a pill, capsule or tablet.

14. The pharmaceutical composition according to claim 2, wherein said Form I of 1-[3-(4-bromo-2-methyl-2H-pyrazol-3-yl)-4-methoxy-phenyl]-3-(2,4-difluoro-phenyl)-urea constitutes at least about 0.1% by weight of said composition.

15. The pharmaceutical composition according to claim 2, wherein said Form I of 1-[3-(4-bromo-2-methyl-2H-pyrazol-3-yl)-4-methoxy-phenyl]-3-(2,4-difluoro-phenyl)-urea constitutes at least about 1% by weight of said composition.

16. The pharmaceutical composition according to claim 2, wherein said Form I of 1-[3-(4-bromo-2-methyl-2H-pyrazol-3-yl)-4-methoxy-phenyl]-3-(2,4-difluoro-phenyl)-urea constitutes at least about 10% by weight of said composition.

17. The pharmaceutical composition according to claim 2, wherein said Form I of 1-[3-(4-bromo-2-methyl-2H-pyrazol-3-yl)-4-methoxy-phenyl]-3-(2,4-difluoro-phenyl)-urea constitutes at least about 30% by weight of said composition.

18. The pharmaceutical composition according to claim 2, wherein said Form I of 1-[3-(4-bromo-2-methyl-2H-pyrazol-3-yl)-4-methoxy-phenyl]-3-(2,4-difluoro-phenyl)-urea constitutes at least about 50% by weight of said composition.

19. The pharmaceutical composition according to claim 2, wherein said Form I of 1-[3-(4-bromo-2-methyl-2H-pyrazol-3-yl)-4-methoxy-phenyl]-3-(2,4-difluoro-phenyl)-urea constitutes at least about 70% by weight of said composition.

20. The pharmaceutical composition according to claim 2, wherein said Form I of 1-[3-(4-bromo-2-methyl-2H-pyrazol-3-yl)-4-methoxy-phenyl]-3-(2,4-difluoro-phenyl)-urea constitutes at least about 90% by weight of said composition.

21. The pharmaceutical composition according to claim 2, further comprising a pharmaceutically acceptable carrier.

22. The pharmaceutical composition according to claim 2, wherein said composition is in the form of a pill, capsule or tablet.

23. A kit for treating a $5\text{-HT}_{2A}$ serotonin receptor-related disorder in an individual comprising a container and a pharmaceutical composition according to claim 1.

24. A method for treating a $5\text{-HT}_{2A}$ serotonin receptor-related disorder in an individual comprising administering to said individual in need thereof a therapeutically effective amount of a pharmaceutical composition according to claim 1.

25. The method according to claim 24, wherein said $5\text{-HT}_{2A}$ serotonin receptor-related disorder is a sleep disorder.

26. The method according to claim 24, wherein said sleep disorder is selected from: a dyssomnia, insomnia, and a parasomnia.

27. A method for increasing slow wave sleep, improving sleep consolidation, improving sleep maintenance, improving sleep quality, or treating nonrestorative sleep in an individual comprising administering to said individual in need thereof a therapeutically effective amount of a pharmaceutical composition according to claim 1.

28. A method for treating a $5\text{-HT}_{2A}$ serotonin receptor-related disorder selected from: coronary artery disease, myocardial infarction, transient ischemic attack, angina, stroke, atrial fibrillation, a condition associated with platelet aggregation, blood clot formation, a diabetic-related disorder, progressive multifocal leukoencephalopathy, hypertension, and pain, in an individual, comprising administering to the individual in need thereof a therapeutically effective amount of a pharmaceutical composition according to claim 1.

* * * * *